(12) United States Patent
Ardecky et al.

(10) Patent No.: US 6,593,493 B1
(45) Date of Patent: Jul. 15, 2003

(54) RXR MODULATORS WITH IMPROVED PHARMACOLOGIC PROFILE

(75) Inventors: Robert J. Ardecky, Encinitas, CA (US); Marcus F. Boehm, San Diego, CA (US); Amy L. Faulkner, San Diego, CA (US); Lawrence G. Hamann, Cherry Hill, NJ (US); Todd K. Jones, Solana Beach, CA (US); Christopher M. Mapes, Del Mar, CA (US); Pierre-Yves Michellys, San Diego, CA (US); John S. Tyhonas, San Diego, CA (US); Anthony W. Thompson, San Diego, CA (US); Jyun-Hung Chen, San Diego, CA (US)

(73) Assignee: Ligand Pharmaceuticals, Inc., San Diego, CA (US)

( * ) Notice: Subject to any disclaimer, the term of this patent is extended or adjusted under 35 U.S.C. 154(b) by 190 days.

(21) Appl. No.: 09/662,211

(22) Filed: Sep. 14, 2000

Related U.S. Application Data

(60) Provisional application No. 60/153,890, filed on Sep. 14, 1999.

(51) Int. Cl.$^7$ .......................... C07C 55/00; A01N 37/12
(52) U.S. Cl. ................. 562/465; 562/444; 562/426; 514/561; 514/562; 514/571; 546/339
(58) Field of Search ................................ 562/426, 444, 562/465; 514/561, 562, 571; 546/339

(56) References Cited

U.S. PATENT DOCUMENTS

| | | | |
|---|---|---|---|
| 3,775,332 A | 11/1973 | Heins et al. | |
| 3,798,031 A | 3/1974 | Janssens et al. | |
| 3,830,647 A | 8/1974 | Janssens et al. | |
| 3,832,171 A | 8/1974 | Janssens et al. | |
| 3,928,686 A | 12/1975 | Poot et al. | |
| 3,936,461 A | 2/1976 | Schwender et al. | |
| 3,979,394 A | 9/1976 | Janssens et al. | |
| 3,993,656 A | 11/1976 | Rooney et al. | |
| 4,138,490 A | 2/1979 | Brittain et al. | |
| 4,193,931 A | 3/1980 | Loeliger | 424/308 |
| 4,326,055 A | 4/1982 | Loeliger | 542/429 |
| 4,415,572 A | 11/1983 | Tominaga et al. | |
| 4,427,654 A | 1/1984 | Austin | |
| 4,505,852 A | 3/1985 | Rasnick et al. | |
| 4,534,979 A | 8/1985 | Loev et al. | 514/529 |
| 4,539,134 A | 9/1985 | Martin et al. | 252/156 |
| 4,578,498 A | 3/1986 | Frickel et al. | 560/8 |
| 4,710,507 A | 12/1987 | Campbell et al. | |
| 4,728,653 A | 3/1988 | Campbell et al. | |
| 4,801,733 A | 1/1989 | Wuest et al. | 560/56 |
| 4,831,052 A | 5/1989 | Shudo | 514/455 |
| 4,833,240 A | 5/1989 | Maignan et al. | 536/55.2 |
| 4,874,747 A | 10/1989 | Shroot et al. | 514/23 |
| 4,879,284 A | 11/1989 | Land et al. | 514/62 |
| 4,898,864 A | 2/1990 | Maignan et al. | 514/237.5 |
| 4,925,979 A | 5/1990 | Shudo | 562/462 |
| 4,933,336 A | 6/1990 | Martin et al. | |
| 4,943,502 A | 7/1990 | Terrell et al. | |
| 4,981,784 A | 1/1991 | Evans et al. | 435/6 |
| 5,004,730 A | 4/1991 | Philippe et al. | 514/29 |
| 5,071,773 A | 12/1991 | Evans et al. | 436/501 |
| 5,081,242 A | 1/1992 | Combs | |
| 5,091,528 A | 2/1992 | Gluchowski et al. | |
| 5,124,473 A | 6/1992 | Shroot et al. | 560/56 |
| 5,147,844 A | 9/1992 | Weber et al. | |
| 5,198,567 A | 3/1993 | Lang et al. | 560/56 |
| 5,320,833 A | 6/1994 | Deckers et al. | 424/59 |
| 5,391,569 A | 2/1995 | Brion et al. | 514/456 |
| 5,391,766 A | 2/1995 | Klaus et al. | |
| 5,688,810 A | 11/1997 | Jones et al. | |
| 5,693,646 A | 12/1997 | Jones et al. | |
| 5,693,647 A | 12/1997 | Jones et al. | |
| 5,696,127 A | 12/1997 | Jones et al. | |
| 5,696,130 A | 12/1997 | Jones et al. | |
| 5,721,103 A | 2/1998 | Boehm et al. | |
| 5,968,908 A | 10/1999 | Epstein et al. | |
| 5,977,108 A | 11/1999 | Kikuchi et al. | |
| 5,977,125 A | 11/1999 | Hibi et al. | |
| 6,030,964 A | 2/2000 | Hibi et al. | |
| 6,133,309 A | 10/2000 | Bollag et al. | |
| 6,147,224 A | 11/2000 | Vuligonda et al. | |

FOREIGN PATENT DOCUMENTS

| | | |
|---|---|---|
| DE | 21 11 938 | 10/1971 |
| DE | 26 11 824 | 9/1976 |
| DE | 38 10 706 | 10/1989 |
| EP | 0 272 910 | 6/1988 |
| EP | 0 356 230 | 2/1990 |
| EP | 0 542 609 | 5/1993 |
| EP | 0718285 A2 | 6/1996 |
| GB | 2 058 788 | 4/1981 |
| SU | 555119 | 4/1977 |
| WO | 89/07441 | 8/1989 |
| WO | 93/21146 | 10/1993 |
| WO | 94/12880 | 6/1994 |
| WO | 94/15901 | 7/1994 |
| WO | 94/15902 | 7/1994 |
| WO | 94/17796 | 8/1994 |

(List continued on next page.)

OTHER PUBLICATIONS

Allegretto, et al., "Transactivation Properties of Retinoic Acid and Retinoid X Receptors in Mammalian Cells and Yeast," *J. Biol. Chem.*, 268(35):26625–26633 (1993).

*Primary Examiner*—Paul J. Killos
(74) *Attorney, Agent, or Firm*—Paul, Hastings, Janofsky & Walker LLP

(57) ABSTRACT

The present invention provides a novel class of RXR modulator compounds that exhibit an improved pharmacologic profile relative to the profile of previously studied RXR modulators, including those that share common structural features with the presently claimed modulators. The present invention also provides synthetic methods for preparing these compounds as well as pharmaceutical compositions incorporating these novel compounds and methods for the therapeutic use of such compounds and pharmaceutical compositions.

85 Claims, No Drawings

FOREIGN PATENT DOCUMENTS

| WO | 94/20093 | 9/1994 |
|---|---|---|
| WO | 95/24394 | 9/1995 |
| WO | 96/05165 | 2/1996 |
| WO | 96/19458 | 6/1996 |
| WO | 97/00876 | 1/1997 |
| WO | 97/12853 | 4/1997 |
| WO | 97/49709 | 12/1997 |
| WO | WO 99/58486 | 11/1999 |
| WO | 00/66680 | 11/2000 |

OTHER PUBLICATIONS

Eyrolles, et al., "Retinoid Antagonists: Molecular Design Based on the Ligand Superfamily Concept," Med. Chem. Res., 2:361–367 (1992).

Jow, et al., "The Human Peroxisome Proliferator–activated Receptor (PPAR) Subtype NUC1 Prepresses the Activation of hPPARα and Thyroid Hormone Receptors," J. Biol. Chem, 270(8):3836–3840 (1995).

Kaneko, et al., "Retinoid Antagonists," Med. Chem. Res., 1:220–225 (1991).

Kurokawa, et al., "Regulation of retinoid signalling by receptor polarity and allosteric control of ligand binding," Nature, 371:528–531 (1994).

Levin, et al., "9–Cis retinoic acid stereoisomer binds and activates the nuclear receptor RXRα," Nature, 355:359–361 (1992).

Atarashi, et al., "Asymmetric Reduction of 7,8–Difluoro–3–methyl–2H–1,4–benzoxazine. Synthesis of a Key Intermediate of (S)–(–)–Ofloxacin (DR–3355)," J. Heterocyclic Chem. 28:329–31 (1991).

Atkins, R.L. et al., "Substituted Coumarins and Azacoumarins. Synthesis and Flourescent Properties," J. Org. Chem., 43(10):1975–1980 (1978).

Barluenga, et al., "A New Method for the Syntheis of Pyridines," Synthesis 191 (1975).

Bissell, E.R. et al., "Synthesis and Chemistry of 7–Amino–4–(trifluormethyl)coumarin and Its Amino Acid and Peptide Derivatives," J. Org. Chem., 45:2283–7 (1980).

Chapelo, et al., "Heteroaromatoc Analogues of the $\alpha_2$–Adrenoreceptor Partial Agonist Clonidine," J. Med. Chem., 32:1627–1630 (1989).

Edwards, et al., "5–Ayrl–2, 2–dihydro–5H–Chromeno[3,4–f]quinolines as Potent, Orally Active, Nonsteriodal Progesterone Receptor Agonists: The Effect of D–Ring Substituents," J. Med. Chem., 41:303–331 (1998).

Edwards, et al., "New Nonsteriodal Androgen Receptor Modulators Based on 4–(Trifluormethyl)–2(1H)–Pyrrolidino[3,2–g]Quinolinone," Bioorg. Med. Chem. Lett. 8:745–750 (1998).

Edwards, J.P., et al., "Preparation, Resolution, and Biological Evaluation of 5–Aryl–1,2–dihydro–5H–chromeno[3,4–f]quinolines: Potent, Orally Active, Nonsteriodal Progesterone Receptor Agonists," J. Med. Chem., 41(15):2779–85 (1998).

Goralski, et al., "Boranes in Synthesis. 3. Conversion of the Morpholine and Pyrrolidine Enamines of Symmetrical Dialkylketones to the Corresponding threo–β–Amino Alcohols via Hydroboration/Oxidation," Tetrahedron Lett. 35(20):3251–54 (1994).

Gromova, G.N. et al., Khim Prom St., 43(2):97–8 (1967).

Hamann, L.G. et al., "Synthesis and biological activity of a novel series of nonsteriodal, peripherally selective androgen receptor antagonists derived from 1, 2–dihydropyridono 5, 6–g!quinolines," J. Med. Chem., 41(4):623–39 (1998).

Hamann, L.G. et al., "Discovery of a Potent, Oraly Active, Nonsteriodal Androgen Receptor Agonist: 4–Ethyl–1,2,3,4–tetrahydro–6–(trifluoromethyl)–8–pyridono[5,6–g ]–quinoline," J. Med. Chem., 42(2):210–12 (1999).

Hershberger, et al., "Myotrophic Activity of 19–Nortestosterone and Other Steroids Determined by Modified Levator Ani Muscle Method" Proc. Soc. Exptl. Biol. Med. 83:175–178 (1953).

Ivanov, et al., Chem Abstracts No. 95:97624, "Synthesis and properties of derivatives of 2,2,4–trimethyl substituted quinolines and some of their analogs," Izv. Akad. Nauk. SSSR Ser. Khim., 3:628–633 (1981).

Jones, "The Structure, Reactions, Synthesis and Uses of Heterocyclic Compounds," Comprehensive Heterocyclic Chemistry vol. 2, Chap. 2.08, 421–426 (1984).

Kong, et al., "Effects of isosteric pyridone replacements in androgen antagonists based on 1,2–dihydro– and 1,2,3,4–tetrahydro–2,2–dimethyl–6–trifluoromethyl–8–pyridono 5,6–g quinolines" Bioorg. Med. Chem. Lett. 10(5), 411–414 (2000).

Labrie, et al., "Science behind total androgen blockade: from gene to combination therapy," Clin. Invest. Med. 16(6):475–492 (1993).

Luke, et al., "The Male Sex Accessory Tissues; Structure, Androgen Action, and Physiology," The Physiology of Reproduction, 1435–1487 (1994).

Matsumoto, et al., "Novel Potassium Channel Activators: Synthesis and Structure–Activity Relationship Studies of 3,4–Dihydro–2H–1,4–benzoxazine Derivatives," Chem. Pharm. Bull., 44(1):103–114 (1996).

Mitscher, et al., "Chiral DNA Gyrase Inhibitors. 2. Asymmetric Synthesis and Biological Activity of the Enantiomers of 9–Fluoro–3–methyl–10–(4–methyl–1–piperazinyl)–7–oxo–2,3–dihydro–7H–pyrido[1,2,3–de]–1,4–benzoxazine–6–carboxylic Acid (Ofloxacin)," J. Med. Chem. 30(12):2283 (1987).

Munk, et al., "Synthesis and Evaluation of 2–[(5–Methylbenz–1–ox–4–azin–6–yl)imino]imidazoline, a Potent, Peripherally Acting $\alpha_2$ Andrenoreceptor Agonist," J. Med. Chem., 39(18):3533–3538 (1996).

Okuda, et al., "Testosterone Dependent Regulation of the Enzymes Involved in DNA Synthesis in the Rat Ventral Prostate," J. Urol. 145:188–191 (1991).

Patent Abstracts of Japan, vol. 4, No. 019, Feb. 16, 1980; JP 54 154797.

Patent Abstracts of Japan, vol. 9, No. 188, Aug. 3, 1985; JP 60 056985.

Patent Abstracts of Japan, vol. 1999, No. 14, Dec. 22, 1999; JP 11 242304.

Pine, et al., "Carbonyl Methylenation Using a Titanium–Aluminum (Tebbe) Complex," J. Org. Chem. 50(8):1212–1216 (1985).

Quast, et al., "Synthesis and reactions of some pyrido 3, 2–g!quinolines (1,8–diazaanthracenes)," Liebigs Ann. Chem., 133–46 (1984).

Rodbard, D. "Mathematics and statistics of ligand assays: an illustrated guide" In: J. Langon and J.J. Clapp, eds., Ligand Assay, Masson Publishing U.S.A, Inc., New York, pp. 45–99, (1981).

Sala, et al., "Depsidone Synthesis. Part 14. The Total Synthesis of Psoromic Acid: Isopropyl Ethers as Useful Phenolic Protective Groups," *J. Chem. Soc. Perkin. Trans.* I:2593 (1979).

Sato, et al., "CsF in Organic Synthesis. Tuning of N– or O–Alkylation of 2–Pyridone," *Synlett* 845–846 (1995).

Shridhar, et al., "A General and Convenient Synthesis of 2H–1,4–Benzoxazin–3(4H)–ones," *Org. Prep. Proc. Int.* 14(3):195 (1982).

Simental, et al., "Transcriptional activation and nuclear targeting signals of the human androgen receptor," *J. Biol. Chem.* 266(1):510–518 (1991).

Tegley, C.M., et al., "5–Benzylidene 1,2–Dihydrochromeno [3,4–f]quinolines, A Novel Class of Nonsteriodal Human Progesterone Receptor Agonists," *J. Med. Chem.*, 41(22):4354–9 (1998).

Voss, "2,4–Bis(4–methoxyphenyl)–1,3,2,4–dithiadiphosphetane 2,4–Disulfide," *Encyclopedia of Reagents for Organic Synthesis*, 1:530–533 (1995).

Wagaw, et al., "Palladuim–Catalyzed Coupling of Optically Active Amines with Aryl Bromides," *J. Am. Chem. Soc.* 119:8451–8458 (1997).

Walsh, et al., "Inhibition of extratesticular stimuli to prostatic growth in the castrated rat by antiandrogens," *Endrocrinology* 86:624 (1970).

Xie, et al., *Chinese Chemical Letters* 6:857 (1995).

Zhi, et al., "5–Aryl–1,2–dihydrochromeno [3,4–f]quinolines: A Novel Class of Nonsteriodal Human Progesterone Receptor Agonists," *J. Med. Chem.*, 41(3):291–302 (1998).

Allegretto, et al., "Retinoid X Receptor Acts as a Hormone Receptor in Vivo to Induce a Key Metabolic Enzyme for 1,25–Dihydroxyvitamin $D_3$," *J.of Biol. Chem* 270:23906 (1995).

Apfel, et al., "A retinoic acid receptor α antagonist selectively counteracts retinoic acid effects," *Proc. Natl. Acad. Sci.* 89:7129 (1992).

Aurell, et al., "Trienediolates of Hexadienoic Acids in Synthesis. Synthesis of Retinoic and nor–Retinoic Acids." *Tetrahedron* 49:6089 (1993).

Beard, et al., "Synthesis and Structure–Activity Relationships of Stilbene Retinoid Analogs Substituted with Heteroaromatic Carboxylic Acids," *J. Med. Chem.* 38:2820 (*1995*).

Berger et al., "Interaction of Glucocorticoid Analogues With The Human Glucocorticoid Receptor," *J. Steroid. Biochem. Molec. Biol.* 41(3–8):733–738 (1992).

Bestmann, et al., "Cumulated Ylides as Building Blocks for the Synthesis of Heterocycles," *Angew. Chem. Int. Ed. Engl.* 15(2):115–116 (1976).

Bissonnette, et al., "9–cis Retinoic Acid Inhibition of Activation–Induced Apoptosis Is Mediated via Regulation of Fas Ligand and Requires Retinoic Acid Receptor and Retinoid X Receptor Activation," *Mol. Cell. Biol.* 15: 5576–5585 (1995).

Biswas, et al., "Montmorillonite clay as condensing agent in Pechmann reaction for the synthesis of courmarin derivatives," *Indian J. Chem.* 31B:628 (1992).

Blatt, The Fries Reaction Chapter II *Org. React.* 1:342 (1942).

Boehm, et al. "Synthesis and Structure–Activity Relationships of Novel Retinoid X Receptor Selective Retinoids," *J. Med. Chem.* 37:2930 (1994).

Boehm, et al., "Synthesis of High Specific Activity [3H]—9–cis Retonoic Acid and Its Application for Identifying Retinoids with Unusual Binding Properties," *J. Med. Chem.* 37:408 (1994).

Boehm, et al., "Design and Synthesis of Potent Retinoid X Receptor Selective Ligands That Induce Apoptosis in Leukemia Cells," *J. Med. Chem.* 38:3146 (1995).

Canan–Koch, et al., "Identification of the First Retinoid X Receptor Homodimer Antagonist," *J. Med. Chem.* 39:3229 (1996).

Strickland et al., "Structure–Activity Relationships of a New Series of Retinoidal Benzoic Acid Derivatives as Measured by Induction of Differentiation of Murine F9 Teratocarcinoma Cells and Human HL–60 Promyelocytic Leukemia Cells," *Cancer Research* 43:5268–5272 (1983).

Catellani, et al., "A New Palladium–catalyzed Synthesis of 3,4–Disubstituted Coumarins from 3–Alkenoates of ortho–Iodophenol, Phenylacetylene and Carbon Monoxide," *Tetrahedron Lett.* 35:5923 (1994).

Clark and Miller, "Hydrogen Bonding in Organic Synthesis V: Potassium Fluoride in Carboxylic Acids as an Alternative To Crown Ether With Acid Salts in The Preparation of Phenacyl Esters," *Tetrahedron Lett.* 7:599 (1977).

Dawson and Hobbs, "Ch. 2—The Synthetic Chemistry of Retinoids," in *The Retinoids: Biology, Chemistry and Medicine*, 2nd edition, edited by Sporn et al., Raven Press, New York, pp. 5–178 (1994).

Dawson, et al., "Effects of Structural Modification in the C7–C11 Region of the Retinoid Skeleton on Biological Activity in a Series of Aromatic Retinoids," *J. Med. Chem.* 32:1504 (1989).

Loeliger, et al., "Arotinoids, a new class of highly active retinoids," *Eur. J. Med. Chem* 15:9 (1980).

Evans, "The Steroid and Thyroid Hormone Receptor Superfamily," *Science* 240:889–895 (1988).

Eyrolles, et al., "Retinobenzoic Acids. 6. Retoid Antagonists with a Heterocyclic Ring," *J. Med. Chem* 37:1508 (1994).

Forman, et al., "Unique Response Pathways Are Established by Allosteric Interactions among Nuclear Hormone Receptors," *Cell* 81:541–550 (1995).

Fries and Fink, "Uber Homologe des Cumaranons und ihre Abkommlinge," *Ber.* 41:4271 (1908).

Fries and Pfaffendorf, "Uber ein Kondensationsprodukt des Cumaranons und seine Umwandlung in Oxindirubin," *Ber.* 43:212 (1910).

Giguere et al., "Identification of a receptor for the morphogen retinoic acid," *Nature* 330:624–629 (1987).

Heyman et al., "9–Cis Retenoic Acid is a High Affinity Ligand for the Retinoid X Receptor," *Cell* 68:397–406 (1992).

Hollenberg and Evans, "Multiple and Cooperative Trans-–Activation Domains of the Human Glucocorticoid Receptor," *Cell* 55:899–906 (1988).

Ishikawa et al., "A Functional Retinoic Acid Receptor Encoded by the Gene on Human Chromosome 12," *Molecular Endocrinology* 4(6):837–844 (1990).

Kagechika, et al. "Retinobenzoic Acids. 2. Structure–Activity Relationship of Chalcone–4–carboxylic Acids and Glavone–4'–carboxylic Acids," *J. Med. Chem.*, 32:834 (1989).

Kagechika, et al., "Retinobenzoic Acids. 3. Structure–Activity Relationships of Retinoidal Azobenzene–4–carboxylic Acids and Stilbene–4–carboxylic Acids," *J. Med. Chem.* 32:1098 (1989).

Kagechika, et al., "Retinobenzoic Acids. 4. Conformation of Aromatic Amides with Retinoidal Activity. Importance of trans–Amide Structure for the Activity," *J. Med. Chem.* 32:2292 (1989).

Keidel, et al., "Different Agonist– and Antagonist–Induced Conformational Changes in Retinoic Acid Receptors Analyzed by Protease Mapping," *Mol. Cell. Biol.* 14:287 (1994).

Kliewer et al., "Convergence of 9–cis retinoic acid and peroxisome proliferator signalling pathways through heterodimer formation of their receptors," *Nature* 358:771–774 (1992).

Lee, et al., "A synthetic retinoid antagonist inhibits the human immunodeficiency virus type 1 promoter," *Proc. Natl. Acad. Sci.* 91:5632 (1994).

Ley et al., "Tetrapropylammonium Perruthenate, $Pr_4N+$ $RuO-_4$, TPAP: A Catalytic Oxidant for Organic Synthesis," *Synthesis* 639 (1994).

Li, et al., "Montmorillonite Clay Catalysts. Part 7. An Environmentally Friendly Procedure for the Synthesis of Coumarins via Pechmann Condensation of Phenols with Ethyl Acetoacetate," *J. Chem. Res.* 38–39 (1998).

Liu and Asato, "Photochemistry and Synthesis of Stereoisomers of Vitamin A," *Tetrahedron* 40(11):1931–1969 (1984).

Mangelsdorf et al., "Ch. 8—The Retinoid Receptors," in *The Retinoids: Biology, Chemistry and Medicine,* 2nd edition, Sporn ed., Raven Press Ltd., New York, pp. 319–349 (1994).

Mangelsdorf et al., "A Direct Repeat in the Cellular Retinol–Binding Protein Type II Gene Confers Differential Regulation by RXR and RAR," *Cell* 66:555–561 (1991).

Mangelsdorf et al., "Nuclear receptor that identifies a novel retinoic acid response pathway," *Nature* 345:224–229 (1990).

Maryanoff and Reitz, *Chem. Rev.* 89:863–927 (1989).

McDonnell, et al., "Analysis of Estrogen Receptor Function in Vitro Reveals Three Distinct Classes of Antiestrogens," *Mol. Endo.* 9:659–669 (1995).

Mukherjee et al., "Human and Rat Peroxisome Proliferator Activated Receptors (PPARs) Demonstrate Similar Tissue Distribution but Different Responsiveness to PPAR Activators," *J. Steroid Biochem. Molec. Biol.* 51(3–4):157–166 (1994).

Mukherjee, et al., "Identification, characterization, and Tissue Distribution of Human Peroxisome Proliferator–activated Receptor (PPAR) Isoforms PPARγ2 versus PPARγ1 and Activation with Retinoid X Receptor Agonists and Antagonists," *Journ. Biol. Chem.* 272: 8071–8076 (1997).

*Chemistry and Biology of Synthetic Retinoids,* Dawson and Okamuna, Eds., CRC Press, Florida: Chapters 3, 8, 14, and 16 (1990).

Petkovich et al., "A human retinoic acid receptor which belongs to the family of nuclear receptors," *Nature* 330:444–450 (1987).

Roy, et al., "Synergistic Activation of Retinoic Acid (RA)–Responsive Genes and Induction of Embryonal Carcinoma Cell Differentiation by an RA Receptor α (RARα)–, RARβ–, or RARγ–Selective Ligand in Combination with a Retinoid X Receptor–Specific Ligand," *Mol. Cell. Biol.* 15:6481–6487 (1995).

Sato and Otera, "CsF in Organic Synthesis. A Practical Method for Inversion of Secondary Mesylates," *Syn. Lett.* 336(1995).

Sethna and Phadke, The Pechmann Reaction *Organic Reactions* 7:1–58 (1953).

Sherman, et al., "Central Hypothyroidism Associated with Retinoid X Receptor–Selective Ligands," *N. Engl. J. Med.* 340(14):1075–1079 (1999).

Trost and Toste, "A New Palladium–Catalyzed Addition: A Mild Method for the Synthesis of Coumarins," *J. Am. Chem. Soc.* 118:6305 (1996).

Tzukerman et al., "Human estrogen receptor transactivational capacity is determined by both cellular and promoter context and mediated by two functionally distinct intramolecular regions," *Molecular Endocrinology* 8:21–30 (1994).

Umesono, et al. "Retinoic acid and thyroid hormone induce gene expression through a common responsive element," *Nature* 336:262 (1988).

Yoshimura, et al. "A Novel Type of Retinoic Acid Receptor Antagonist: Synthesis and Structure–Activity Relationships of Heterocyclic Ring Containing Benzoic Acid Derivatives," *J. Med. Chem.* 38:3163 (1995).

RXR MODULATORS WITH IMPROVED PHARMACOLOGIC PROFILE

This application claims priority to U.S. Provisional Application Ser. No. 60/153,890, filed Sep. 14, 1999, the entire disclosure of which is incorporated by reference herein.

FIELD OF THE INVENTION

The present invention relates to small molecule compounds that are able to modulate the biological activity of retinoid X receptors, and to methods for the production and therapeutic use of such compounds.

BACKGROUND OF THE INVENTION

The vitamin A metabolite, retinoic acid, has long been recognized to induce a broad spectrum of biological effects. For example, retinoic acid-containing products, such as Retin-A® and Accutane®, have found utility as therapeutic agents for the treatment of various pathological conditions. In addition, a variety of structural analogues of retinoic acid have been synthesized that also have been found to be bioactive. Many of these synthetic retinoids have been found to mimic many of the pharmacological actions of retinoic acid, and thus have therapeutic potential for the treatment of numerous disease states.

Medical professionals have become very interested in the therapeutic applications of retinoids. Among their uses approved by the FDA is the treatment of severe forms of acne and psoriasis as well as cancers such as Kaposi's Sarcoma. A large body of evidence also exists that these compounds can be used to arrest and, to an extent, reverse the effects of skin damage arising from prolonged exposure to the sun. Other evidence exists that these compounds have clear effects on cellular proliferation, differentiation and programmed cell death (apoptosis), and thus, may be useful in the treatment and prevention of a variety of cancerous and pre-cancerous conditions, such as acute promyleocytic leukemia (APL), epithelial cancers, squamous cell carcinomas, including cervical and skin cancers and renal cell carcinoma. Furthermore, retinoids may have beneficial activity in treating and preventing diseases of the eye, cardiovascular disease and skin disorders.

Major insight into the molecular mechanism of retinoic acid signal transduction was gained in 1988, when a member of the steroid/thyroid hormone intracellular receptor superfamily was shown to transduce a retinoic acid signal. V. Giguere et al., *Nature*, 330:624–29 (1987); M. Petkovich et al., *Nature*, 330: 444–50 (1987); for a review, see R. M. Evans, *Science*, 240:889–95 (1988). It is now known that retinoids regulate the activity of two distinct intracellular receptor subfamilies: the Retinoic Acid Receptors (RARs) and the Retinoid X Receptors (RXRs), including their subtypes, RARα,β,γ and RXRα,β,γ. All-trans-retinoic acid (ATRA) is an endogenous low-molecular-weight ligand that modulates the transcriptional activity of the RARs, while 9-cis retinoic acid (9-cis) is the endogenous ligand for the RXRs. R. A. Heyman et al., *Cell*, 68:397–406 (1992); and A. A. Levin et al., *Nature*, 355:359–61 (1992).

Although both the RARs and RXRs respond to ATRA in vivo, due to the in vivo conversion of some of the ATRA to 9-cis, the receptors differ in several important aspects. First, the RARs and RXRs are significantly divergent in primary structure (e.g., the ligand binding domains of RARα and RXRα have only approximately 30% amino acid homology). These structural differences are reflected in the different relative degrees of responsiveness of RARs and RXRs to various vitamin A metabolites and synthetic retinoids. In addition, distinctly different patterns of tissue distribution are seen for RARs and RXRs. For example, RXRα mRNA is expressed at high levels in the visceral tissues, e.g., liver, kidney, lung, muscle and intestine, while RARα mRNA is not. Finally, the RARs and RXRs have different target gene specificity. In this regard, RARs and RXRs regulate transcription by binding to response elements in target genes that generally consist of two direct repeat half-sites of the consensus sequence AGGTCA. RAR:RXR heterodimers activate transcription ligand by binding to direct repeats spaced by five base pairs (a DR5) or by two base pairs (a DR2). However, RXR:RXR homodimers bind to a direct repeat with a spacing of one nucleotide (a DR1). D. J. Mangelsdorf et al., "The Retinoid Receptors" in *The Retinoids: Biology, Chemistry and Medicine*, M. B. Sporn, A. B. Roberts and D. S. Goodman, Eds., Raven Press, New York, N.Y., 2nd Edition (1994). For example, response elements have been identified in the cellular retinal binding protein type II (CRBPII), which consists of a DR1, and in Apolipoprotein AI genes that confer responsiveness to RXR, but not to RAR. Further, RAR has also been shown to repress RXR-mediated activation through the CRBPII RXR response element (D. J. Manglesdorf et al., *Cell*, 66:555–61 (1991)). Also, RAR specific target genes have been identified, including target genes specific for RARβ (e.g., βRE), that consist of a DR5. These data indicate that two retinoic acid responsive pathways are not simply redundant, but instead manifest a complex interplay.

RXR agonists in the context of an RXR:RXR homodimer display unique transcriptional activity in contrast to the activity of the same compounds through an RXR heterodimer. Activation of a RXR homodimer is a ligand dependent event, i.e., the RXR agonist must be present to bring about the activation of the RXR homodimer. In contrast, RXR working through a heterodimer (e.g., RXR:RAR, RXR:VDR) is often the silent partner, i.e., no RXR agonist will activate the RXR-containing heterodimer without the corresponding ligand for the heterodimeric partner. However, for other heterodimers, (e.g., PPAR:RXR) a ligand for either or both of the heterodimer partners can activate the heterodimeric complex. Furthermore, in some instances, the presence of both an RXR agonist and the agonist for the other heterodimeric partner (e.g., gemfibrizol for PPARα and TTNPB for RARα) leads to at least an additive, and often a synergistic enhancement of the activation pathway of the other IR of the heterodimer pair (e.g., the PPARα pathway). See e.g., WO 94/15902, published Jul. 21, 1994; R. Mukherjee et al., *J. Steroid Biochem. Molec. Biol.*, 51:157–166 (1994); and L. Jow and R. Mukherjee, *J. Biol. Chem.*, 270:3836–40 (1995).

RAR and RXR retinoid agonists, including both RAR specific and RXR specific agonists have been previously identified. See e.g., WO 94/15902, WO 93/21146, WO 94/15901, WO 94/12880, WO 94/17796, WO 94/20093, WO 96/05165 and Application No. PCT/US93/10166; EPO Patent Application Nos. 87110303.2, 87309681.2 and EP 0718285; U.S. Pat. Nos. 4,193,931, 4,539,134, 4,801,733, 4,831,052, 4,833,240, 4,874,747, 4,879,284, 4,898,864, 4,925,979, 5,004,730, 5,124, 473, 5,198,567, 5,391,569 and Re 33,533; and H. Kagechika et al., "Retinobenzoic Acids. 2. Structure-Activity Relationship of Chalcone-4-carboxylic Acids and Flavone-4'-carboxylic Acids", *J. Med. Chem.*, 32:834 (1989); H. Kagechika et al., "Retinobenzoic Acids. 3. Structure-Activity Relationships of Retinoidal Azobenzene-4-carboxylic Acids and Stilbene-4-carboxylic Acids", *J. Med. Chem.*, 32:1098 (1989); H. Kagechika et al., "Retinobenzoic Acids. 4. Conformation of Aromatic Amides with Retinoidal Activity. Importance of trans-Amide Structure for the Activity", *J. Med. Chem.*, 32:2292 (1989); M. Boehm et al., *J. Med. Chem.*, 37:2930 (1994); M. Boehm et al., *J. Med. Chem.*, 38:3146 (1995); E. Allegretto et al., *Journal of Biol. Chem.*, 270:23906 (1995); R. Bissonnette et al., *Mol. & Cellular Bio.*, 15:5576 (1995); R. Beard et al., *J. Med. Chem.*, 38:2820 (1995); and M. I. Dawson et al., "Effect of Structural Modifications in the C7–C11 Region of the Retinoid Skeleton on Biological Activity in a Series of Aromatic Retinoids", *J. Med. Chem.*, 32:1504 (1989).

Further, antagonists to the RAR subfamily of receptors have been identified. See e.g., C. Apfel et al., *Proc. Natl. Acad. Sci.*, 89:7129 (1992); S. Keidel et al., *Mol. Cell. Biol.*, 14:287 (1994); S. Kaneko et al., *Med. Chem. Res.*, 1:220 (1991); L. Eyrolles et al., *Med. Chem. Res.*, 2:361 (1992); J. Eyrolles et al., *J. Med. Chem.*, 37:1508 (1994); M-O Lee et al., *Proc. Natl. Acad. Sci.*, 91:5632 (1994); Yoshimura et al., *J. Med. Chem.*, 38:3163 (1995); and U.S. Pat. No. 5,391,766. In addition, various polyene compounds have been disclosed to be useful in the treatment of inflammatory conditions, psoriasis, allergic reactions, and for use in sunscreens in cosmetic preparations. See e.g., U.S. Pat. Nos. 4,534,979 and 5,320,833. Also, trienediolates of hexadienoic acids have proved useful in the synthesis of retinoic and nor-retinoic acids. See M. J. Aurell, et al., *Tetrahedron*, 49:6089 (1993).

Compounds have also been found that are RXR antagonist (e.g., that bind to RXR and do not activate, but antagonize transcription) and/or RXR selective compounds that have distinct heterodimer selective properties, such that they are capable of manifesting agonist, partial agonist and antagonist properties. See WO 97/12853, published Apr. 10, 1997. RXR agonists compounds which have been identified so far have exhibited significant therapeutic utility, but they have also exhibited some undesirable side effects, such as elevation of triglycerides and suppression of the thyroid hormone axis (see, e.g., Sherman, S. I. et al., *N. Engl. J. Med.* 340(14):1075–1079 (1999).

The entire disclosures of the publications and references referenced to above and hereafter in this specification are incorporated herein by reference.

SUMMARY OF THE INVENTION

The present invention provides a novel class of RXR modulator compounds having the structure:

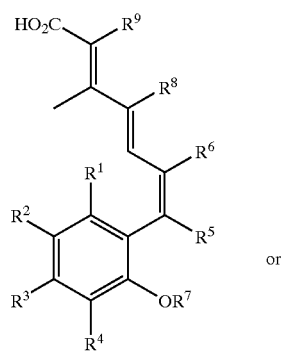

or

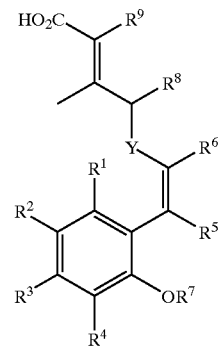

wherein $R^1$ is selected from the group of hydrogen, F, Cl, Br, I, $C_1$–$C_3$ alkyl, $C_1$–$C_3$ haloalkyl, $C_2$–$C_3$ alkenyl, $C_2$–$C_3$ haloalkenyl, $C_2$–$C_3$ alkynyl, $C_2$–$C_3$ haloalkynyl, and $C_1$–$C_3$ alkoxy, wherein said alkyl, haloalkyl, alkenyl, haloalkenyl, alkynyl, haloalkynyl, and alkoxy groups may be optionally substituted;

$R^2$ and $R^4$ are independently selected from the group of hydrogen, $NR^{10}R^{11}$, $C_1$–$C_6$ alkyl, $C_1$–$C_6$ haloalkyl, $C_3$–$C_8$ cycloalkyl, $C_2$–$C_6$ alkenyl, $C_2$–$C_6$ haloalkenyl, $C_2$–$C_6$ alkynyl, $C_2$–$C_6$ haloalkynyl, aryl, heteroaryl, $C_1$–$C_6$ alkoxy, and aryloxy, wherein said alkyl, haloalkyl, cycloalkyl, alkenyl, haloalkenyl, alkynyl, haloalkynyl, aryl, heteroaryl, alkoxy, aryloxy groups may be optionally substituted;

$R^3$ is selected from the group of hydrogen, $C_1$–$C_6$ alkyl, $C_1$–$C_6$ haloalkyl, $C_3$–$C_8$ cycloalkyl, $C_2$–$C_6$ alkenyl, $C_2$–$C_6$ haloalkenyl, $C_2$–$C_6$ alkynyl, $C_2$–$C_6$ haloalkynyl, aryl, heteroaryl, $C_1$–$C_6$ alkoxy, and aryloxy, wherein said alkyl, haloalkyl, cycloalkyl, alkenyl, haloalkenyl, alkynyl, haloalkynyl, aryl, heteroaryl, alkoxy, aryloxy groups may be optionally substituted;

$R^5$ and $R^6$ are independently selected from the group of hydrogen, F, Cl, Br, I, CN, $NH_2$, OH, SH, $C_1$–$C_6$ alkyl, $C_1$–$C_6$ haloalkyl, $C_2$–$C_6$ alkenyl, $C_1$–$C_6$ haloalkenyl, $C_1$–$C_6$ alkoxy, and aryloxy wherein said alkyl, haloalkyl, alkenyl, haloalkenyl, alkoxy and aryloxy groups may be optionally substituted; or $R^5$ and $R^6$ taken together form a three- to eight-membered carbocyclic ring, a three- to eight-membered heterocyclic ring, an aryl group or a heteroaryl group, wherein said carbocyclic ring, heterocyclic ring, aryl and heteroaryl groups may be optionally substituted;

$R^7$ is selected from the group of $C_2$–$C_6$ alkyl, $C_2$–$C_6$ alkenyl, and $C_2$–$C_6$ haloalkyl, wherein said alkyl, alkenyl, and haloalkyl groups may be optionally substituted;

$R^8$ is selected from the group of hydrogen, F, Cl, Br, I, CN, $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_1$–$C_6$ alkoxy, and aryloxy, wherein said alkyl, haloalkyl, alkenyl, haloalkenyl, alkynyl, alkoxy, and aryloxy groups may be optionally substituted;

$R^9$ is selected from the group of hydrogen, F, Cl, Br, I, methyl, and optionally substituted methyl;

$R^{10}$ and $R^{11}$ each independently is hydrogen or optionally substituted $C_1$–$C_6$ alkyl; or $R^{10}$ and $R^{11}$ taken together with nitrogen form an optionally substituted five- or six-membered heterocyclic ring;

Y is selected from the group of $NR^{12}$; O and S;

$R^{12}$ is selected from the group of hydrogen, optionally substituted $C_1$–$C_6$ alkyl, and optionally substituted $C_1$–$C_6$ haloalkyl; and pharmaceutically acceptable salts thereof.

Compounds of the present invention exhibit an improved pharmacologic profile relative to the profile of previously studied RXR modulators, including those that share common structural features with the presently disclosed modulator compounds. The present invention also provides synthetic methods for preparing these compounds as well as pharmaceutical compositions incorporating these novel compounds and methods for the therapeutic use of such compounds and pharmaceutical compositions.

These and various other advantages and features of novelty that characterize the invention are pointed out with particularity in the claims annexed hereto and forming a part hereof. However, for a better understanding of the invention, its advantages, and objects obtained by its use, reference should be had to the accompanying descriptive matter, in which there is described preferred embodiments of the invention.

DETAILED DESCRIPTION OF THE INVENTION

The present invention is based on the discovery of a group of compounds that modulate the activity of the RXR receptor and unexpectedly exhibit a significantly improved pharmacologic profile. This new group of compounds does not exhibit the undesirable side effects of substantially raising triglyceride levels and substantially suppressing thyroid hormone axis, which have been associated with previously characterized RXR modulators.

In accordance with the present invention and as used herein, the following terms are defined with the following meanings, unless explicitly stated otherwise.

The term "alkyl", alone or in combination, refers to a straight-chain or branched-chain alkyl radical having from 1 to about 10 carbon atoms. Examples of alkyl radical include methyl, ethyl, n-propyl, isopropyl, n-butyl, isobutyl, sec-butyl, tert-butyl, tert-amyl, pentyl, hexyl, heptyl, octyl and the like.

The term "alkenyl", alone or in combination, refers to a straight-chain or branched-chain hydrocarbon radical having one or more carbon-carbon double-bonds and having from 2 to about 18 carbon atoms. Examples of alkenyl radicals include ethenyl, propenyl, 1,4-butadienyl and the like.

The term "alkynyl", alone or in combination, refers to a straight-chain or branched-chain hydrocarbon radical having one or more carbon-carbon triple-bonds and having from 2 to about 10 carbon atoms. Examples of alkynyl radicals include ethynyl, propynyl, butynyl and the like.

The term "aryl", alone or in combination, refers to an optionally substituted aromatic ring. The term aryl includes monocyclic aromatic rings, polyaromatic rings and polycyclic ring systems. The polyaromatic and polycyclic rings systems may contain from two to four, more preferably two to three, and most preferably two rings. Preferred aryl groups include five or six-membered aromatic ring systems. Examples of aryl groups include, without limitation, phenyl, biphenyl, naphthyl and anthryl ring systems. Preferably the aryl groups of the present invention contain from five to about twenty carbon atoms.

The term "alkoxy", alone or in combination, refers to an alkyl ether radical wherein the term alkyl is defined as above. Examples of alkoxy radicals include methoxy, ethoxy, n-propoxy, isopropoxy, n-butoxy, iso-butoxy, sec-butoxy, tert-butoxy and the like.

The term "aryloxy", alone or in combination, refers to an aryl ether radical wherein the term aryl is defined as above. Examples of aryloxy radicals include phenoxy, benyloxy and the like.

The term "cycloalkyl", alone or in combination, refers to a saturated or partially saturated monocyclic, bicyclic or tricyclic alkyl radical wherein each cyclic moiety has about 3 to about 8 carbon atoms. Examples of cycloalkyl radicals include cyclopropyl, cyclobutyl, cyclopentyl, cyclohexyl and the like.

The term "aralkyl", alone or in combination, refers to an alkyl radical as defined above in which one hydrogen atom is replaced by an aryl radical as defined above, such as, for example, benzyl, 2-phenylethyl and the like.

The terms alkyl, alkenyl and alkynyl include straight-chain, branched-chain, saturated and/or unsaturated structures, and combinations thereof.

The terms haloalkyl, haloalkenyl and haloalkynyl include alkyl, alkenyl and alkynyl structures, as described above, that are substituted with one or more fluorines, chlorines, bromines or iodines, or with combinations thereof.

The terms cycloalkyl and cycloalkene include optionally substituted, saturated and/or unsaturated $C_3$–$C_7$ carbocyclic structures.

The terms cycloalkyl, allyl, aryl, arylalkyl, heteroaryl, alkynyl, and alkenyl include optionally substituted cycloalkyl, allyl, aryl, arylalkyl, heteroaryl, alkynyl, and alkenyl groups.

The term carbocycle includes optionally substituted, saturated and/or unsaturated, three- to seven-membered cyclic structures in which all of the skeletal atoms are carbon.

The term heterocycle includes optionally substituted, saturated and/or unsaturated, three- to seven-membered cyclic structures in which one or more skeletal atoms is oxygen, nitrogen, sulfur, or combinations thereof.

The term "heteroaryl" refers to optionally substituted aromatic ring systems having one or more heteroatoms such as, for example, oxygen, nitrogen and sulfur. The term heteroaryl may include five- or six-membered heterocyclic rings, polycyclic heteroaromatic ring systems, and polyheteroaromatic ring systems where the ring system has from two to four, more preferably two to three, and most preferably two, rings. The terms heterocyclic, polycyclic heteroaromatic, and polyheteroaromatic include ring systems containing optionally substituted heteroaromatic rings having more than one heteroatom as described above (e.g., a six membered ring with two nitrogens), including polyheterocyclic ring systems from two to four, more preferably two to three, and most preferably two, rings. The term heteroaryl includes ring systems such as, for example, pyridine, quinoline, furan, thiophene, pyrrole, pyrrolidine, piperidine, indole, imidazole, thiazole, benzthiazole, triazole and pyrazole. Preferably the heteroaryl groups of the present invention contain from about five to about 20 skeletal ring atoms.

The term acyl includes alkyl, aryl, heteroaryl, arylalkyl or heteroarylalkyl substituents attached to a compound via a carbonyl functionality (e.g., —CO-alkyl, —CO-aryl, —CO-arylalkyl or heteroarylalkyl etc. . . . ).

The substituents of an "optionally substituted" structure may include, without limitation, one or more , preferably one to four, and more preferably one to two of the following preferred substituents: alkyl, alkenyl, alkynyl, aryl, heteroaryl, alkoxy, aryloxy, alkylthio, arylthio, cycloalkyl, arylalkyl, amino, alkylamino, dialkylamino, F, Cl, Br, I, CN, $NO_2$, $NH_2$, $NHCH_3$, $N(CH_3)_2$, S, SH, $SCH_3$, OH, $OCH_3$, $OCF_3$, $CH_3$, $CF_3$.

The term halogen refers to F, Cl, Br or I.

Protecting groups that may be used in the present invention include those that are commonly known to those skilled in the art, such groups include, but are not limited to, TBDMS, TBS, and BNZ.

RXR refers to RXRα, RXRβ, RXRγ and combinations thereof.

PPAR refers to PPARα, PPARβ, PPARγ1, PPARγ2 and combinations thereof.

The term RXR modulator compound refers to a compound that binds to one or more Retinoid X Receptors and modulates (i.e., increases or decreases the transcriptional activity and/or biological properties of the given receptor dimer) the transcriptional activity of an RXR homodimer (i.e., RXR:RXR) and/or RXR in the context of a heterodimer, including but not limited to heterodimer formation with peroxisome proliferator activated receptors (e.g., RXR:PPARα,β,γ1 or γ2), thyroid receptors (e.g., RXR:TRα or β), vitamin D receptors (e.g., RXR:VDR), retinoic acid receptors (e.g., RXR:RARα,β or γ), NGFIB receptors (e.g., RXR:NGFIB), NURR1 receptors (e.g., RXR:NURR1) LXR receptors (e.g., RXR:LXRα,β), DAX receptors (e.g., RXR:DAX), as well as other orphan receptors that form heterodimers with RXR, as either an agonist, partial agonist and/or antagonist. The particular effect of an RXR modulator as an agonist, partial agonist and/or antagonist will depend upon the cellular context as well as the heterodimer partner in which the modulator compounds acts.

Compounds of the present invention that do not substantially raise triglyceride levels do not raise triglyceride levels by more than 50% in individuals having normal triglyceride plasma levels when such compounds are administered to such individuals in a pharmaceutically effective amount. Preferably, such compounds do not raise triglyceride levels by more than 25%. More preferably, such compounds do not raise triglyceride levels by more than 15%. Most preferably, such compounds decrease triglyceride levels when administered to such individuals in a pharmaceutically effective amount.

Compounds of the present invention that do not substantially suppress thyroid hormone axis do not decrease T4 levels in the blood by more than 50% in individuals having normal T4 levels when such compounds are administered to such individuals in a pharmaceutically effective amount. Preferably, such compounds do not decrease T4 levels in the blood by more than 25%. More preferably, such compounds do not decrease T4 levels in the blood by more than 15%. Most preferably, compounds of the present invention do not substantially increase or decrease T4 levels in the blood.

As used herein, the term disease includes, but is not limited to, syndrome X, NIDDM, diabetes, obesity, and cardiovascular disease.

As used herein, persons at risk for developing a disease condition are those who have one or more, preferably two or more risk factors for developing such a disease. Such risk factors include, but are not limited to, insulin resistance, obesity, hyperlipidemia, hypercholesterolemia, and hypertension.

In accordance with a first aspect of the present invention, we have developed compounds of the formulae:

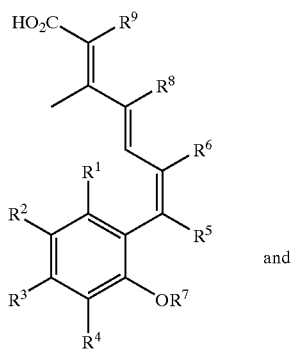

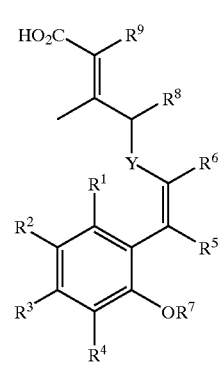

wherein
  $R^1$ is selected from the group of hydrogen, F, Cl, Br, I, $C_1$–$C_3$ alkyl, $C_1$–$C_3$ haloalkyl, $C_2$–$C_3$ alkenyl, $C_2$–$C_3$ haloalkenyl, $C_2$–$C_3$ alkynyl, $C_2$–$C_3$ haloalkynyl, and $C_1$–$C_3$ alkoxy, wherein said alkyl, haloalkyl, alkenyl, haloalkenyl, alkynyl, haloalkynyl, and alkoxy groups may be optionally substituted;
  $R^2$ and $R^4$ are independently selected from the group of hydrogen, $NR^{10}OR^{11}$, $C_1$–$C_6$ alkyl, $C_1$–$C_6$ haloalkyl, $C_3$–$C_8$ cycloalkyl, $C_2$–$C_6$ alkenyl, $C_2$–$C_6$ haloalkenyl, $C_2$–$C_6$ alkynyl, $C_2$–$C_6$ haloalkynyl, aryl, heteroaryl, $C_1$–$C_6$ alkoxy, and aryloxy, wherein said alkyl, haloalkyl, cycloalkyl, alkenyl, haloalkenyl, alkynyl, haloalkynyl, aryl, heteroaryl, alkoxy, aryloxy groups may be optionally substituted;
  $R^3$ is selected from the group of hydrogen, $C_1$–$C_6$ alkyl, $C_1$–$C_6$ haloalkyl, $C_3$–$C_8$ cycloalkyl, $C_2$–$C_6$ alkenyl, $C_2$–$C_6$ haloalkenyl, $C_2$–$C_6$ alkynyl, $C_2$–$C_6$ haloalkynyl, aryl, heteroaryl, $C_1$–$C_6$ alkoxy, and aryloxy, wherein said alkyl, haloalkyl, cycloalkyl, alkenyl, haloalkenyl, alkynyl, haloalkynyl, aryl, heteroaryl, alkoxy, aryloxy groups may be optionally substituted;
  $R^5$ and $R^6$ are independently selected from the group of hydrogen, F, Cl, Br, I, CN, $NH_2$, OH, SH, $C_1$–$C_6$ alkyl, $C_1$–$C_6$ haloalkyl, $C_2$–$C_6$ alkenyl, $C_1$–$C_6$ haloalkenyl, $C_1$–$C_6$ alkoxy, and aryloxy wherein said alkyl, haloalkyl, alkenyl, haloalkenyl, alkoxy and aryloxy groups may be optionally substituted; or
  $R^5$ and $R^6$ taken together form a three- to eight-membered carbocyclic ring, a three- to eight-membered heterocyclic ring, an aryl group or a heteroaryl group, wherein said carbocyclic ring, heterocyclic ring, aryl and heteroaryl groups may be optionally substituted;
  $R^7$ is selected from the group of $C_2$–$C_6$ alkyl, $C_2$–$C_6$ alkenyl, and $C_2$–$C_6$ haloalkyl, wherein said alkyl, alkenyl, and haloalkyl groups may be optionally substituted;

$R^8$ is selected from the group of hydrogen, F, Cl, Br, I, CN, $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_1$–$C_6$ alkoxy, and aryloxy, wherein said alkyl, haloalkyl, alkenyl, haloalkenyl, alkynyl, alkoxy, and aryloxy groups may be optionally substituted;

$R^9$ is selected from the group of hydrogen, F, Cl, Br, I, methyl, and optionally substituted methyl;

$R^{10}$ and $R^{11}$ each independently is hydrogen or optionally substituted $C_1$–$C_6$ alkyl; or $R^{10}$ and $R^{11}$ taken together with nitrogen form an optionally substituted five- or six-membered heterocyclic ring;

Y is selected from the group of $NR^{12}$, O and S;

$R^{12}$ is selected from the group of hydrogen, optionally substituted $C_1$–$C_6$ alkyl, and optionally substituted $C_1$–$C_6$ haloalkyl; and pharmaceutically acceptable salts thereof.

In one embodiment, the present invention provides a method for preparing compounds of formula 1 using a coumarin intermediate. Such a method includes treating a coumarin intermediate of structural formula 4:

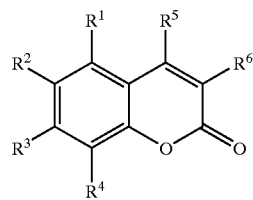

(4)

with a reducing agent to form a diol of structural formula 7:

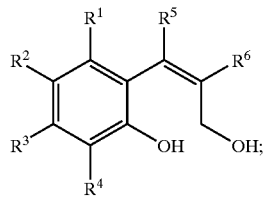

(7)

wherein $R^1$, $R^2$, $R^3$, $R^4$, $R^5$, and $R^6$ are as previously defined. Preferably, such a method further includes the step of selectively alkylating the phenol oxygen of the diol of structural formula 7 with $R^7X$ in the presence of a base to form a primary allylic alcohol of structural formula 8:

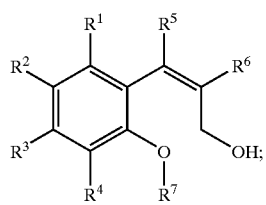

(8)

treating the allylic alcohol of structural formula 8 with an oxidant to form an aldehyde of structural formula 9:

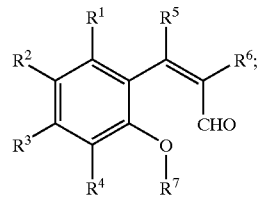

(9)

treating the aldehyde of structural formula 9 with a phosphonate of structural formula 10:

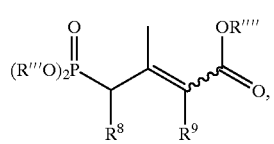

(10)

to form an ester of formula 1-E:

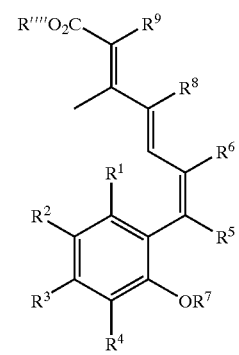

(1-E)

and hydrolyzing the ester, 1-E; wherein $R^1$, $R^2$, $R^3$, $R^4$, $R^5$, $R^6$, $R^7$, $R^8$, and $R^9$ are as previously defined. Preferably, R''' and R'''' each independently is methyl, ethyl or iso-propyl.

In another embodiment, the present invention provides a method for preparing compounds of formula 1, which includes the steps of treating alkoxyarylhalide 12

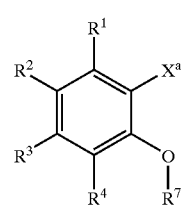

(12)

with a trialkyl borate and a base under Pd-catalysis to form a compound of structural formula 14

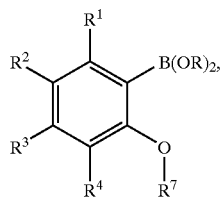
(14)

treating a compound of structural formula 14 with a compound of structural formula 15:

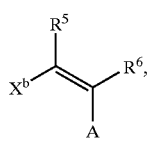
(15)

to form a compound of structural formula 16:

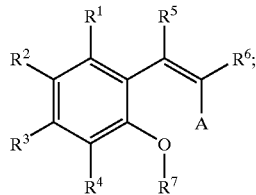
(16)

wherein A is COOR' or COP$^g$, P$^g$ is a protecting group, R and R' each is hydrogen or alkyl; X$^a$ and X$^b$ each independently is halogen; and R$^1$, R$^2$, R$^3$, R$^4$, R$^5$, R$^6$, and R$^7$ are as previously defined. In this embodiment, it is preferred where R is hydrogen and R' is methyl or ethyl.

In yet another embodiment, the present invention provides a method for preparing compounds of formula 1, which includes the steps of treating a ketone of structural formula VI:

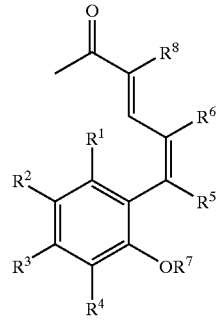
(VI)

with a phosphonate of structural formula 10b:

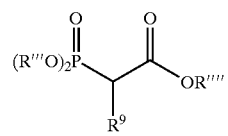
(10b)

wherein R''' and R'''' each independently is alkyl or aryl and R$^1$, R$^2$, R$^3$, R$^4$, R$^5$, R$^6$, R$^7$, R$^8$, and R$^9$ are as previously defined. In this embodiment, it is preferred where R$^9$ is halogen, most preferably F.

In still another embodiment, the present invention provides a method for preparing a compound of structural formula 1b:

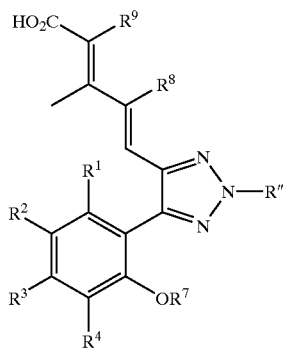
(1b)

which includes the step of treating a compound of the structural formula I:

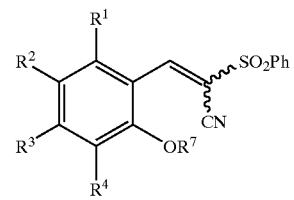
(I)

with sodium azide to form a triazole of formula II:

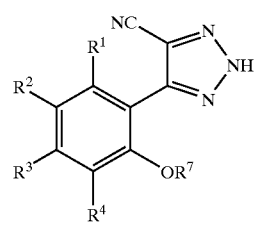
(II)

wherein R'' is C$_1$–C$_6$ alkyl and R$^1$, R$^2$, R$^3$, R$^4$, R$^5$, R$^6$, R$^7$, R$^8$, and R$^9$ are as previously defined.

In yet another embodiment, the present invention provides a method for preparing a compound of structural formula 1a:

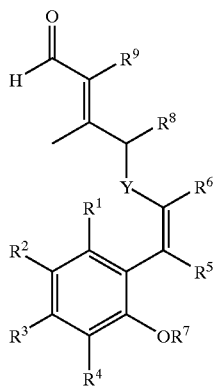

which includes the steps of
(a) treating an arylboronic acid of structural formula I:

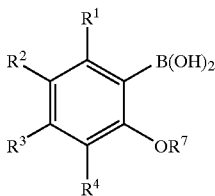

with a compound of structural formula XI:

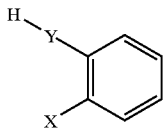

to form a compound of structural formula II:

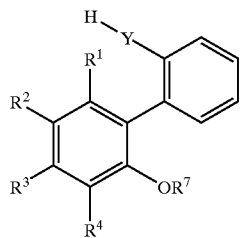

wherein X is halogen and $R^1$, $R^2$, $R^3$, $R^4$, $R^5$, $R^6$, $R^7$, $R^8$, $R^9$, $R^{12}$, and Y are as previously defined. In this embodiment, Y is preferably $NR^{12}$.

Preferred $R^1$ groups include hydrogen, optionally substituted $C_1$–$C_3$ alkyl, and optionally substituted $C_1$–$C_3$ haloalkyl. Most preferably, $R^1$ is hydrogen.

Preferred $R^2$ groups include $NR^{10}OR^{11}$, $C_1$–$C_6$ alkyl, $C_1$–$C_6$ haloalkyl, $C_3$–$C_8$ cycloalkyl, aryl and heteroaryl, wherein the alkyl, haloalkyl, cycloalkyl, aryl, and heteroaryl groups are optionally substituted. More preferred $R^2$ groups include $C_1$–$C_6$ alkyl, $C_1$–$C_6$ haloalkyl, and aryl. Most preferably $R^2$ is optionally substituted $C_1$–$C_6$ alkyl, such as, for example, ethyl, iso-propyl, tert-butyl, and tert-amyl.

Preferred $R^3$ groups include hydrogen, optionally substituted $C_1$–$C_6$ alkyl, and optionally substituted $C_1$–$C_6$ haloalkyl. Most preferably, $R^3$ is hydrogen.

Preferred $R^4$ groups include $NR^{10}OR^{11}$, $C_1$–$C_6$ alkyl, $C_1$–$C_6$ haloalkyl, $C_3$–$C_8$ cycloalkyl, aryl and heteroaryl, wherein the alkyl, haloalkyl, cycloalkyl, aryl, and heteroaryl groups are optionally substituted. More preferred $R^4$ groups include $C_1$–$C_6$ alkyl, $C_1$–$C_6$ haloalkyl, and aryl. Most preferably $R^4$ is $NR^{10}OR^{11}$ or optionally substituted $C_1$–$C_6$ alkyl, such as, for example, iso-propyl, tert-butyl, and tert-amyl.

Preferred $R^5$ groups include hydrogen, F, Cl, Br, I, and optionally substituted $C_1$–$C_4$ alkyl. Also preferred are compounds of formulae 1 and 1a where $R^5$ is taken with $R^6$ to form a five- to six-membered carbocyclic, a five- to six-membered heterocyclic ring, an aryl group or a heteroaryl group, wherein the carbocyclic, heterocyclic, aryl and heteroaryl groups are optionally substituted. More preferably $R^5$ is optionally substituted $C_1$–$C_4$ alkyl or is taken together with $R^6$ to form a five- to six-membered carbocyclic, a five- to six-membered heterocyclic ring, an aryl group or a heteroaryl group, wherein the carbocyclic, heterocyclic, aryl and heteroaryl groups are optionally substituted.

Preferred $R^6$ groups include hydrogen, F, Cl, Br, I, and optionally substituted $C_1$–$C_4$ alkyl. More preferably, $R^6$ is hydrogen or is taken together with $R^5$ to form a five- to six-membered carbocyclic, a five- to six-membered heterocyclic ring, an aryl group or a heteroaryl group, wherein the carbocyclic, heterocyclic, aryl and heteroaryl groups are optionally substituted.

Preferred $R^7$ groups include $C_2$–$C_5$ alkyl and $C_2$–$C_5$ haloalkyl, wherein the alkyl, and haloalkyl groups are optionally substituted. More preferably $R^7$ is optionally substituted $C_2$–$C_5$ haloalkyl.

Preferred $R^8$ groups include hydrogen, F, $C_1$–$C_6$ alkyl, and $C_1$–$C_6$ haloalkyl, wherein the alkyl and haloalkyl groups are optionally substituted. More preferably $R^8$ is hydrogen.

Preferred $R^9$ groups include hydrogen and halogen. More preferably $R^9$ is hydrogen.

Preferred $R^{10}$ groups include hydrogen and optionally substituted $C_1$–$C_6$ alkyl. Also preferred is $R^{10}$ and $R^{11}$ taken with nitrogen to form a five or six membered heterocyclic ring.

Preferred $R^{11}$ groups include hydrogen and optionally substituted $C_1$–$C_6$ alkyl.

Preferred Y groups include $NR^{12}$, O or S. More preferably Y is $NR^{12}$.

Preferred $R^{12}$ groups include hydrogen and optionally substituted $C_1$–$C_6$ alkyl.

In one preferred embodiment of the invention, $R^1$ is selected from the group of hydrogen, optionally substituted $C_1$–$C_3$ alkyl, and optionally substituted $C_1$–$C_3$ haloalkyl; $R^3$, $R^6$, and $R^8$ each independently is selected from the group of hydrogen, optionally substituted $C_1$–$C_6$ alkyl, and optionally substituted $C_1$–$C_6$ haloalkyl; $R^2$ and $R^4$ each independently is selected from the group of $C_1$–$C_6$ alkyl, $C_1$–$C_6$ haloalkyl, $C_5$–$C_6$ cycloalkyl, aryl, and heteroaryl, wherein said alkyl, haloalkyl, cycloalkyl, aryl and heteroaryl groups are optionally substituted; $R^5$ is optionally substituted $C_1$–$C_6$ alkyl; $R^7$ is optionally substituted $C_2$–$C_5$ alkyl; and $R^9$ is hydrogen or halogen.

In another preferred embodiment of the invention, $R^1$ is selected from the group of hydrogen, optionally substituted $C_1$–$C_3$ alkyl, and optionally substituted $C_1$–$C_3$ haloalkyl;

$R^3$, $R^6$, and $R^8$ each independently is selected from the group of hydrogen, optionally substituted $C_1$–$C_6$ alkyl, and optionally substituted $C_1$–$C_6$ haloalkyl; $R^2$ and $R^4$ each independently is selected from the group of $C_1$–$C_6$ alkyl, $C_1$–$C_6$ haloalkyl, $C_5$–$C_6$ cycloalkyl, aryl, and heteroaryl, wherein said alkyl, haloalkyl, cycloalkyl, aryl and heteroaryl groups are optionally substituted; $R^5$ is optionally substituted $C_1$–$C_6$ alkyl; $R^7$ is optionally substituted $C_2$–$C_5$ haloalkyl; and $R^9$ is hydrogen or halogen.

In yet another preferred embodiment of the invention, $R^1$, $R^3$, $R^8$ and $R^9$ are hydrogen; $R^2$ and $R^4$ each independently is selected from the group of $C_1$–$C_6$ alkyl, $C_1$–$C_6$ haloalkyl, $C_3$–$C_6$ cycloalkyl, aryl and heteroaryl, wherein the alkyl, haloalkyl, cycloalkyl, aryl and heteroaryl groups are optionally substituted; $R^5$ and $R^6$ taken together form a five- to six-membered carbocyclic ring, a five- to six-membered heterocyclic ring, an aryl group or a heteroaryl group, wherein said carbocyclic ring, heterocyclic ring, aryl and heteroaryl groups are optionally substituted; and $R^7$ is optionally substituted $C_2$–$C_5$ alkyl.

In still another preferred embodiment of the invention, $R^1$, $R^3$, $R^8$ and $R^9$ are hydrogen; $R^2$ and $R^4$ each independently is selected from the group of $C_1$–$C_6$ alkyl, $C_1$–$C_6$ haloalkyl, $C_3$–$C_6$ cycloalkyl, aryl and heteroaryl, wherein alkyl, haloalkyl, cycloalkyl, aryl and heteroaryl; $R^5$ and $R^6$ taken together form a five- to six-membered carbocyclic ring, a five- to six-membered heterocyclic ring, an aryl group or a heteroaryl group, wherein said carbocyclic ring, heterocyclic ring, aryl and heteroaryl groups are optionally substituted; and $R^7$ is optionally substituted $C_2$–$C_5$ haloalkyl.

The compounds of formulae 1 and 1a represent a novel group of compounds RXR modulator compounds that have insulin sensitizing activity, but do not substantially suppress the thyroid axis and do not substantially elevate triglycerides. These compounds are heterodimer selective modulators of RXR activity. They bind to RXR with high affinity ($K_i$<20 nM) and produce potent activation of the RXR:P-PARγ heterodimer, but preferably do not activate the RXR:RAR heterodimer. This activation of PPARγ in vitro is contemplated to be a major determinant of the antidiabetic efficacy of the compounds in vivo.

In a conventional cell-based co-transfection assay, the compounds of the invention act as partial agonists with respect to RXR homodimers and, together with PPAR modulators such as BRL, synergistically activate RXR:P-PAR heterodimers. In contrast to their effect upon RXR:P-PAR heterodimers, the compounds of the present invention do not significantly activate RXR:RAR heterodimers and in fact exhibit substantial RXR:RAR antagonist activity. In animal models of diabetes, such as the db/db mouse, the Sprague-Dawley rat and the ZDF rat, these compounds have been shown to regulate glucose and triglyceride levels. In contrast to previously characterized retinoids, these compounds are also contemplated to be non-teratogenic.

Applicants have discovered that one feature for achieving RXR modulator compounds with the desired activity is the length of the carbon chain at the $R^7$ position. The preferred length of the carbon chain at this position is from 2 to 5 carbons. The most preferred or optimal length of the carbon chain within this range of 2 to 5 carbons will vary, depending upon the specific substitutions made at the other positions in Formula 1 or in Formula 1a. By varying the length of the carbon chain at the $R^7$ position, the substituents at $R^2$ and $R^4$, and testing for desired activity, the preferred chain length for any specific compound within the scope of Formula 1 and 1a can be determined.

Table 1 shows a comparison of the activity of compounds of Formula 1 that are identical except for the length of the carbon chain at the $R^7$ position or the presence of an oxygen linking the $R^7$ substituent to the ring.

TABLE 1

| Compound | Bind RXRα $K_i$ (nM) | PPARγ CV-1 (%) Synergy | RXR:RXR CV-1 (%) Ag. | RXR:RXR CV-1 (%) Antag. | RXR:RAR CV-1 (%) Ag. | RXR:RAR CV-1 (%) Antag. | db/db mouse Glu. (D 14) | db/db mouse Trigs. (D 3) | db/db mouse Trigs. (D 14) | db/db mouse T4 (D 3) |
|---|---|---|---|---|---|---|---|---|---|---|
| LG100268 | 3 | 183 | 73 | — | 6 | 0 | 73 | 195 | 82 | 43 |
| L1 | 1.1 | 166 | 62 | 7 | 21 | 19 | 96 | 300 | 54 | NT |
| L2 | 13 | 69 | 11 | 62 | 6 | 49 | 91 | NC | 116 | 45 |
| L3 | 1 | 25 | 2 | 90 | 5 | 84 | 75 | NC | 133 | NC |
| L4 | 1 | 20 | 1 | 92 | 2 | 88 | 50 | NC | 105 | NC |
| L5 | 0.6 | 6 | 0 | 94 | 5 | 68 | 0 | NC | NC | NT |

NC = no change
NT = not tested
$K_i$ = Determined from $IC_{50}$ values by the Cheng-Prussof equation using tritiated LGD1069.
Synergy = Efficacy calculated as the maximal response in presence of 100 nM BRL49653 (RXR:PPARγ) relative to maximal response of BRL49653 alone.
Ag. = Efficacy calculated as the maximal response relative to maximal response of ATRA.
Antag. = Efficacy calculated as the maximal repression (100%) in the presence of 32 nM LGD1069 (RXR:RXR) or 10 nM TTNPB (RXR:RAR).
Glu. = Plasma glucose as a % correction relative to lean values on day 14 of treatment.
Trigs. = Plasma triglycerides as a % correction relative to lean values on the indicated day of treatment.
T4 = Total T4 as a % of obese control values on day 3 of treatment.

Table 2 shows an additional comparison of the activity of compounds of formulae 1 and 1a that have variations of the length of the carbon chain at the $R^7$ position, variations of the substituents at $R^2$ and $R^4$ and ring systems incorporated at $R^5$ and $R^6$ taken together. Increased levels of triglycerides measured using the db/db mouse model were found not to correlate to increased triglyceride levels measured in the accepted Sprague-Dawley rat model. Data for Sprague-Dawley rats were included in Table 2 to indicate the profile of selected compounds of the invention in an accepted model for triglyceride measurements.

TABLE 2

| Compound | Bind RXRα $K_i$(nM) | PPARγ CV-1 (%) Synergy | RXR:RXR CV-1 (%) | | RXR:RAR CV-1 (%) Ag. | db/db mouse | | SD rat Trigs. (R 2) |
|---|---|---|---|---|---|---|---|---|
| | | | Ag. | Antag. | | Glu. (D 7) | Trigs. (D 3) | |
| LG100268 | 3 | 183 | 73 | — | 6 | 73 | 195 | 225 |
| L13 | 3 | 54 | 4 | 84 | 1 | 54 | 109 | NC |
| L14 | 5 | 135 | 3 | 80 | 2 | 45 | 138 | NC |
| L15 | 6 | 99 | 44 | 39 | 1 | 80 | 156 | NT |
| L16 | 2 | 64 | 1 | 93 | 2 | 37 | 79 | NT |
| L17 | 8 | 88 | 3 | 76 | 4 | 29 | 75 | NT |
| L18 | 29 | 69 | 2 | 90 | 1 | 45 | 134 | NC |
| L19 | 1 | 47 | 3 | 90 | 2 | 68 | 187 | NC |
| L23 | 27 | 38 | 1 | 93 | 7 | 53 | NT | NC |

NC = no change
NT = not tested
$K_i$ = Determined from IC50 values by the Cheng-Prussof equation using tritiated LGD1069.
Synergy = Efficacy calculated as the maximal response in presence of 100 nM BRL49653 (RXR:PPARγ) relative to maximal response of BRL49653 alone.
Ag. = Efficacy calculated as the maximal response relative to maximal response of ATRA.
Antag. = Efficacy calculated as the maximal repression (100%) in the presence of 32 nM LGD1069 (RXR:RXR) or 10 nM TTNPB (RXR:RAR).
Glu. = Plasma glucose as a % correction relative to lean values on day 7 of treatment with 30 mg/kg/day using db/db mouse study.
db/db mouse Trigs. = Plasma triglycerides as a % of control values on day 3 of treatment with 30 mg/kg/day using db/db mouse study.
SD rat Trigs. = Plasma triglycerides as a % of control values at hour 2 of treatment using Sprague Dawley rat study.

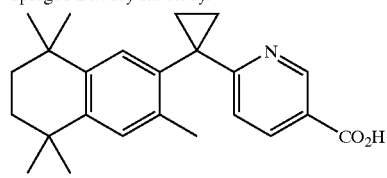

LG100268

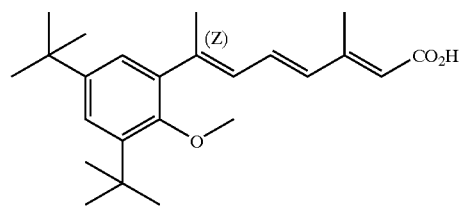

L1

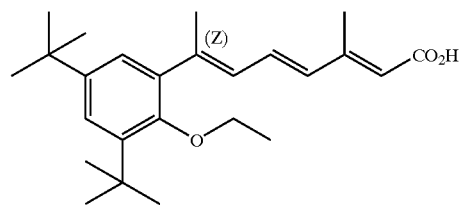

L2

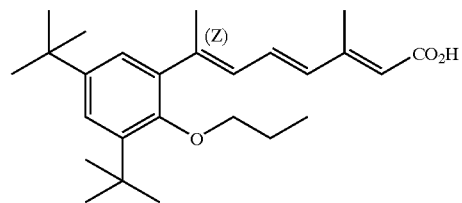

L3

TABLE 2-continued
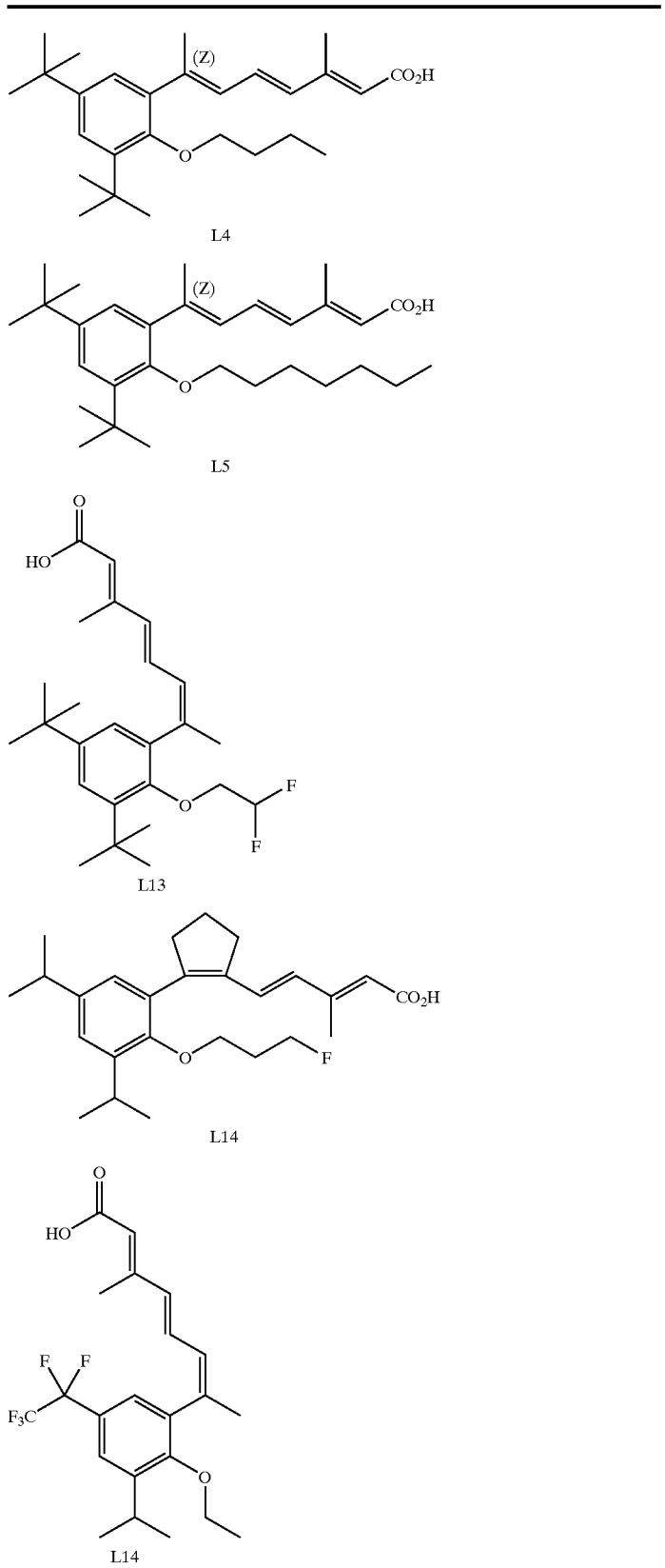

TABLE 2-continued
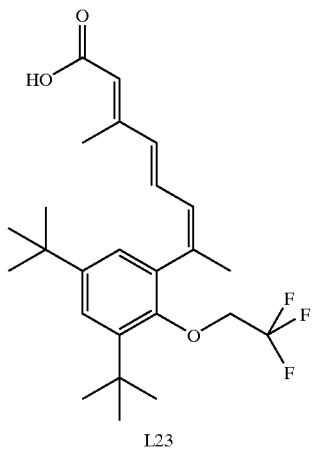
L23
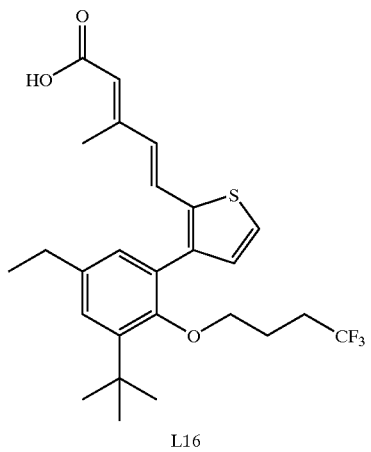
L16
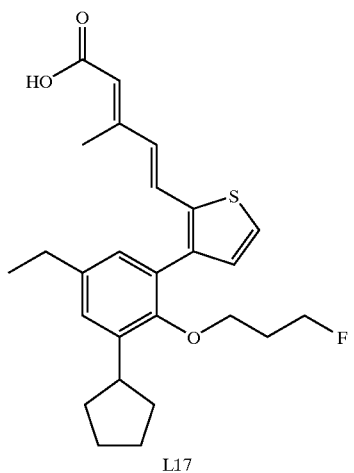
L17

TABLE 2-continued

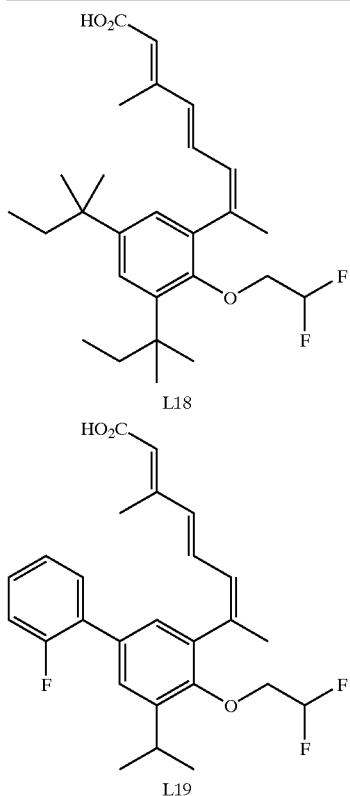

L18

L19

The rexinoids depicted above where $R^7$ is less than 2 carbons in length and/or do not have an oxygen linking the $R^7$ substituent to the ring (LG100268 and L1) are full RXR homodimer agonists. These compounds are efficacious insulin sensitizers in rodent models of Type II Diabetes, but they also raise triglycerides and suppress the thyroid hormone axis in these animals. On the other hand, a rexinoid such as L5, depicted above, where $R^7$ is greater than 5 carbons is a full antagonist and has no effect on glucose, triglycerides or thyroid status in these same model systems. The activity of the compounds is dependent on the chain length of $R^7$ and on the identity of $R^1$, $R^2$, $R^3$, and $R^4$, all of which can be substituted to affect the behavior of the rexinoid.

Those compounds that have a carbon chain length at the $R^7$ position and appropriate substituents at $R^1$, $R^2$, $R^3$, and $R^4$ within the scope of the present invention maintain the desirable insulin sensitizing activity and eliminate or reduce both the suppression of the thyroid axis and triglyceride elevations (e.g., L3, L4, L6, L7). These compounds are heterodimer selective modulators of RXR activity. They bind to RXR with high affinity ($K_i$<20 nM) and produce potent activation of the RXR:PPARγ heterodimer. Among these compounds, L3 and L4, having a chain length of 3 and 4 carbons, respectively, can be identified as the more preferred embodiments in this group based on the absence of detectable suppression of the thyroid hormone axis.

To minimize the undesirable increases in triglyceride levels and suppression of thyroid hormone axis, the modulators must not significantly activate the RXR:RAR heterodimer and must have substantial RXR:RAR antagonist activity. This requirement is clearly demonstrated by the two related compounds L2 and L3. The striking in vitro characteristic for these two compounds is that L3 has approximately twice the RXR:RAR antagonist activity as L2; this correlates with the distinction in vivo where L2 suppresses thyroid hormone axis while L3 does not.

When administered to obese, insulin resistant db/db mice (100 mg/kg by daily oral gavage for 14 days) these heterodimer selective RXR modulators lower both plasma glucose and triglyceride levels. However, unlike either full agonists (e.g., LG100268, L1) or partial agonists that exhibit less than 50% activity at the RXR:RAR heterodimer (e.g., L2), they do not substantially suppress total circulating levels of T4, or substantially increase triglyceride levels.

When administered to transgenic mice carrying the human apo A-I gene all of these compounds increase HDL cholesterol, but both LG100268 and L1 also raise triglycerides. Among the modulators that do not significantly activate the RAR:RXR heterodimer are those which do not raise triglyceride levels in the transgenic mouse model, consistent with their heterodimer selectivity. This effect is consistent with activation of PPARα, and, in fact, in vivo these compounds synergize with the weak PPARα agonist fenofibrate.

The compounds of the present invention possess particular application as RXR modulators and in particular as dimer-selective RXR modulators including, but not limited to, RXR homodimer antagonists, and agonists, partial agonists and antagonists of RXRs in the context of a heterodimer.

In a second aspect, the present invention provides a method of modulating processes mediated by RXR homodimers and/or RXR heterodimers comprising administering to a patient an effective amount of a compound of the invention as set forth above. The compounds of the present invention also include all pharmaceutically acceptable salts, as well as esters and amides. As used in this disclosure, pharmaceutically acceptable salts include, but are not limited to: pyridine, ammonium, piperazine, diethylamine, nicotinamide, formic, urea, sodium, potassium, calcium, magnesium, zinc, lithium, cinnamic, methylamino, methanesulfonic, picric, tartaric, triethylamino, dimethylamino, and tris(hydoxymethyl) aminomethane. Additional pharmaceutically acceptable salts are known to those skilled in the art.

The compounds of the present invention are useful in the modulation of transcriptional activity through RXR in the context of heterodimers other than RXR:RARα,β,γ (e.g., RXR:.PPARα,β,γ; RXR:TR; RXR:VDR; RXR:NGFIB; RXR:NURR1; RXR:LXRα,β, RXR:DAX), including any other intracellular receptors (IRs) that form a heterodimer with RXR. For example, application of the compounds of the present invention to modulate a RXRα:PPARα heterodimer is useful to modulate, i.e. increase, HDL cholesterol levels and reduce triglyceride levels. Yet, application of many of the same compounds of the present invention to a RXRα:PPARγ heterodimer modulates a distinct activity, i.e., modulation of adipocyte biology, including effects on the differentiation and apoptosis of adipocytes, which will have implications in the treatment and/or prevention of diabetes and obesity. In addition, use of the modulator compounds of the present invention with activators of the other heterodimer partner (e.g., fibrates for PPARα and thiazolidinediones for PPARγ) can lead to a synergistic enhancement of the desired response. Likewise, application of the modulator compounds of the present invention in the context of a RXRα:VDR heterodimer will be useful to modulate skin related processes (e.g., photoaging, acne, psoriasis), malignant and pre-malignant conditions and programmed cell death (apoptosis). Further, it will be understood by those skilled in the art that the modulator compounds of the present invention will also prove useful in the modulation of other heteromer interactions that include RXR, e.g., trimers, tetramers and the like.

In the context of an RXR homodimer, the compounds of the present invention function as partial agonists. Further, when the modulator compounds of the present invention are combined with a corresponding modulator of the other heterodimeric partner, a surprising synergistic enhancement of the activation of the heterodimer pathway can occur. For example, with respect to a RXRα:PPARα heterodimer, the combination of a compound of the present invention with clofibric acid or gemfibrozil unexpectedly leads to a greater than additive (i.e. synergistic) activation of PPARα responsive genes, which in turn is useful to modulate serum cholesterol and triglyceride levels and other conditions associated with lipid metabolism.

Whether acting on an RXR heterodimer pathway, or the RXR homodimer pathway, it will also be understood by those skilled in the art that the dimer-selective RXR modulator compounds of the present invention will prove useful in any therapy in which agonists, partial agonists and/or full antagonists of such pathways will find application. Importantly, because the compounds of the present invention can differentially activate RXR homodimers and RXR heterodimers, their effects will be tissue and/or cell type specific, depending upon the cellular context of the different tissue types in a given patient. For example, compounds of the present invention will exert an RXR antagonist effect in tissues where RXR homodimers prevail, and partial agonist or full agonist activity on the PPAR pathway where RXRα:PPARα heterodimers prevail (e.g., in liver tissue). Thus, the compounds of the present invention will exert a differential effect in various tissues in an analogous fashion to the manner in which various classes of estrogens and antiestrogens (e.g., Estrogen, Tamoxifen, Raloxifen) exert differential effects in different tissue and/or cell types (e.g., bone, breast, uterus). See e.g., M. T. Tzukerman et al., *Mol. Endo*, 8:21–30 (1994); D. P. McDonnell et al., *Mol. Endo.*, 9:659–669 (1995). However, in the present case, it is believed that the differential effects of the compounds of the present invention are based upon the particular dimer pair through which the compound acts, rather than through different transactivating regions of the estrogen receptor in the case of estrogens and antiestrogens. However, it is possible that they also function, in part, by tissue selectivity.

The particular conditions that may be treated with the compounds of the present invention include, but are not limited to, skin-related diseases, such as actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical antimicrobial, as skin pigmentation agents and to treat and reverse the effects of age and photo damage to the skin. With respect to the modulation of malignant and pre-malignant conditions, the compounds may also prove useful for the prevention and treatment of cancerous and pre-cancerous conditions, including, premalignant and malignant hyperproliferative diseases and cancers of epithelial origin such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of *Kaposis sarcoma*. In addition, the present compounds may be used as agents to treat and prevent various cardiovascular diseases, including, without limitation, diseases associated with lipid metabolism such as dyslipidemias, prevention of restenosis and as an agent to increase the level of circulating tissue plasminogen activator (TPA), metabolic diseases such as obesity and diabetes (i.e., non-insulin dependent diabetes mellitus and insulin dependent diabetes mellitus), the modulation of differentiation and proliferation disorders, as well as the prevention and treatment of neurodegenerative diseases such as Alzheimer's disease, Parkinson's disease and Amyotrophic Lateral Sclerosis (ALS), and in the modulation of apoptosis, including both the induction of apoptosis and inhibition of T-Cell activated apoptosis.

The RXR modulator compounds, their pharmaceutically acceptable salts or hydrolyzable esters of the present invention may be combined with a pharmaceutically acceptable carrier to provide pharmaceutical compositions useful for treating the biological conditions or disorders noted herein in mammalian species, and more preferably, in humans. The particular carrier employed in these pharmaceutical compositions may vary depending upon the type of administration desired (e.g. intravenous, oral, topical, suppository, or parenteral).

In preparing the compositions in oral liquid dosage forms (e.g. suspensions, elixirs and solutions), typical pharmaceutical media, such as water, glycols, oils, alcohols, flavoring agents, preservatives, coloring agents and the like can be employed. Similarly, when preparing oral solid dosage forms (e.g. powders, tablets and capsules), carriers such as starches, sugars, diluents, granulating agents, lubricants, binders, disintegrating agents and the like can be employed.

For parenteral administration, the carrier will typically comprise sterile water, although other ingredients that aid solubility or serve as preservatives can also be included. Furthermore, injectable suspensions can also be prepared, in which case appropriate liquid carriers, suspending agents and the like can be employed.

For topical administration, the compounds of the present invention can be formulated using bland, moisturizing bases such as ointments or creams.

The pharmaceutical compositions and compounds of the present invention can generally be administered in the form of a dosage unit (e.g. tablet, capsule, etc.) in an amount from about 1 μg/kg of body weight to about 1 g/kg of body weight, preferably from about 5 μg/kg of body weight to about 500 mg/kg of body weight, more preferably from about 10 μg/kg of body weight to about 250 mg/kg of body weight, most preferably from about 20 μg/kg of body weight to about 100 mg/kg of body weight. Those skilled in the art will recognize that the particular quantity of pharmaceutical composition and/or compounds of the present invention administered to an individual will depend upon a number of factors including, without limitation, the biological effect desired, the condition of the individual and the individual's tolerance for the compound.

Furthermore, it will be understood by those skilled in the art that the compounds of the present invention, including pharmaceutical compositions and formulations containing these compounds, can be used in a wide variety of combination therapies to treat the conditions and diseases described above. Thus, the compounds of the present invention can be used in combination with modulators of the other heterodimeric partner with RXR (i.e., in combination with PPARα modulators, such as fibrates, in the treatment of cardiovascular disease, and in combination with PPARγ modulators, such thiazolidinediones, in the treatment of diabetes, including non-insulin dependent diabetes mellitus and insulin dependent diabetes mellitus, and with agents used to treat obesity) and with other therapies, including, without limitation, chemotherapeutic agents such as cytostatic and cytotoxic agents, immunological modifiers such as interferons, interleukins, growth hormones and other cytokines, hormone therapies, surgery and radiation therapy.

By utilizing the compounds of the present invention with modulators of the other heterodimeric partner one is able to utilize lower dosages of either or both modulators, thereby leading to a significant decrease in the side-effects associated with such modulators when employed alone at the strengths required to achieve the desired effect. Thus, the modulator compounds of the present invention, when utilized in combination therapies, provide an enhanced therapeutic index (i.e., significantly enhanced efficacy and/or decrease side-effect profiles) over utilization of the compounds by themselves.

Representative modulator compounds of the present invention include, without limitation those depicted below.

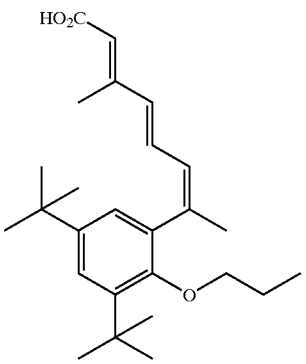

L3

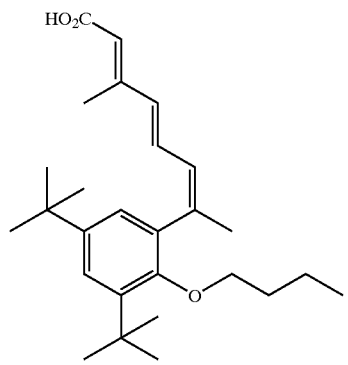

L4

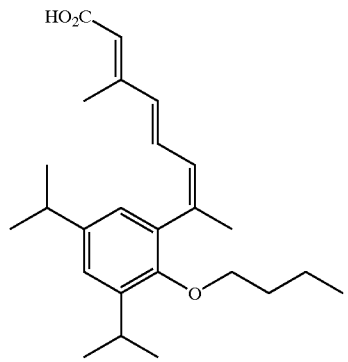

L6

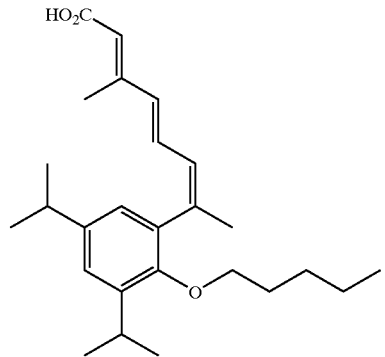

L7

L8
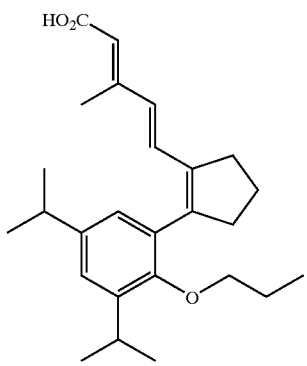
L9
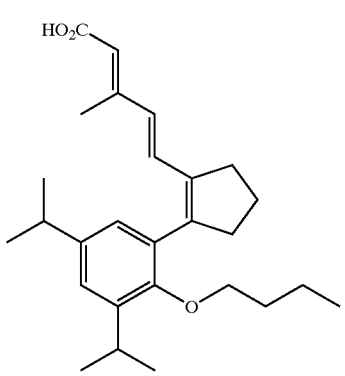
L10
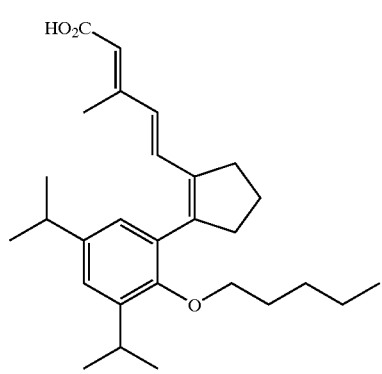
L11
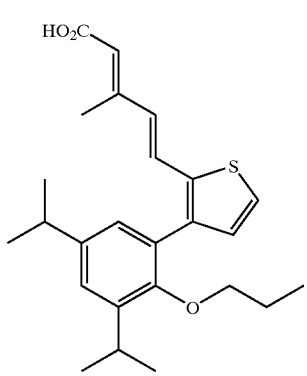
L12
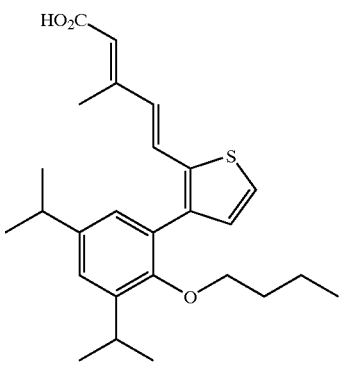
L13
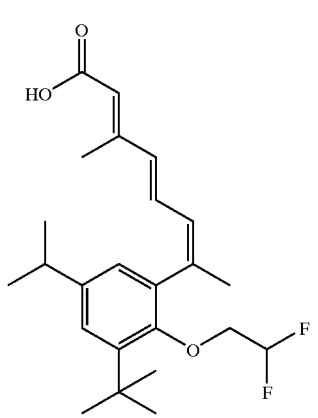
L14
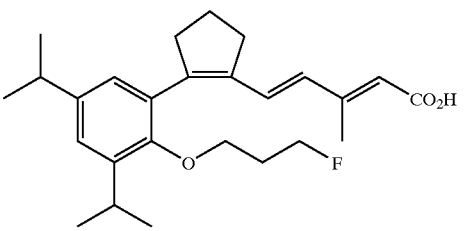
L15
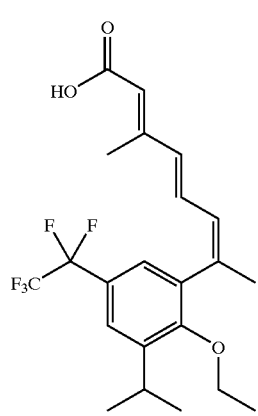

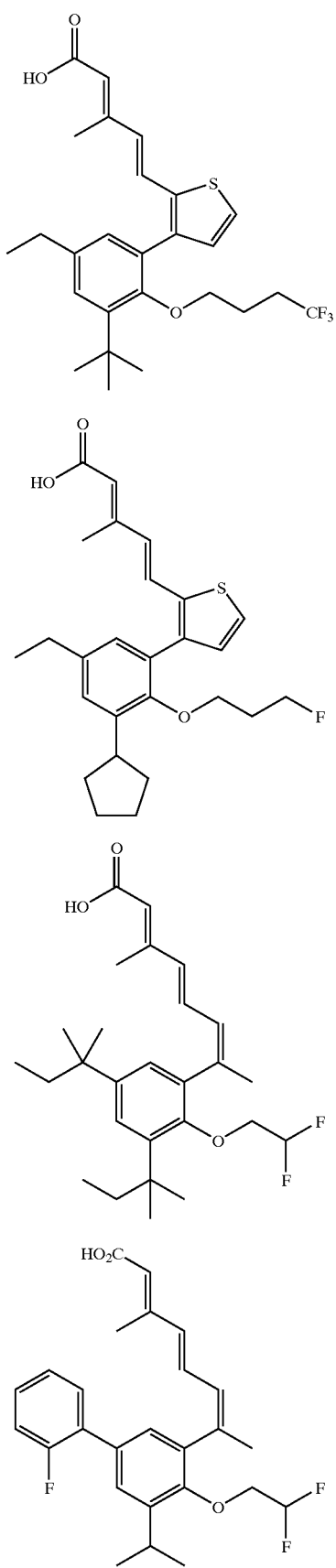
L16
L17
L18
L19
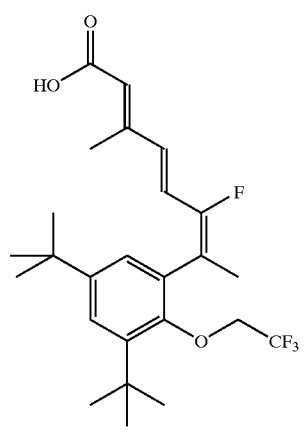
L20
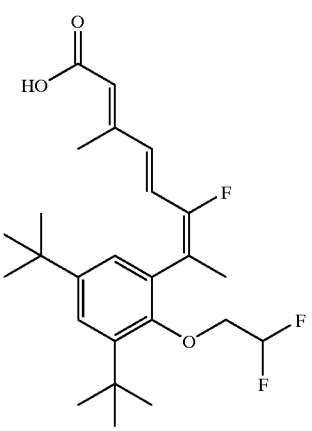
L21
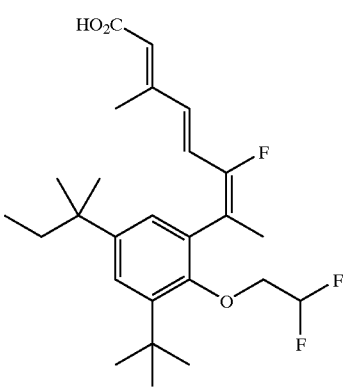
L22
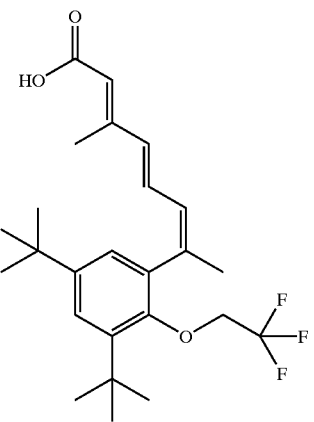
L23

L24
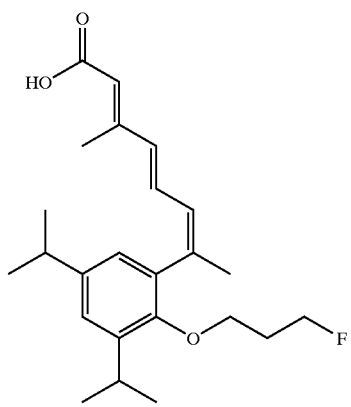
L25
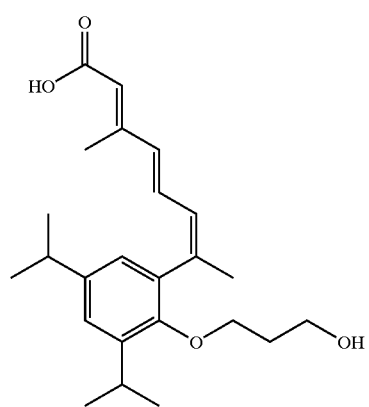
L26
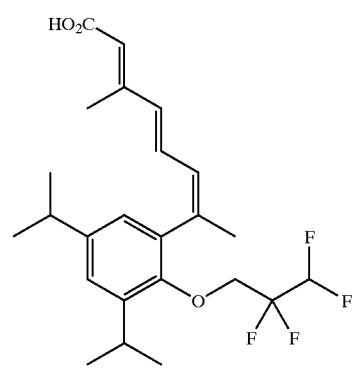
L27
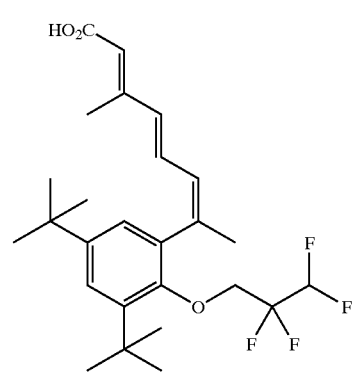
L28
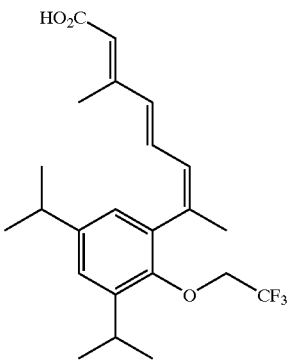
L29
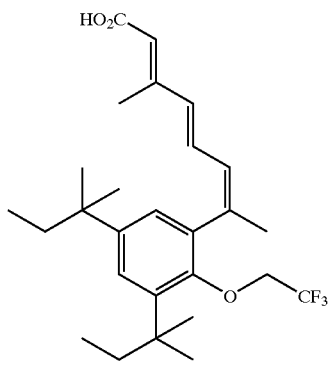
L30
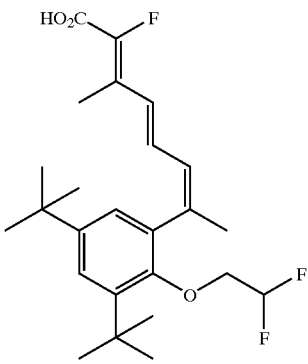
L31
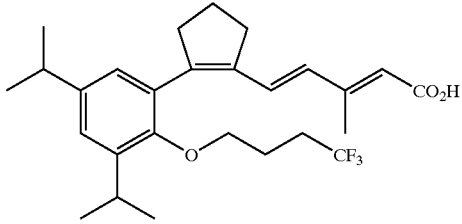
L32
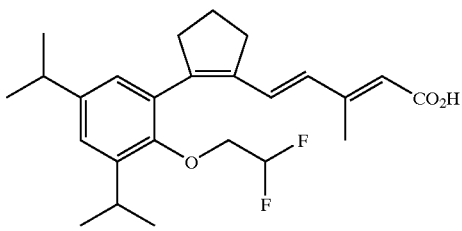

L33 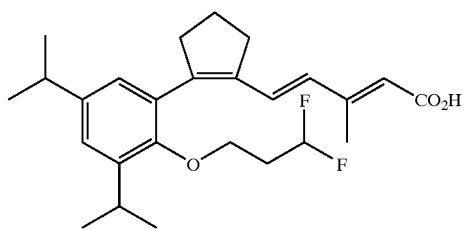
L34 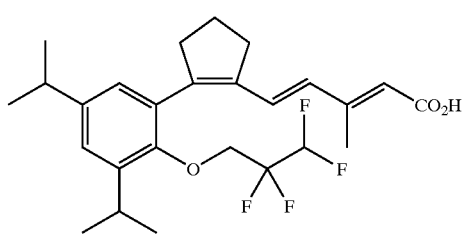
L35 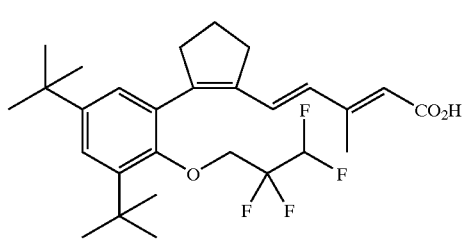
L36 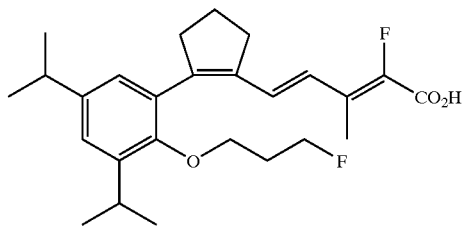
L37 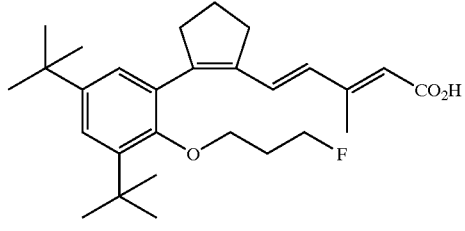
L38 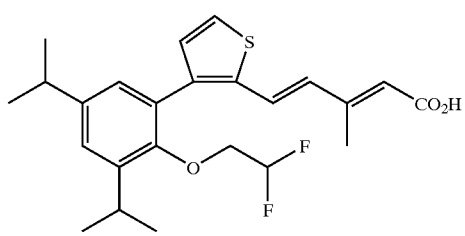
L39 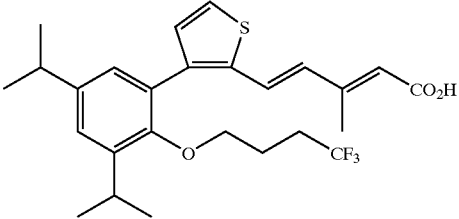
L40 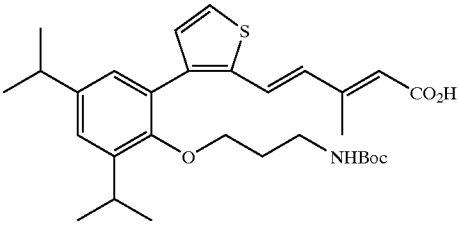
L41 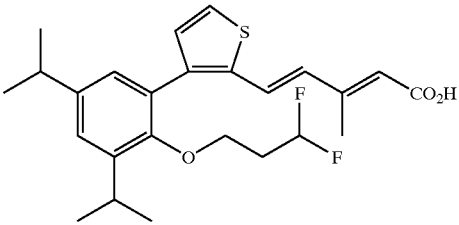
L42 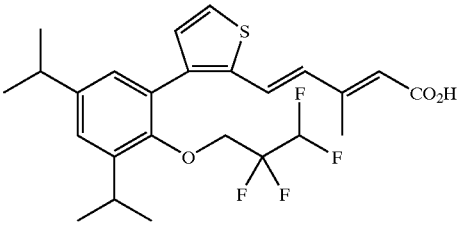
L43 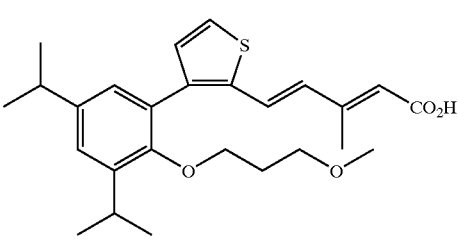
L45 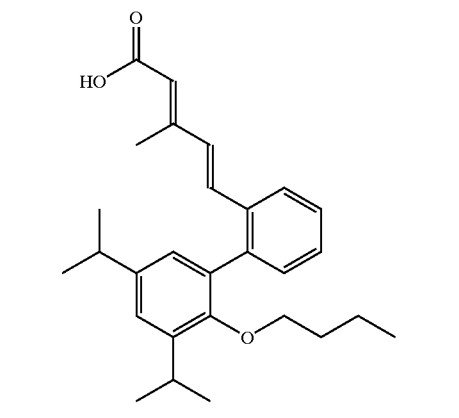

L46
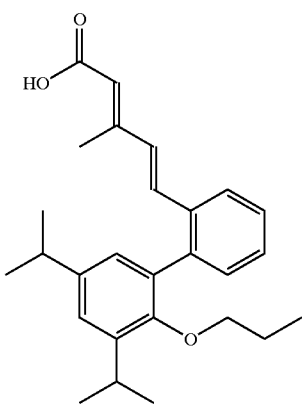
L47
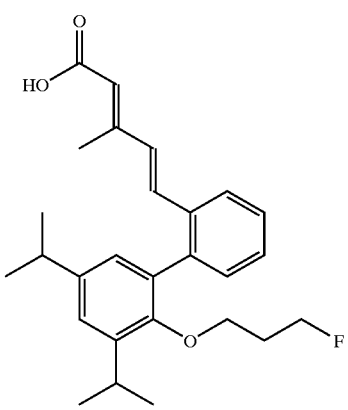
L48
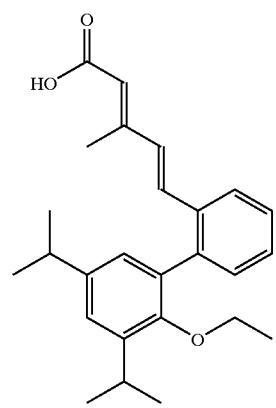
L49
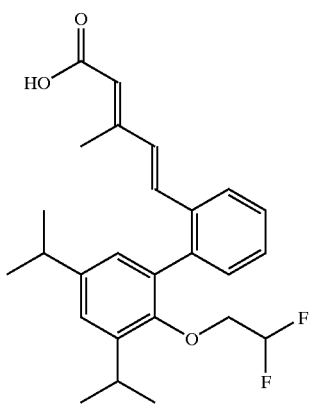
L51
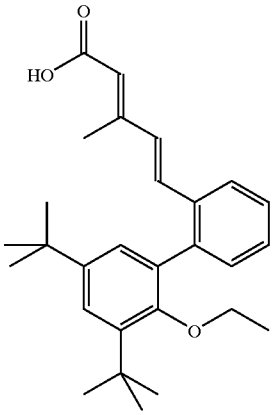
L52
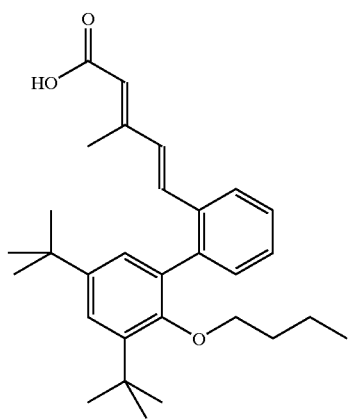
L53
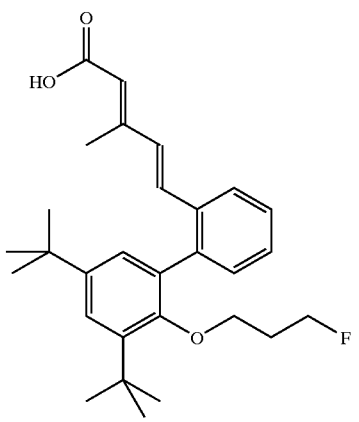
L54
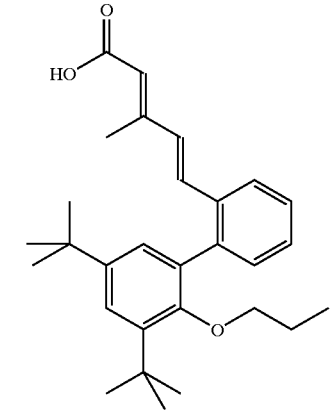

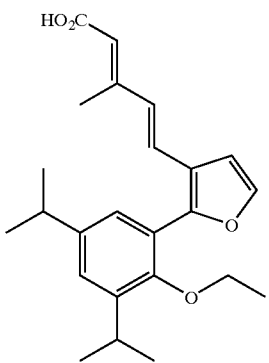
L55
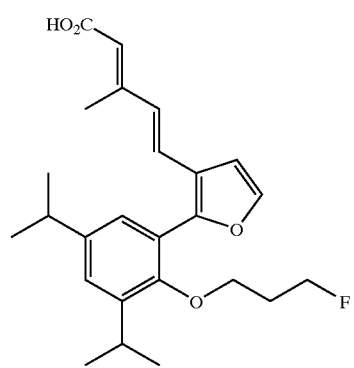
L56
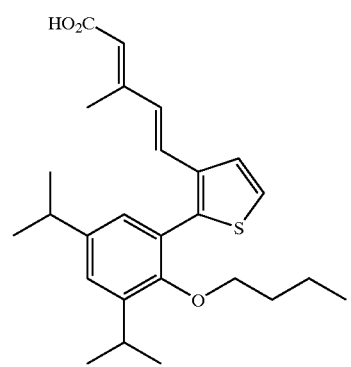
L57
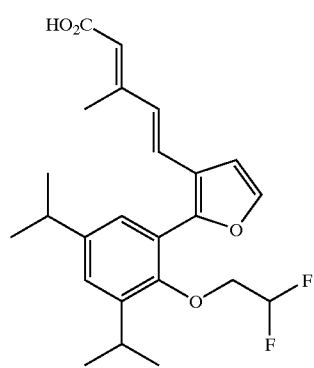
L58
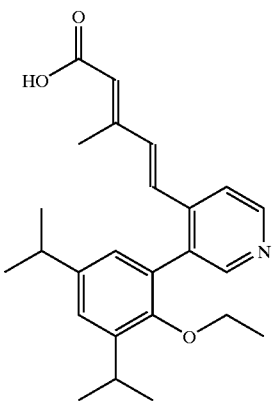
L59
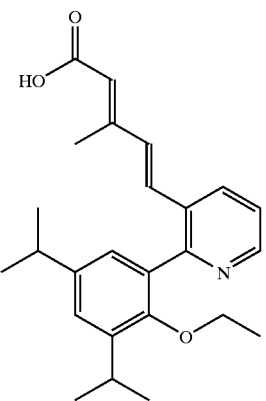
L60
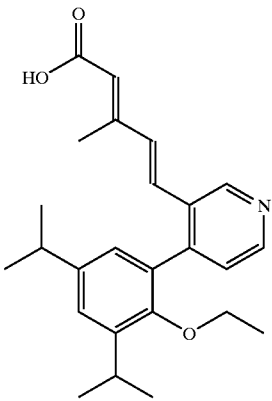
L61
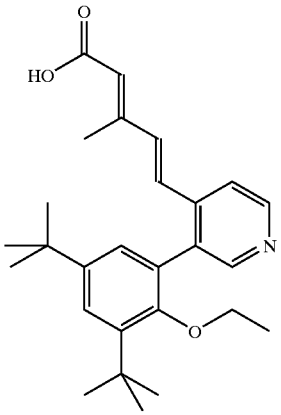
L62

-continued
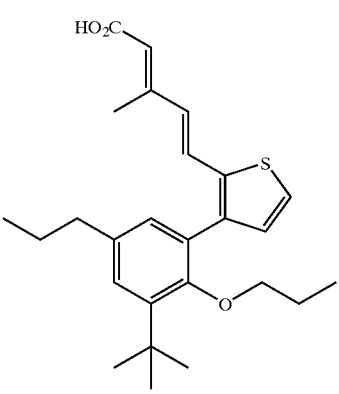
L64
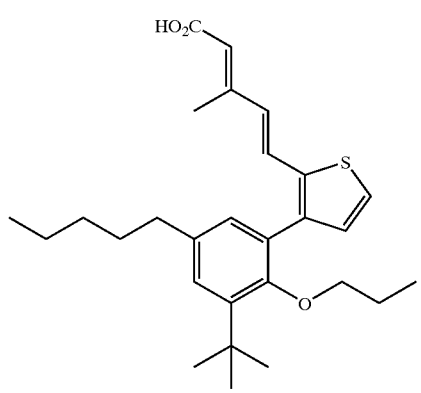
L65
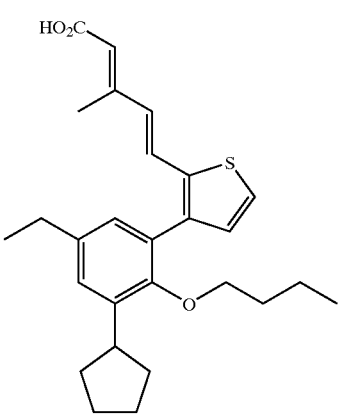
L66
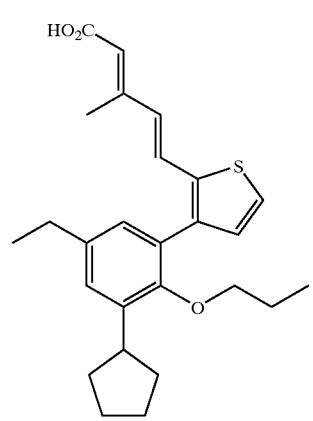
L67
-continued
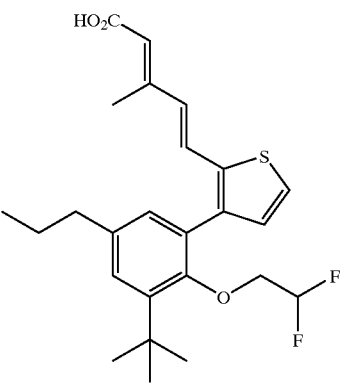
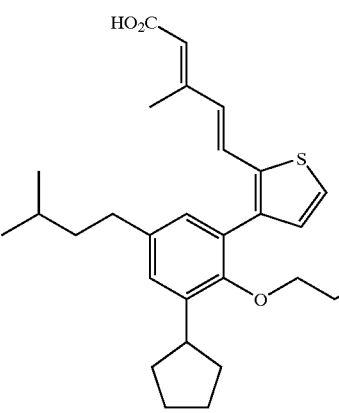
L69
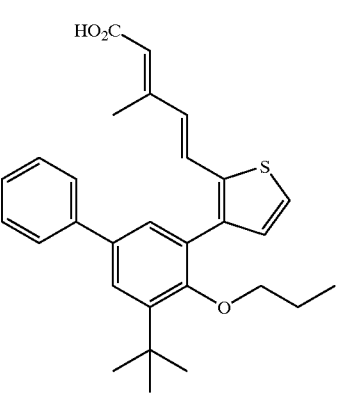
L70
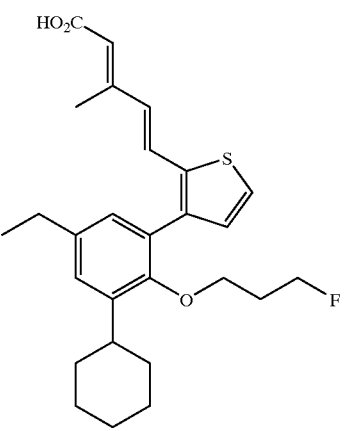
L71

-continued
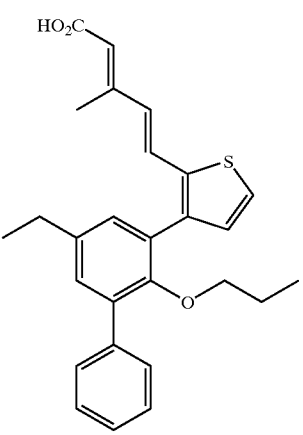
L72
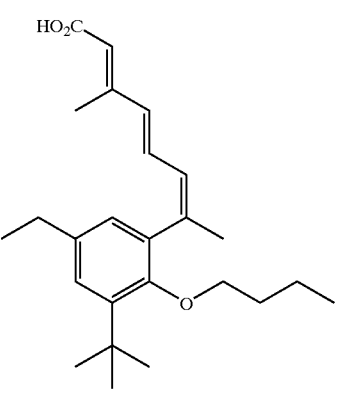
L76
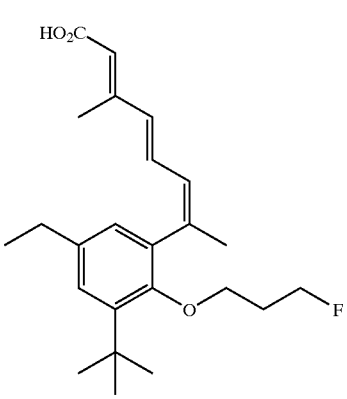
L77
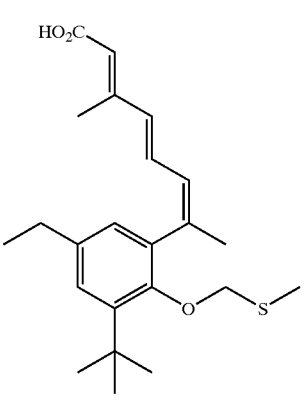
L78
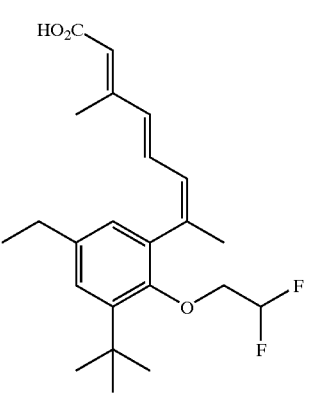
L79

L80
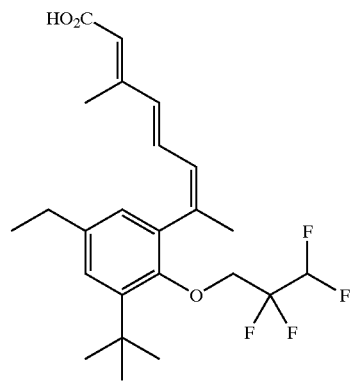
L81
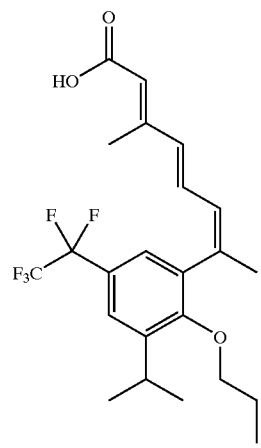
L82
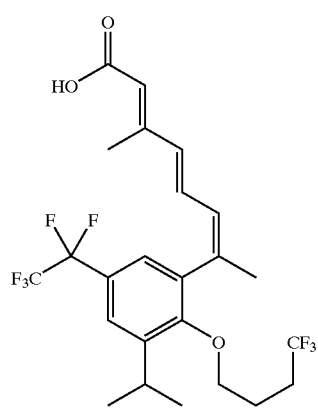
L83
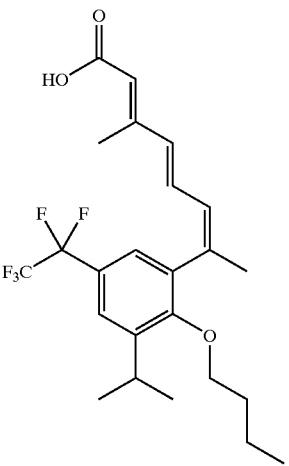
L84
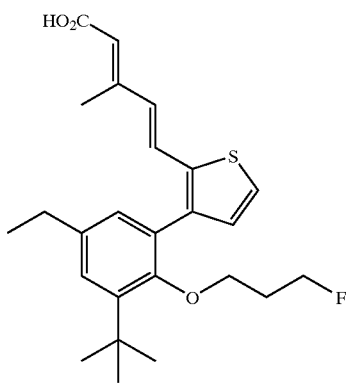
L85
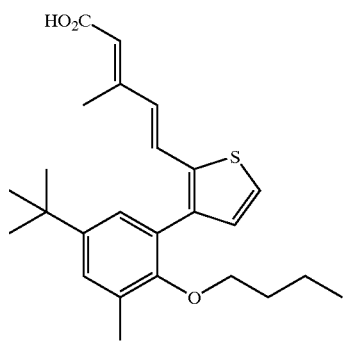
L86
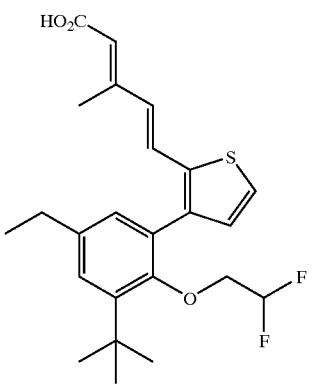

L87

L88

L89

L90

L91

L92

L93

L94

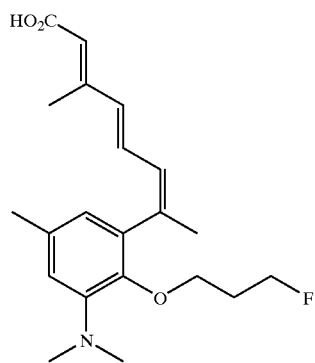 L95
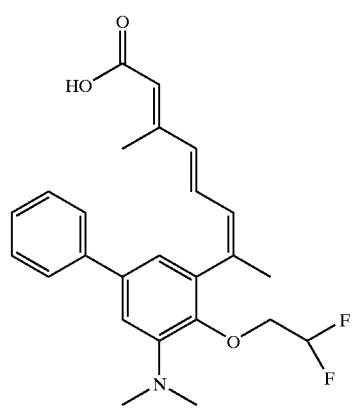 L96
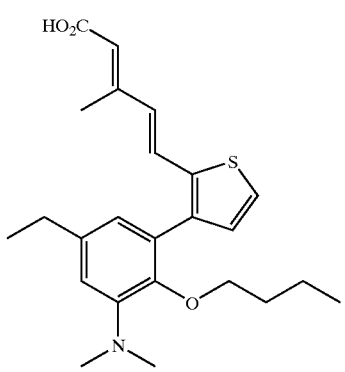 L97
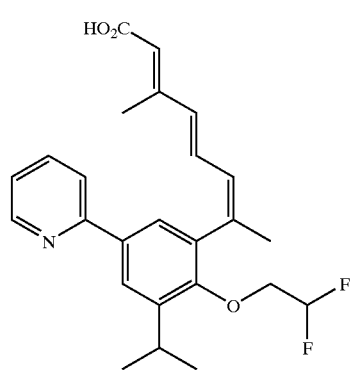 L98
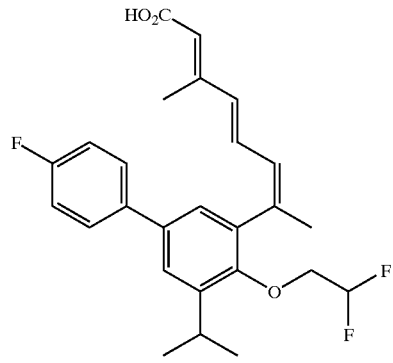 L99
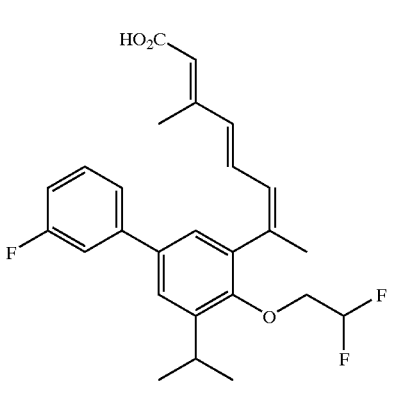 L100
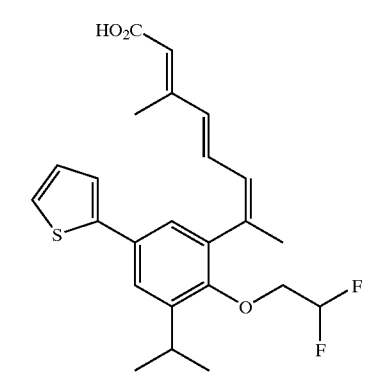 L101
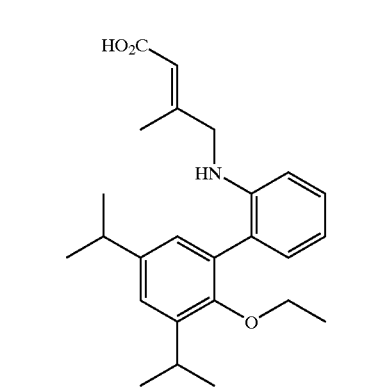 L102

51
-continued

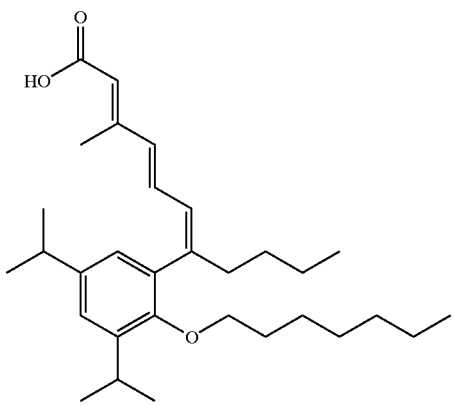

L103

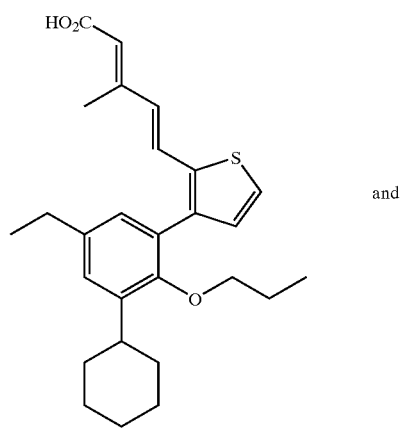

and

L104

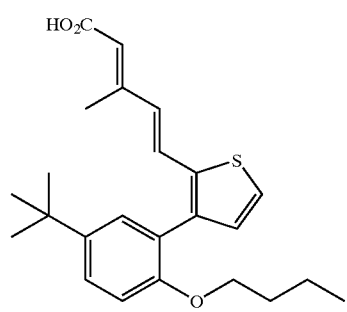

L105

The compounds of the present invention can be obtained by modification of the compounds disclosed herein or by a total synthesis approach using techniques known to those skilled in the art. In this regard, the synthesis of the dimer-specific RXR modulator compounds of the present invention follow established retinoid synthesis schemes and techniques as described in U.S. Pat. Nos. 4,326,055 and 4,578,498, the disclosures of which are herein incorporated by reference. See also, M. I. Dawson and W. H. Okamura, "Chemistry and Biology of Synthetic Retinoids", Chapters 3, 8, 14 and 16, CRC Press, Inc., Florida (1990); M. I. Dawson and P. D. Hobbs, The Synthetic Chemistry of Retinoids, In Chapter 2: "The Retinoids, Biology, Chemistry and Medicine", M. B. Sporn et al., eds. (2nd ed.), Raven Press, New York, N.Y., pp. 5–178 (1994); R. S. H. Liu and A. E. Asato, "Photochemistry and Synthesis of Stereoisomers of Vitamin A," Tetrahedron, 40:1931 (1984); Cancer Res., 43:5268 (1983); Eur. J. Med. Chem., 15:9 (1980); M. Boehm et al., J. Med. Chem., 37:2930 (1994); M. Boehm et al., J. Med. Chem., 38:3146 (1995); E. Allegretto et al., J. Biol. Chem., 270:23906 (1995); R. Bissonette et al., Mol. & Cellular Bio., 15:5576 (1995); R. Beard et al., J. Med. Chem., 38:2820 (1995); S. Canan-Koch et al., J. Med. Chem., 39:3229 (1996); WO 97/12853.

Novel Method of Synthesis

In addition to the synthetic techniques available in the prior art, the present invention further provides an improved method for making the claimed compounds, as well as structurally related RXR modulators, that efficiently and stereospecifically introduces the desired triene moiety with the correct olefin geometry. Scheme 1 describes a general method for producing RXR modulators of the present invention via a coumarin intermediate which is then ring opened to a diol and then further modified to the desired compounds. The new synthetic route is versatile, and can be adapted to the synthesis of an entire class of molecules with the appropriate variations.

The key sequence of reactions in this synthetic route involves utilizing an existing arylalcohol group as a functional handle to annulate a lactone ring on to the existing aromatic ring, forming a coumarin. The coumarin, by virtue of its cyclic structure, necessarily locks the olefin geometry as cis. The cis-geometry established in this step is then preserved throughout the remainder of the synthesis, yielding compounds of high isomeric purity without the need for isomerization of or discarding of the undesired isomers. Access to coumarin intermediates of the type required for construction of this important class of RXR modulators (e.g., Structure 4) can be achieved through either of two distinct strategies.

A coumarin such as 4 can be formed directly from an arylalcohol such as 2 through a von Pechmann or related cyclization reaction with a β-keto ester such as 3. Alternately, the coumarin may be introduced from an ortho-hydroxyacetophenone such as 5 by condensation with a stabilized phosphorous ylide as shown in Structure 6. For further reference see, S. Sethna and R. Phadke, Organic Reactions, 7:1–58 (1953); H. J. Bestmann, et al., Angew. Chem. Int. Ed. Engl. 15(2):115–116 (1976).

After this cyclization step to form a coumarin such as 4, the lactone ring of the coumarin is then reductively opened to form a diol as shown in Structure 7. The diol then undergoes selective alkylation at the arylalcohol oxygen and mild oxidation of the allylic alcohol to the corresponding aldehyde (e.g., Structure 9). The synthesis is then completed by a standard Horner-Emmons/ester hydrolysis protocol. For further reference see, WO 97/12853, S. Canan-Koch et al., J. Med. Chem. 39:3229–34 (1996).

Scheme 1: General Synthesis of RXR Modulator Compounds via Coumarin Intermediates.

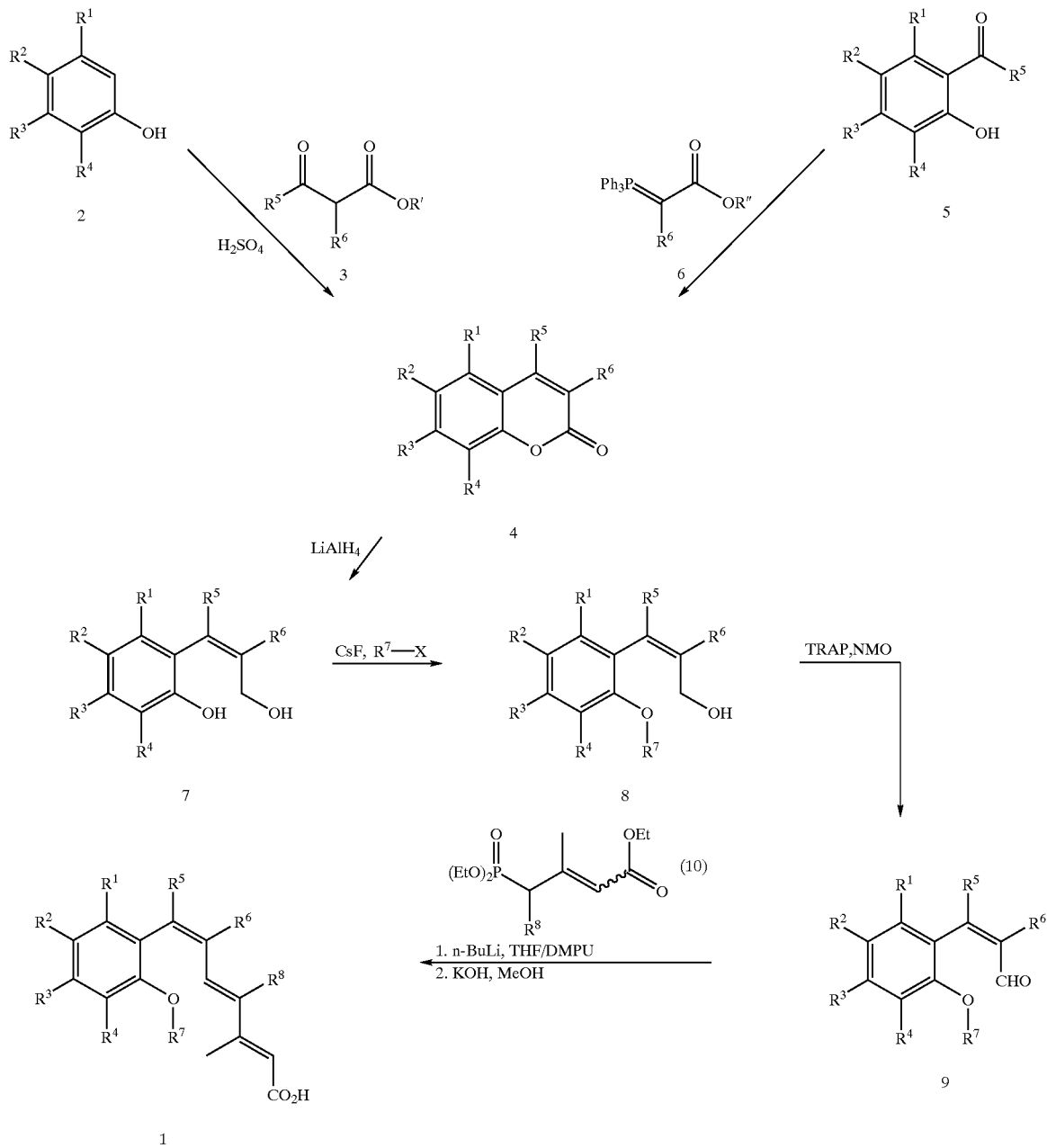

Scheme 2 provides an example of the first method for producing a desired RXR modulator of the present invention. Beginning with a previously described tetramethyltetrahydronaphthol (e.g., Structure 2), a classical von Pechmann cyclization strategy using ethyl acetoacetate in 75% aqueous $H_2SO_4$ is used to regioselectively generate the 4-methylcoumarin ring system such as 4 in one step, setting the olefin geometry of the target compound. For further reference see, S. Canan-Koch et al., *J. Med. Chem.* 39: 3229–3234 (1996)); S. Sethna and R. Phadke, *Organic Reactions*, 7:1–58 (1953). Reductive ring opening of the lactone ring in 4 with $LiAlH_4$ cleanly provides a diol such as 7. Selective alkylation of the phenol oxygen under extremely mild conditions is achieved using excess cesium fluoride and stoichiometric 1-iodopropane in DMF yields a primary allylic alcohol such as Structure 8. For further reference see, T. Sato and J. Otera, *Syn. Lett.*, 336 (1995); J. H. Clark and J. M. Miller, *Tetrahedron Lett.*, 18:599 (1977). Oxidation to an aldehyde such as 9 is accomplished with TPAP and NMO in $CH_2Cl_2$ (S. V. Ley et al., *Synthesis*, 639 (1994)). Horner-Wadsworth-Emmons olefination of 9 a with phosphonate such as 10 provides the remainder of the triene chain (See, B. E. Maryanoff and A. B. Reitz, *Chem. Rev.*, 89:863 (1989)). Phosphonate 10 may be subjected to saponification with KOH in methanol to reveal the free acid target compound 1.

Scheme 2: Example Synthesis of the RXR Modulator Compound LG100754.

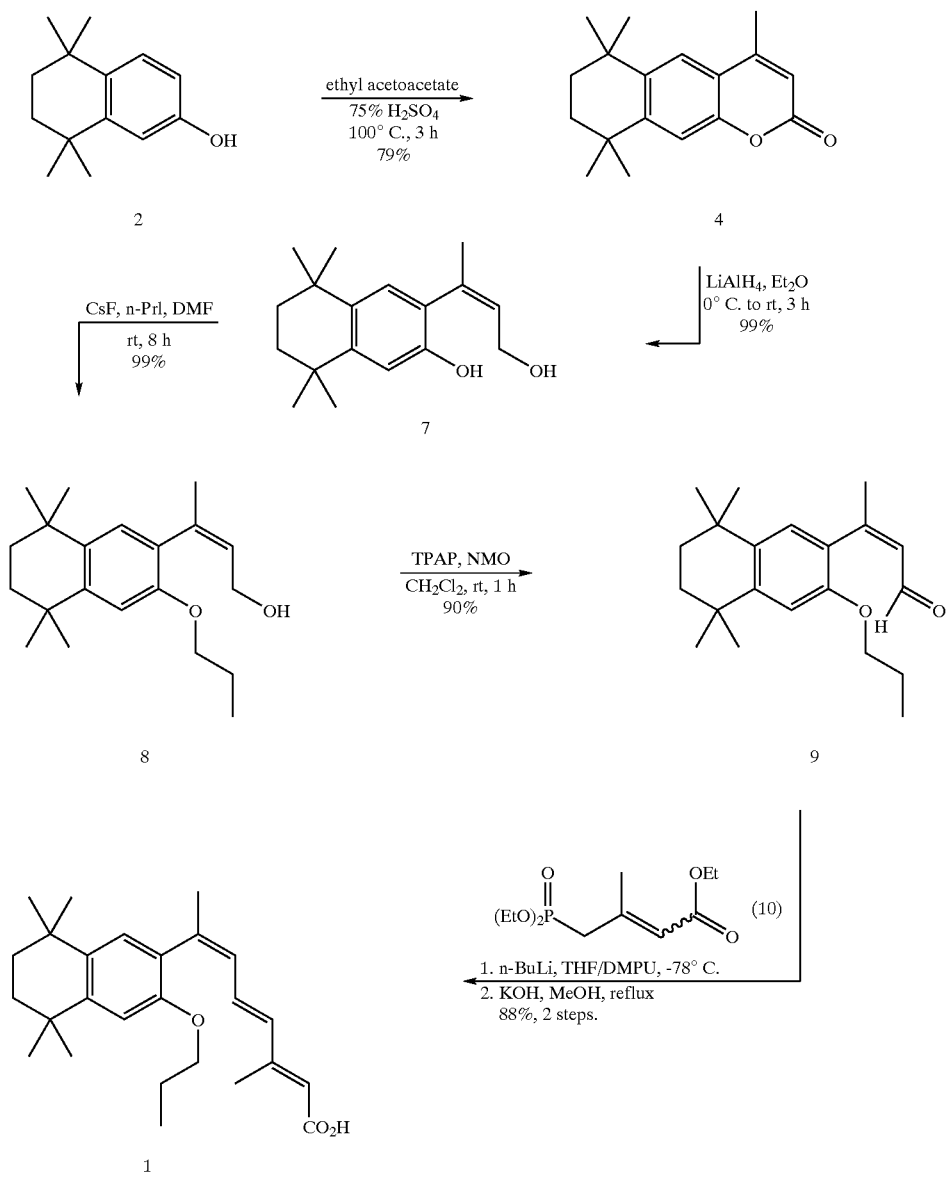

Certain related molecules in this series of RXR modulators (e.g., See, WO 97/12853) that contain branched alkyl-substituted phenyl moieties in place of the tetramethyltetrahydronaphthyl group of 1 proved incompatible with the strongly acidic conditions employed in the von Pechmann cyclization step. Unwanted alkyl migrations occurred under these reaction conditions. Milder alternative routes to the coumarin intermediates were explored using the present substrate as a model. It was reasoned that construction of the lactone ring under neutral conditions would circumvent these undesired side reactions. Recently published routes to coumarins involving montmorillonite clays (e.g., See, T.-S. Li et al., *J. Chem. Res.*, 38 (1998); G. K. Biswas et al, *Indian J. Chem.*, 31B:628 (1992)) or Pd-catalyzed reaction of unsaturated esters (e.g., See B. M. Trost and F. D. Toste, *J. Am. Chem. Soc.*, 118:6305 (1996); M. Catellani et al., *Tetrahedron Lett.*, 35:5923 (1994)) generally required highly electron-rich aryls for efficient C—C bond formation to close the coumarin ring. Therefore, a potentially more generally applicable stabilized ylide approach was investigated. For further reference see, H. J. Bestmann et al., *Angew. Chem. Int. Ed. Engl.*, 15(2):115 (1976).

As shown in Scheme 3, treatment of hydroxyacetophenone 5, which is prepared by acylation/Fries rearrangement of arylalcohol 2, with excess carbethoxymethylenetriphenylphosphorane in refluxing toluene cleanly produces coumarin 4. See, e.g., K. Fries and G. Fink, *Ber.*, 41:4271 (1908); K. Fries and W. Pfaffendorf, *Ber.*, 43:212 (1910); A. H. Blatt, *Org. React.*, 1:342 (1942). This compound is identical in every respect to the compound obtained by the von Pechmann cyclization route. Given the ready availability of acetophenones and related precursors with varied alkyl substitution, this two-step approach to the key coumarin intermediate complements the von Pechmann cyclization method.

Scheme 3: Alternate Method for Synthesis of Coumarin Intermediate 4.

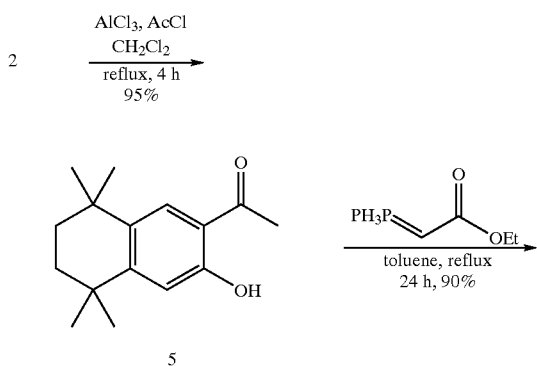

as 11 to its corresponding arylboronic acid or arylboronate e.g., Structure 13 under Pd-catalysis in DMF. Subsequent Suzuki coupling of the resultant arylboronic acid or arylboronate with an ethyl cis-3-halocrotonate represented by Structure 15 produces coumarin intermediate 4. Concomitant cyclization to the corresponding coumarin ensues under the basic hydrolytic conditions employed for the Suzuki coupling chemistry (2 M $K_2CO_3$).

In a variant of the above described synthetic scheme, Suzuki coupling of the same ethyl cis-3-halocrotonate (15) fragment to a 2-alkoxyarylboronate 14 results in Z-ester 16. Alkoxyarylboranate 14 is prepared by alkylation of a 2-haloarylalcohol such as 11 to a 2-alkoxyaryhalide 12 prior to conversion to the arylboronic acid or arylboronate 14. Z-ester 16 may then be treated with $LiAlH_4$ to intercept the coumarin based routes at the stage of allylic alcohol Scheme 4: Alternate General Syntheses of Intermediates 4 and 8.

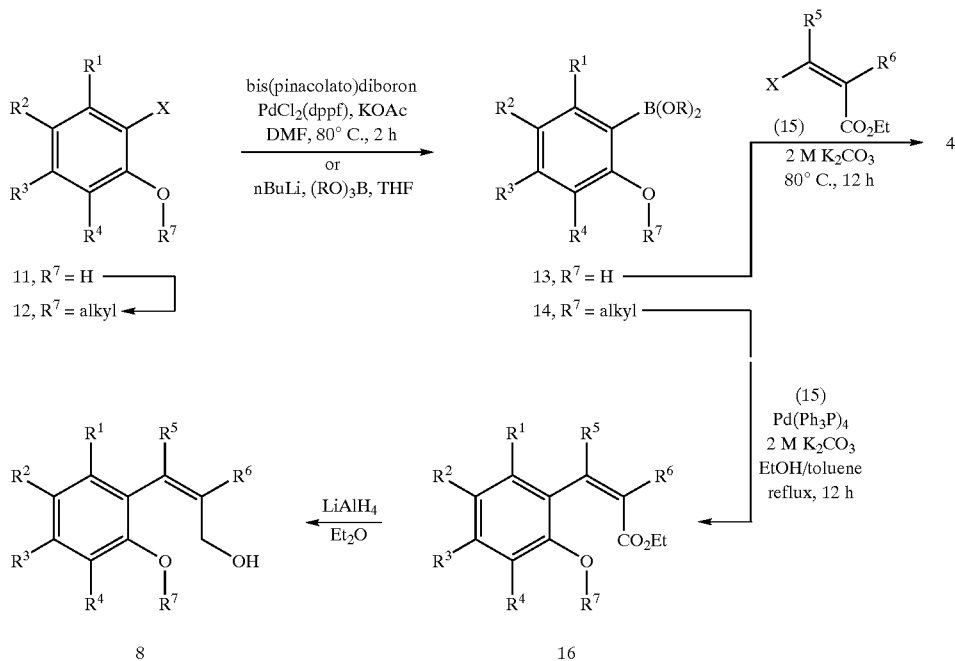

LG100754, Compound 1 of Scheme 2, was synthesized in six steps in 61% overall yield from tetrahydronaphthol 2, with stereospecific introduction of the 6-cis-olefin through a coumarin intermediate. Employing the alternate synthetic route of Scheme 3, Compound 1 of Scheme 2 was prepared in seven steps, 66% overall yield via the stabilized ylide variation of Scheme 3. All of the reactions in this synthesis are amenable to multigram scale execution without significant loss of yield or stereochemical purity, and intermediates require minimal purification.

Scheme 4 describes a third method for preparation of the coumarin intermediates described by general Structure 4. The method involves conversion of a haloarylalcohol such The concept of using a coumarin intermediate to set the key cis-olefin geometry of an important new class of RXR modulating drugs constitutes an efficient general synthetic route, of which several variations are demonstrated herein.

EXAMPLES

Experimental Section

General Experimental Chemical Procedures. Proton nuclear magnetic resonance ($^1$H NMR) spectra were recorded on a Brüker AC 400 or a Varian VXR 500 S spectrometer. Chemical shifts are given in parts per million (ppm) downfield from internal reference tetramethylsilane in δ-units, and coupling constants (J-values) are given in hertz (Hz). Selected data are reported in the following manner: chemical shift, multiplicity, and coupling constants. Melting points were taken on an Electrothermal IA9100 Digital apparatus and are uncorrected. "Brine" refers to a saturated aqueous solution of NaCl. Unless otherwise specified, solutions of common inorganic salts used in work-ups are aqueous solutions. All moisture sensitive reactions were carried out using oven-dried or flame-dried round-bottomed (r.b.) flasks and glassware under an atmosphere of dry nitrogen.

General Procedure A: von Pechmann Cyclization/ Coumarin Intermediate Method for Synthesis of RXR Modulators (2E,4E,6Z)-7-[5,6,7,8-Tetrahydro-5,5,8,8-tetramethyl-2-(n-propyloxy)-naphthalen-3-yl]-3-methylocta-2,4,6-trienoic acid (LG100754, Structure 1 of Schemes 1 and 2, where $R^1$, $R^4$, $R^6$, $R^8$=H, $R^2$ and $R^3$ together form a tetramethyl saturated six-membered carbocyclic ring, $R^5$=methyl, $R^7$=n-propyl).

5,6,7,8-Tetrahydro-5,5,8,8-tetramethylnaphth-2-ol (Structure 2 of Schemes 1 and 2, where $R^1$, $R^4$=H, $R^2$ and $R^3$ together form a tetramethyl saturated six-membered carbocyclic ring). This compound was prepared as previously described (S. S. Canan-Koch et al., *J. Med. Chem.* 39: 3229–34 (1996)): mp 146–149° C. $^1$H NMR (400 MHz, CDCl$_3$) 7.17 (d, 1H, J=8.5 Hz), 6.75 (d, 1H, J=2.8 Hz), 6.62 (dd, 1H, J=8.5, 2.8 Hz), 4.49 (s, 1H), 1.66 (s, 4H), 1.25 and 1.24 (2s, 2×3H). $^{13}$C NMR (100 MHz, CDCl$_3$) 153.0, 146.6, 137.3, 127.7, 113.1, 112.7, 35.2, 35.1, 34.4, 33.7, 32.0, 31.8. IR (thin film) 3143 (br, s), 2917 (m), 1455 (m). Anal. Calcd for C$_{14}$H$_{20}$O: C, 82.30; H, 9.87. Found: C, 82.25; H, 10.07.

1,2,3,4-Tetrahydro-1,1,4,4,6-pentamethylbenzo[5,6-g] coumarin (Structure 4 of Schemes 1 and 2, where $R^1$, $R^4$, $R^6$=H, $R^2$ and $R^3$ together form a tetramethyl saturated six-membered carbocyclic ring, $R^5$=methyl). To a flame-dried 50-mL r.b. flask containing 5,6,7,8-tetrahydro-5,5,8,8-tetramethylnaphth-2-ol (2.03 g, 9.94 mmol) in 4 mL 75% H$_2$SO$_4$ was added ethyl acetoacetate (Structure 3 of Scheme 1, where $R^5$=methyl, $R^6$=H, R'=ethyl) (3.19 mL, 25.0 mmol, 2.52 equiv), and the mixture was heated to 100° C. for 3 h. Upon cooling to room temperature, the mixture was poured over ice (50 g), diluted with saturated NaHCO$_3$ (50 mL), and stirred for 30 min. The mixture was then extracted with EtOAc (3×50 mL) and the organic layer was washed with brine (50 mL), dried (Na$_2$SO$_4$), and concentrated under reduced pressure. The crude product mixture was purified by flash column chromatography (silica gel, hexanes/EtOAc, 4:1) to remove residual ethyl acetoacetate, providing the desired coumarin as a white solid (R$_f$0.62, hexanes/EtOAc, 2:1). Recrystallization from hexanes/EtOAc afforded 2.12 g (79%) of 1,2,3,4-tetrahydro-1,1,4,4,6-pentamethylbenzo[5, 6-g]coumarin as white prisms (mp 126–128° C.). $^1$H NMR (400 MHz, CDCl$_3$) 7.51 (s, 1H), 7.25 (s, 1H), 6.20 (d, 1H, J=0.8 Hz), 2.43 (d, 3H, J=0.9 Hz), 1.72 (s, 4H), 1.33 and 1.31 (2s, 2×3H). $^{13}$C NMR (100 MHz, CDCl$_3$) 161.2, 152.2, 151.4, 150.4, 141.5, 122.2, 117.9, 114.3, 107.1, 34.92, 34.84, 34.58, 34.20, 32.22, 31.83, 18.49. IR (thin film) 2923 (m), 1716 (s), 1612 (m). Anal. Calcd for C$_{18}$H$_{22}$O: C, 79.96; H, 8.20. Found: C, 80.06; H, 8.06.

(2Z)-3-(4-Hydroxy-2-buten-2-yl)-5,6,7,8-tetrahydro-5,5, 8,8-tetramethylnaphth-2-ol (Structure 7 of Schemes 1 and 2, where $R^1$, $R^4$, $R^6$=H, $R^2$ and $R^3$ together form a tetramethyl saturated six-membered carbocyclic ring, $R^5$=methyl). To a flame-dried 100-mL r.b. flask containing 1,2,3,4-tetrahydro-1,1,4,4,6-pentamethylbenzo[5,6-g]coumarin (564 mg, 2.09 mmol) in 30 mL Et$_2$O at 0° C. was added LiAlH4 (79.0 mg, 2.08 mmol, 1.00 equiv), and the mixture was stirred and allowed to gradually warm to room temperature over 2 h. The mixture was then cooled to 0° C. before the cautious addition of 1.0M NaHSO$_4$ (10 mL). The mixture was extracted with EtOAc (30 mL) and the organic layer was washed with brine (50 mL), dried (Na$_2$SO$_4$), and concentrated under reduced pressure to afford 568 mg (99%) of (2Z)-3-(4-hydroxy-2-buten-2-yl)-5,6,7,8-tetrahydro-5,5,8, 8-tetramethylnaphth-2-ol as a white solid (mp 144–145° C. ). $^1$H NMR (400 MHz, CDCl$_3$) 6.92 (s, 1H), 6.82 (s, 1H), 5.92 (t, 1H, J=7.4 Hz), 3.96 (d, 2H, J=7.4 Hz), 2.05 (s, 3H), 1.66 (s, 4H), 1.26 and 1.23 (2s, 2×3H). $^{13}$C NMR (100 MHz, CDCl$_3$) 149.4, 145.8, 137.3, 137.2, 127.4, 126.6, 124.8, 113.3, 60.4, 35.2, 35.1, 34.2, 33.6, 32.0, 31.8, 25.6. IR (thin film) 3147 (br, m), 2919 (m), 1218 (s). Anal. Calcd for C$_{18}$H$_{26}$O$_2$: C, 78.79; H, 9.55. Found: C, 78.71; H,9.71.

(2Z)-3-(4-Hydroxy-2-buten-2-yl)-5,6,7,8-tetrahydro-5,5, 8,8-tetramethyl-2-(n-propyloxy)naphthalene (Structure 8 of Schemes 1 and 2, where $R^1$, $R^4$, $R^6$=H, $R^2$ and $R^3$ together form a tetramethyl saturated six-membered carbocyclic ring, $R^5$=methyl, $R^7$=n-propyl). To a flame-dried 25-mL r.b. flask containing 3-(4-hydroxy-2-buten-2-yl)-5,6,7,8-tetrahydro-5,5,8,8-tetramethylnaphth-2-ol (133 mg, 0.48 mmol) in 2 mL anhydrous DMF at room temperature was added cesium fluoride (365 mg, 2.40 mmol, 5.00 equiv) and 1-iodopropane (52.0 μL, 0.53 mmol, 1.10 equiv), and the mixture was stirred for 12 h. The reaction mixture was then diluted with EtOAc (20 mL) and the resultant organic layer was washed with water (2×10 mL), brine (10 mL), dried (Na$_2$SO$_4$), and concentrated under reduced pressure to afford 150 mg (99%) of (2Z)-3-(4-hydroxy-2-buten-2-yl)-5,6,7,8-tetrahydro-5,5, 8,8-tetramethyl-2-(n-propyloxy) naphthalene as a colorless viscous oil. $^1$H NMR (400 MHz, CDCl$_3$) 6.91 (s, 1H), 6.77 (s, 1H), 5.78 (dt, 1H, J=6.6, 1.4 Hz), 3.88 (m, 4H), 2.04 (s, 3H), 1.75 (m, 2H), 1.28 and 1.23 (2s, 2×3H), 1.01 (t, 3H, J=7.5 Hz). $^{13}$C NMR (100 MHz, CDCl$_3$) 153.3, 144.9, 138.4, 137.0, 127.7, 126.5, 110.1, 70.3, 60.7 35.2, 35.1, 34.4, 33.6, 31.9, 31.8, 25.1, 22.8, 10.7. IR (thin film) 3336 (br, s), 2919 (s), 1498 (m), 1455 (m). Anal. Calcd for C$_{21}$H$_{32}$O$_2$: C, 79.70; H, 10.19. Found: C, 79.60; H, 10.44.

(2Z)-3-[5,6,7,8-Tetrahydro-5,5,8,8-tetramethyl-2-(n-propyloxy)naphthalen-3-yl]-but-2-en-1-al (Structure 9 of Schemes 1 and 2, where $R^1$, $R^4$, $R^6$=H, $R^1$and $R^3$ together form a tetramethyl saturated six-membered carbocyclic ring, $R^5$=methyl, $R^7$=n-propyl). To an oven-dried 10-mL r.b. flask containing (2Z)-3-(4-hydroxy-2-buten-2-yl)-5,6,7,8-tetrahydro-5,5,8,8-tetramethyl-2-(n-propyloxy)naphthalene (25.0 mg, 0.08 mmol) and N-methylmorpholine N-oxide (NMO, 14 mg, 0.12 mmol, 1.5 equiv) in 0.5 mL CH$_2$Cl$_2$ at 0° C. was added tetra-n-propylammonium perruthenate (TPAP, 1.3 mg, 5 mol%), and the mixture was allowed to warm to room temperature. After 1 h at room temperature, the reaction mixture was filtered through a pad of silica gel, washing with an additional 50 mL CH$_2$Cl$_2$. The solvent was then removed under reduced pressure to afford 25 mg (99%) of (2Z)-3-[5,6,7,8-tetrahydro-5,5,8,8-tetramethyl-2-(n-propyloxy)naphthalen-3-yl]-but-2-en-1-al as a colorless low-melting solid. The aldehyde thus obtained was of greater than 98% purity as judged by the $^1$H NMR spectrum, and was used directly in the next step without further purification. $^1$H NMR (400 MHz, CDCl$_3$) 9.36 (d, 1H, J=8.1 Hz), 6.99 (s, 1H), 6.79 (s, 1H), 6.09 (dd, 1H, J=8.4, 1.1 Hz), 3.90 (t, 2H, J=6.4 Hz), 2.29 (d, 3H, J=1.1 Hz), 1.76 (m, 2H), 1.68 (d, 4H, J=1.6Hz), 1.30 and 1.23 (2s, 2×3H) 1.00 (t, 3H, J=7.5Hz). $^{13}$C NMR (100 MHz, CDCl$_3$) 194.0, 161.7, 153.3, 146.9, 136.6, 129.7, 128.6, 125.3, 109.5, 69.7, 35.1, 35.0, 34.6, 33.6, 31.9, 31.8, 25.9, 22.6, 10.7. IR (thin film) 2922 (br, m), 1674 (s), 1202 (s), 1147 (s).

(2E,4E,6Z)-7-[5,6,7,8-Tetrahydro-5,5,8,8-tetramethyl-2-(n-propyloxy)-naphthalen-3-yl]-3-methylocta-2,4,6-trienoic acid (LG100754, Structure 1 of Schemes 1 and 2, where $R^1$, $R^4$, $R^6$, $R^8$=H, $R^2$ and $R^3$ together form a tetramethyl saturated six-membered carbocyclic ring, $R^5$=methyl, $R^7$=n-propyl). This compound was prepared from (2Z)-3-[5,6,7,8-tetrahydro-5,5,8,8-tetramethyl-2-(n-propyloxy) naphthalen-3-yl]-but-2-en-1-al as previously described (S. S. Canan-Koch et al., *J. Med. Chem.* 39: 3229–34 (1996)). The $^1$H NMR spectral data, TLC elution properties, and melting point of this product thus obtained matched those previously reported.

General Procedure B: Stabilized Ylide Procedure for Preparation of a Coumarin Intermediate of General Structure 4

1,2,3,4-Tetrahydro-1,1,4,4,6-pentamethylbenzo[5,6-g] coumarin (Structure 4 of Schemes 1 and 3, where $R^1$, $R^4$, $R^6$=H, $R^2$ and $R^3$ together form a tetramethyl saturated six-membered carbocyclic ring, $R^5$=methyl).

3-Acetyl-5,6,7,8-tetrahydro-5,5,8,8-tetramethylnaphth-2-ol (Structure 5 of Schemes 1 and 3, where $R^1$, $R^4$=H, $R^2$ and $R^3$ together form a tetramethyl saturated six-membered carbocyclic ring, $R^5$=methyl). This compound was prepared as previously described (S. S. Canan-Koch et al., *J. Med. Chem.* 39: 3229–34 (1996)): mp 101–103° C. $^1$H NMR(400 MHz, CDCl$_3$) 11.65 (folded over s, 1H), 7.65 (s, 1H), 6.90 (s, 1H), 2.61 (s, 3H), 1.68 (s, 4H), 1.29 and 1.27 (2s, 2×3H). $^{13}$C NMR (100 MHz, CDCl$_3$) 203.9, 159.5, 136.2, 128.7, 118.3, 115.4, 107.1, 35.1, 34.9, 34.6, 33.7,32.2, 31.6, 26.4. IR (thin film) 2923 (m), 1654 (s), 1459 (m). Anal. Calcd for C$_{16}$H$_{22}$O: C, 78.01; H, 9.00. Found: C, 78.28; H, 9.09.

1,2,3,4-Tetrahydro-1,1,4,4,6-pentamethylbenzo[5,6-g] coumarin (Structure 4 of Schemes 1 and 3, where $R^1$, $R^4$, $R^6$=H, $R^2$ and $R^3$ together form a tetramethyl saturated six-membered carbocyclic.ring, $R^5$=methyl). To a flame-dried 50-mL r.b. flask containing 3-acetyl-5,6,7,8-tetrahydro-5,5,8,8-tetramethylnaphth-2-ol (1.579 g, 6.41 mmol) in 10 mL toluene was added carbethoxymethylenetriphenylphosphorane (Structure 6 of Scheme 1, where $R^6$=H, R'=ethyl) (3.35 g, 9.62 mmol, 1.50 equiv), and the mixture was heated to reflux for 24 h. Upon cooling to room temperature, the solvent was removed under diminished pressure, and the remaining solid was purified by trituration with cold hexanes (3×50 mL) to afford 1.54 g (90%) of 1,2,3,4-tetrahydro-1,1,4,4,6-pentamethylbenzo[5,6-g] coumarin as a white solid. The $^1$H NMR spectral data, TLC elution properties, and melting point of this compound thus obtained matched those of the same compound obtained using General Procedure A (von Pechmann cyclization).

General Procedure C: Suzuki Coupling Procedure for Preparation of a Coumarin Intermediate of General Structure 4

Variant 1: 6,8-Di-(tert)-butyl-4-methylcoumarin (Structure 4 of Scheme 1, where $R^1$, $R^3$, $R^6$=H, $R^2$, $R^4$=tert-butyl, $R^5$=methyl). To a 100-mL r.b. flask containing 4,6-di-tert-butyl-2-iodophenol (Structure 11 of Scheme 4, where $R^1$, $R^3$=H, $R^2$, $R^4$=tert-butyl, $R^7$=H) (1.10 g, 3.00 mmol) in 30 mL DMF was added bis(pinacolato)diboron (0.83 g, 3.30 mmol, 1.10 equiv), and potassium acetate (0.88 g, 9.00 mmol), and a stream of nitrogen gas was bubbled through the solution for 15 min. To this solution was added PdCl$_2$ (dppf) (0.22 g, 0.33 mmol, 10 mol %), and the reaction was heated to 80° C. for 2 h. The reaction mixture was then cooled to room temperature, ethyl cis-3-iodocrotonate (Compound 15 of Scheme 4, where $R^5$=methyl, $R^6$=H) (1.44 g, 6.00 mmol) and 15 mL of 2 M K$_2$CO$_3$ was added, and the reaction was heated to 80° C. overnight. The mixture was cooled, concentrated under reduced pressure, water was added, and the organics were extracted with 200 mL CH$_2$Cl$_2$. The organic layer was washed successively with water then brine, dried (MgSO$_4$), concentrated under reduced pressure, and purified by flash column chromatography (silica gel, CH$_2$Cl$_2$/hexanes, 1:1) to give 0.38 g (47%) of 6,8-di-(tert)-butyl-4-methylcoumarin. $^1$H NMR (500 MHz, CDCl$_3$) 7.59 (d, 1H, J=2.0 Hz), 7.44 (d, 1H, J=2.0 Hz), 6.27 (s, 1H), 2.45 (s, 3H), 1.51 (s, 9H), 1.36 (s, 9H).

Variant 2: 6,8-Di-(tert)-butyl-4-methylcoumarin (Structure 4 of Scheme 1, where $R^1$, $R^3$, $R^6$=H, $R^2$, $R^4$=tert-butyl, $R^5$=methyl). To a 100-mL r.b. flask containing 3,5-di-(tert)-butyl-2-hydroxyphenylboronic acid (Structure 13 of Scheme 4, where $R^1$and $R^3$=H, $R^2$ and $R^4$=tert-butyl, $R^7$=H) (0.54 g, 1.9 mmol) in 20 mL of ethanol and 20 mL of toluene was added (Ph$_3$P)$_4$Pd (0.1 g, 0.1 mmol, 5 mol %), ethyl cis-3-iodocrotonate (Compound 15 of Scheme 4, where $R^5$=methyl, $R^6$=H) (0.70 g, 2.9 mmol, 1.5 equiv), and 10 mL of 2 M K$_2$CO$_3$, and a stream of nitrogen gas was bubbled through the solution for 10 min. The reaction mixture was then heated to reflux overnight. The reaction mixture was then cooled to room temperature, concentrated under reduced pressure, water was added, and the organics were extracted with 200 mL CH$_2$Cl$_2$. The organic layer was washed successively with water then brine, dried (MgSO$_4$), concentrated under reduced pressure, and purified by flash column chromatography (silica gel, CH$_2$Cl$_2$/hexanes, 1:1) to give 0.33 g (55%) of 6,8-di-(tert)-butyl-4-methylcoumarin. $^1$H NMR (500 MHz, CDCl$_3$) 7.59 (d, 1H, J=2.0 Hz), 7.44 (d, 1H, J=2.0 Hz), 6.27 (s, 1H), 2.45 (s, 3H), 1.51 (s, 9H), 1.36 (s, 9H).

General Procedure D: Preparation of a Z-3-Arylbutenoate of General Structure 16

(2Z)-Ethyl 3-[4,6-di-(tert)-butyl-1-methoxyphen-2-yl] but-2-enoate (Structure 16 of Scheme 4, where $R^1$, $R^3$, $R^6$=H, $R^2$, $R^4$=tert-butyl, $R^5$, $R^7$=methyl). To a 50-mL r.b. flask containing 3,5-di-(tert)-butyl-2-methoxyphenylboronic acid (Structure 14 of Scheme 4, where R, $R^1$, $R^3$=H, $R^2$, $R^4$=tert-butyl, $R^7$=methyl) (0.97 g, 3.20 mmol) in 10 mL of EtOH and 6 mL of toluene was added (Ph$_3$P)$_4$Pd (0.1 g, 0.1 mmol, 3 mol %), ethyl cis-3-iodocrotonate (Compound 15 of Scheme 4, where $R^5$=methyl, $R^6$=H) (1.01 g, 4.2 mmol, 1.31 equiv), and 6 mL of 2 M K$_2$CO$_3$, and a stream of nitrogen gas was bubbled through the solution for 10 min. The reaction mixture was then heated to reflux overnight. The reaction mixture was then cooled to room temperature, concentrated under reduced pressure, water was added, and the organics were extracted with 200 mL of CH$_2$Cl$_2$. The organic layer was washed successively with water then brine), dried (MgSO$_4$), concentrated under reduced pressure, and purified by flash column chromatography (silica gel, CH$_2$Cl$_2$/hexanes, 1:1) to give 0.35 g (56%) of (2Z)-ethyl 3-[4,6-di-(tert)-butyl-1-methoxyphen-2-yl]but-2-enoate. $^1$H NMR (500 MHz, CDCl$_3$) 7.11 (d, 1H, J=2.0 Hz), 5.91 (s, 1H), 4.16 (q, 2H), 3.71 (s, 3H), 2.19 (s, 3H), 1.51 (s, 9H), 1.36 (s, 9H), 0.84 (t, 3H).

(2'Z)-4,6-Di-(tert)-butyl-2-(4-hydroxy-2-buten-2-yl) anisole (Structure 8 of Schemes 1 and 4, where $R^1$, $R^3$, $R^6$=H, $R^2$, $R^4$=tert-butyl, $R^5$, $R^7$=methyl). To a 50-mL r.b. flask containing (2Z)-ethyl 3-[4,6-di-(tert)-butyl-1- methoxyphen-2-yl]but-2-enoate (Structure 16, where $R^1$, $R^3$, $R^6$=H, $R^2$, $R^4$=tert-butyl, $R^5$, $R^7$=methyl) (0.35 g, 0.72 mmol) in 5 mL of $Et_2O$ at −78° C. was added $LiAlH_4$ (0.03 g, 0.7 mmol), and the reaction was warmed to room temperature and stirred for 1 h. Ethyl acetate (20 mL) and 2 mL of 6 N HCl were added and stirred for 1 h. The organic layer was then washed successively with water then brine, dried ($MgSO_4$), concentrated under reduced pressure, and purified by flash column chromatography (silica gel, $CH_2Cl_2$/hexanes, 1:1) to give 0.20 g (90%) of (2'Z)-4,6-di-(tert-butyl)-3-(4-hydroxy-2-buten-2-yl)anisole. $^1H$ NMR (500 MHz, $CDCl_3$) 7.26 (d, 1H, J=2.0 Hz), 6.91 (d, 1H, J=2.0 Hz), 5.82 (dt, 1H, J=7.0 Hz, 2.0 Hz), 3.81 (m, 2H), 3.79 (s, 3H), 2.16 (d, 3H, J=2.0 Hz), 1.41 (s, 9H), 1.30 (s, 9H).

Scheme 5

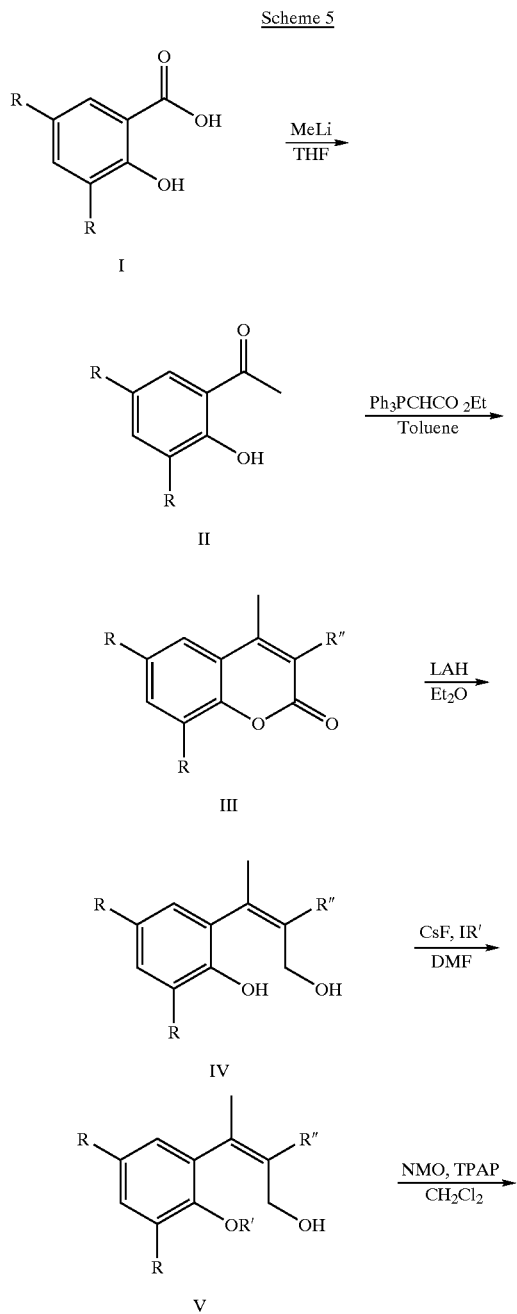

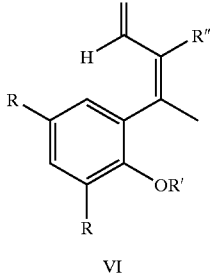

VI

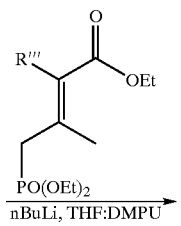

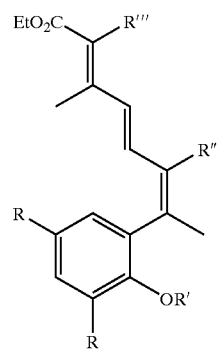

VII

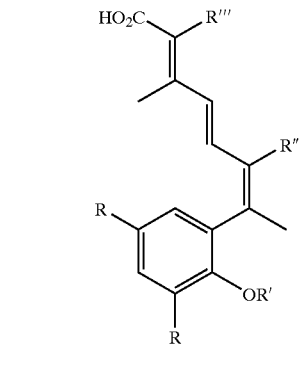

VIII

Scheme 5 shows a general synthetic method for the production of coumarin intermediates (e.g., Structure III). This synthetic method is also described in Scheme I. The synthetic process of these schemes describes the production of a coumarin from a hydroxyacetophenone by condensation with a phosphorous ylide. The coumarin intermediates are then ring opened and alkylated to produce the desired RXR modulator compounds. Examples 1–13 show a preferred embodiment for the synthetic method shown in Schemes I and 5.

Example 1

(Compound II of Scheme 5, where R=tert-butyl). To 110 gm (0.44 mol) of 3,5 Di-tert-butyl-4-hydroxybenzoic acid I in 500 mL of THF at 0° C. was added 1.6 L (1.76 mol) of 1.4 M MeLi. The reaction was stirred for 2 h while slowly warming to room temperature. One liter of EtOAc was slowly added to the reaction mixture which was subsequently washed (1 L of 1 N HCl, 1 L of water and 500 mL of brine), dried ($MgSO_4$), concentrated and purified by $SiO_2$ chromatography (10% EtOAc-hexanes) to give 83.0 gm (0.33 mol) of II. $^1$H-NMR (CDCl$_3$) δ 7.56 (m, 2H, Ar—H), 2.65 (s, 3H, CH$_3$), 1.42 (s, 9H, t-butyl), 1.32 (s, 9H, t-butyl).

Example 1a (Compound IIa of Scheme 5, where R=isobutyl). To a mixture of 15.64 g (0.0625 mol) of 2-hydroxy-2,4-di-tert-isopropylbenzoic acid and 300 ml of dry THF at −78° C. was added 100 ml of 2.5 M n-butyllithium slowly (Note: Scheme 5 demonstrates use of methyl lithium, however in this synthesis butyl lithium was used). The resulting mixture was warmned to room temperature. The reaction was checked by TLC and after 3 hours 100 ml of EtOAc and 20 ml of water were added. The reaction was stirred for 30 minutes and then extracted with 500 ml of ETOAc. The organic fractions were combined and dried over MgSO$_4$. The solvents were evaporated under reduced pressure and the resulting oil was purified over silica gel (eluent: methylene chloride/hexane: 50/50) to give 17.82 g (yield: 98%) of IIa. $^1$H NMR (CDCl$_3$): 7.62 (s, 1 H), 7.54 (s, 1H), 2.98 (t, 2H), 1.76 (m, 2H), 1.55 (m, 4H), 1.54 (d, 6H), 1.43 (d, 6H), 0.96 (t, 3H).

Example 2

(Compound III of Scheme 5, where R=tert-butyl, R"=H). To 83.0 gm (0.34 mol) of methyl ketone II suspended in 500 mL of toluene was added 232.9 gm (0.67 mol) of (carbethoxymethylene)triphenylphosphorane. The mixture was heated to reflux and allowed to stir overnight. The mixture was cooled, water was added, and the organics were extracted with 500 mL of EtOAc. The organic layer was washed (water then brine), dried (MgSO$_4$), concentrated and purified by SiO$_2$ chromatography (10% EtOAc-hexanes) to give 73.4 gm (0.27 mol) of III. $^1$H-NMR (CDCl$_3$) δ 7.59 (d, J=2.0 Hz, 1H, Ar—H), 7.44 (d, J=2.0 Hz, 1H, Ar—H), 6.27 (s, 1H, =CH), 2.45 (s, 3H, CH3), 1.51 (s, 9H, t-butyl), 1.36 (s, 9H, t-butyl).

Example 3

(Compound IV of Scheme 5, where R=tert-butyl, R"=H). To 9.3 gm (34.2 mmol) of coumarin III in 120 mL of Et$_2$O at −78° C. was added 34.2 mL (34.2 mmol) of 1.0 M lithium aluminum hydride (LAH). The reaction was stirred for 3 h or until complete by TLC (20% EtOAc-hexanes) while slowly warming to room temperature. Upon completion, the mixture was cooled to 0° C. and quenched with water. The organics were extracted (250 mL of EtOAc), washed (50 mL of brine), dried (MgSO$_4$), concentrated and purified by SiO$_2$ chromatography (20% EtOAc-hexanes) to give 9.1 g (32.97 mmol) of IV. $^1$H-NMR (CDCl$_3$) δ 7.26 (d, J=2.0 Hz, 1H, Ar—H), 6.91 (d, J=2.0 Hz, 1H, Ar—H), 5.98 (dt, J=7.0 Hz, J=2.0 Hz, 1H, =CH), 3.94 (m, 2H, CH$_2$-OH), 2.14 (d, J=1 Hz, 3H, =CHCH$_3$), 1.30 (s, 9H, t-butyl), 1.41 (s, 9H, t-butyl).

Example 4

(Compound V of Scheme 5, where R=tert-butyl, R'=ethyl, R"=H). To 9.00 g (32.0 mmol) of diol IV in 120 mL of DMF was added 14.58 g (96.0 mmol) of cesium fluoride. The solution was stirred for 15 min and then 2.8 mL (35.2 mmol) of iodoethane was added and the mixture was allowed to stir overnight. Water was added (250 mL) and the organics were extracted (500 mL EtOAc), dried (MgSO$_4$), concentrated and purified by SiO$_2$ chromatography (10% EtOAc-hexanes) to give 9.2 g (30.5 mmol) of V. $^1$H-NMR (CDCl$_3$) δ 7.26 (d, J=2.0 Hz, 1H, Ar—H), 6.91 (d, J=2.0 Hz, 1H, Ar—H), 5.82 (dt, J=7.0 Hz, J=7.0 Hz, 2.0 Hz, 1H=CH), 3.81 (m, 4H, CH$_2$-OH, —OCH$_2$CH$_3$), 2.16 (d, J=2.0 Hz, 3H, CH$_3$), 1.41 (s, 9H, t-butyl), 1.36 (t, J=7.0 Hz, 3H, —OCH$_2$CH$_3$), 1.30 (s, 9H, t-butyl).

Example 5

(Compound VI of Scheme 5, where R=tert butyl, R'=ethyl, R"=H). To 10.3 g (33.9 mmol) of the alcohol V stirring in 150 mL of CH$_2$Cl$_2$ was added 600 mg (1.69 mmol) of tetrapropylammonium perruthenate (TPAP) and 5.95 g (50.82 mmol) of 4-methylmorpholine-N-oxide (MMNO). The reaction stirred overnight and the filtered through a SiO$_2$ plug and washed with CH$_2$Cl$_2$. In vacuo concentration gave 8.49 g (28.11 mmol) of VI. $^1$H-NMR (CDCl$_3$) δ 9.47 (d, J=8.5 Hz, 1H, HCO), 7.37 (d, J=2.0 Hz, 1H, Ar—H), 6.96 (d, J=2.0 Hz, 1H, Ar—H), 6.10 (d, J=8.5 Hz, 1H, =CH), 3.87 (t, J=6.3 Hz, 1H, CH$_2$CH$_3$), 3.73 (t, J=6.3 Hz, 1H, CH$_2$CH$_3$), 2.36 (s, 3H, =CCH$_3$), 1,41 (s, 9H, t-butyl), 1.31 (t, 6.3 Hz, 3H, —OCH2CH$_3$), 1.308 (s, 9H, t-butyl).

Example 6

(Compound VII of Scheme 5, where R=tert-butyl, R'=ethyl, R"=H, R'''=H). To 20.5 mL (84.34 mmol) of triethyl 3-methyl-4-phosphonocrotonate in 50 mL of THF at −78° C., was added 52.7 mL (84.34 mmol) of 1.6 M n-BuLi. This solution was stirred for 30 min and then 8.49 g (28.11 mmol) of aldehyde VI was added in 50 mL of THF. The reaction was slowly warmed to room temperature while stirring overnight. Water (300 mL) was added, and extracted with EtOAc (300 mL), dried (MgSO$_4$), concentrated and purified by SiO$_2$ chromatography (10% EtOAc-hexanes) to give 10.5 gm (24.53 mmol) of VII. $^1$H-NMR (CDCl$_3$) δ 7.29 (d, J=2.0 Hz, 1H, Ar=H), 6.92 (d, J=2.0 Hz, 1H, Ar—H), 6.68 (dd, J=15.0 Hz, J=11 Hz, 1H, =CH), 6.26 (d, J=15 Hz, 1H, =CH), 6.23 (d, J=11 Hz, 1H, =CH), 5.76 (s, 1H, =CH), 4.15 (m, 2H, CO$_2$CH$_2$CH$_3$), 3.87 (t, J=6.3 Hz, 1H, =OCH$_2$CH$_3$), 3.69 (t, J=6.3 Hz, 1H, OCH$_2$CH$_3$), 2:21 (s, 3H, CH$_3$), 1.41 (s, 9, t-butyl), 1.31 (s, 3H, t-butyl), 1.25 (m, 6H, CO$_2$CH$_2$CH$_3$, OCH$_2$CH$_3$).

Example 7

(L2, Compound VIII of Scheme 5, where R=tert-butyl, R'=ethyl, R"=H, R'''H). To 10.00 g (23.36 mmol) of the ethyl ester VII in 80 mL of MeOH, was added 23.4 mL (70.1 mmol) of 3N aqueous KOH and the suspension was refluxed overnight. After acidification (20% aqueous HCl), the organics were extracted with EtOAc (300 mL), dried (MgSO$_4$), concentrated and the solid recrystallized from EtOH to give 3.8 gm (9.90 mmol) of the carboxylic acid VIII. $^1$H-NMR (CDCl$_3$) δ 7.29 (d, J=2.0 Hz, 1H, Ar—H), 6.92 (d, J=2.0 Hz, 1H, Ar—H), 6.68 (dd, J=15 Hz, J=11 Hz, 1H, =CH), 6.26 (d, J=15 Hz, 1H, =CH), 6.23 (d, J=11 Hz, 1H, =CH), 5.77 (s, 1H, COCH), 3.87 (t, J=6.3 Hz, 1H, CH$_2$CH$_3$), 3.69 (t, J=6.3 Hz, 1H, CH$_2$CH$_3$), 2.24 (s, 3H, CH$_3$), 2.16 (d, J=1 Hz, 3H, CH$_3$), 1.42 (s, 9H, t-butyl), 1.31 (s, 9H, t-butyl), 1.28 (t, J=6.3 Hz, 3H, CH$_3$).

Example 8

(L1, Compound VIII of Scheme 5, where R=tert-butyl, R'=methyl, R"=H, R'''=H). This compound was prepared in the manner previously described for compound VIII in Example 7, except that iodomethane was used instead of iodoethane in Example 4. $^1$H-NMR (CDCl$_3$) δ 7.29 (d, J=2.2 Hz, 1H, Ar—H), 6.95 (d, J=2.0 Hz, 1H, Ar—H), 6.67 (dd, J=15 Hz, J=11 Hz, 1H, =CH), 6.26 (d, J=15 Hz, 1H, =CH), 6.23 (d, J=11 Hz, 1H, =CH), 5.79 (s, 1H, COCH), 3.62 (s, 3H, CH$_3$), 2.30 (s, 3H, CH$_3$), 2.16 (s, 3H, CH$_3$), 1.42 (s, 9H, t-butyl), 1.29 (s, 9H, t-butyl).

Example 9

(L3, Compound VIII of Scheme 5, where R=tert-butyl, R'=n-propyl, R"=H, R'''=H). This compound was prepared in the manner previously described for Compound VIII in Example 7, except that iodopropane was used instead of iodoethane in Example 4. $^1$H-NMR (CDCl$_3$) δ 7.30 (d, J=2.0 Hz, 1H, Ar—H), 6.92 (d, J=2.0 Hz, 1H, Ar—H), 6.67 (dd, J=15 Hz, J=11 Hz, 1H, =CH), 6.26 (d, J=15 Hz, 1H, =CH), 6.23 (d, J=11 Hz, 1H, =CH), 5.75 (s, 1H, COCH), 3.89 (m, 1H, CH$_2$CH$_3$), 3.69 (m, 1H, CH$_2$CH$_3$), 2.27(s, 3H, CH$_3$), 2.18 (s, 3H, CH$_3$), 1.68 (m, 2H, CH$_3$), 1.42 (s, 9H, t-butyl), 1.29 (s, 9H, t-butyl), 0.97 (t, J=6.3 Hz, 3H, CH$_3$).

Example 10

(L4, Compound VIII of Scheme 5, where R=tert-butyl, R'=n-butyl, R"=H, R'''=H). This compound was prepared in the manner previously described for Compound VIII in Example 7, except that iodobutane (or bromobutane) was used instead of iodoethane in Example 4. $^1$H-NMR (CDCl$_3$) δ 7.29 (d, J=2.2 Hz, 1H, Ar—H), 6.96 (d, J=2.2 Hz, 1H, Ar—H), 6.60 (dd, J=15 Hz, J=11 Hz, 1H, =CH), 6.26 (d, J=15 Hz, 1H, =CH), 6.23 (d, J=11 Hz, 1H, =CH), 5.70 (s, 1H, COCH), 3.87 (m, 1H, CH$_2$CH$_3$), 3.63 (m, 1H, CH$_2$CH$_3$), 2.30(s, 3H, CH$_3$), 2.21 (s, 3H, CH$_3$), 1.62 (m, 2H, CH$_3$), 1.42 (s, 9H, t-butyl), 1.29 (s, 9H, t-butyl), 1.27 (m, 2H, CH$_3$), 0.91 (t, J=6.3 Hz, 3H, CH$_3$).

Example 11

(L5, Compound VIII of Scheme 5, where R=tert-butyl, R'=n-heptyl, R"=H, R'''=H). This compound was prepared in the manner previously described for Compound VIII in Example 7, except that bromoheptane was used instead of iodoethane in Example 4. $^1$H-NMR (CDCl$_3$) δ 7.30 (d, J=2.2 Hz, 1H, Ar—H), 6.90 (d, J=2.2 Hz, 1H, Ar—H), 6.66 (dd, J=15 Hz, J=11 Hz, 1H, =CH), 6.26 (d, J=15 Hz, 1H, =CH), 6.23 (d, J=11 Hz, 1H, =CH), 5.70 (s, 1H, COCH), 3.90 (m, 1H, CH$_2$CH$_3$), 3.60 (m, 1H, CH$_2$CH$_3$), 2.22(s, 3H, CH$_3$), 2.16 (s, 3H, CH$_3$), 1.68–1.29 (m, 8H, CH$_2$), 1.40 (s, 9H, t-butyl), 1.30 (s, 9H, t-butyl), 1.27 (m, 2H, CH$_3$), 0.86 (t, J=6.3 Hz, 3H, CH$_3$).

Example 11a (L104, Compound VIIIa of Scheme 5 where R=isopropyl, R'=heptyl, R"=H, .and R'''=H). Note: This compound was synthesized using the procedures illustrated in Scheme 5 starting from Compound IIa from Example 1a, the synthesis of which employed n-butyl lithium instead of methyl lithium as in Example 1. To a mixture of 710 mg of the ester of Compound VIIa in 10 ml of ethanol was added 1 ml of 6 N NaOH. The solution was heated to reflux until completion (TLC monitoring). After cooling, water was added and the mixture as extracted with ethyl acetate. The organic layer was washed with water and brine and dried over MgSO$_4$. The solvents were evaporated under reduced pressure, and the residual oil was crystallized from acetonitrile to yield 120 mg of Compound VIIIa. $^1$H NMR (CDCl$_3$): 6.92 (d, 1H), 6.66 (m, 1H), 6.22 (m, 3H), 6.72 (s, 1H), 3.88 (m, 1H), 3.62 (m, 1H), 2.68 (m, 1H), 2.44 (m, 1H), 1.77 (m, 2H), 1.53 (d, 6H), 1.44 (m, 6H), 2.98 (t, 2H), 1.76 (m, 2H), 1.55 (m, 4H), 1.54 (d, 6H), 1.43 (d, 6H),1.27 (d, 6H), 0.96 (m, 6H).

Example 12

(L6, Compound VIII of Scheme 5, where R=isopropyl, R'=n-butyl, R"=H, R'''=H). This compound was prepared in the manner previously described for Compound VIII in Example 7, except that 3,5 di-isopropyl-4-hydroxybenzoic acid was used instead of 3,5 di-tert-butyl-4-hydroxybenzoic acid in Example 1, and iodobutane was used instead of iodoethane in Example 4. $^1$H-NMR (CDCl$_3$) δ 7.02 (d, J=2.2 Hz, 1H, Ar—H), 6.72 (d, J=2.2 Hz, 1H, Ar—H), 6.57 (dd, J=15 Hz, J=11 Hz, 1H, =CH), 6.24 (d, J=15 Hz, 1H, =CH), 6.18 (d, J=11 Hz, 1H, =CH), 5.73 (s, 1H, COCH), 3.62 (mb, 2H, CH$_2$CH$_3$), 3.37 (m, 1H, CH), 2.85 (m, 1H, CH), 2.20(s, 3H, CH$_3$), 2.13 (s, 3H, CH$_3$), 1.62 (m, 2H, CH$_2$), 1.44 (m, 2H, CH$_2$), 1.27 (d, 6H, CH$_3$), 1.24 (d, 6H, CH$_3$), 0.91 (t, J=6.3 Hz, 3H, CH$_3$).

Example 13

(L7, Compound VIII of Scheme 5, where R=isopropyl, R'=n-pentyl, R"=H, R'''=H) This compound was prepared in the manner previously described for Compound VIII in Example 7, except that 3,5 di-isopropyl-4-hydroxybenzoic acid was used instead of 3,5 di-tert-butyl-4-hydroxybenzoic acid in Example 1, and iodopentane (or bromopentane) was used instead of iodoethane in Example 4. $^1$H-NMR (CDCl$_3$) δ 7.04 (d, J=2.2 Hz, 1H, Ar—H), 6.74 (d, J=2.2 Hz, 1H, Ar—H), 6.57 (dd, J=15 Hz, J=11 Hz, 1H, =CH), 6.24 (d, J=15Hz, 1H, =CH), 6.18 (d, J=11 Hz, 1H, =CH), 5.73 (s, 1H, COCH), 3.62 (mb, 2H, CH$_2$CH$_3$), 3.33 (m, 1H, CH), 2.89 (m, 1H, CH), 2.20(s, 3H, CH$_3$), 2.13 (s, 3H, CH$_3$), 1.62 (m, 2H, CH$_2$), 1.44 (m, 4H, CH$_2$), 1.27 (d, 6H, CH$_3$), 1.24 (d, 6H , CH$_3$), 0.91 (t, J=6.3 Hz, 3H, CH$_3$).

Example 14

(Compound III of Scheme 5, where R=tert-butyl, R"=F). This compound was prepared in the manner previously described for Compound III in Example 2, except that triethyl-2-fluoro phosphono acetate was used instead of (carbethoxymethylene)triphenylphosphorane. $^1$H-NMR (CDCl$_3$) δ 7.56 (d, J=2.1 Hz, 1H, Ar—H), 7.40 (d, J=2.1 Hz, 1H, Ar—H), 2.42 (d, J=3 Hz, 3H, CH3), 1.51 (s, 9H, t-butyl), 1.36 (s, 9H, t-butyl).

Example 15

(L20, Compound VII of Scheme 5, where R=tert-butyl, R'=1,1,1-trifluoroethyl, R'=F, R'''=H). This compound was prepared in the manner previously described for Compound VIII in Example 7, except that 1,1,1-trifluoro, 2-iodoethane was used instead of iodoethane in Example 4. $^1$H NMR (400 MHz, CDCl$_3$) 7.35 (d, J=2.4 Hz, 1H), 6.99 (d, J=2.4 Hz, 1H), 6.59 (d, J=15.6 Hz, 1H), 6.41 (dd, J=25.9, 15.6 Hz, 1H), 5.90 (s, 1H), 4.15 (quintet, J=8.4 Hz, 1H), 4.02 (quintet, J=8.4 Hz, 1H), 2.17 (d, J=3.5 Hz, 3H), 2.14 (s, 3H), 1.41 (s, 9H), 1.30 (s, 9H).

Example 16

(Compound IV of Scheme 5, where R=tert-butyl, R"=F). This compound was prepared in the manner previously described for Compound IV in Example 3, except that 3-fluoro-4-methyl-7,9-di-tert-butyl coumarin was used instead 4-methyl-7,9-di-tert-butyl coumarin in Example 2. IV was directly used in the next step. $^1$H NMR (400 MHz, CDCl$_3$), δ 7.25 (d, J=2.1 Hz, 1H), 6.90 (d, J=2.1 Hz, 1H), 4.95 (broad s, 1H), 4.09 (m, 2H), 2.00 (d, J=3.6 Hz, 3H), 1.98 (broad m, 1H), 1.41 (s, 9H), 1.28 (s, 9H).

Example 17

(Compound V of Scheme 5, where R=tert-butyl, R'=1,1-difluoroethyl, R"=F). This compound was prepared in the manner previously described for Compound V in Example 4, except that of Z-2-fluoro-3-[2-(2,2-difluoroethoxy)-3,5-di-tert-butylbenzene]crotyl alcohol was used instead of 3-[2-(2,2-difluoroethoxy)-3,5-di-tert-butylbenzene]crotyl alcohol IV in Example 3 (4.7 mmol, yield=88%) of V. $^1$H NMR (400 MHz, CDCl$_3$) δ: 7.29 (d, J=2.1 Hz, 1H), 6.99 (d, J=2.1 Hz, 1H), 6.08 (dt, J=55.3, 4.0 Hz, 1H), 4.00 (m, 4H), 2.08 (d, J=3.6 Hz, 3H), 2.01 (broad s, 1H), 1.39 (s, 9H), 1.29 (s, 9H).

Example 18

(Compound VII of Scheme 5, where R=tert-butyl, R'=1,1-difluoroethyl, R"=F, R'"=H). To a mixture of 365 mg (1.02 mmol) of VI and 179 mg (1.52 mmol) of NMO in 10 ml of CH$_2$Cl$_2$ was added 18 g (0.05 mmol) of TPAP in one time. The mixture was stirred at room temperature until the reaction was complete (TLC analysis). The mixture is filtrated over a short pad of silica gel and the solvent evaporated. The crude aldehyde was directly treated with the anion of ethyl-3-methylphosphono crotonate (prepared from 1.0 g—3.8 mmol—of triethyl-3-methylphosphonocrotonate and 2.9 ml of nBuLi in a 10/1 THF/DMPU mixture at −78° C.) at −78° C. The mixture is allowed to warm-up to room temperature and the solvents are evaporated. The crude ester was purified over a short silica gel plug (eluent: 5/95 ethyl acetate/hexane) to afford 414 mg (0.89 mmol, yield=87%, 2 steps) of VII. $^1$H NMR (400 MHz, CDCl$_3$) δ: 7.33 (d, J=2.4 Hz, 1H), 6.99 (d, J=2.4 Hz, 1H), 6.56 (d, J=15.7 Hz, 1H), 6.37 (dd, J=26.3, 15.7 Hz, 1H), 5.97 (dt, J=55.1, 3.9 Hz, 1H), 5.87 (s, 1H), 4.15 (dd, J=15.6, 7.2 Hz, 2H), 4.07 (m, 1H), 3.89 (m, 1H), 2.16 (d, J=3.5 Hz, 3H), 2.12 (s, 3H), 1.40 (s, 9H), 1.26 (s, 9H), 1.24 (t, J=7.2H, 3H).

Example 19

(L21, Compound VIII of Scheme 5, where R=tert-butyl, R'=1,1-difluoroethyl, R"=F, R'"=H). This compound was prepared in the manner previously described for Compound VIII in Example 7, except that ethyl (2E, 4E, 6E)-3-methyl-6-fluoro-7-[2-(2,2-difluoroethoxy)-3,5-di-tert-butylbenzene]octatrienoate was used instead of ethyl (2E, 4E, 6E)-3-methyl-7-[2-(2,2-difluoroethoxy)-3,5-di-tert-butylbenzene]octatrienoate in Example 6 (yield: 58%) of VII. $^1$H NMR (400 MHz, CDCl$_3$) δ: 7.34 (d, J=2.5 Hz, 1H), 6.99 (d, J=2.4 Hz, 1H), 6.59 (d, J=15.7 Hz, 1H), 6.44 (dd, J=25.8, 15.7 Hz, 1H), 5.97 (dt, J=55.1, 3.9 Hz, 1H), 5.90 (s, 1H), 4.05 (m, 1H), 3.88 (m, 1H), 2.18 (d, J=3.6 Hz, 3H), 2.13 (s, 3H), 1.40 (s, 9H), 1.30 (s, 9H).

Example 20

(L22, Compound VIII of Scheme 5, where R=tert-amyl, R'=1,1-difluoroethyl, R"=F, R'"=H). This compound was prepared in the manner previously described for Compound VIII in Example 7, except that 3,5 di-tert-amyl-4-hydroxybenzoic acid was used instead of 3,5 di-tert-butyl-4-hydroxybenzoic acid in Example 1, and difluoroethyl bromide was used instead of iodoethane in Example 4. $^1$H NMR (400 MHz, CDCl$_3$) δ: 7.19 (d, J=2.4 Hz, 1H), 6.91 (d, J=2.3 Hz, 1H), 6.58 (d, J=15.6 Hz, 1H), 6.39 (dd, J=26.1, 15.7 Hz, 1H), 5.96 (dt, J=55.2, 3.9 Hz, 1H), 5.89 (s, 1H), 3.99 (m, 1H), 3.81 (m, 1H), 2.16 (d, J=3.5 Hz, 3H), 2.11 (s, 3H), 1.78 (dd, J=15.0, 7.5 Hz, 2H), 1.59 (dd, J=15.0, 7.5 Hz, 2H), 1.37 (s, 3H), 1.36 (s, 3H), 1.26 (s, 3H), 1.25 (s, 3H), 0.67 (dd, J=7.5, 2.8 Hz, 3H), 0.65 (dd, J=7.5, 2.8 Hz, 3H).

Example 20a (L18, Compound VIII of Scheme 5, where R=tert-amyl, R'=1,1-difluoroethyl, R"=H, R'"H). This compound was prepared in the manner previously described for Compound VIII in Example 7, except that 3,5 di-tert-amyl-4-hydroxybenzoic acid was used instead of 3,5 di-tert-butyl-4-hydroxybenzoic acid in Example 1, and difluoroethyl bromide was used instead of iodoethane in Example 4. 1H NMR (CDCl3): 6.92 (s, 1H), 6.96 (s, 1H), 6.66 (m, 3H), 6.28 (m, 3H), 6.06 (m, 1H), 5.95 (m, 1H), 5.42 (m, 1H), 3.88 (bm, 2H), 2.22 (s, 3H), 2.07 (s, 3H), 1.77 (m, 2H), 1.64 (m, 2H),) 1.38 (s, 6H), 1.28 (s, 6H), 0.68 (m, 6H).

Example 21

(L23, Compound VIII of Scheme 5, where R=tert-butyl, R'=1,1,1-trifluoroethyl, R"=H, R'"=H). This compound was prepared in the manner previously described for Compound VIII in Example 7, except that 2,2,2-difluoro-bromoethane was used instead of iodoethane in Example 4. $^1$H NMR (400 MHz, CDCl$_3$) δ: 7.31 (d, J=2.4Hz, 1H), 6.95 (d, J=2.4Hz, 1H), 6.59 (dd, J=15.3 Hz, 11.0 Hz, 1H), 6.29 (d, J=4.3 Hz, 1H), 6.28 (d, J=14.7 Hz, 1H), 5.96 (dt, J=55.3 Hz, 4.3 Hz, 1H), 5.78 (s, 1H), 3.95 (m, 2H), 2.22 (s, 3H), 2.15 (s, 3H), 1.41 (s, 9H), 1.30 (s, 9H).

Example 22

(L13, Compound VIII of Scheme 5, where R=tert-butyl, R'=1,1-difluoroethyl, R"=H, R'"=H). This compound was prepared in the manner previously described for Compound VIII in Example 7, except that 2,2-difluoro-bromoethane was used instead of iodoethane in Example 4. $^1$H NMR (400 MHz, CDCl$_3$) δ: 7.31 (d, J=2.4Hz, 1H), 6.95 (d, J=2.4Hz, 1H), 6.59 (dd, J=15.3 Hz, 11.0 Hz, 1H), 6.29 (d, J=4.3 Hz, 1H), 6.28 (d, J=14.7 Hz, 1H), 5.96 (dt, J=55.3 Hz, 4.3 Hz, 1H), 5.78 (s, 1H), 3.95 (m, 2H), 2.22 (s, 3H), 2.15 (s, 3H), 1.41 (s, 9H), 1.30 (s, 9H).

Example 23

(L24, Compound VIII of Scheme 5, where R=isopropyl, R'=1-fluoropropyl, R"=H, R'"=H). This compound was prepared in the manner previously described for Compound VIII in Example 7, except that 3,5 di-isopropyl-4-hydroxybenzoic acid was used instead of 3,5 di-tert-butyl-4-hydroxybenzoic acid in Example 1, and 3-fluoro-1-bromopropane was used instead of iodoethane in Example 4. $^1$H-NMR (CDCl$_3$) δ 7.02 (d, J=2.2 Hz, 1H, Ar—H), 6.72 (d, J=2.2 Hz, 1H, Ar—H), 6.57 (dd, J=15 Hz, J=11 Hz, 1H, =CH), 6.24 (d, J=15 Hz, 1H, =CH), 6.20 (d, J=11 Hz, 1H, =CH), 5.73 (s, 1H, COCH), 4.65 (m, 1H), 4.55 (m, 1H), 3.75 (m, 2H), ), 3.25 (m, 1H, CH$_3$—CH—CH$_3$), 2.85 (m, 1H, CH$_3$—CH—CH$_3$), 2.22 (s, 3H), 2.22 (s, 3H), 2.01 (m, 2H), 1.25 (m, 12H).

Example 24

(L25, Compound VIII of Scheme 5, where R=isopropyl, R'=3-hydroxypropyl, R"=H, R'"=H). This compound was prepared in the manner previously described for Compound VIII in Example 7, except that 3,5 di-isopropyl-4-hydroxybenzoic acid was used instead of 3,5 di-tert-butyl-4-hydroxybenzoic acid in Example 1, and 3-fluoro-1- bromopropane was used instead of iodoethane in Example 4. ¹H-NMR (CDCl₃) δ 7.02 (d, J=2.2 Hz, 1H, Ar—H), 6.72 (d, J=2.2 Hz, 1H, Ar—H), 6.57 (dd, J=15 Hz, J=11 Hz, 1H, =CH), 6.24 (d, J=15 Hz, 1H, =CH), 6.20 (d, J=11 Hz, 1H, =CH), 5.73 (s, 1H, COCH), 3.75 (m, 2H,), 3.25 (m, 1H, CH₃—CH—CH₃), 2.85 (m, 1H, CH₃—CH—CH₃), 2.22 (s, 3H), 2.22 (s, 3H), 2.01 (m, 2H), 1.25 (m, 12H).

Example 25

(L26, Compound VIII of Scheme 5, where R=isopropyl, R'=1,1,2,2-tetrafluoropropyl, R"=H, R'"=H). This compound was prepared in the manner previously described for Compound VIII in Example 7, except that 3,5 di-isopropyl-4-hydroxybenzoic acid was used instead of 3,5 di-tert-butyl-4-hydroxybenzoic acid in Example 1, and 1,1,2,2-tetrafluoro-bromo-propane was used instead of iodoethane in Example 4. ¹H NMR (400 MHz, CDCl₃) δ 7.07 (d, J=2.1 Hz, 1H, Ar—H), 6.79 (d, J=2.1 Hz, 1H, Ar—H), 6.51 (dd, J=15.3 Hz, J=10.9 Hz, 1H, C=C—H), 6.30 (d, J=15.3 Hz, 1H, C=CH), 6.28 (d, J=15.3 Hz, 1H, C=C—H), 5.98 (tt, J=53.1 Hz, J=5.2 Hz, 1H, R—O—CH₂—CF₂—CF₂H), 5.78 (s, 1H, C=C—H), 3.99 (m, 2H, R—O—CH₂—CF₂—CF₂H), 3.27 (m, 1H, CH₃—CH—CH₃), 2.88 (m, 1H, CH₃—CH—CH₃), 2.19 (s, 3H, CH₃), 2.13 (s, 3H, CH₃), 1.25 (d, J=5.3 Hz, 6H, CH₃—CH—CH₃), 1.23 (d, J=7.4 Hz, 6H, CH₃—CH—CH₃).

Example 26

(L27, Compound VIII of Scheme 5, where R=tert-butyl, R'=1,1,2,2-tetrafluoropropyl, R"=H, R'"=H). This compound was prepared in the manner previously described for Compound VIII in Example 7, except that 1,1,2,2-tetrafluoro-bromo-propane was used instead of iodoethane in Example 4. ¹H NMR (400 MHz, CDCl₃) δ 7.32 (d, J=2.4 Hz, 1H, Ar—H), 6.95 (d, J=2.4 Hz, 1H, Ar—H), 6.52 (dd, J=14.9 Hz, J=11.3 Hz, 1H, C=C—H), 6.29 (d, J=15.3 Hz, 1H, C=CH), 6.28 (d, J=9.3 Hz, 1H, C=C-H), 5.91 (tt, J=53.0 Hz, J=5.0 Hz, 1H, R—O—CH₂—CF₂—CF₂H), 5.79 (s, 1H, C=C—H), 4.10 (m, 2H, R—O—CH₂—CF₂—CF₂H), 2.21 (s, 3H, CH₃), 2.13 (s, 3H, CH₃), 1.41 (s, 9H, ᵗbutyl), 1.30 (s, 9H, ᵗbutyl).

Example 27

(L28, Compound VIII of Scheme 5, where R=isopropyl, R'=1,1,1-trifluoroethyl, R"=H, R'"=H). This compound was prepared in the manner previously described for Compound VIII in Example 7, except that 3,5 di-isopropyl-4-hydroxybenzoic acid was used instead of 3,5 di-tert-butyl-4-hydroxybenzoic acid in Example 1, and 1,1,1-trifluoro-bromo-ethane was used instead of iodoethane in Example 4. ¹H NMR (400 MHz, CDCl₃) δ 7.07 (d, J=2.1 Hz, 1H, Ar—H), 6.77 (d, J=2.0 Hz, 1H, Ar—H), 6.55 (dd, J=15.3 Hz, J=11.0 Hz, 1H, C=C—H), 6.30 (d, J=10.3 Hz, 1H, C=CH), 6.28 (d, J=15.3 Hz, 1H, C=C—H), 5.78 (s, 1H, C=C—H), 3.99 (m, 2H, R—O—CH₂—CF₃), 3.35 (m, 1H, CH₃—CH—CH₃), 2.87 (m, 1H, CH₃—CH—CH₃), 2.21 (s, 3H, CH₃), 2.14 (s, 3H, CH₃), 1.25 (d, J=6.1 Hz, 6H, CH₃—CH—CH₃), 1.23 (d, J=6.9 Hz, 6H, CH₃—CH—CH₃).

Example 28

(L29, Compound VIII of Scheme 5, where R=tert-amyl, R'=1,1,1-trifluoroethyl, R"=H, R'"=H). This compound was prepared in the manner previously described for Compound VIII in Example 7, except that 3,5 di-isoamyl-4-hydroxybenzoic acid was used instead of 3,5 di-tert-butyl-4-hydroxybenzoic acid in Example 1, and 1,1,1-trifluoro-bromo-ethane was used instead of iodoethane in Example 4. ¹H NMR (400 MHz, CDCl₃) δ 7.19 (d, J=2.4 Hz, 1H, Ar—H), 6.86 (d, J=2.4 Hz, 1H, Ar—H), 6.58 (dd, J=15.4 Hz, J=10.9 Hz, 1H, C=C—H), 6.29 (d, J=11.0 Hz, 1H, C=CH), 6.28 (d, J=15.4 Hz, 1H, C=C—H), 5.78 (s, 1H, C=C—H), 4.09 (m, 2H, R—O—CH₂—CF₃), 2.20 (s, 3H, CH₃), 2.13 (s, 3H, CH₃), 1.79 (m, 2H, ᵗamyl-CH₂—CH₃), 1.60 (q, J=7.4 Hz, 2H, ᵗamyl-CH₂—CH₃), 1.38 (s, 3H, ᵗamyl-CH₃), 1.37 (s, 3H, ᵗamyl-CH₃), 1.26 (s, 3H, ᵗamyl-CH₃), 0.66 (t, J=7.46, 6H, ᵗamyl-CH₂—CH₃).

Scheme 6

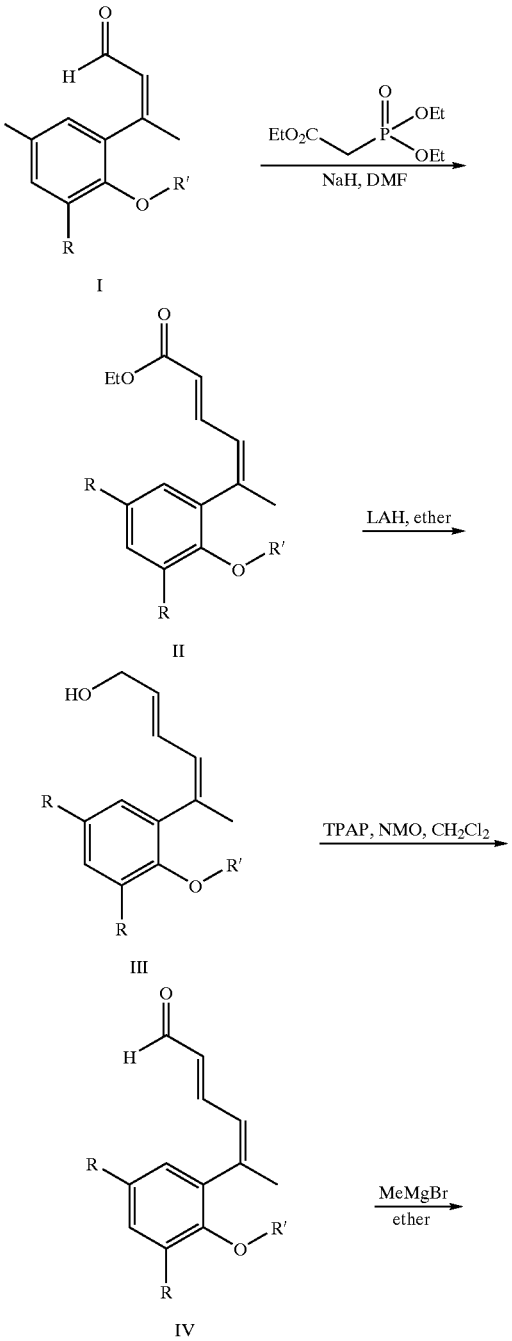

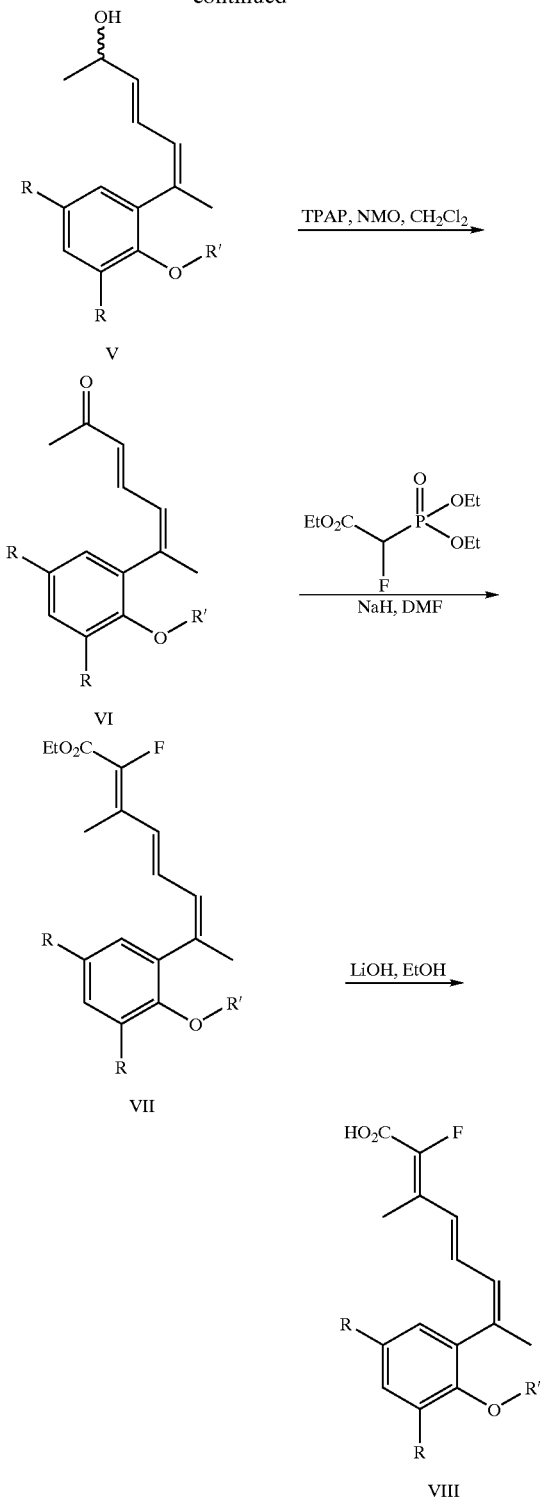

Scheme 6 is an alternate route to that suggested in Scheme 5 for introduction of fluorine at the $R^9$ position of the modulator compound.

Example 29

(Compound II of Scheme 6, where R=tert-butyl, R'=1,1-difluoropropyl). To 0.103 g of sodium hydride (2.14 mmol) suspended in anhydrous DMF (10 ml) in a flame dried 25 ml r.b. flask at 0° C. is added triethyl-phosphonoacetate (0.449 g, 2.01 mmol) dropwise. The mixture is allowed to stir for 0.2 hours. Compound I is then added dropwise (0.452 g, 1.34 mmol) via solvation in anhydrous DMF (5.0 ml). The resultant mixture is allowed to warm to ambient temperature, and stirred for 18.0 hours. After such time, water (10.0 ml) is added and the mixture is allowed to stir for 0.3 hours. The aqueous layer was extracted with EtOAc. All organic layers were combined, washed (brine), dried (MgSO$_4$), and concentrated under reduced pressure. Purification by flash column chromatography (silica gel, hexanes/EtOAc, 9:1) yielded 0.47 g of II (86%) in a 9:1 E to Z isomer ratio. Data for compound II. $^1$H NMR (400 MHz, CDCl$_3$) δ 7.32 (d, J=2.4 Hz, 1H), 7.25 (dd, J=15.3 Hz, J=10.5 Hz, 1H), 6.90 (d, J=2.5 Hz, 1H), 6.30 (d, J=11.5 Hz, 1H), 5.98 (tt, J=55.2 Hz, 4.1 Hz, 1H), 5.87 (d, J=15.4 Hz, 1H), 4.13 (q, J=7.2 Hz, 2H), 3.95 (m, 2H), 2.24 (s, 3H), 1.41 (s, 9H), 1.30 (s, 9H), 1.25 (t, J=7.1 Hz, 3H).

Example 30

(Compound III of Scheme 6, where R=tert-butyl, R'=1,1-difluoropropyl). To 0.47 g of II (1.15 mmol) dissolved in anhydrous diethyl ether (15 ml) in a flame dried 25 ml r.b. flask at 0° C. is added lithium aluminum hydride (0.043 g, 1.15 mmol) portion wise. The resultant mixture is allowed to slowly warm to ambient temperature, and stirred for 4.0 hours. After such time, water (10.0 ml) is added and the mixture is allowed to stir for 0.3 hours. The aqueous layer was extracted with EtOAc. All organic layers were combined, washed (brine), dried (MgSO$_4$), and concentrated under reduced pressure. Purification by flash column chromatography (silica gel, hexanes/EtOAc, 9:1) yielded 0.335 g of III (80%). Data for compound III. $^1$H NMR (400 MHz, CDCl$_3$) δ 7.28 (d, J=2.5 Hz, 1H), 6.92 (d, J=2.5 Hz, 1H), 6.15 (m, 1H), 5.99 (tt, J=55.7 Hz, 4.1 Hz, 1H), 5.82 (d, J=10.9 Hz, 1H), 5.81 (d, J=12.0 Hz, 1H), 3.86 (m, 4H), 2.14 (s, 3H), 1.40 (s, 9H), 1.30 (s, 9H).

Example 31

(Compound IV of Scheme 6, where R=tert-butyl, R'=1,1-difluoropropyl). To 0.335 g of compound III (0.914 mmol) dissolved in anhydrous CH$_2$Cl$_2$ (10.0 ml) in a flame dried 25 ml r.b. flask is added 4-Methylmorpholine N-oxide (0.161 g, 1.37 mmol) followed by Tetrapropylammonium perruthenate (0.016 g, 0.046 mmol). The resulting mixture is stirred at ambient temperature for 1.0 hours. After such time, the reaction mixture is filtered through a plug of silica gel (eluding with CH$_2$Cl$_2$) and concentrated under reduced pressure to yield 0.261 g of IV (80%). Data for compound IV. $^1$H NMR (400 MHz, CDCl$_3$) δ 9.40 (d, J=8.0 Hz, 1H), 7.37 (d, J=2.5 Hz, 1H), 7.04 (dd, J=15.2 Hz, J=11.4 Hz, 1H), 6.93 (d, J=2.4 Hz, 1H), 6.46 (d, J=11.0 Hz, 1H), 6.15 (dd, J=15.3 Hz, 8.0 Hz, 1H), 5.97 (tt, J=55.1 Hz, J=4.1 Hz, 1H), 3.94 (m, 2H), 2.30 (s, 3H), 1.42 (s, 9H), 1.31 (s, 9H).

Example 32

(Compound V of Scheme 6, where R=tert-butyl, R'=1,1-difluoropropyl). To 0.261 g of compound IV (0.717 mmol) dissolved in anhydrous diethyl ether (15.0 ml) in a flame dried 25 ml r.b. flask at 0° C. is added methyl magnesium bromide (0.789 mmol, 0.26 ml of 3.0 M solution in ether) dropwise via syringe. The resultant mixture is kept at 0° C. for 2.0 hours. After such time sat. NH$_4$Cl (5.0 ml) is added and the mixture is allowed to warm to room temperature. At room temperature, the mixture is filtered through a plug of silica gel (eluding with hexanes/EtOAc 9:1) and concentrated under reduced pressure to yield the crude product mixture. Purification by flash column chromatography (silica gel, hexanes/EtOAc, 9:1) yielded 0.232 g of V (85%). Data for compound V. $^1$H NMR (400 MHz, CDCl$_3$) δ 7.28 (d, J=2.5 Hz, 1H), 6.93 (d, J=2.3 Hz, 1H), 6.05 (m, 2H), 5.85 (tt, J=56.3 Hz, J=4.1 Hz, 1H), 5.74 (dd, J=13.9 Hz, J=6.3 Hz, 1H), 4.26 (m, 1H), 3.98 (m, 2H), 2.14 (s, 3H), 1.40 (s, 9H), 1.30 (s, 9H), 1.24 (d, J=6.4 Hz, 3H).

Example 33

(Compound VI of Scheme 6, where R=tert-butyl, R'=1,1-difluoropropyl). To 0.232 g of compound V (0.612 mmol) dissolved in anhydrous CH$_2$Cl$_2$ (10.0 ml) in a flame dried 25 ml r.b. flask is added 4-Methylmorpholine N-oxide (0.107 g, 0.92 mmol) followed by Tetrapropylammonium perruthenate (0.011 g, 0.031 mmol). The resulting mixture is stirred at ambient temperature for 1.5 hours. After such time, the reaction mixture is filtered through a plug of silica gel (eluding with CH$_2$Cl$_2$) and concentrated under reduced pressure to yield 0.120 g of VI (52%). Data for compound VI. $^1$H NMR (400 MHz, CDCl$_3$) δ 7.34 (d, J=2.5 Hz, 1H), 7.06 (dd, J=15.7 Hz, J=11.2 Hz, 1H), 6.93 (d, J=2.5 Hz, 1H), 6.32 (d, J=11.0 Hz, 1H), 6.12 (d, J=15.7 Hz, 1H), 5.96 (tt, J=55.1 Hz, J=4.1 Hz, 1H), 3.95 (m, 2H), 2.27 (s, 3H), 2.15 (s, 3H), 1.42 (s, 9H), 1.31 (s, 9H).

Example 34

(Compound VII of Scheme 6, where R=tert-butyl, R'=1,1-difluoropropyl). To 0.019 g of sodium hydride (0.411 mmol) suspended in anhydrous DMF (2.0 ml) in a flame dried 10 ml r.b. flask at 0° C. is added triethyl-2-fluoro-2-phosphonoacetate (0.092 g, 0.379 mmol) dropwise. The mixture is allowed to stir for 0.3 hours. Compound VI is then added dropwise (0.120 g, 0.316 mmol) via solvation in anhydrous DMF (3.0 ml). The resultant mixture is allowed to stir at 0° C. for 2.0 hours. After such time, water (5.0 ml) is added and the mixture is allowed to stir for 0.3 hours. The aqueous layer was extracted with EtOAc. All organic layers were combined, washed (brine), dried (MgSO$_4$), and concentrated under reduced pressure. Purification by flash column chromatography (silica gel, hexanes/EtOAc, 9:1) yielded 0.135 g of VII (92%) as a 1:1 E to Z isomer ratio. Data for compound VII. $^1$H NMR (400 MHz, CDCl$_3$) δ 7.31 (d, J=2.6 Hz, 1H), 6.96 (d, J=2.3 Hz, 1H), 6.79 (d, J=15.5 Hz, 1H), 6.49 (dd, J=15.4 Hz, J=11.1 Hz, 1H), 6.35 (d, J=11.0 Hz, 1H), 5.97 (tt, J=55.3 Hz, J=4.1 Hz, 1H), 4.30 (q, J=7.3 Hz, 2H), 3.95 (m, 2H), 2.21 (s, 3H), 2.07 (d, J=3.0 Hz, 3H), 1.41 (s, 9H), 1.36 (t, J=7.1 Hz, 3H), 1.31 (s, 9H).

Example 35

(L30, Compound VII of Scheme 6, where R=tert-butyl, R'=1,1-difluoroethyl). To 0.135 g of compound VII (0.289 mmol) dissolved in ethanol (10.0 ml) in a 25.0 ml r.b. flask is added 2 M aqueous LiOH (0.868 mmol). The resultant mixture is heated to 60° C. for 7.0 hours. After such time, the reaction is cooled and concentrated under reduced pressure. The residue is taken up in 1 N aqueous HCl (10.0 ml). The flask is sealed and shaken for 1.0 minute. The resultant suspension was extracted with EtOAc. All organic layers were combined, washed (brine), dried (MgSO$_4$), and concentrated under reduced pressure. The crude reaction mixture is purified using HPLC (80:20:0.1 MeOH, H$_2$O, TFA). The purified 2-Z isomer is recrystallized from Acetonitrile to yield VIII as a white crystalline solid. Data for compound VIII. $^1$H NMR (400 MHz, CDCl$_3$) δ 7.32 (d, J=2.5 Hz, 1H), 6.95 (d, J=2.4 Hz, 1H), 6.76 (d, J=15.3 Hz, 1H), 6.56 (dd, J=15.4 Hz, J=11.0 Hz, 1H), 6.35 (d, J=10.8 Hz, 1H), 5.96 (tt, J=55.3 Hz, J=4.1 Hz, 1H), 3.96 (m, 2H), 2.23 (s, 3H), 2.08 (d, J=3.1 Hz, 3H), 1.41 (s, 9H), 1.30 (s, 9H).

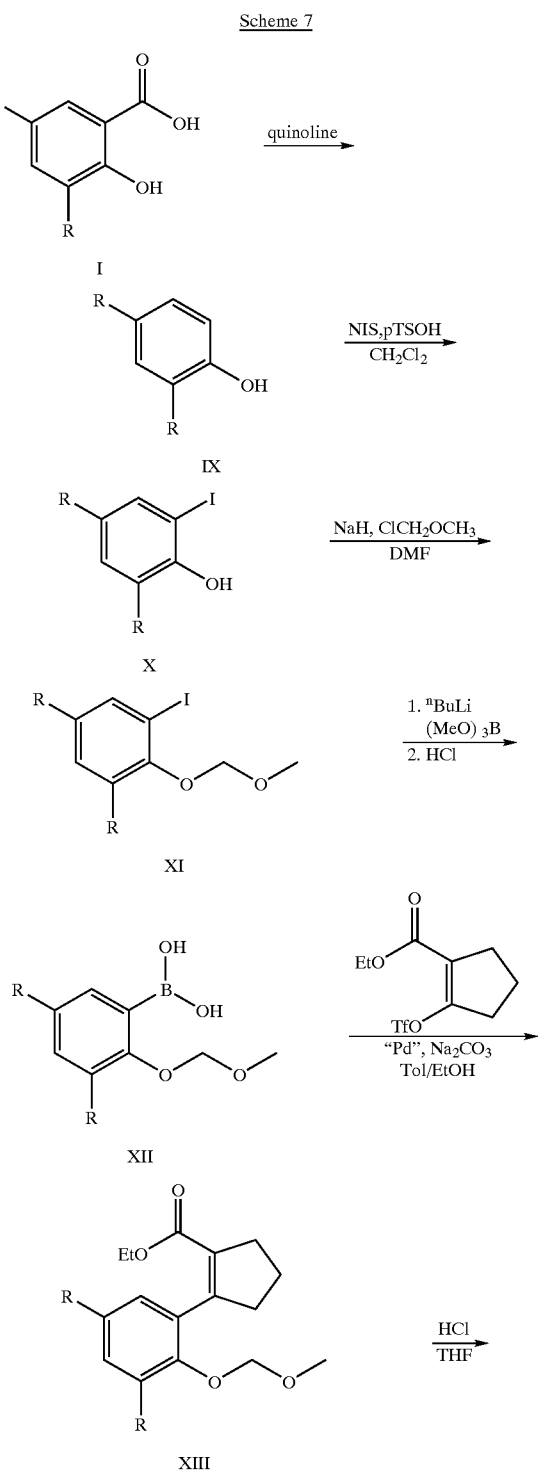

Scheme 7

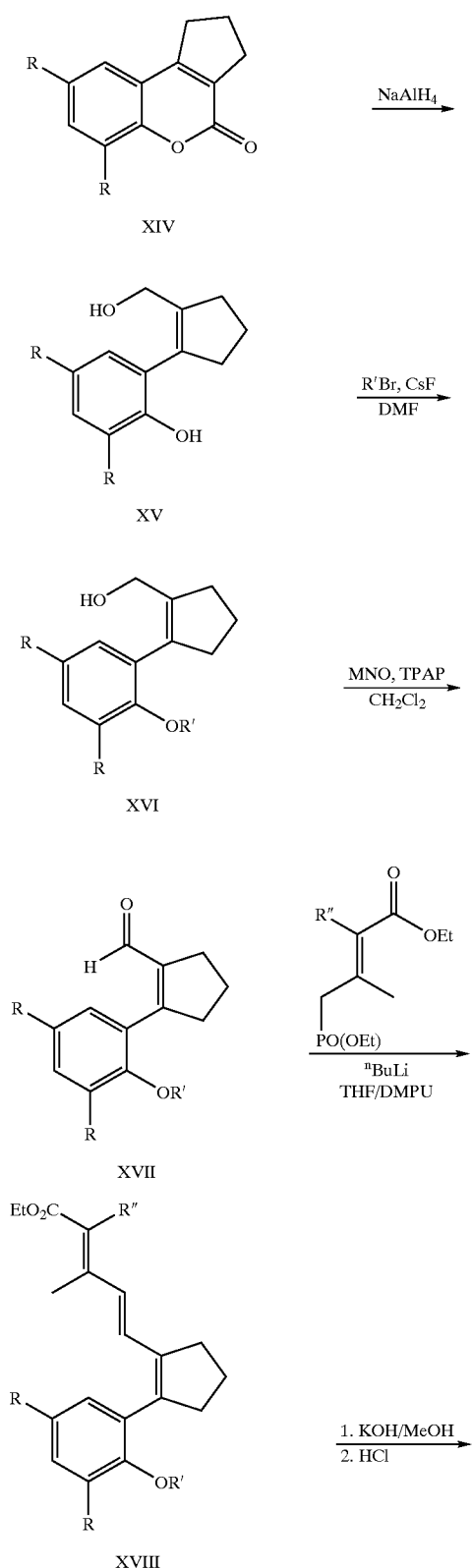

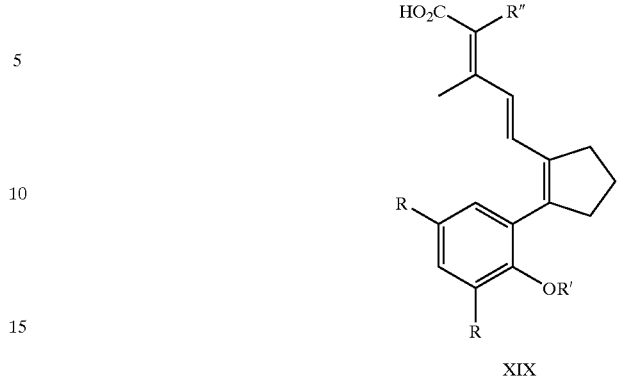

In a preferred embodiment, Scheme 7 shows the synthetic method employed in Examples 36–46. Scheme 7 corresponds to the general synthetic method shown in Scheme 4 for the production of coumarin intermediates (e.g., Structure XIV). The coumarin intermediates as shown above are then converted to the desired RXR modulator compounds as previously described and as shown in the following examples.

Example 36

(Compound IX of Scheme 7, where R=isopropyl). To 3,5-Diisopropylsalicylic acid I (75.0 g, 0.34 mol) in a 300 mL round bottom flask was added 150 mL of quinoline. The resulting mixture was heated to 210° C. for 4.0 hours, cooled to room temperature, dissolved in EtOAc (500 mL), and extracted with 1N HCl (2×500 mL). The organic layer was washed (water then brine), dried (MgSO$_4$), and concentrated under reduced pressure. The crude product was purified by vacuum distillation (1 mm Hg, collecting the fraction between 100–102° C.) to yield 50.0 g (0.28 mol) of Compound IX as a clear, pale yellow oil (82% yield). $^1$H NMR (400 MHz, CDCl$_3$) δ 7.05 (d, J=2.1 Hz, 1H, Ar—H), 6.93 (dd, J=8.2 Hz, J=2.2 Hz, 1H, Ar—H), 6.68 (d, J=8.2 Hz, 1H, Ar—H), 4.53 (s, 1H, R—OH), 3.19 (m, 1H, CH$_3$—CH—CH$_3$), 2.85 (m, 1H, CH$_3$—CH—CH$_3$), 1.27 (d, J=6.8 Hz, 6H, CH$_3$—CH—CH$_3$), 1.23 (d, J=6.8 Hz, 6H, CH$_3$—CH—CH$_3$).

Example 37

(Compound X of Scheme 7, where R=isopropyl). To 52.2 g (0.293 mol) of Compound IX dissolved in 400 mL of CH$_2$Cl$_2$ in a 1 liter round bottom flask was added 72.6 g (0.322 mol) of N-Iodosuccinimide (NIS) and 5.6 g (0.029 mol) of p-toluene sulfuric acid (pTSOH). The resultant mixture was stirred at ambient temperature for 3.0 hours. After such time, 500 ml of 10% aqueous Na$_2$S$_2$O$_3$ was added and the reaction mixture was stirred for an additional 0.5 hours. The aqueous layer was then separated and extracted with CH$_2$Cl$_2$ (2×400 mL). The organic layers were combined, washed (10% aqueous Na$_2$S$_2$O$_3$, then water, then brine), dried (MgSO$_4$) and concentrated under reduced pressure to give 89.1 g (0.29 mol) of X as a deep red oil (99% yield). $^1$H NMR (400 MHz, CDCl$_3$) δ 7.33 (d, J=2.1 Hz, 1H, Ar—H), 7.00 (d, J=2.0 Hz, 1H, Ar—H), 4.83 (s, 1H, R—OH), 3.28 (m, 1H, CH$_3$—CH—CH$_3$), 2.80 (m, 1H, CH$_3$—CH—CH$_3$), 1.23 (d, J=6.8 Hz, 6H, CH$_3$—CH—CH$_3$), 1.21 (d, J=6.8 Hz, 6H, CH$_3$—CH—CH$_3$).

Example 38

(Compound XI of Scheme 7, where R=isopropyl). To 1.6 g (0.04 mol) of sodium hydride dissolved in 225 ml of anhydrous N,N-Dimethyl-formamide (DMF) in a flame dried 500 ml round bottom flask at 0° C., was added dropwise 10.0 g (0.033 mol) of Compound X in 25 mL DMF. The mixture was stirred at 0° C. for 0.5 hours followed by dropwise addition of 3.22 g (0.04 mol) of methyl chloromethyl ether. The resultant reaction mixture was allowed to warm to ambient temperature and stirred for 3.0 hours. The contents of the flask were poured into iced brine (200 ml) and stirred for 0.5 hours. The aqueous layer was extracted with diethyl ether (2×200 mL) and the organic layers were combined, washed (brine), dried (MgSO$_4$) and concentrated under reduced pressure. The concentrated product was filtered through a silica gel plug (eluting with diethyl ether) and concentrated under reduced pressure to give 11.3 g (0.032 mol) of XI as a red oil (97% yield). $^1$H NMR (400 MHz, CDCl$_3$) δ 7.42 (d, J=1.8 Hz, 1H, Ar—H), 7.06 (d, J=1.8 Hz, 1H, Ar—H), 5.05 (s, 2H, R—O—CH$_2$—O—CH$_3$), 3.65 (s, 3H, R—O—CH$_2$—O—CH$_3$), 3.40 (m, 1H, CH$_3$—CH—CH$_3$), 2.81 (m, 1H, CH$_3$—CH—CH$_3$), 1.26 (d, J=6.5, 6H, CH$_3$—CH—CH$_3$), 1.21 (d, J=6.6, 6H, CH$_3$—CH—CH$_3$).

Example 39

(Compound XII of Scheme 7, where R=isopropyl). To 10.0 g (0.029 mol) of Compound XI dissolved in 150 ml of a 1:2 mixture of diethyl ether-THF in a flame dried 300 ml round bottom flask at −78° C., was added 21.9 mL (0.035 mol) of a 1.6 M solution of nBuLi in hexanes. The mixture was stirred at −78 ° C. for 0.3 h followed by addition of 6.6 mL (0.058 mol) of trimethyl borate in one portion via syringe. The resultant mixture is allowed to stir at −78° C. for 0.5 h, warmed to ambient temperature, and stirred for a further 2 h. Aqueous HCl was added (30 ml of 1N HCl) and the mixture stirred for an additional 0.5 h. The organic layer was separated and the aqueous layer was extracted with EtOAc (2×30 ml). The organic layers were combined, washed (water, then 10% aqueous Na$_2$S$_2$O$_3$, then brine), dried (MgSO$_4$), and concentrated under reduced pressure. Purification by flash column chromatography (silica gel, hexanes/EtOAc, 9:1) yielded 6.6 g (0.025 mol) of XII as a pale yellow oil (86% yield). $^1$H NMR (400 MHz, CDCl$_3$) δ 7.50 (d, J=2.3 Hz, 1H, Ar—H), 7.23 (d, J=2.3 Hz, 1H, Ar—H), 5.94 (s, 2H, B(OH)$_2$), 5.00 (s, 2H, R—O—CH$_2$—O—CH$_3$), 3.57 (s, 3H, R—O—CH$_2$—O—CH$_3$), 3.21 (m, 1H, CH$_3$—CH—CH$_3$), 2.89 (m, 1H, CH$_3$—CH—CH$_3$), 1.25 (d, J=6.9, 6H, CH$_3$—CH—CH$_3$), 1.24 (d, J=6.9, 6H, CH$_3$—CH—CH$_3$).

Example 40

(Compound XIII of Scheme 7, where R=isopropyl). To 6.6 g (0.025 mol) of Compound XII dissolved in 300 ml of 1:1 toluene-ethanol in a 500 ml round bottom flask, was added 7.86 g (0.027 mol) of ethyl-2-(trifluoromethyl sulfonyloxy)-1-cyclopentene-1-carboxylate, 5.3 g (0.05 mol) of 2 N aqueous Na$_2$CO$_3$ and 2.89 g (0.0025 mol) of tetrakis(triphenylphosphine) palladium (0). The reaction mixture was heated to 90° C. for 15.0 hours, then cooled to room temperature, poured into brine (200 ml), and stirred for 0.3 hours. The aqueous layer was extracted with EtOAc (2×200 mL) and the organic layers were combined, dried (MgSO$_4$), and concentrated under reduced pressure. Purification by flash column chromatography (silica gel, 9:1 hexanes-EtOAc) gave 8.0 g (0.022 mol) of XIII as a yellow oil (89% yield). $^1$H NMR (400 MHz, CDCl$_3$) δ 7.03 (d, J=2.2 Hz, 1H, Ar—H), 6.77 (d, J=2.2 Hz, 1H, Ar—H), 4.81 (s, 2H, R—O—CH$_2$—O—CH$_3$), 3.98 (q, J=7.1 Hz, 2H, CO$_2$—CH$_2$—CH$_3$), 3.49 (s, 3H, R—O—CH$_2$—O—CH$_3$), 3.38 (m, 1H, CH$_3$—CH—CH$_3$), 2.82 (m, 5H, ring CH$_2$, ring CH$_2$, CH$_3$—CH—CH$_3$), 1.99 (m, 2H, ring CH$_2$), 1.22 (d, J=6.8 Hz, 6H, CH$_3$—CH—CH$_3$), 1.21 (d, J=6.8 Hz, 6H, CH$_3$—CH—CH$_3$), 0.95 (t, J=7.1 Hz, 3H, CO$_2$—CH$_2$—CH$_3$).

Example 41

(Compound XIV of Scheme 7, where R=isopropyl). To 8.0 g (0.022 mol) of Compound XIII dissolved in 150 ml of THF in a 300 ml round bottom flask was added 6 N aqueous HCl (25.0 ml, 0.15 mol). The resulting mixture was stirred at ambient temperature for 65.0 hours. After such time, the solvent was removed under reduced pressure and the residue was taken up in water (100 ml). The aqueous layer was extracted with EtOAc (2×100 mL) and the organic layers were combined, washed (water then brine), dried (MgSO$_4$), and concentrated under reduced pressure. Purification by flash column chromatography (silica gel, 9:1 hexanes-EtOAc) gave 5.9 g (0.022 mmol) of XIV as a yellow-orange oil which crystallized upon standing (99% yield). $^1$H NMR (400 MHz, CDCl$_3$) δ 7.28 (d, J=1.7 Hz, 1H, Ar—H), 7.10 (d, J=1.8 Hz, 1H, Ar—H) 3.65 (m, 1H, CH$_3$—CH—CH$_3$), 3.08 (t, J=7.6 Hz, 2H, ring CH$_2$) 2.93 (m, 3H, ring CH$_2$, CH$_3$—CH—CH$_3$), 2.21 (m, 2H, ring CH$_2$), 1.29 (d, J=7.4 Hz, 6H, CH$_3$—CH—CH$_3$), 1.28 (d, J=7.2 Hz, 6H, CH$_3$—CH—CH$_3$).

Example 42

(Compound XV of Scheme 7, where R=isopropyl). To 2.0 g (7.4 mmol) of Compound XIV dissolved in 75 mL of anhydrous THF in a flame dried 200 ml round bottom flask at 0° C. was added 400 mg (7.4 mmol) of sodium aluminum hydride portion-wise. The resultant mixture is allowed to warm to ambient temperature and stirred for 4.0 hours. After such time, water (0.14 ml, 7.4 mmol) was added, followed by 6 N aqueous sodium hydroxide (2.5 ml, 14.8 mmol). The resultant mixture was allowed to stir for 0.5 hours, filtered through a plug of silica gel (eluting with diethyl ether) and concentrated under reduced pressure to give 2.0 g (7.3 mmol) of XV as a colorless oil (99% yield). $^1$H NMR (400 MHz, CDCl$_3$) δ 6.97 (d, J=2.1 Hz, Ar—H), 6.75 (d, J=2.2 Hz, 1H, Ar—H), 5.55 (s, 1H, Ar—OH), 5.07 (s, 2H, R—CH$_2$—OH), 3.29 (m, 1H, CH$_3$—CH—CH$_3$), 2.82 (m, 1H, CH$_3$—CH—CH$_3$), 2.70 (m, 4H, ring CH$_2$), 2.02 (m, 2H, ring CH$_2$), 1.62 (br s, 1H, R—CH$_2$—OH), 1.25 (d, J=6.9 Hz, 6H, CH$_3$—CH—CH$_3$), 1.22 (d, J=7.1 Hz, 6H, CH$_3$—CH—CH$_3$).

Example 43

(Compound XVI of Scheme 7, where R=isopropyl, R'=n-propyl). To 2.0 g (7.30 mmol) of Compound XV dissolved in 75 mL of anhydrous N,N-dimethylformamide (DMF) in a flame dried 200 ml round bottom flask, was added 1.00 g (8.1 mmol) of 1-bromopropane followed by 4.5 g (29.6 mmol) of cesium fluoride. The mixture was allowed to stir at ambient temperature for 18.0 h. Water (100 ml) was added and the mixture was allowed to stir for an additional 0.5 h. The aqueous layer was extracted with EtOAc (2×100 mL) and the organic layers were combined, washed (brine), dried (MgSO$_4$), and concentrated under reduced pressure. Purification by flash column chromatography (silica gel, 9:1 hexanes-EtOAc) yielded 2.15 g (6.79 mmol) of XVI as a brown oil (93% yield). $^1$H NMR (400 MHz, CDCl$_3$) δ 6.99 (d, J=2.2 Hz, 1H, Ar—H), 6.78 (d, J=2.2 Hz, 1H, Ar—H), 3.98 (d, J=5.0 Hz, 2H, CH$_2$—OH), 3.57 (t, J=6.7 Hz, 2H, R—O—CH$_2$—CH$_2$—CH$_3$), 3.32 (m, 1H, CH$_3$—CH—CH$_3$), 2.84 (m, 1H, CH$_3$—CH—CH$_3$), 2.74 (t, J=7.3 Hz, 2H, ring CH$_2$), 2.64 (t, J=7.3 Hz, 2H, ring CH$_2$), 2.00 (m, 2H, ring CH$_2$), 1.71 (m, 2H, R—O—CH$_2$—CH$_2$—CH$_3$), 1.22 (d, J=6.9 Hz, 6H, CH$_3$—CH—CH$_3$), 1.17 (d, J=6.9 Hz, 6H, CH$_3$—CH—CH$_3$), 0.97 (t, J=7.4 Hz, 3H, R—O—CH$_2$—CH$_2$—CH$_3$).

Example 44

(Compound XVII of Scheme 7, where R=isopropyl, R'=n-propyl). To 2.15 g (6.80 mmol) of Compound XVI dissolved in 70 mL of anhydrous CH$_2$Cl$_2$ in a flame dried 200 ml round bottom flask, was added 1.19 g (10.2 mmol) of 4-methylmorpholine N-oxide (MMNO) followed by 0.119 g (0.34 mmol) of tetrapropylammonium perruthenate (TPAP). The resulting mixture was stirred at ambient temperature for 1.5 h. After such time, the reaction mixture was filtered through a plug of silica gel (eluting with CH$_2$Cl$_2$) and concentrated under reduced pressure to yield 2.13 g (6.21 mmol) of XVII as a pale yellow oil (91% yield). $^1$H NMR (400 MHz, CDCl$_3$) δ 9.69 (s, 1H, CHO), 7.11 (d, J=2.1 Hz, 1H, Ar—H), 6.85 (d, J=2.0 Hz, 1H, Ar—H), 3.55 (t, J=6.4 Hz, 2H, R—O—CH$_2$—CH$_2$—CH$_3$), 3.33 (m, 1H, CH$_3$—CH—CH$_3$), 2.99 (t, J=7.4 Hz, 2H, ring CH$_2$), 2.87 (m, 1H, CH$_3$—CH—CH$_3$), 2.72 (t, J=7.5 Hz, 2H, ring CH$_2$), 2.03 (m, 2H, ring CH$_2$), 1.67 (m, 2H, R—O—CH$_2$—CH$_2$—CH$_3$), 1.28 (d, J=7.1 Hz, 6H, CH$_3$—CH—CH$_3$), 1.23 (d, J=7.0 Hz, 6H, CH$_3$—CH—CH$_3$), 0.96 (t, J=7.4 Hz, 3H, R—O—CH$_2$—CH$_2$—CH$_3$).

Example 45

(Compound XVIII of Scheme 7, where R=isopropyl, R'=n-propyl, R"=H). To 5.38 g (20.4 mmol) of triethyl 3-methyl-4-phosphonocrotonate dissolved in 60.0 ml of a 1:2 mixture of THF-DMPU in a flame dried 200 ml round bottom flask at –78° C., was added dropwise 13.6 mL (21.7 mmol) of 1.6 M nBuLi in hexanes. The mixture was allowed to stir for 0.3 h followed by dropwise addition of 2.33 g (6.80 mmol) of Compound XVII in 10 mL of a 1:2 THF-DMPU solution. The reaction mixture was allowed to stir at –78° C. for 0.5 h, warmed to ambient temperature, and stirred for an additional 2 h. Water (100 ml) was added and the mixture was stirred for 0.5 h. The aqueous layer was separated and extracted with EtOAc (2×100 mL), and the organic layers were combined, washed (brine), dried (MgSO$_4$), and concentrated under reduced pressure. Purification by flash column chromatography (silica gel, 9:1 hexanes-EtOAc) gave 2.74 g (6.45 mmol) of XVIII as a yellow oil (95% yield). $^1$H NMR (400 MHz, CDCl3) δ 7.03 (d, J=2.2 Hz, 1H, Ar—H), 6.85 (d, J=15.8 Hz, 1H, =CH) 6.79 (d, J=2.2 Hz, 1H, Ar—H), 6.21 (d, J=15.8 Hz, 1H, =CH), 5.79 (s, 1H, =CH), 4.15 (q, J=7.1 Hz, 2H, —CO$_2$—CH$_2$—CH$_3$) 3.53 (t, J=6.5 Hz, 2H, R—O—CH$_2$—CH$_2$—CH$_3$), 3.34 (m, 1H, CH$_3$—CH—CH$_3$), 2.86 (m, 3H, CH$_3$—CH—CH$_3$, ring CH$_2$), 2.66 (t, J=7.3 Hz, 2H, ring CH$_2$), 2.22 (s, 3H, CH$_3$), 2.01 (m, 2H, ring CH$_2$), 1.65 (m, 2H, R—O—CH$_2$—CH$_2$—CH$_3$), 1.27 (t, J=7.1 Hz, 3H, —CO$_2$—CH$_2$—CH$_3$) 1.24 (d, J=7.0 Hz, 6H, CH$_3$—CH—CH$_3$), 1.23 (d, J=6.8 Hz, 6H, CH$_3$—CH—CH$_3$), 0.950 (t, J=7.4 Hz, 3H, R—O—CH$_2$—CH$_2$—CH$_3$).

Example 46

(L8, Compound XIX of Scheme 7, where R=isopropyl, R'=n-propyl, R"=H). To 2.74 g (6.45 mmol) of Compound XVIII dissolved in 75 mL of ethanol in a 200 ml round bottom flask was added 10 mL (20.0 mmol) of a 2 M aqueous LiOH solution. The mixture was heated to 90° C. for 3.0 hours, then cooled and concentrated under reduced pressure. The residue was taken up in 100 mL of 1 N aqueous HCl and the flask was shaken for 1 min. The resultant suspension was extracted with EtOAc (2×100 mL) and the organic layers were combined, washed (brine), dried (MgSO$_4$), and concentrated under reduced pressure. The concentrate was filtered through a short plug of silica gel (eluting with EtOAc), concentrated under reduced pressure and crystallized from acetonitrile to give 2.41 g (5.68 mmol) of XIX as light yellow crystals (88% yield). $^1$H NMR (400 MHz, CDCl$_3$) δ 7.03 (d, J=2.1 Hz, 1H, Ar—H), 6.90 (d, J=15.8 Hz, 1H, =CH) 6.79 (d, J=2.1 Hz, 1H, Ar—H), 6.23 (d, J=15.7 Hz, 1H, =CH), 5.81 (s, 1H, =CH), 3.53 (t, J=6.5 Hz, 2H, R—O—CH$_2$—CH$_2$—CH$_3$), 3.33 (m, 1H, CH$_3$—CH—CH$_3$), 2.88 (m, 3H, CH$_3$—CH—CH$_3$, ring CH$_2$), 2.66 (t, J=7.3 Hz, 2H, ring CH$_2$), 2.23 (s, 3H, CH$_3$), 2.03 (m, 2H, ring CH$_2$), 1.65 (m, 2H, R—O—CH$_2$—CH$_2$—CH$_3$), 1.24 (d, J=6.8 Hz, 6H, CH$_3$—CH—CH$_3$), 1.23 (d, J=6.9 Hz, 6H, CH$_3$—CH—CH$_3$), 0.951 (t, J=7.4 Hz, 3H, R—O—CH$_2$—CH$_2$—CH$_3$).

Example 47

(L9, Compound XIX of Scheme 7, where R=isopropyl, R'=n-butyl, R"=H). This compound was prepared in the manner previously described for Compound XIX in Example 46, except that bromobutane was used instead of bromopropane in Example 43. $^1$H NMR (400 MHz, CDCl$_3$) δ 7.03 (d, J=2.1 Hz, 1H, Ar—H), 6.90 (d, J=15.7 Hz, 1H, =CH) 6.79 (d, J=2.1 Hz, 1H, Ar—H), 6.23 (d, J=15.8 Hz, 1H, =CH), 5.81 (s, 1H, =CH), 3.57 (t, J=6.4 Hz, 2H, R—O—CH$_2$—CH$_2$—CH$_2$—CH$_3$), 3.33 (m, 1H, CH$_3$—CH—CH$_3$), 2.88 (m, 3H, CH$_3$—CH—CH$_3$, ring CH$_2$), 2.67 (t, J=7.2 Hz, 2H, ring CH$_2$), 2.23 (s, 3H, CH$_3$), 2.02 (m, 2H, ring CH$_2$), 1.60 (m, 2H, R—O—CH$_2$—CH$_2$—CH$_2$—CH$_3$), 1.41 (m, 2H, R—O—CH$_2$—CH$_2$—CH$_2$—CH$_3$) 1.24 (d, J=7.0 Hz, 6H, CH$_3$—CH—CH$_3$), 1.23 (d, J=6.9 Hz, 6H, CH$_3$—CH—CH$_3$), 0.906 (t, J=7.4 Hz, 3H, R—O—CH$_2$—CH$_2$—CH$_3$).

Example 48

(L10, Compound XIX of Scheme 7, where R=isopropyl, R'=n-pentyl, R"=H). This compound was prepared in the manner previously described for Compound XIX in Example 46, except that bromopentane was used instead of bromopropane in Example 43. $^1$H NMR (400 MHz, CDCl$_3$) δ 7.03 (d, J=2.3 Hz, 1H, Ar—H), 6.90 (d, J=15.8 Hz, 1H, =CH) 6.79 (d, J=2.3 Hz, 1H, Ar—H), 6.23 (d, J=15.8 Hz, 1H, =CH), 5.82 (s, 1H, =CH), 3.56 (t, J=6.5 Hz, 2H, R-O—CH$_2$—CH$_2$—CH$_2$—CH$_2$—CH$_3$), 3.33 (m, 1H, CH$_3$—CH—CH$_3$), 2.88 (m, 3H, CH$_3$—CH—CH$_3$, ring CH$_2$), 2.67 (t, J=7.4 Hz, 2H, ring CH$_2$), 2.22 (s, 3H, CH$_3$), 2.02 (m, 2H, ring CH$_2$), 1.63 (m, 2H, R—O—CH$_2$—CH$_2$—CH$_2$—CH$_2$—CH$_3$), 1.32 (m, 4H, R—O—CH$_2$—CH$_2$—CH$_2$—CH$_2$—CH$_3$) 1.24 (d, J=6.9 Hz, 6H, CH$_3$—CH—CH$_3$), 1.23 (d, J=6.9 Hz, 6H, CH$_3$—CH—CH$_3$), 0.89 (t, J=7.0 Hz, 3H, R-O—CH$_2$—CH$_2$—CH$_2$—CH$_2$—CH$_3$).

Example 49

(L31, Compound XIX of Scheme 7, where R=isopropyl, R'=1,1,1-trifluorobutyl, R"=H). This compound was prepared in the manner previously described for Compound XIX in Example 46, except that 4,4,4-trifluoro-1-bromobutane was used instead of bromopropane in Example 43. $^1$H NMR (400 MHz, CDCl$_3$) δ 7.04 (d, J=2.2 Hz, 1H, Ar—H), 6.84 (d, J=15.8 Hz, 1H, C=CH), 6.80 (d, J=2.2 Hz, 1H, Ar—H), 6.24 (d, J=15.8 Hz, 1H, C=CH), 5.82 (s, 1H, C=CH), 3.62 (t, J=5.9 Hz, 2H, R—O—CH$_2$—CH$_2$—CH$_2$—CF$_3$), 3.26 (m, 1H, CH$_3$—CH—CH$_3$), 2.86 (m, 3H, CH$_3$—CH—CH$_3$, ring CH$_2$), 2.68 (t, J=7.3 Hz, 2H, ring CH$_2$), 2.22 (s, 3H, CH$_3$), 2.21 (m, 2H, R—O—CH$_2$—CH$_2$—CH$_2$—CF$_3$), 2.03 (dt, J=14.9 Hz, J=7.4 Hz, 2H, ring CH$_2$), 1.87 (dt, J=15.8 Hz, J=5.9 Hz, 2H, R—O—CH$_2$—CH$_2$—CH$_2$—CF$_3$), 1.24 (d, J=6.8 Hz, 6H, CH$_3$—CH—CH$_3$), 1.23 (d, J=6.9 Hz, 6H, CH$_3$—CH—CH$_3$).

Example 50

(L32, Compound XIX of Scheme 7, where R=isopropyl, R'=1,1-difluoroethyl, R"=H). This compound was prepared in the manner previously described for Compound XIX in Example 46, except that 2,2-difluoro-1-bromo-ethane was used instead of bromopropane in Example 43. $^1$H NMR (400 MHz, CDCl$_3$) δ 7.06 (d, J=2.1 Hz, 1H, Ar—H), 6.84 (d, J=16.5 Hz, 1H, C=CH), 6.81 (d, J=2.3 Hz, 1H, Ar—H), 6.27 (d, J=15.8 Hz, 1H, C=CH), 5.90 (tt, J=55.2 Hz, J=4.1 Hz, 1H, R-O—CH$_2$—CF$_2$H), 5.83 (s, 1H, C=CH), 3.80 (td, J=13.8 Hz, J=4.1 Hz, 2H, R—O—CH$_2$—CF$_2$H), 3.33 (m, 1H, CH$_3$—CH—CH$_3$), 2.87 (m, 3H, CH$_3$—CH—CH$_3$, ring CH$_2$), 2.69 (t, J=7.4 Hz, 2H, ring CH$_2$), 2.22 (s, 3H, CH$_3$), 2.04 (dt, J=14.9 Hz, J=7.5 Hz, 2H, ring CH$_2$), 1.25 (d, J=6.9 Hz, 6H, CH$_3$—CH—CH$_3$), 1.24 (d, J=6.8 Hz, 6H, CH$_3$—CH—CH$_3$).

Example 51

(L33, Compound XIX of Scheme 7, where R=isopropyl, R'=1,1-difluoropropyl, R"=H). This compound was prepared in the manner previously described for Compound XIX in Example 46, except that 3,3-difluoro-1-bromopropane was used instead of bromopropane in Example 43. $^1$H NMR (400 MHz, CDCl$_3$) δ 7.05 (d, J=2.0 Hz, 1H, Ar—H), 6.83 (d, J=14.9 Hz, 1H, C=CH), 6.81 (d, J=2.3 Hz, 1H, Ar—H), 6.25 (d, J=15.8 Hz, 1H, C=CH), 5.99 (tt, J=56.8 Hz, J=4.8 Hz, 1H, R-O—CH$_2$—CH$_2$—CF$_2$H), 5.83 (s, 1H, C=CH), 3.71 (t, J=5.8 Hz, 2H, R—O—CH$_2$—CH$_2$—CF$_2$H), 3.24 (m, 1H, CH$_3$—CH—CH$_3$), 2.86 (m, 3H, CH$_3$—CH—CH$_3$, ring CH$_2$), 2.69 (t, J=7.2 Hz, 2H, ring CH$_2$), 2.21 (s, 3H, CH$_3$), 2.10 (m, 4H, R—O—CH$_2$—CH$_2$—CF$_2$H, ring CH$_2$), 1.24 (d, J=6.9 Hz, 6H, CH$_3$—CH—CH$_3$), 1.23 (d, J=6.8 Hz, 6H, CH$_3$—CH—CH$_3$).

Example 52

(L34, Compound XIX of Scheme 7, where R=isopropyl, R'=1,1,2,2-tetrafluoropropyl, R"=H). This compound was prepared in the manner previously described for Compound XIX in Example 46, except that 1,1,2,2-tetrafluoro-bromopropane was used instead of bromopropane in Example 43. $^1$H NMR (400 MHz, CDCl$_3$) δ 7.07 (d, J=2.2 Hz, 1H, Ar—H), 6.82 (d, J=2.2 Hz, 1H, Ar—H), 6.77 (d, J=15.8 Hz, 1H, C=CH), 6.27 (d, J=15.8 Hz, 1H, C=CH), 5.96 (tt, J=53.2 Hz, J=5.1 Hz, 1H, R—O—CH$_2$—CF$_2$—CF$_2$H), 5.84 (s, 1H, C=CH), 3.93 (t, J=12.1 Hz, 2H, R—O—CH$_2$—CF$_2$—CF$_2$H), 3.27 (m, 1H, CH$_3$—CH—CH$_3$), 2.87 (m, 3H, CH$_3$—CH—CH$_3$, ring CH$_2$), 2.69 (t, J=7.5 Hz, 2H, ring CH$_2$), 2.21 (s, 3H, CH$_3$), 2.04 (dt, J=14.9 Hz, J=7.4 Hz, 2H, ring CH$_2$), 1.25 (d, J=6.9 Hz, 6H, CH$_3$—CH—CH$_3$), 1.24 (d, J=6.8 Hz, 6H, CH$_3$—CH—CH$_3$).

Example 53

(L35, Compound XIX of Scheme 7, where R=tert-butyl, R'=1,1,2,2-tetrafluoropropyl. R"=H). This compound was prepared in the manner previously described for Compound XIX in Example 46, except that 3,5-ditert-butylsalicylic acid was used instead of 3,5-diisopropylsalicylic acid in Example 36 and 1,1,2,2-tetrafluoro-bromopropane was used instead of bromopropane in Example 43. $^1$H NMR (400 MHz, CDCl$_3$) δ 7.32 (d, J=2.6 Hz, 1H, Ar—H), 6.97 (d, J=2.5 Hz, 1H, Ar—H), 6.74 (d, J=15.8 Hz, 1H, C=CH), 6.26 (d, J=15.8 Hz, 1H, C=CH), 5.85 (tt, J=53.1 Hz, J=4.9 Hz, 1H, R—O—CH$_2$—CF$_2$—CF$_2$H), 5.83 (s, 1H, C=CH), 4.03 (m, 2H, R—O—CH$_2$—CF$_2$—CF$_2$H), 2.87 (m, 2H, ring CH$_2$), 2.68 (m, 2H, ring CH$_2$), 2.19 (d, J=0.8 Hz, 3H, CH$_3$), 2.07 (m, 2H, ring CH$_2$), 1.41 (s, 9H, $^t$butyl), 1.31 (s, 9H, $^t$butyl).

Example 54

(L14, Compound XIX of Scheme 7, where R=isopropyl, R'=1-fluoropropyl, R"=H). This compound was prepared in the manner previously described for Compound XIX in Example 46, except that 3-fluoro-1-bromopropane was used instead of bromopropane in Example 43. $^1$H NMR (400 MHz, CDCl$_3$) δ 7.04 (d, J=2.2 Hz, 1H, Ar—H), 6.86 (d, J=15.8 Hz, 1H, C=CH), 6.81 (d, J=2.2 Hz, 1H, Ar—H), 6.24 (d, J=15.7 Hz, 1H, C=CH), 5.82 (s, 1H, C=CH), 4.57 (dt, J=47.1 Hz, J=5.8 Hz, 2H, R—O—CH$_2$—CH$_2$—CH$_2$F), 3.69 (t, J=5.9 Hz, 2H, R—O—CH$_2$—CH$_2$—CH$_2$F), 3.28 (m, 1H, CH$_3$—CH—CH$_3$), 2.86 (m, 3H, CH$_3$—CH—CH$_3$, ring CH$_2$), 2.68 (t, J=7.4 Hz, 2H, ring CH$_2$), 2.22 (s, 3H, CH$_3$), 2.00 (m, 4H, R—O—CH$_2$—CH$_2$—CH$_2$F, ring CH$_2$), 1.25 (d, J=6.9 Hz, 6H, CH$_3$—CH—CH$_3$), 1.24 (d, J=6.8 Hz, 6H, CH$_3$—CH—CH$_3$).

Example 55

(L36, Compound XIX of Scheme 7, where R=isopropyl, R'=1-fluoropropyl, R"=F). This compound was prepared in the manner previously described for Compound XIX in Example 46, except that triethyl 2-fluoro-3-methyl-4-phosphonocrotonate was used instead of triethyl 3-methyl-4-phosphonocrotonate in Example 45 and 3-fluoro-1-bromopropane was used instead of bromopropane in Example 43. $^1$H NMR (400 MHz, CDCl$_3$) δ 7.05 (d, J=2.2 Hz, 1H; Ar—H), 6.85 (d, J=15.9 Hz, 1H, C=CH), 6.81 (d, J=2.1 Hz, 1H, Ar—H), 6.69 (d, J=15.8 Hz, 1H, C=CH), 4.57 (dt, J=47.2 Hz, J=5.8 Hz, 2H, R-O—CH$_2$—CH$_2$—CH$_2$F), 3.69 (t, J=5.9 Hz, 2H, R—O—CH$_2$—CH$_2$—CH$_2$F), 3.29 (m, 1H, CH$_3$—CH—CH$_3$), 2.86 (m, 3H, CH$_3$—CH—CH$_3$, ring CH$_2$), 2.73 (t, J=7.4 Hz, 2H, ring CH$_2$), 2.16 (d, J=3.2 Hz, 3H, CH$_3$), 2.01 (m, 4H, R—O—CH$_2$—CH$_2$—CH$_2$F, ring CH$_2$), 1.24 (d, J=6.9 Hz, 6H, CH$_3$—CH—CH$_3$), 1.23 (d, J=6.8 Hz, 6H, CH$_3$—CH—CH$_3$).

Example 55a (L37, Compound XIX of Scheme 7, where R=tert-butyl, R'=1-fluoropropyl, R"=H). This compound was prepared in the manner previously described for Compound XIX in Example 46, except that 3,5-ditert-butylsalicylic acid was used instead of 3,5-diisopropylsalicylic acid in Example 36 and 3-fluoro-1-bromopropane was used instead of bromopropane in Example 43. $^1$H NMR (400 MHz, CDCl$_3$) δ

7.28 (d, J=2.4 Hz, 1H, Ar—H), 6.97 (d, J=2.4 Hz, 1H, Ar—H), 6.85 (d, J=15.8 Hz, 1H, C═CH), 6.23 (d, J=15.8 Hz, 1H, C═CH), 5.82 (s, 1H, C═CH), 4.54 (dt, J=47.1 Hz, J=5.9 Hz, 2H, R—O—CH$_2$—CF$_2$—CH$_2$F), 3.75 (m, 2H, R—O—CH$_2$—CF$_2$—CH$_2$F), 2.88 (m, 2H, ring CH$_2$), 2.68 (t, J=7.3, 2H, ring CH$_2$), 2.21 (s, 3H, CH$_3$), 1.99 (m, 4H, R-O—CH$_2$—CH$_2$—CH$_2$F, ring CH$_2$), 1.40 (s, 9H, $^t$butyl), 1.30 (s, 9H, $^t$butyl).

Scheme 8

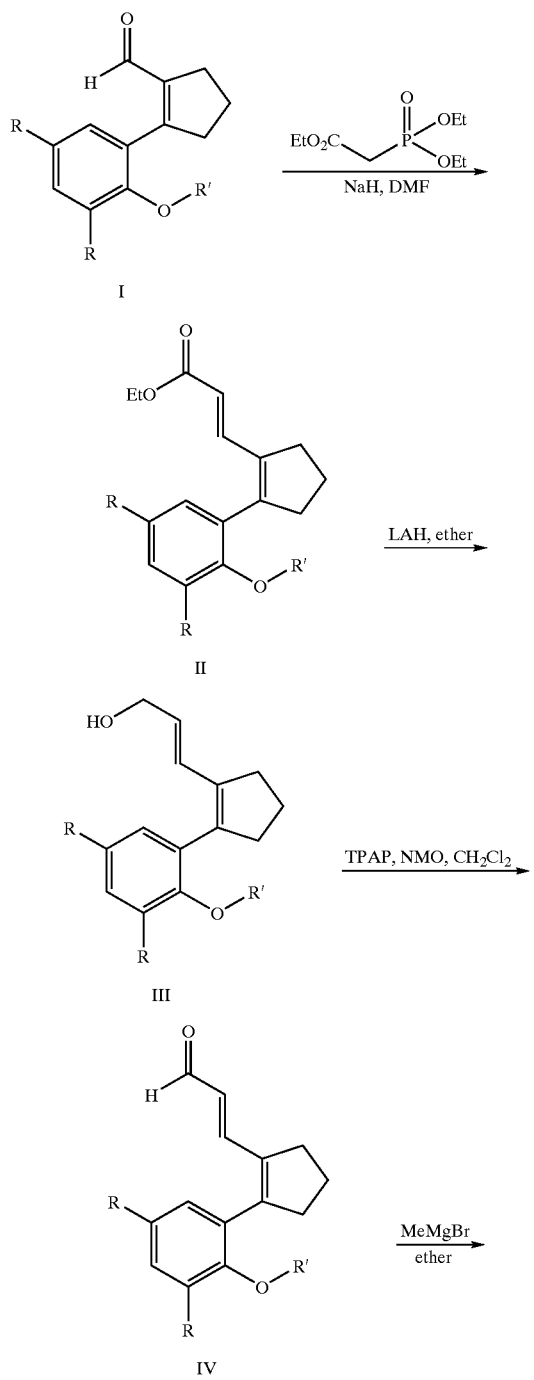

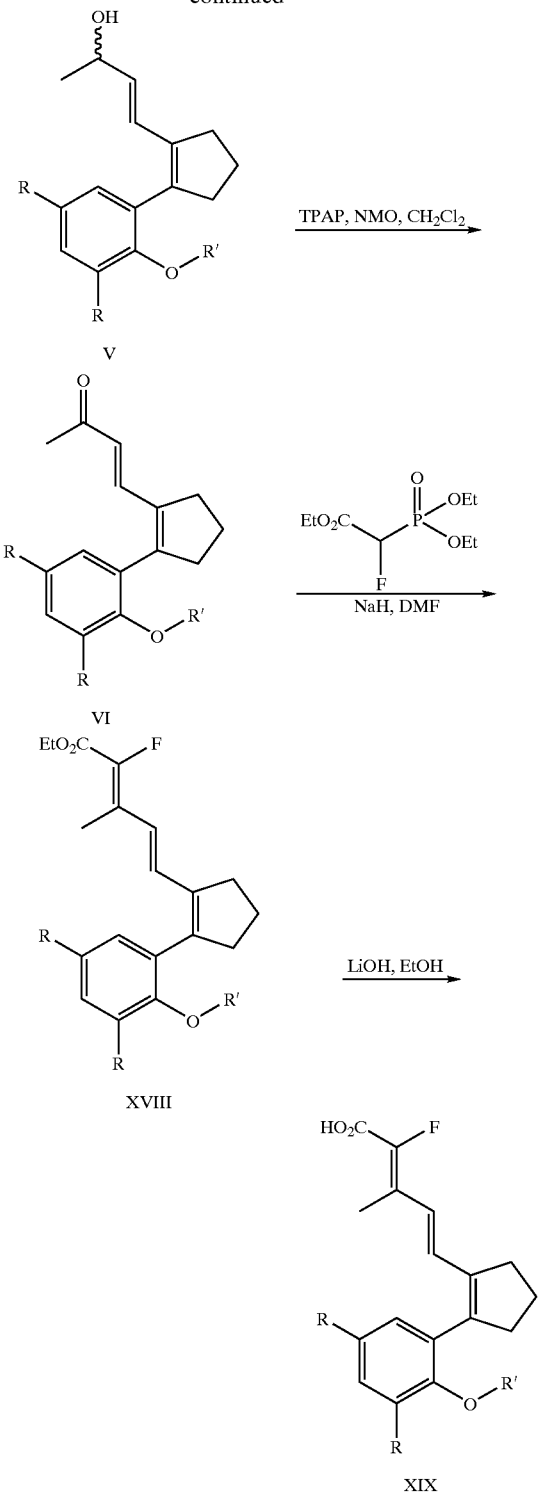

Scheme 8 provides an alternate route to that proposed in Scheme 7 for introduction of fluorine at position $R^9$ of the modulator compounds.

Example 56

(Compound II of Scheme 8, where R=propyl, R'=1-fluoropropyl). To 0.114 g of sodium hydride (2.38 mmol)

suspended in anhydrous DMF (10 ml) in a flame dried 25 ml r.b. flask at 0° C. is added triethyl-phosphonoacetate (0.501 g, 2.23 mmol) dropwise. The mixture is allowed to stir for 0.2 hours. Compound I is then added dropwise (0.495 g, 1.49 mmol) via solvation in anhydrous DMF (5.0 ml). The resultant mixture is allowed to warm to ambient temperature, and stirred for 2.0 hours. After such time, water (10.0 ml) is added and the mixture is allowed to stir for 0.3 hours. The aqueous layer was extracted with EtOAc. All organic layers were combined, washed (brine), dried ($MgSO_4$), and concentrated under reduced pressure. Purification by flash column chromatography (silica gel, hexanes/EtOAc, 9:1) yielded 0.60 g of II (100%) as the E-isomer exclusively. Data for compound II. $^1$H NMR (400 MHz, $CDCl_3$) δ 7.48 (d, J=15.6 Hz, 1H), 7.05 (d, J=2.0 Hz, 1H), 6.76 (d, J=2.2 Hz, 1H), 5.80 (d, J=15.7 Hz, 1H), 4.58 (dt, J=47.1 Hz, 5.9 Hz, 2H), 4.16 (q, J=7.1 Hz, 2H), 3.68 (t, J=6.0 Hz, 2H), 3.28 (m, 1H), 2.85 (m, 3H), 2.65 (t, J=7.5 Hz, 2H), 2.01 (m, 4H), 1.25 (t, J=7.1 Hz, 3H), 1.24 (d, J=7.3 Hz, 6H), 1.23 (d, J=7.1 Hz, 6H).

Example 57

(Compound III of Scheme 8, where R=isopropyl, R'=1-fluoropropyl). To 0.61 g of II (1.51 mmol) suspended in anhydrous diethyl ether (15 ml) in a flame dried 25 ml r.b. flask at 0° C. is added lithium aluminum hydride (0.057 g, 1.51 mmol)-portion wise. The resultant mixture is allowed to slowly warm to ambient temperature, and stirred for 4.0 hours. After such time, water (10.0 ml) is added and the mixture is allowed to stir for 0.3 hours. The aqueous layer was extracted with EtOAc. All organic layers were combined, washed (brine), dried ($MgSO_4$), and concentrated under reduced pressure. Purification by flash column chromatography (silica gel, hexanes/EtOAc, 9:1) yielded 0.441 g of III (83%). Data for compound III. $^1$H NMR (400 MHz, $CDCl_3$) δ 7.05 (d, J=2.2 Hz, 1H), 6.77 (d, J=2.2 Hz, 1H), 6.40 (d, J=15.4 Hz, 1H), 5.78 (dt, J=15.7 Hz, J=6.2 Hz, 1H),), 5.59 (dt, J=47.2 Hz, 5.9 Hz, 2H), 4.17 (t, J=5.7 Hz, 2H), 3.70 (t, J=5.9 Hz, 2H), 3.30 (m, 1H) 2.86 (m, 3H), 2.82 (t, J=7.4 Hz, 2H), 2.63 (t, J=7.3 Hz, 2H), 1.84 (m, 4H), 1.23 (d, J=6.8 Hz, 12H).

Example 58

(Compound IV of Scheme 8, where R=isopropyl, R'=1-fluoropropyl). To 0.441 g of compound III (1.22 mmol) dissolved in anhydrous $CH_2Cl_2$ (10.0 ml) in a flame dried 25 ml r.b. flask is added 4-Methylmorpholine N-oxide (0.215 g, 1.84 mmol) followed by Tetrapropylammonium perruthenate (0.021 g, 0.061 mmol). The resulting mixture is stirred at ambient temperature for 1.0 hours. After such time, the reaction mixture is filtered through a plug of silica gel (eluding with $CH_2Cl_2$) and concentrated under reduced pressure to yield 0.437 g of IV (100%). Data for compound IV. $^1$H NMR (400 MHz, $CDCl_3$) δ 9.49 (d, J=8.0 Hz, 1H), 7.28 (d, J=16.1 Hz, 1H), 7.10 (d, J=2.2 Hz, 1H), 6.79 (d, J=2.2 Hz, 1H), 6.09 (dd, J=15.4 Hz, J=8.0 Hz, 1H),), 4.34 (dt, J=47.1 Hz, J=5.7 Hz, 2H), 3.69 (t, J=5.9 Hz, 2H), 3.30 (m, 1H) 2.88 (m, 3H), 2.70 (t, J=7.5 Hz, 2H), 2.20 (m, 4H), 1.25 (d, J=7.0 Hz, 6H), 1.24 (d, J=6.8 Hz, 6H).

Example 59

(Compound V of Scheme 8, where R=isopropyl, R'=1-fluoropropyl). To 0.437 g of compound IV (1.22 mmol) dissolved in anhydrous diethyl ether (15.0 ml) in a flame dried 25 ml r.b. flask at 0° C. is added methyl magnesium-bromide (1.34 mmol, 0.45 ml of 3.0 M solution in ether) dropwise via syringe. The resultant mixture is kept at 0° C. for 2.0 hours. After such time sat. $NH_4Cl$ (10 ml) is added and the mixture is allowed to warm to room temperature. Once at room temperature, the mixture is filtered through a plug of silica gel (eluding with hexanes/EtOAc 9:1) and concentrated under reduced pressure to yield 0.233 g of V (51%). Data for compound V. $^1$H NMR (400 MHz, $CDCl_3$) δ 7.01 (d, J=2.0 Hz, 1H), 6.78 (d, J=2.1 Hz, 1H), 6.36 (d, J=15.7 Hz, 1H), 5.66 (dd, J=15.8 Hz, J=6.8 Hz, 1H),), 4.59 (dt, J=, 47.2 Hz, J=5.9 Hz, 2H), 4.32 (m, 1H), 3.70 (t, J=6.0 Hz, 2H), 3.29 (m, 1H) 2.84 (m, 3H), 2.62 (t, J=7.4 Hz, 2H), 2.01 (m, 4H), 1.27 (d, J=6.3 Hz, 3H), 1.23 (d, J=6.9 Hz, 12H).

Example 60

(Compound VI of Scheme 8, where R=isopropyl, R'=1-fluoropropyl). To 0.233 g of compound V (0.62 mmol) dissolved in anhydrous $CH_2Cl_2$ (10.0 ml) in a flame dried 25 ml r.b. flask is added 4-Methylmorpholine N-oxide (0.109 g, 0.93 mmol) followed by Tetrapropylammonium perruthenate (0.011 g, 0.031 mmol). The resulting mixture is stirred at ambient temperature for 1.0 hours. After such time, the reaction mixture is filtered through a plug of silica gel (eluding with $CH_2Cl_2$) and concentrated under reduced pressure to yield 0.204 g of VI (100%). Data for compound VI. $^1$H NMR (400 MHz, $CDCl_3$) δ 7.31 (d, J=16.1 Hz, 1H), 7.07 (d, J=2.2 Hz, 1H), 6.79 (d, J=2.1 Hz, 1H), 6.06 (d, J=16.1 Hz, 1H), 4.57 (dt, J=47.1 Hz, J=5.8 Hz, 2H), 3.68 (t, J=5.9 Hz, 2H), 3.29 (m, 1H), 2.90 (m, 3H), 2.67 (t, J=7.4 Hz, 2H), 2.21 (s, 3H), 2.01 (m, 4H), 1.25 (d, J=7.0 Hz, 6H), 1.24 (d, J=6.9 Hz, 6H).

Example 61

(Compound XVIII of Scheme 8, where R=isopropyl, R'=1-fluoropropyl). To 0.034 g of sodium hydride (0.713 mmol) suspended in anhydrous DMF (4.0 ml) in a flame dried 15 ml r.b. flask at 0° C. is added triethyl-2-fluoro-2-phosphonoacetate (0.159 g, 0.659 mmol) dropwise. The mixture is allowed to stir for 0.3 hours. Compound VI is then added dropwise (0.204 g, 0.549 mmol) via solvation in anhydrous DMF (3.0 ml). The resultant mixture is allowed to stir at 0° C. for 0.75 hours. After such time, water (10.0 ml) is added and the mixture is allowed to stir for 0.3 hours. The aqueous layer was extracted with EtOAc. All organic layers were combined, washed (brine), dried ($MgSO_4$), and concentrated under reduced pressure. Purification by flash column chromatography (silica gel, hexanes/EtOAc, 9:1) yielded 0.267 g of XVIII (100%) as a 1:1 E to Z isomer ratio. Data for compound XVIII. $^1$H NMR (400 MHz, $CDCl_3$) δ 7.04 (s, 1H), 6.82 (s, 1H), 6.78 (d, J=16.2 Hz, 1H), 6.69 (d, J=16.1 Hz, 1H), 4.58 (dt, J=47.2 Hz, J=5.9 Hz, 2H), 4.31 (q, J=7.1 Hz, 2H), 3.70 (t, J=5.8 Hz, 2H), 3.30 (m, 1H), 2.85 (m, 3H), 2.73 (t, J=7.1 Hz, 2H), 2.14 (d, J=3.0 Hz, 3H), 2.00 (m, 4H), 1.38 (t, J=7.1 Hz, 3H), 1.25 (d, J=6.9 Hz, 6H), 1.24 (d, J=6.8 Hz, 6H).

Example 62

(L36, Compound XIX of Scheme 8, where R=isopropyl, R'=1-fluoropropyl). To 0.267 g of compound XVIII (0.580 mmol) dissolved in ethanol (10.0 ml) in a 25.0 ml r.b. flask is added 2 M aqueous LiOH (1.16 mmol). The resultant mixture is heated to 60° C. for 7.0 hours. After such time, the reaction is cooled and concentrated under reduced pressure. The residue is taken up in 1 N aqueous HCl (10.0 ml). The flask is sealed and shaken for 1.0 minute. The resultant suspension was extracted with EtOAc. All organic layers were combined, washed (brine), dried (MgSO$_4$), and concentrated under reduced pressure. The crude reaction mixture is purified using HPLC (85:15:0.1 MeOH, H$_2$O, TFA). The purified 2-Z isomer is recrystallized from acetonitrile to yield 0.107 g of XIX (42.8%) as a pale yellow crystalline solid. Data for compound XIX. $^1$H NMR (400 MHz, CDCl$_3$) δ 7.05 (d, J=2.2 Hz, 1H), 6.85 (d, J=15.9 Hz, 1H), 6.81 (d, J=2.1 Hz, 1H), 6.69 (d, J=15.8 Hz, 1H), 4.57 (dt, J=47.2 Hz, J=5.8 Hz, 2H), 3.69 (t, J=5.9 Hz, 2H), 3.29 (m, 1H), 2.86 (m, 3H), 2.73 (t, J=7.4 Hz, 2H), 2.16 (d, J=3.2 Hz, 3H), 2.01 (m, 4H), 1.24 (d, J=6.9 Hz, 6H), 1.23 (d, J=6.8 Hz).

Scheme 9

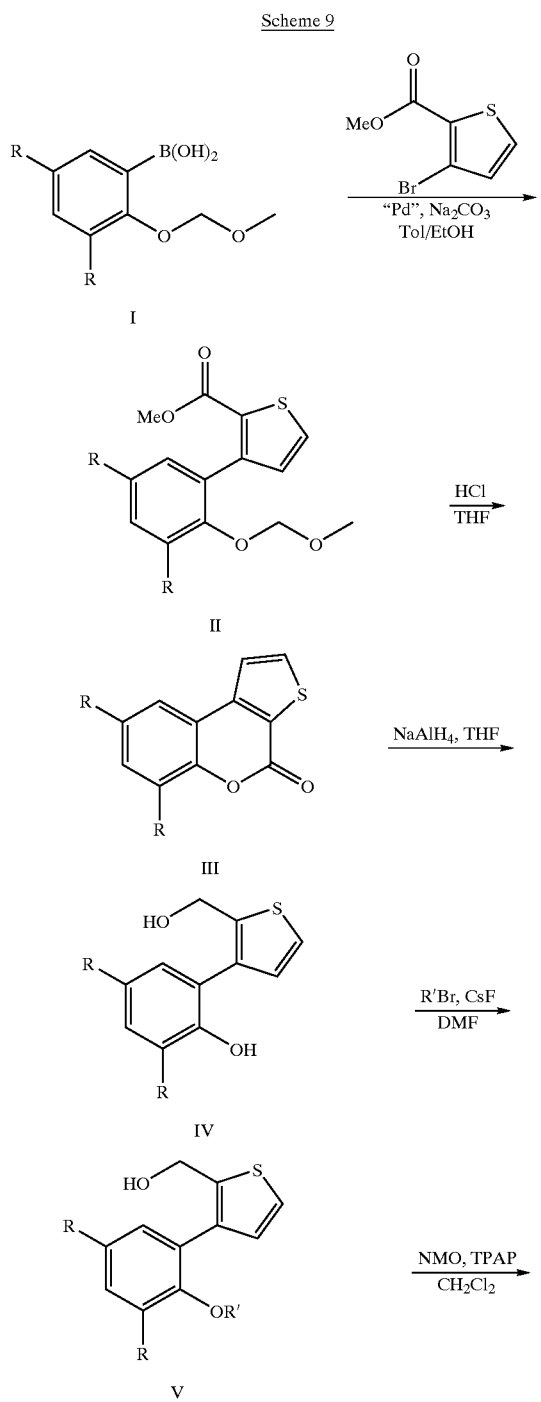

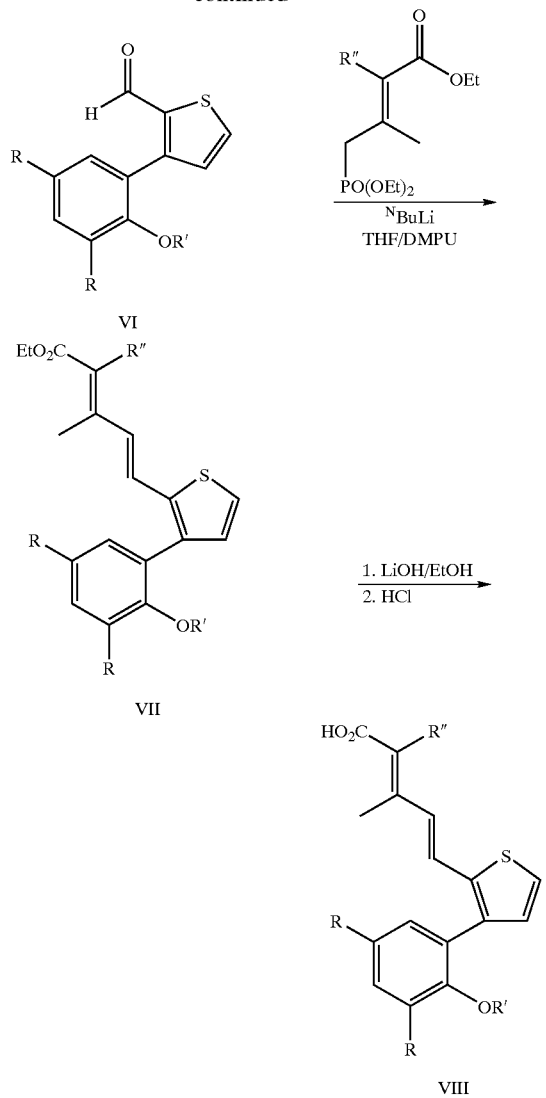

Scheme 9 shows the preparation of additional coumarin intermediates (e.g., Structure III) in another preferred aspect of the invention. The coumarin intermediates may then be converted to the desired RXR modulator compounds as previously described and as further described in Examples 63–69.

Example 63

(Compound II of Scheme 9, where R=isopropyl). To 0.45 g of Compound I (1.68 mmol) dissolved in toluene/ethanol (1:1, 20.0 ml) in a 50 ml r.b. flask was added Methyl-3-bromothiophene-2-carboxylate (0.37 g, 1.68 mmol), 2 N aqueous Na$_2$CO$_3$ (0.36 g, 3.36 mmol,), and Tetrakis(triphenylphosphine) palladium(0) (0.194 g, 0.17 mmol). The reaction mixture was heated to 90° C. for 15.0 hours. The mixture was then cooled, poured into brine (20.0 ml), and stirred for 0.3 hours. The aqueous layer was extracted with EtOAc. All organic layers were combined, dried (MgSO$_4$), and concentrated under reduced pressure. Purification by flash column chromatography (silica gel, hexanes/EtOAc, 9:1) yielded 0.17 g of II (28%) as a yellow solid. Data for Compound II. $^1$H NMR (400 MHz, CDCl$_3$) δ 7.50 (d, J=5.2 Hz, 1H, thiophene-H), 7.13 (d, J=5.4 Hz, 1H, thiophene-H), 7.12 (d, J=2.5 Hz, 1H, Ar—H), 6.95 (d, J=2.2 Hz, 1H, Ar—H), 4.55 (s, 2H, R—O—CH$_2$—O—CH$_3$), 3.78 (s, 3H, R—O—CH$_2$—O—CH$_3$), 3.39 (m, 1H, CH$_3$—CH—CH$_3$), 3.18 (s, 3H, CO$_2$CH$_3$), 2.89 (m, 1H, CH$_3$—CH—CH$_3$), 1.26 (d, J=6.7 Hz, 6H, CH$_3$—CH—CH$_3$), 1.25 (d, J=6.8 Hz, 6H, CH$_3$—CH—CH$_3$).

Example 64

(Compound III of Scheme 9, where R=isopropyl). To 0.17 g of Compound II (0.46 mmol) dissolved in THF (15.0 ml) in a 25 ml r.b. flask was added 6 N aqueous HCl (2.0 ml, 0.012 mol). The resulting mixture is allowed to stir at ambient temperature for 65.0 hours. After such time, the solvent is removed under reduced pressure. The residue was taken up in water (25.0 ml). The aqueous layer was extracted with EtOAc. All organic layers were combined, washed (water then brine), dried (MgSO$_4$), and concentrated under reduced pressure. Purification by flash column chromatography (silica gel, hexanes/EtOAc, 9:1) yielded 0.101 g of III (77%) as a yellow oil. Data for Compound III. $^1$H NMR (400 MHz, CDCl$_3$) δ 7.89 (d, J=5.0 Hz, 1H, thiophene-H), 7.67 (d, J=5.3 Hz, 1H, thiophene-H) 7.51 (d, J=2.1 Hz, 1H, Ar—H), 7.21 (d, J=1.9 Hz, 1H, Ar—H) 3.70 (m, 1H, CH$_3$—CH—CH$_3$), 3.01 (m, 1H, CH$_3$—CH—CH$_3$), 1.34 (d, J=7.1 Hz, 6H, CH$_3$—CH—CH$_3$), 1.32 (d, J=6.9 Hz, 6H, CH$_3$—CH—CH$_3$).

Example 65

(Compound IV of Scheme 9, where R=isopropyl). To 0.101 g of Compound III (0.35 mmol) dissolved in anhydrous THF (10.0 ml) in a flame dried 25 ml r.b. flask at 0° C. is added Sodium aluminum hydride (0.02 g, 0.35 mmol) portion wise. The resultant reaction mixture is allowed to slowly warm to ambient temperature and stirred for 2.0 hours. After such time, water (0.01 ml, 0.35 mmol) is added followed by 6 N aqueous sodium hydroxide (0.12 ml, 0.70 mmol). The resultant mixture is allowed to stir for 0.5 hours, filtered through a plug of silica gel (eluding with diethyl ether) and concentrated under reduced pressure to yield 0.102 g of IV (100%) as a clear, colorless oil. Data for Compound IV. $^1$H NMR (400 MHz, CDCl$_3$) δ 7.40 (d, J=5.1 Hz, 1H, thiophene-H), 7.07 (d, J=2.2 Hz, 1H, Ar—H), 7.03 (d, J=5.1 Hz, 1H, thiophene-H), 6.86 (d, J=2.2 Hz, Ar—H), 5.43 (s, 1H, Ar—OH), 4.69 (d, J=5.2 Hz, 2H, R—CH$_2$—OH), 3.74 (t, J=6.6 Hz, 1H, R—CH$_2$—OH), 3.31 (m, 1H, CH$_3$—CH—CH$_3$), 2.86 (m, 1H, CH$_3$—CH—CH$_3$), 1.28 (d, J=6.8 Hz, 6H, CH$_3$—CH—CH$_3$), 1.24 (d, J=7.1 Hz, 6H, CH$_3$—CH—CH$_3$).

Example 66

(Compound V of Scheme 9, where R=isopropyl, R'=n-butyl). To 0.102 g of Compound IV (0.34 mmol) dissolved in anhydrous N,N-Dimethylformamide (10.0 ml) in a flame dried 25 ml r.b. flask is added 1-Bromobutane (0.052 g, 0.378 mmol) followed by Cesium fluoride (0.21 g, 1.38 mmol). The resulting mixture is allowed to stir at ambient temperature for 18.0 hours. Water (15.0 ml) is added and the mixture is allowed to stir for 0.5 hours. The aqueous layer was extracted with EtOAc. All organic layers were combined, washed (brine), dried (MgSO$_4$), and concentrated under reduced pressure. Purification by flash column chromatography (silica gel, hexanes/EtOAc, 9:1) yielded 0.0748 g of V (63%) as a pale yellow oil. Data for Compound V. $^1$H NMR (400 MHz, CDCl$_3$) δ 7.32 (d, J=5.0 Hz, 1H, thiophene-H), 7.10 (d, J=2.2 Hz, 1H, Ar—H), 7.01 (d, J=5.0 Hz, 1H, thiophene-H), 6.92 (d, J=2.3 Hz, 1H, Ar—H), 4.52 (d, J=6.3 Hz, 2H, R—CH$_2$—OH), 3.66 (t, J=6.4 Hz, 1H, R—CH$_2$—OH), 3.39 (t, J=6.7 Hz, 2H, R—O—CH$_2$—CH$_2$—CH$_2$CH$_3$), 3.34 (m, 1H, CH$_3$—CH—CH$_3$), 2.89 (m, 1H, CH$_3$—CH—CH$_3$), 1.44 (m, 2H, R—O—CH$_2$—CH$_2$—CH$_2$—CH$_3$), 1.25 (m, 14H, CH$_3$—CH—CH$_3$, R—O—CH$_2$—CH$_2$—CH$_2$—CH$_3$), 0.80 (t, J=7.3 Hz, 3H, R—O—CH$_2$—CH$_2$—CH$_2$—CH$_3$).

Example 67

(Compound VI of Scheme 9, where R=isopropyl, R'=n-butyl). To 0.0748 g of Compound V (0.22 mmol) dissolved in anhydrous CH$_2$Cl$_2$ (3.0 ml) in a flame dried 10 ml r.b. flask is added 4-Methylmorpholine N-oxide (0.04 g, 0.32 mmol) followed by Tetrapropylammonium perruthenate (0.004 g, 0.011 mmol). The resulting mixture is stirred at ambient temperature for 1.0 hour. After such time, the reaction mixture is filtered through a plug of silica gel (eluding with CH$_2$Cl$_2$) and concentrated under reduced pressure to yield 0.075 g of VI (100%) as a yellow oil. Data for Compound VI. $^1$H NMR (400 MHz, CDCl$_3$) δ 9.78 (s, 1H, CHO), 7.71 (d, J=5.0 Hz, 1H, thiophene-H), 7.25 (d, J=5.5 Hz, 1H, thiophene-H), 7.17 (d, J=2.0 Hz, 1H, Ar—H), 6.99 (d, J=2.0 Hz, 1H, Ar—H), 3.36 (m, 3H, R—O—CH$_2$—CH$_2$—CH$_2$—CH$_3$, CH$_3$—CH—CH$_3$), 2.91 (m, 1H, CH$_3$—CH—CH$_3$), 1.45 (m, 2H, R—O—CH$_2$—CH$_2$—CH$_2$—CH$_3$), 1.26 (m, 14H, CH$_3$—CH—CH$_3$, R—O—CH$_2$—CH$_2$—CH$_2$—CH$_3$), 0.79 (t, J=7.3 Hz, 3H, R—O—CH$_2$—CH$_2$—CH$_2$—CH$_3$).

Example 68

(Compound VII of Scheme 9, where R=isopropyl, R'=n-butyl, R"=H). To 0.17 g of Triethyl 3-methyl-4-phosphonocrotonate (0.65 mmol) dissolved in THF/DMPU (1:2, 2.5 ml) in a flame dried 15 ml r.b. flask at −78° C. is added $^n$BuLi (0.69 mmol, in hexanes) dropwise. The mixture is allowed to stir for 0.1 hours. Compound VI is then added dropwise (0.075 g, 0.22 mmol) via solvation in THF/DMPU (1:2, 2.5 ml). The resultant mixture is allowed to stir at −78° C. for 0.3 hours, warmed to ambient temperature, and stirred for 2.0 hours. After such time, water (10.0 ml) is added and the mixture is allowed to stir for 0.3 hours. The aqueous layer was extracted with diethyl ether. All organic layers were combined, washed (brine), dried (MgSO$_4$), and concentrated under reduced pressure. Purification by flash column chromatography (silica gel, hexanes/EtOAc, 9:1) yielded 0.084 g of VII (85%) as a yellow oil. Data for Compound VII. $^1$H NMR (400 MHz, CDCl$_3$) δ 7.23 (d, J=5.2 Hz, 1H, thiophene-H), 7.16 (d, J=5.0 Hz, 1H, thiophene-H), 7.10 (d, J=2.2 Hz, 1H, Ar—H), 7.05 (d, J=15.8 Hz, 1H, =CH) 6.90 (d, J=2.2 Hz, 1H, Ar—H), 6.64 (d, J=15.8 Hz, 1H, =CH), 5.85 (s, 1H, =CH), 4.17 (q, J=7.1 Hz, 2H, R—CO$_2$—CH$_2$—CH$_3$) 3.37 (m, 3H, R—O—CH$_2$—CH$_2$—CH$_2$—CH$_3$, CH$_3$—CH—CH$_3$), 2.89 (m, 1H, CH$_3$—CH—CH$_3$), 2.26 (s, 3H, CH$_3$), 1.43 (m, 2H, R—O—CH$_2$—CH$_2$—CH$_2$—CH$_3$), 1.26 (m, 15H, R—CO$_2$—CH$_2$—CH$_3$, CH$_3$—CH—CH$_3$), 0.79 (t, J=7.4 Hz, 3H, R—O—CH$_2$—CH$_2$—CH$_2$—CH$_3$).

Example 69

(L12, Compound VIII of Scheme 9, where R=isopropyl, R'=n-butyl, R"=H). To 0.084 g of Compound VII (0.18 mmol) dissolved in ethanol (5.0 ml) in a 15.0 ml r.b. flask is added 2 M aqueous LiOH (0.55 mmol). The resultant mixture is heated to 90° C. for 3.0 hours. After such time, the reaction is cooled and concentrated under reduced pressure. The residue is taken up in 1 N aqueous HCl (10.0 ml). The flask is sealed and shaken for 1.0 minute. The resultant suspension was extracted with EtOAc. All organic layers were combined, washed (brine), dried (MgSO$_4$), and concentrated under reduced pressure. The concentrate is filtered through a short plug of silica gel (eluding with EtOAc), concentrated under reduced pressure and recrystallized from Acetonitrile to yield 0.08 g of VIII (100%) as a yellow crystalline solid. Data for Compound VIII. $^1$H NMR (400 MHz, CDCl$_3$) δ 7.26 (d, J=5.1 Hz, 1H, thiophene-H), 7.17 (d, J=5.0 Hz, 1H, thiophene-H), 7.11 (d, J=2.0 Hz, 1H, Ar—H), 7.11 (d, J=15.8 Hz, 1H, =CH), 6.91 (d, J=2.1 Hz, 1H, Ar—H), 6.57 (d, J=15.8 Hz, 1H, =CH), 5.87 (s, 1H, =CH), 3.37 (m, 3H, R—O—CH$_2$—CH$_2$—CH$_2$—CH$_3$, CH$_3$—CH—CH$_3$), 2.90 (m, 1H, CH$_3$—CH—CH$_3$), 2.28 (s, 3H, CH$_3$), 1.44 (m, 2H, R—O—CH$_2$—CH$_2$—CH$_2$—CH$_3$), 1.26 (m, 14H, CH$_3$—CH—CH$_3$, R—O—CH$_2$—CH$_2$—CH$_2$—CH$_3$), 0.79 (t, J=7.3 Hz, 3H, R—O—CH$_2$—CH$_2$—CH$_2$—CH$_3$).

Example 70

(L38, Compound VIII of Scheme 9, where R=isopropyl, R'=1,1-difluoroethyl, R"=H). This compound was prepared in the manner previously described for Compound VIII in Example 69, except that 2,2-difluoro-1-bromoethane was used instead of bromobutane in Example 66. $^1$H NMR (400 MHz, CDCl$_3$) δ 7.31 (d, J=5.1 Hz, 1H, thiophene-H), 7.16 (d, J=5.0 Hz, 1H, thiophene-H), 7.13 (d, J=2.1 Hz, 1H, Ar—H), 7.05 (d, J=15.8 Hz, 1H, C=CH), 6.93 (d, J=2.2 Hz, 1H, Ar—H), 6.69 (d, J=15.8 Hz, 1H, C=CH), 5.89 (s, 1H, C=CH), 5.68 (tt, J=55.4 Hz, J=4.2 Hz, 1H, R—O—CH$_2$—CF$_2$H) 3.56 (dt, J=13.7 Hz, J=4.1 Hz, 2H, R—O—CH$_2$—CF$_2$H), 3.37 (m, 1H, CH$_3$—CH—CH$_3$), 2.91 (m, 1H, CH$_3$3CH—CH$_3$), 2.27 (s, 3H, CH$_3$), 1.28 (d, J=6.9 Hz, 6H, CH$_3$—CH—CH$_3$), 1.26 (d, J=7.1 Hz, 6H, CH$_3$—CH—CH$_3$).

Example 71

(L39, Compound VIII of Scheme 9, where R=isopropyl, R'=1,1,1-trifluorobutyl, R"=H). This compound was prepared in the manner previously described for Compound VIII in Example 69, except that 4,4,4-trifluoro-1-bromobutane was used instead of bromobutane in Example 66. $^1$H NMR (400 MHz, CDCl$_3$) δ 7.28 (d, J=5.1 Hz, 1H, thiophene-H), 7.13 (d, J=5.2 Hz, 1H, thiophene-H), 7.12 (d, J=2.0 Hz, 1H, Ar—H), 7.04 (d, J=15.8 Hz, 1H, C=CH), 6.92 (d, J=2.0 Hz, 1H, Ar—H), 6.66 (d, J=15.8 Hz, 1H, C=CH), 5.88 (s, 1H, C=CH), 3.42 (t, J=5.8 Hz, 2H, R—O—CH$_2$—CH$_2$—CH$_2$—CF$_3$), 3.29 (m, 1H, CH$_3$—CH—CH$_3$), 2.90 (m, 1H, CH$_3$—CH—CH$_3$), 2.26 (s, 3H, CH$_3$), 2.02 (m, 2H, R—O—CH$_2$—CH$_2$—CH$_2$—CF$_3$), 1.69 (m, 2H, R—O—CH$_2$—CH$_2$—CH$_2$—CF$_3$), 1.28 (d, J=7.3 Hz, 6H, CH$_3$—CH—CH$_3$), 1.26 (d, J=7.4 Hz, 6H, CH$_3$—CH—CH$_3$).

Example 72

(L40, Compound VIII of Scheme 9, where R=isopropyl, R'=NHBoc-propyl, R"=H). This compound was prepared in the manner previously described for Compound VIII in Example 69, except 3-NHBoc-propylbromide was used instead of bromobutane in Example 66. $^1$H NMR (400 MHz, CDCl$_3$) δ 7.29 (d, J=5.0 Hz, 1H, thiophene-H), 7.16 (d, J=5.2 Hz, 1H, thiophene-H), 7.12 (d, J=2.0 Hz, 1H, Ar—H), 7.05 (d, J=15.8 Hz, 1H, C=CH), 6.91 (d, J=2.0 Hz, 1H, Ar—H), 6.67 (d, J=15.8 Hz, 1H, C=CH), 5.88 (s, 1H, C=CH), 4.57 (s, 1H, NH), 3.43 (t, J=5.6 Hz, 2H, R—O—CH$_2$—CH$_2$—CH$_2$-O—NHBoc), 3.30 (m, 1H, CH$_3$—CH—CH$_3$), 3.09 (m, 2H, R—O—CH$_2$—CH$_2$—CH$_2$-NHBoc), 2.90 (m, 1H,CH$_3$—CH—CH$_3$), 2.65 (m, 2H, R—O—CH$_2$—CH$_2$—CH$_2$-NHBoc), 2.26 (s, 3H, CH$_3$), 1.42 (s, 9H, NHCO$_2$$^t$butyl), 1.27 (d, J=7.6 Hz, 6H, CH$_3$—CH—CH$_3$), 1.25 (d, J=7.8 Hz, 6H, CH$_3$—CH—CH$_3$).

Example 73

(L41, Compound VIII of Scheme 9, where R=isopropyl, R'=1,1-difluoropropyl, R"=H). This compound was prepared in the manner previously described for Compound VIII in Example 69, except that 3,3-difluoro-1-bromopropane was used instead of bromobutane in Example 66. $^1$H NMR (400 MHz, CDCl$_3$) δ 7.30 (d, J=5.2 Hz, 1H, thiophene-H), 7.14 (d, J=5.3 Hz, 1H, thiophene-H), 7.12 (d, J=2.4 Hz, 1H, Ar—H), 7.05 (d, J=15.8 Hz, 1H, C=CH), 6.93 (d, J=2.3 Hz, 1H, Ar—H), 6.81 (d, J=15.8 Hz, 1H, C=CH), 5.89 (s, 1H, C=CH), 5.84 (tt, J=56.9 Hz, J=4.8 Hz, 1H, R—O—CH$_2$—CH$_2$—CF$_2$H), 3.52 (t, J=5.8 Hz, 2H, R—O—CH$_2$—CH$_2$—CF$_2$H), 3.28 (m, 1H, CH$_3$—CH—CH$_3$), 2.90 (m, 1H, CH$_3$—CH—CH$_3$), 2.26 (d, J=0.8 Hz, 3H, CH$_3$), 1.28 (d, J=8.2 Hz, 6H, CH$_3$—CH—CH$_3$), 1.25 (d, J=7.0 Hz, 6H, CH$_3$—CH—CH$_3$).

Example 74

(L42, Compound VIII of Scheme 9, where R=isopropyl, R'=1,1,2,2-tetrafluoropropyl, R"=H). This compound was prepared in the manner previously described for Compound VIII in Example 69, except that 3,3,2,2-tetrafluoro-1-bromopropane was used instead of bromobutane in Example 66. $^1$H NMR (400 MHz, CDCl$_3$) δ 7.32 (d, J=5.2 Hz, 1H, thiophene-H), 7.15 (d, J=2.0 Hz, 1H, Ar—H), 7.11 (d, J=5.0 Hz, 1H, thiophene-H), 7.00 (d, J=15.8 Hz, 1H, C=CH), 6.94 (d, J=2.1 Hz, 1H, Ar—H), 6.69 (d, J=15.8 Hz, 1H, C=CH), 5.89 (s, 1H, C=CH), 5.82 (tt, J=53.2 Hz, J=5.1 Hz, 1H, R—O—CH$_2$—CF$_2$—CF2H), 3.70 (t, J=12.1 Hz, 2H, R—O—CH$_2$—CF$_2$—CF$_2$H), 3.32 (m, 1H, CH$_3$—CH—CH$_3$), 2.91 (m, 1H, CH$_3$—CH—CH$_3$), 2.26 (s, 3H, CH$_3$), 1.28 (d, J=7.3 Hz, 6H, CH$_3$—CH—CH$_3$), 1.26 (d, J=7.4 Hz, 6H, CH$_3$—CH—CH$_3$).

Example 75

(L43, Compound VIII of Scheme 9, where R=isopropyl, R'=3-methoxy-propyl, R"=H). This compound was prepared in the manner previously described for Compound VIII in Example 69, except that 3-methoxy-1-bromopropane was used instead of bromobutane in Example 66. $^1$H NMR (400 MHz, CDCl$_3$) δ 7.27 (d, J=5.8 Hz, 1H, thiophene-H), 7.15 (d, J=5.1 Hz, 1H, thiophene-H), 7.11 (d, J=2.1 Hz, 1H, Ar—H), 7.09 (d, J=15.6 Hz, 1H, C=CH), 6.91 (d, J=2.2 Hz, 1H, Ar—H), 6.66 (d, J=15.8 Hz, 1H, C=CH), 5.88 (s, 1H, C=CH), 3.45 (t, J=6.04 Hz, 2H, R—O—CH$_2$—CH$_2$—O—CH$_3$), 3.34 (m, 3H, CH$_3$—CH—CH$_3$, R—O—CH$_2$—CH$_2$—CH$_2$—O—CH$_3$), 3.26 (s, 3H, R—O—CH$_2$—CH$_2$—CH$_2$—O—CH$_3$), 2.89 (m, 1H, CH$_3$—CH—CH$_3$), 2.27 (s, 3H, CH$_3$), 1.72 (dt, J=12.6 Hz, J=6.3 Hz, 2H, R—O—CH$_2$—CH$_2$—CH$_2$—O—CH$_3$), 1.27 (d, J=8.1 Hz, 6H, CH$_3$—CH—CH$_3$), 1.25 (d, J=7.9 Hz, 6H, CH$_3$—CH—CH$_3$).

Scheme 10

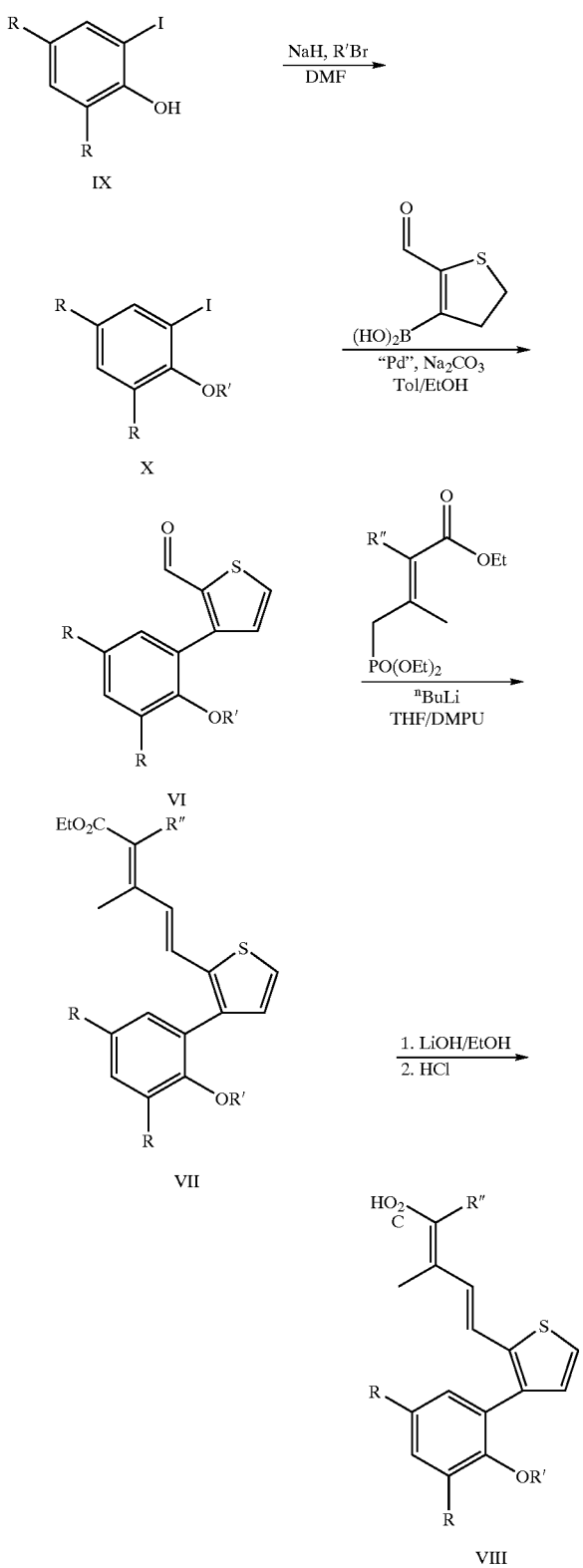

Scheme 10 describes an alternate synthetic method for producing the desired RXR modulator compounds in another preferred aspect of the invention. Scheme 10 shows the coupling of an arylboronic acid with a haloarylalkoxide (e.g., Structure X). The resulting alkoxyaryl-formylthiophene compound (e.g., Structure VI) is then coupled with a phosphonate and reduced to produce the desired RXR modulator compounds.

Example 76

(Compound X of Scheme 10, where R=isopropyl, R'=n-propyl). To 0.48 g of Sodium hydride (0.02 mol) dissolved in anhydrous N,N-Dimethyl-formamide (150.0 ml) in a flame dried 300 ml r.b. flask at 0° C. was added dropwise Compound IX (5.0 g, 0.016 mol) via solvation in anhydrous N,N-Dimethyl-formamide (15.0 ml). The mixture was stirred at 0° C. for 0.5 hours. After such time, 1-Bromopropane (2.22 g, 0.018 mol) was added dropwise via syringe. The resultant reaction mixture was allowed to warm to ambient temperature and stirred for 24.0 hours. Upon completion, the contents of the flask are poured into iced brine (200.0 ml) and stirred for 0.5 hours. The aqueous layer was extracted with diethyl ether. All organic layers were combined, washed (brine), dried (MgSO$_4$) and concentrated under reduced pressure. Purification by flash column chromatography (silica gel, hexanes/EtOAc, 9:1) yielded 5.18 g of X (91.2%) as a clear, colorless oil. Data for Compound X. $^1$H NMR (400 MHz, CDCl$_3$) δ 7.46 (d, J=1.9 Hz, 1H, Ar—H), 7.05 (d, J=1.9 Hz; 1H, Ar—H), 3.79 (t, J=6.6 Hz, 2H, R—O—CH$_2$—CH$_2$—CH$_3$), 3.31 (m, 1H, CH$_3$—CH—CH$_3$), 2.81 (m, 1H, CH$_3$—CH—CH$_3$), 1.89 (m, 2H, R—O—CH$_2$—CH$_2$—CH$_3$), 1.22 (d, J=6.8 Hz, 6H, CH$_3$—CH—CH$_3$), 1.21 (d, J=6.9 Hz, 6H, CH$_3$—CH—CH$_3$), 1.09 (t, J=7.4 Hz, 3H, R—O—CH$_2$—CH$_2$—CH$_3$).

Example 77

(Compound VI of Scheme 10, where R=isopropyl, R'=n-propyl). To 0.20 g of Compound X (0.578 mmol) dissolved in toluene/ethanol (1:1, 10.0 ml) in a 25 ml r.b. flask was added 2-Formylthiophene-3-boronic acid(0.082 g, 0.525 mmol), 2 N aqueous Na$_2$CO$_3$ (0.11 g, 1.05 mmol), and Tetrakis(triphenylphosphine) palladium(0) (0.061 g, 0.053 mmol). The reaction mixture was heated to 90° C. for 15.0 hours. The mixture was then cooled, poured into brine (25.0 ml), and stirred for 0.3 hours. The aqueous layer was extracted with EtOAc. All organic layers were combined, dried (MgSO$_4$), and concentrated under reduced pressure. Purification by flash column chromatography (silica gel, hexanes/EtOAc, 9:1) yielded 0.133 g of VI (70%) as a yellow oil. Data for Compound VI. $^1$H NMR (400 MHz, CDCl$_3$) δ 9.79 (d, J=0.9 Hz, 1H, R—COH), 7.71 (dd, J=4.9 Hz, J=0.9 Hz, 1H, thiophene-H), 7.25 (d, J=4.9 Hz, 1H, thiophene-H), 7.17 (d, J=2.2 Hz, 1H, Ar—H), 7.00 (d, J=2.2 Hz, 1H, Ar—H), 3.35 (m, 3H, R—O—CH$_2$—CH$_2$—CH$_3$, CH$_3$—CH—CH$_3$), 2.91 (m, 1H, CH$_3$—CH—CH$_3$), 1.47 (m, 2H, R—O—CH$_2$—CH$_2$—CH$_3$), 1.26 (d, J=6.9 Hz, 12H, CH$_3$—CH—CH$_3$), 0.79 (t, J=7.4 Hz, 3H, R—O—CH$_2$—CH$_2$—CH$_3$).

Example 78

(Compound VII of Scheme 10, where R=isopropyl, R'=n-propyl, R"=H). To 0.319 g of Triethyl 3-methyl-4-phosphonocrotonate (1.21 mmol) dissolved in THF/DMPU (1:2, 5.0 ml) in a flame dried 25 ml r.b. flask at −78° C. is added "BuLi (1.29 mmol, in Hexanes) dropwise. The mixture is allowed to stir for 0.3 hours. Compound VI is then added dropwise via solvation in THF/DMPU (1:2, 5.0 ml). The resultant mixture is allowed to stir at −78° C. for 0.5 hours, warmed to ambient temperature, and stirred for 3.0 hours. After such time, water (20.0 ml) is added and the mixture is allowed to stir for 0.2 hours. The aqueous layer was extracted with EtOAc. All organic layers were combined, washed (brine), dried (MgSO$_4$), and concentrated under reduced pressure. Purification by flash column chromatography (silica gel, hexanes/EtOAc, 9:1) yielded 0.154 g of VII (87%) as a yellow oil Data for Compound VII. $^1$H NMR (400 MHz, CDCl$_3$) δ 7.23 (d, J=5.2 Hz, 1H, thiophene-H), 7.16 (d, J=4.9 Hz, 1H, thiophene-H), 7.10 (d, J=2.1 Hz, 1H, Ar—H), 7.05 (d, J=15.8 Hz, 1H, =CH), 6.91 (d, J=2.2 Hz, 1H, Ar—H), 6.64 (d, J=15.8 Hz, 1H, =CH), 5.58 (s, 3H, =CH), 4.17 (q, J=7.6 Hz, 2H, CO$_2$—CH$_2$—CH$_3$), 3.36 (m, 3H, R—O—CH$_2$—CH$_2$—CH$_3$, CH$_3$—CH—CH$_3$), 2.89 (m, 1H, CH$_3$—CH—CH$_3$), 2.26 (s, 3H, CH$_3$), 1.48 (m, 2H, R—O—CH$_2$—CH$_2$—CH$_3$), 1.28 (m, 15H, CH$_3$—CH—CH$_3$, CO$_2$—CH$_2$—CH$_3$), 0.80 (t, J=7.4 Hz, 3H, R—O—CH$_2$—CH$_2$—CH$_3$).

EXAMPLE 79

(L11, Compound VIII of Scheme 10, where R=isopropyl, R'=n-propyl, R"=H). To 0.154 g of Compound VII (0.35 mmol) dissolved in ethanol (10.0 ml) in a 25 ml r.b. flask is added 2 M aqueous LiOH (1.05 mmol). The resultant mixture is heated to 90° C. for 3.0 hours. After such time, the reaction is cooled and concentrated under reduced pressure. The residue is taken up in 1 N aqueous HCl (25.0 ml). The flask is sealed and shaken for 1.0 minute. The resultant suspension was extracted with EtOAc. All organic layers were combined, washed (brine), dried (MgSO$_4$), and concentrated under reduced pressure. The concentrate is filtered through a short plug of silica gel (eluding with EtOAc), concentrated under reduced pressure and recrystallized from Acetonitrile to yield 0.142 g of VIII (98%) as a light yellow crystalline solid. Data for Compound VIII. $^1$H NMR (400 MHz, CDCl$_3$) δ 7.25 (d, J=4.8 Hz, 1H, thiophene-H), 7.17 (d, J=5.0 Hz, 1H, thiophene-H), 7.11 (d, J=2.2 Hz, 1H, Ar—H), 7.10 (d, J=15.8 Hz, 1H, =CH), 6.91 (d, J=2.2 Hz, 1H, Ar—H), 6.66 (d, J=15.8 Hz, 1H, =CH), 5.87 (s, 3H, =CH), 3.35 (m, 3H, R—O—CH$_2$—CH$_2$—CH$_3$, CH$_3$—CH—CH$_3$), 2.90 (m, 1H, CH$_3$—CH—CH$_3$), 2.28 (s, 3H, CH$_3$), 1.48 (m, 2H, R—O—CH$_2$—CH$_2$—CH$_3$), 1.27 (d, J=6.8 Hz, 6H, CH$_3$—CH—CH$_3$), 1.26 (d, J=6.9 Hz, 6H, CH$_3$—CH—CH$_3$), 0.80 (t, J=7.4 Hz, 3H, R-O—CH$_2$—CH$_2$—CH$_3$).

Scheme 11a

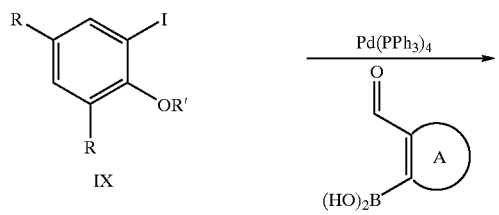

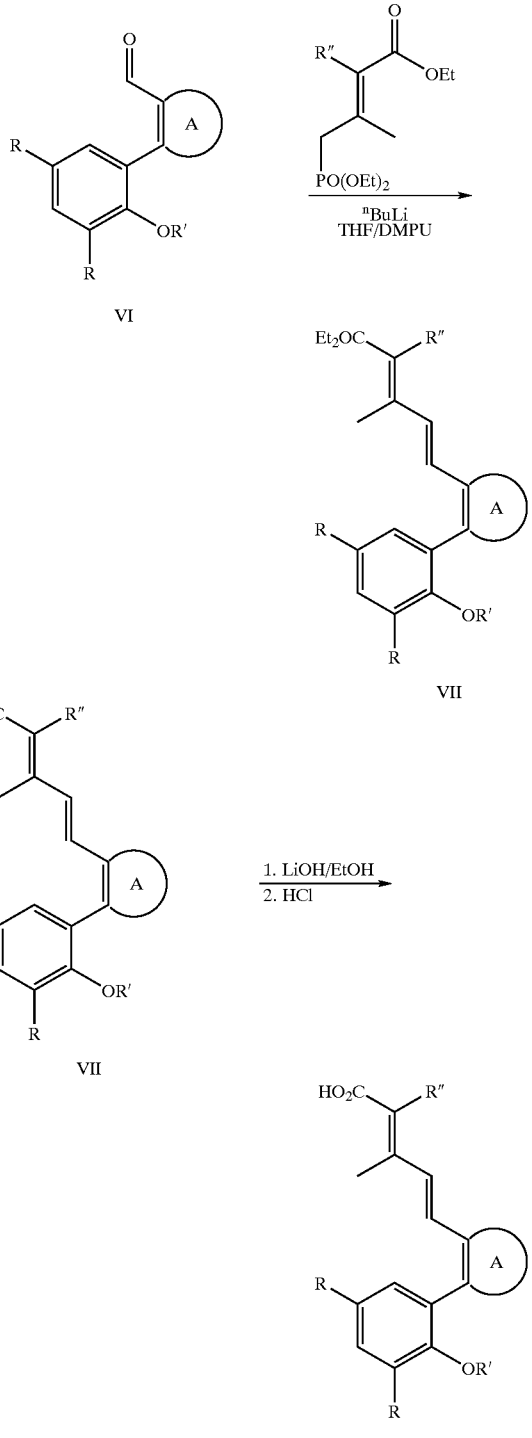

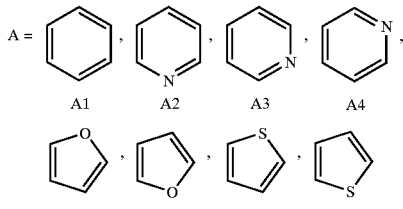

The following acids were prepared according to Scheme 11a (procedure described in Schemes 1 and 2). Scheme 11a depicts the preparation of compound having various cyclic A substituents. The methodology employed here is similar to that depicted in Scheme 10.

Example 80

(Compound VI of Scheme 11a, where R=isopropyl R'=methyl A=A1). A mixture of 1.1478 g (3.6 mmol) of 3,5-diisopropyl-2-methoxy iodobenzene, 593 mg (3.97 mmol) of 2-formylbenzeneboronic acid and 208 mg (0.18 mmol) of tetrakistriphenylphosphine palladium, 2 ml of 2N aqueous sodium carbonate in 20 ml of toluene and 20 ml ethanol was heated to reflux. After completion (TLC), 40 mL of 10% EtOAc/hexane was added and the solution was filtered through a short plug of silica gel and rinsed with 300 mL of 10% ethyl acetate/hexane. The filtrate was concentrated in vacuo. The residue was purified by flash column chromatography (SiO$_2$, 4×20 cm, 10% EtOAc/hexane as eluent) to afford 931 mg (87% yield, theoretical 1.0692 g) of VI as a colorless oil. R$_f$ 0.50 (SiO$_2$, 10% EtOAc-hexane). $^1$H NMR (400 MHz, CDCl$_3$) 9.83 (s, 1H), 8.03 (d, J=7.7 Hz, 1H), 7.65 (dd, J=8.8, 6.3 Hz, 1H), 7.48 (m, 2H), 7.17 (d, J=2.2 Hz, 1H), 7.00 (d, J=2.2 Hz, 1H), 3.34 (septet, J=6.9 Hz, 1H), 3.19 (s, 3H), 2.92 (septet, J=6.9 Hz, 1H), 1.27 (d, J=6.9 Hz, 12H).

Example 81

(Compound VII of Scheme 11a, where R=isopropyl, R'=methyl, R"=H, A=A1). A solution of 2.17 g (8.2 mmol) of triethyl 3-methyl-4-phosphonocrotonate in a 2:1 mixture of tetrahydrofuran/1,3-dimethyl-3,4,5,6-tetrahydro-2(1H)-pyrimidinone (THF/DMPU) (15 mL) was cooled to −78° C. and treated with 3.3 mL of n-butyllithium (2.5 M in hexane, 8.25 mmol). The resulting solution was stirred at −78° C. for 15 min. To this solution was added slowly a solution of 925 mg (2.7 mmol) of VI in a 2:1 mixture of THF/DMPU (10 mL) via syringe. The resulting mixture was stirred at −78° C. for additional 1 h and allowed to warm to 0° C. After completion (TLC), the reaction mixture was quenched with water (20 mL) and extracted with EtOAc (3×50 mL). The combined organic layers was washed with saturated aqueous sodium chloride solution (100 mL), dried (MgSO$_4$), filtered and concentrated in vacuo. The crude residue was purified by flash column chromatography (SiO$_2$, 4×20 cm, 5% ethyl acetate/hexane as eluent) to afford 467 mg (37% yield, theoretical 1.28g) of VII as a colorless oil. R$_f$ 0.73 (SiO$_2$, 10% EtOAc-hexane). $^1$H NMR (400 MHz, CDCl$_3$) 7.70 (dd, J=7.5, 2.1 Hz, 1H), 7.40–7.32 (m, 3H), 7.11 (d, J=2.1 Hz, 1H), 6.87 (d, J=16 Hz, 1H), 6.85 (d, J=2.1 Hz, 1H), 6.74 (d, J=16 Hz, 1H), 5.85 (s, 1H), 4.16 (q, J=7.1 Hz, 2H), 3.34 (septet, J=6.9 Hz, 1H), 3.24 (s, 3H), 2.89 (septet, J=6.9 Hz, 1H), 2.17 (s, 3H), 1.31 (t, J=7.1 Hz, 3H), 1.27 (d, J=6.9 Hz, 6H), 1.24 (d, J=6.9 Hz, 6H).

Example 82

(L44, Compound VIII of Scheme 11a, where R=isopropyl, R'=methyl, R"=H, A=A1). To a solution of 295 mg (0.73 mmol) of VII in a 2:2:1 mixture of THF/EtOH/H$_2$O (10 mL) was added 91 mg (2.18 mmol) of LiOH. The resulting mixture was heated to reflux for 3 hours. After cooling to room temperature, the mixture was acidified with HCl (1N aqueous) to pH=2 and extracted with EtOAc (2×20 mL). The combined organic layers was dried (MgSO$_4$), filtered and concentrated in vacuo. The crude acid was recrystallized from acetonitrile to give 142 mg (52%, theoretical 275 mg) of VIII as a white solid. $^1$H NMR (400 MHz, CDCl$_3$) 7.71 (dd, J=6.4, 2.6 Hz, 1H), 7.42–7.34 (m, 3H), 7.11 (d, J=2.2 Hz, 1H), 6.92 (d, J=16 Hz, 1H), 6.86 (d, J=2.2 Hz, 1H), 6.76 (d, J=16 Hz, 1H), 5.87 (s, 1H), 3.34 (septet, J=6.9 Hz, 1H), 3.24 (s, 3H), 2.89 (septet, J=6.9 Hz, 1H), 2.18 (s, 3H), 1.24 (d, J=6.9 Hz, 12H).

Example 83

(L45, Compound VIII of Scheme 11a, where R=isopropyl, R'=n-butyl, R"=H, A=A1). This compound was prepared in the manner previously described for Compound VIII of Example 82, starting from the intermediate IX where R'=n-butyl, synthesized in the manner described in Example 76 using 1-bromobutane instead of 1-bromopropane. $^1$H NMR (400 MHz, CDCl$_3$) 7.71 (dd, J=6.3, 2.7 Hz, 1H), 7.42–7.32 (m, 3H), 7.11 (d, J=2.1 Hz, 1H), 6.95 (d, J=16 Hz, 1H), 6.85 (d, J=2.1 Hz, 1H), 6.75 (d, J=16 Hz, 1H), 5.87 (s, 1H), 3.40–3.20 (m, 3H), 2.88 (septet, J=6.9 Hz, 1H), 2.19 (s, 3H), 1.27 (m, 2H), 1.24 (d, J=6.9 Hz, 12H), 1.09 (m, 2H), 0.68 (t, J=7.4 Hz, 3H).

Example 84

(L46, Compound VIII of Scheme 11a, where R=isopropyl, R'=n-propyl, R"=H, A=A1). This compound was prepared in the manner previously described for Compound VIII of Example 82, starting from the intermediate IX where R'=n-propyl, synthesized in the manner described in Example 76. $^1$H NMR (400 MHz, CDCl$_3$) 7.71 (dd, J=6.3, 2.7 Hz, 1H), 7.42–7.32 (m, 3H), 7.11 (d, J=2.2 Hz, 1H), 6.95 (d, J=16 Hz, 1H), 6.85 (d, J=2.2 Hz, 1H), 6.75 (d, J=16 Hz, 1H), 5.87 (s, 1H), 3.40–3.20 (m, 3H), 2.89 (septet, J=6.9 Hz, 1H), 2.19 (s, 3H), 1.34 (m, 2H), 1.24 (d, J=6.9 Hz, 12H), 0.64 (t, J=7.4 Hz, 3H).

Example 85

(L47, Compound VIII of Scheme 11a, where R=isopropyl, R'=1-fluoropropyl, R"=H, A=A1). This compound was prepared in the manner previously described for Compound VIII of Example 82, starting from the intermediate IX where R'=1-fluoropropyl, synthesized in the manner described in Example 76 using 1-fluoro-3-bromopropane instead of 1-bromopropane. $^1$H NMR (400 MHz, CDCl$_3$) 7.71 (d, 1H, J=7.5 Hz, 1H), 7.40–7.35 (m, 3H), 7.12 (d, J=2.1 Hz, 1H), 6.91 (d, J=16 Hz, 1H), 6.87 (d, J=2.1 Hz, 1H), 6.76 (d, J=16 Hz, 1H), 5.87 (s, 1H), 4.29 (dt, J=17.9, 6.1 Hz, 1H), 4.18 (dt, J=17.9, 6.1 Hz, 1H), 3.45 (t, J=6.0 Hz, 1H), 3.40 (t, J=6.0 Hz, 1H), 3.30 (septet, J=6.9 Hz, 1H), 2.89 (septet, J=6.9 Hz, 1H), 2.18 (s, 3H), 1.69 (m, 2H), 1.25 (d, J=6.9 Hz, 12H).

Example 86

(L48, Compound VIII of Scheme 11a, where R=isopropyl, R'=ethyl, R"=H, A=A1). This compound was prepared in the manner previously described for Compound VIII of Example 82, starting from the intermediate IX where R'=ethyl, synthesized in the manner described in Example 76 using 1-bromoethane instead of 1-bromopropane. $^1$H NMR (400 MHz, CDCl$_3$) 7.72 (dd, J=6.1, 2.7 Hz, 1H), 7.43–7.32 (m, 3H), 7.11 (d, J=2.1 Hz, 1H), 6.95 (d, J=16 Hz, 1H), 6.85 (d, J=2.1 Hz, 1H), 6.75 (d, J=16 Hz, 1H), 5.87 (s, 1H), 3.37 (m, 3H), 2.88 (septet, J=6.9 Hz, 1H), 2.19 (s, 3H), 1.24 (d, J=6.9 Hz, 12H), 0.94 (t, J=7.1 Hz, 3H).

Example 87

(L49, Compound VIII of Scheme 11a, where R=isopropyl, R'=1,1-difluoroethyl, R"=H, A=A1). This compound was prepared in the manner previously described for Compound VIII of Example 82, starting from the intermediate IX where R'=1,1-difluoroethyl, synthesized in the manner described in Example 76 using 1,1-difluoro-2-bromoethane instead of 1-bromopropane. $^1$H NMR (400 MHz, CDCl$_3$) 7.72 (dd, J=7.2, 2.3 Hz, 1H), 7.43–7.35 (m, 3H), 7.14 (d, J=2.2 Hz, 1H), 6.89 (d, J=2.2 Hz, 1H), 6.88 (d, J=16 Hz, 1H), 6.76 (d, J=16 Hz, 1H), 5.88 (s, 1H), 5.48 (tt, J=55.5, 4.2 Hz, 1H), 3.48 (dtd, J=27, 12.8, 4.2 Hz, 2H), 3.35 (septet, J=6.9 Hz, 1H), 2.90 (septet, J=6.9 Hz, 1H), 2.18 (s, 3H), 1.25 (d, J=6.9 Hz, 12H).

Example 88

(L50, Compound VIII of Scheme 11a, where R=tert-butyl, R'=methyl, R"=H, A=A1). This compound was prepared in the manner previously described for Compound VIII in Example 82 except that 3,5-ditertbutyl-2-methoxy iodobenzene was used instead of 3,5-diisopropyl-2-methoxy-iodobenzene in Example 80. $^1$H NMR (400 MHz, CDCl$_3$) 7.73 (dd, J=5.5, 3.7 Hz, 1H), 7.44–7.34 (m, 4H), 7.02 (d, J=2.4 Hz, 1H), 6.96 (d, J=16 Hz, 1H), 6.78 (d, J=16 Hz, 1H), 5.88 (s, 1H), 3.16 (s, 3H), 2.19 (s, 3H), 1.43 (s, 9H), 1.31 (s, 9H).

Example 89

(L51, Compound VIII of Scheme 11a, where R=tert-butyl, R'=ethyl, R"=H, A=A1). This compound was prepared in the manner previously described for Compound VIII in Example 82 except that 3,5-ditertbutyl-2-methoxy iodobenzene was used instead of 3,5-diisopropyl-2-methoxy-iodobenzene in Example 80 and Compound IX was synthesized in the manner described in Example 76 using 1,1-difluoro-2-bromoethane instead of 1-bromopropane. $^1$H NMR (500 MHz, CDCl$_3$) 7.72 (dd, J=5.6, 3.7 Hz, 1H), 7.42 (dd, J=5.6, 3.7 Hz, 1H), 7.36 (m, 3H), 7.01 (d, J=2.8 Hz, 1H), 6.99 (d, J=15.9 Hz, 1H), 6.77 (d, J=15.9 Hz, 1H), 5.88 (s, 1H), 3.35 (dq, J=5.8 Hz, 2H), 2.21 (s, 3H), 1.44 (s, 9H), 1.30 (s, 9H), 0.92 (t, J=7.0 Hz, 3H).

Example 90

(L52, Compound VIII of Scheme 11a, where R=tert-butyl, R'=n-butyl, R"=H, A=A1). This compound was prepared in the manner previously described for Compound VIII in Example 82 except that 3,5-ditertbutyl-2-methoxy iodobenzene was used instead of 3,5-diisopropyl-2-methoxy-iodobenzene in Example 80 and Compound IX was synthesized in the manner described in Example 76 using 1-bromobutane instead of 1-bromopropane. $^1$H NMR (500 MHz, CDCl$_3$) 7.71 (m, 1H), 7.40 (m, 1H), 7.36 (m, 3H), 7.00 (d, J=2.7 Hz, 1H), 6.97 (d, J=16 Hz, 1H), 6.76 (d, J=16 Hz, 1H), 5.88 (s, 1H), 3.31 (m, 2H), 2.20 (d, J=1.0 Hz, 3H), 1.43 (s, 9H), 1.31 (s, 9H), 1.07 (m, 2H), 0.67 (t, J=7.3 Hz, 3H).

Example 91

(L53, Compound VIII of Scheme 11a, where R=tert-butyl, R'=1-fluoropropyl, R"=H, A=A1). This compound was prepared in the manner previously described for Compound VIII in Example 82 except that 3,5-ditertbutyl-2-methoxy iodobenzene was used instead of 3,5-diisopropyl-2-methoxy-iodobenzene in Example 80 and Compound IX was synthesized in the manner described in Example 76 using 1-fluoro-3-bromopropane instead of 1-bromopropane. $^1$H NMR (500 MHz, CDCl$_3$) 7.73 (m, 1H), 7.38 (m, 4H), 7.02 (d, J=2.4 Hz, 1H), 6.93 (d, J=15.9 Hz, 1H), 6.78 (d, J=15.9 Hz, 1H), 5.89 (s, 1H), 4.26 (m, 2H), 3.44 (m, 2H), 2.19 (d, J=0.7 Hz, 3H), 1.68 (m, 2H), 1.43 (s, 9H), 1.31 (s, 9H).

Example 92

(L54, Compound VIII of Scheme 11a, where R=tert-butyl, R'=n-propyl, R"=H, A=A1). This compound was prepared in the manner previously described for Compound VIII in Example 82 except that 3,5-ditertbutyl-2-methoxy iodobenzene was used instead of 3,5-diisopropyl-2-methoxy-iodobenzene in Example 80 and Compound IX was synthesized in the manner described in Example 76. $^1$H NMR (500 MHz, CDCl$_3$) 7.71 (dd, J=5.6, 3.7 Hz, 1H), 7.41 (dd, J=5.6, 3.7 Hz, 1H), 7.36 (d, J=2.4 Hz, 1H), 7.35 (m, 2H), 7.00 (d, J=2.4 Hz, 1H), 6.97 (d, J=15.9 Hz, 1H), 6.76 (d, J=15.9 Hz, 1H), 5.87 (s, 1H), 3.27 (m, 2H), 2.20 (d, J=0.9 Hz, 3H), 1.43 (s, 9H), 1.34 (m, 2H), 1.31 (s, 9H), 0.64 (t, J=7.3 Hz, 3H).

Example 93

(L55, Compound VIII of Scheme 11a, where R=isopropyl, R'=ethyl, R"=H, A=A6). This compound was prepared in the manner previously described for Compound VIII in Example 82 except that Compound IX was synthesized in the manner described in Example 76 using 1-bromoethane instead of 1-bromopropane and 2-formylfuran boronic acid was used instead of 2-formylbenzene boronic acid in Example 80. $^1$H NMR (400 MHz, CDCl$_3$) δ 7.49 (d, J=1.9 Hz, 1H), 7.16 (d, J=2.2 Hz, 1H), 7.09 (d, J=2.2 Hz, 1H), 7.07 (d, J=15.9 Hz, 1H), 6.71 (d, J=1.9 Hz, 1H), 6.57 (d, J=15.9 Hz, 1H), 5.86 (s, 1H), 3.57 (dd, J=14.0, 6.9 Hz, 2H), 3.39 (dt, J=13.9, 6.9 Hz, 1H), 2.90 (dt, J=13.9, 6.9 Hz, 1H), 2.33 (s, 3H), 1.26 (d, J=6.9 Hz, 6H), 1.25 (d, J=6.9 Hz, 6H), 1.16 (t, J=7.1 Hz, 3H).

Example 94

(L56, Compound VIII of Scheme 11a, where R=isopropyl, R'=1-fluoropropyl, R"=H, A=A6). This compound was prepared in the manner previously described for Compound VIII in Example 82 except that Compound IX was synthesized in the manner described in Example 76 using 1-fluoro-3-bromopropane instead of 1-bromopropane and 2-formylfuran boronic acid was used instead of 2-formylbenzene boronic acid in Example 80. $^1$H NMR (400 MHz, CDCl$_3$) δ 7.50 (d, J=1.9 Hz, 1H), 7.17 (d, J=2.3 Hz, 1H), 7.09 (d, J=2.3 Hz, 1H), 6.99 (d, J=15.9 Hz, 1H), 6.72 (d, J=1.9 Hz, 1H), 6.57 (d J=15.9 Hz, 1H), 5.86 (s, 1H), 4.57 (t, J=5.9 Hz, 1H), 4.45 (t, J=5.8 Hz, 1H), 3.63 (t, J=6.0 Hz, 2H), 3.34 (dt, J=13.9, 6.9 Hz, 1H), 2.91 (dt, J=13.9, 6.9 Hz, 1H), 2.31 (s, 3H), 1.95 (m, 1H), 1.90 (m, 1H), 1.27 (d, J=6.9 Hz, 6H), 1.26 (d, J=6.9 Hz, 6H).

Example 95

(L57, Compound VIII of Scheme 11a, where R=isopropyl, R'=n-butyl, R"=H, A=A8). This compound was prepared in the manner previously described for Compound VIII in Example 82 except that Compound IX was synthesized in the manner described in Example 76 using 1-bromobutane instead of 1-bromopropane and 2-formylthiophene boronic acid was used instead of 2-formylbenzene boronic acid in Example 80. $^1$H NMR (400 MHz, CDCl$_3$) δ: 7.33 (m, 2H), 7.13 (d, J=2.2 Hz, 1H), 6.97 (d, J=2.2 Hz, 1H), 6.95 (d, J=15.9 Hz, 1H), 6.68 (d, J=16.0 Hz, 1H), 5.87 (s, 1H), 3.42 (t, J=6.4 Hz, 2H), 3.35 (dt, J=13.8, 6.9 Hz, 1H), 2.88 (dt, J=13.8, 6.9 Hz, 1H), 2.28 (s, 3H), 1.55 (m, 2H), 1.26 (d, J=6.9 Hz, 6H), 1.25 (d, J=6.9 Hz, 6H), 1.24 (m, 2H), 0.79 (t, J=7.3 Hz, 3H).

Example 96

(L58, Compound VIII of Scheme 11a, where R=1-ethyl, 1,1-dimethylbutyl, R'=1-difluoroethyl, R''=H, A=A6). This compound was prepared in the manner previously described for Compound VIII in Example 82 except that Compound IX was synthesized in the manner described in Example 76 using 1,1-difluoro-2-bromoethane instead of 1-bromopropane and 2-formylfuran boronic acid was used instead of 2-formylbenzene boronic acid in Example 80. $^1$H NMR (400 MHz, CDCl$_3$) δ: 7.53 (d, J=2.2 Hz, 1H), 7.29 (d, J=2.0 Hz, 1H), 7.19 (d, J=2.0 Hz, 1H), 6.89 (d, J=15.9 Hz, 1H), 6.73 (d, J=2.2 Hz, 1H), 6.58 (d, J=15.9 Hz, 1H), 5.87 (s, 1H), 5.77 (dt, J=55.2, 4.0 Hz, 1H), 3.59 (dt, J=13.5, 4.0, 2H), 2.30 (s, 3H), 1.84 (dd, J=15.0, 7.5 Hz, 2H), 1.63 (dd, J=15.0, 7.5 Hz, 2H), 1.40 (s, 3H), 1.28 (s, 6H), 1.27 (d, J=7.2 Hz, 3H), 0.88 (t, J=6.6 Hz, 3H), 0.69 (dd, J=14.4, 7.4 Hz, 3H).

Scheme 11b

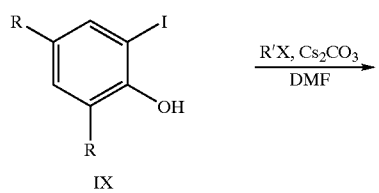

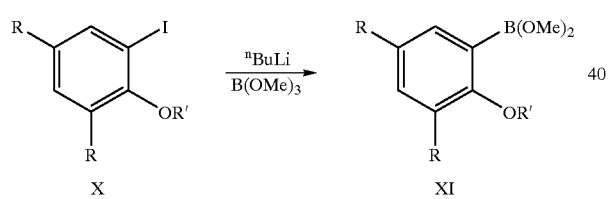

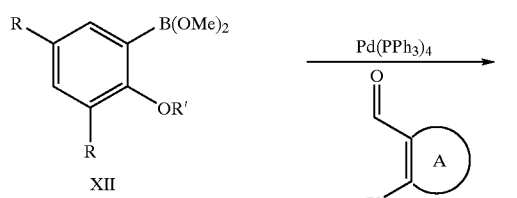

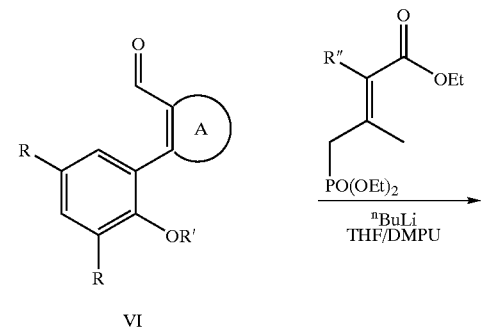

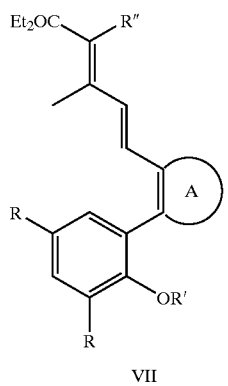

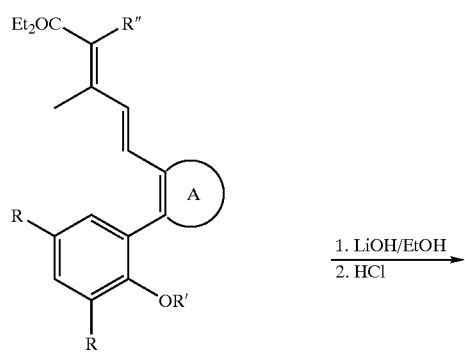

Example 97

(Compound VI of Scheme 11b where R=isopropyl, R'=ethyl, A=A3). A mixture of 740 mg (3.0 mmol) of 3-5-diisopropyl-2-ethoxy benzeneboronic acid, 500 mg (2.7 mmol) of 3-bromo-4-formylpyridine and 155 mg (0.13 mmol) of tetrakistriphenylphosphine palladium, 1.5 ml of 2N aqueous sodium carbonate in 10 ml of toluene and 10 ml ethanol was heated to reflux. After completion (TLC), 40 mL of 10% EtOAc/hexane was added and the solution was filtered through a short plug of silica gel and rinsed with additional 10% ethyl acetate/hexane (300 mL). The filtrate was concentrated in vacuo. The residue was purified by flash column chromatography (SiO$_2$, 3×20 cm, 10% EtOAc/hexane as eluent) to afford 731 mg (91%, theoretical 805 mg) of VI as a colorless oil. R$_f$ 0.26 (SiO$_2$, 10% EtOAc-hexane). $^1$H NMR (400 MHz, CDCl$_3$) 9.86 (s, 1H), 8.81 (s, 1H), 8.80 (d, J=7.0 Hz, 1H), 7.78 (d, J=4.9 Hz, 1H), 7.23 (d, J=2.2 Hz, 1H), 7.06 (d, J=2.2 Hz, 1H), 3.47 (br. s, 1H), 3.34 (septet, J=6.9 Hz, 1H), 3.17 (br. s, 1H), 2.95 (septet, J=6.9 Hz, 1H), 1.29 (d, J=6.9 Hz, 12H), 0.94 (t, J=6.9 Hz, 3H).

Example 98

(Compound VII of Scheme 11b where R=isopropyl, R'=ethyl, A=A3, R"=H). A solution of 1.935 g (7.3 mmol) of triethyl 3-methyl-4-phosphonocrotonate in a 2:1 mixture of tetrahydrofuran/1,3-dimethyl-3,4,5,6-tetrahydro-2(1H)-pyrimidinone (THF/DMPU) (20 mL) was cooled to −78° C. and treated with 3.0 mL of n-butyllithium (2.5 M in hexane, 7.5 mmol). The resulting solution was stirred under nitrogen atmosphere at −78° C. for 15 min. To this solution was added slowly a solution of 731 mg (2.4 mmol) of VI in a 2:1 mixture of THF/DMPU (15 mL) via syringe. The resulting mixture was stirred at −78° C. for additional 1 hour. After completion (TLC), the reaction mixture was quenched with water (20 mL) and extracted with EtOAc (3×50 mL). The combined organic layers was washed with saturated aqueous sodium chloride solution (100 mL), dried (MgSO$_4$), filtered and concentrated in vacuo. The crude residue was purified by flash column chromatography (SiO$_2$, 4×20 cm, 10% ethyl acetate/hexane as eluent) to afford 766 mg (74%, theoretical 1.029 g) of VII as a colorless oil. R$_f$ 0.27 (SiO$_2$, 20% EtOAc-hexane). $^1$H NMR (400 MHz, CDCl$_3$) 8.62 (s, 1H), 8.56 (d, J=5.3 Hz, 1H), 7.52 (d, J=5.3Hz, 1H), 7.16 (d, J=2.2 Hz, 1H), 6.88 (d, J=16 Hz, 1H), 6.86 (d, J=2.2 Hz, 1H), 6.81 (d, J=16 Hz, 1H), 5.92 (s, 1H), 4.18 (q, J=7.1 Hz, 2H), 3.36 (m, 3H), 2.90 (septet, J=6.9 Hz, 1H), 2.19 (s, 3H), 1.28 (d, J=6.9 Hz, 6H), 1.25 (d, J=6.9 Hz, 6H), 0.95 (t, J=6.9 Hz, 3H).

Example 99

(L59, Compound VIII of Scheme 11b where R=isopropyl, R'=ethyl, R"=H, A=A3). To a solution of 766 mg (1.8 mmol) of VII in a 2:2:1 mixture of THF/EtOH/H$_2$O (30 mL) was added 381 mg (9.1 mmol) of LiOH. The resulting mixture was heated to reflux for 3 hours. After cooling to room temperature, the mixture was acidified with HCl (1N aqueous) to pH=2 and extracted with EtOAc (2×50 mL). The combined organic layers was dried (MgSO$_4$), filtered and concentrated in vacuo. The crude acid was recrystallized from acetonitrile to give 372 mg (52%, theoretical 715 mg) of VIII as a white solid. $^1$H NMR (400 MHz, CDCl$_3$) 8.63 (s, 1H), 8.58 (d, J=5.3 Hz, 1H), 7.55 (d, J=5.3 Hz, 1H), 7.16 (d, J=2.2 Hz, 1H), 6.91 (d, J=16 Hz, 1H), 6.87 (d, J=2.2 Hz, 1H), 6.85 (d, J=16 Hz, 1H), 5.97 (s, 1H), 3.36 (m, 3H), 2.90 (septet, J=6.9 Hz, 1H), 2.21 (s, 3H), 1.25 (d, J=6.9 Hz, 12H), 0.95 (t, J=6.9 Hz, 3H).

Example 100

(L60, Compound VIII of Scheme 11b where R=isopropyl, R'=ethyl, R"=H, A=A2). This compound was prepared in the manner previously described for Compound VIII in Example 99. $^1$H NMR (400 MHz, CDCl$_3$) 8.65 (dd, J=4.7, 1.4 Hz, 1H), 7.99 (dd, J=8.0, 1.4 Hz, 1H), 7.31 (dd, J=8.0, 4.7 Hz, 1H), 7.16 (d, J=2.3 Hz, 1H), 7.03 (d, J=2.3 Hz, 1H), 6.86 (d, J=16.1 Hz, 1H), 6.74 (d, J=16.1 Hz, 1H), 5.88 (s, 1H), 3.47 (br. s, 1H), 3.37 (br. s, 1H), 3.35 (septet, J=6.9 Hz, 1H), 2.90 (septet, J=6.9 Hz, 1H), 2.18 (s, 3H), 1.25 (d, J=6.9 Hz, 12H), 0.92 (t, J=7.0 Hz, 3H).

Example 101

(L61, Compound VIII of Scheme 11b where R=isopropyl, R'=ethyl, R"=H, A=A4). This compound was prepared in the manner previously described for Compound VIII in Example 99. $^1$H NMR (400 MHz, CDCl$_3$) 8.94 (s, 1H), 8.55 (d, J=5.0 Hz, 1H), 7.39 (d, J=5.0 Hz, 1H), 7.17 (d, J=2.2 Hz, 1H), 6.88 (d, J=16.3 Hz, 1H), 6.84 (d, J=2.2 Hz, 1H), 6.83 (d, J=16.3 Hz, 1H), 5.96 (s, 1H), 3.90 (q, 2H, J=6.9 Hz, 2H), 3.36 (septet, J=6.9 Hz, 1H), 2.89 (septet, J=6.9 Hz, 1H), 2.24 (s, 3H), 1.27 (d, J=6.9 Hz, 6H), 1.24 (d, J=6.9 Hz, 6H), 0.99 (t, J=6.9 Hz, 3H).

Example 102

(L62, Compound VIII of Scheme 11b where R=tert-butyl, R'=ethyl, R"=H, A=A3). This compound was prepared in the manner previously described for Compound VIII in Example 99. $^1$H NMR (400 MHz, CDCl$_3$) 8.66 (s, 1H), 8.59 (d, J=5.4 Hz, 1H), 7.57 (d, J=5.4 Hz, 1H), 7.41 (d, J=2.4 Hz, 1H), 7.01 (d, J=2.4 Hz, 1H), 6.94 (d, J=16.1 Hz, 1H), 6.89 (d, J=16.1 Hz, 1H), 5.98 (s, 1H), 3.38 (quintet, J=7.0 Hz, 1H), 3.32 (quintet, J=7.0 Hz, 1H), 2.23 (s, 3H), 1.44 (s, 9H), 1.32 (s, 9H), 0.93 (t, J=7.0 Hz, 3H).

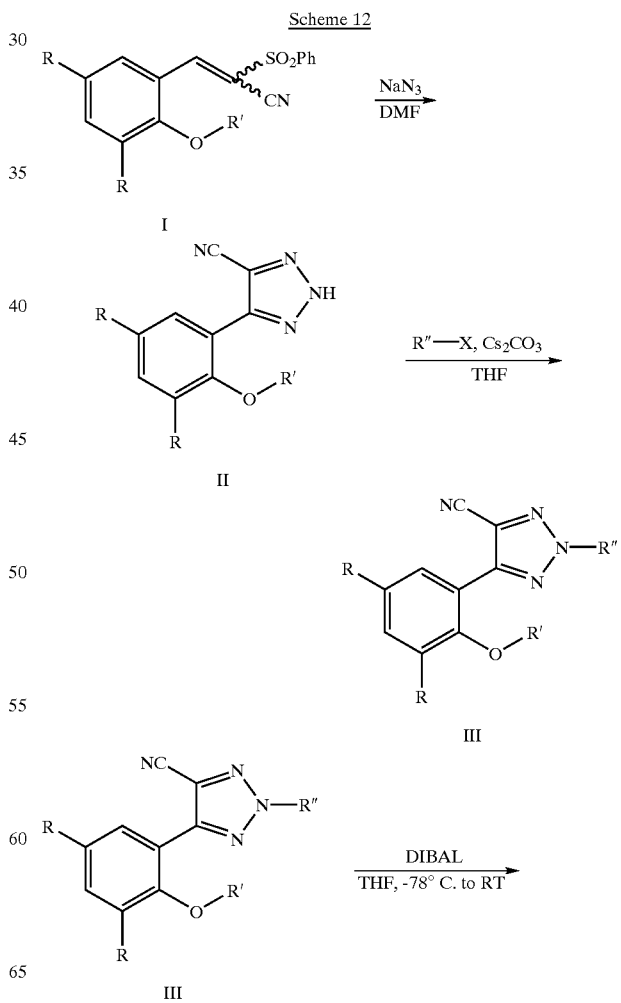

Scheme 12

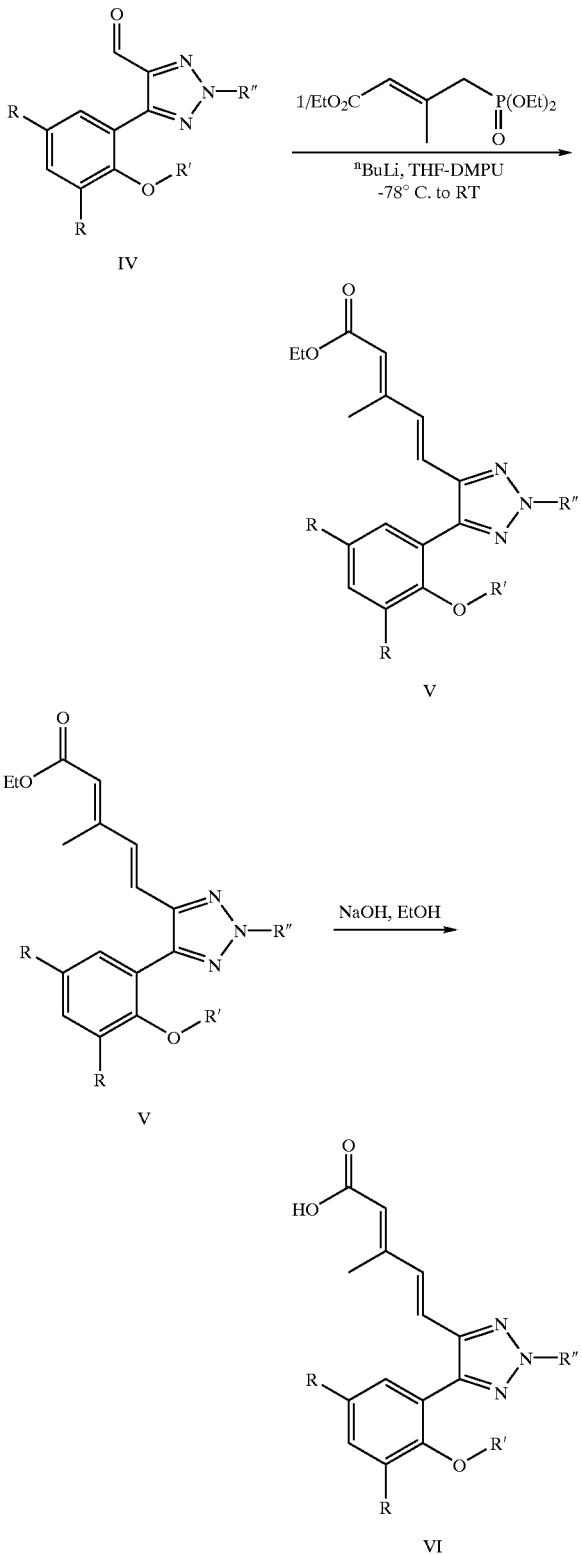

Scheme 12 depicts the preparation of triazole derivatives of type VI employed in Examples 103–108.

Example 103

(Compound I of Scheme 12, where R=tert-butyl, R'=methyl). To a mixture of 5.92 g (0.02474 mol) of 1-methoxy-2,4-di-tert-butyl benzaldehyde and 4.48 g (0.02474 mol) of thiophenysulfonylacetonitrile in DMF (20 ml) and benzene (40 ml) was added 1 ml of piperidine. The resulting mixture was heated to reflux until completion. After cooling to room temperature, water was added and the mixture was extracted with ethyl acetate (2×50 ml). The organic fractions were combined and dried over $MgSO_4$. The solvents were evaporated under reduced pressure and the resulting oil was purified over silica gel (eluent:methylene chloride/hexane: 50/50) to give 6.31 g (yield: 62%) of I. $^1$H NMR (CDCl$_3$): 8.51 (s, 1H), 8.05 (m, 2H), 7.96 (s, 1H), 7.63 (m, 3H), 7.58 (s, 1H), 3.80 (s, 3H), 1.40 (s, 9H), 1.30 (s, 3H).

Example 104

(Compound II of Scheme 12, where R=tert-butyl, R'=methyl). To a mixture of 6.31 g (0.01533 mol) of Compound I and 1.00 g (0.01533 mol)) of sodium azide in 40 ml DMF was heated to 100° C. behind an explosion shield. The mixture was stirred at this temperature until complexion and the solvents were evaporated under reduced pressure. Water was added and the solution was extracted with ethyl acetate. The organic layer was dried over a $MgSO_4$ and the residue purified over silica gel (eluent:ethyl acetate/methylene chloride: 0/100 to 10/90% gradient to give 3.50 g (54% yield) of II. $^1$H NMR (CDCl$_3$): 7.95 (m, 2H), 7.66 (b, 1H), 7.53 (m, s, 4H), 3.46 (s, 3H), 1.44 (s, 9H), 1.35 (s, 9H).

Example 105

(Compound III of Scheme 12 where R=tert-butyl, R'=methyl, R"=methyl). A mixture of 600 mg (0.06 mmol) of Compound II in 10 ml of dry THF, 1 ml of methyliodide and 2 g of cesium carbonate was stirred until complete consumption of starting material. The solvents were evaporated under reduced pressure and the residue was purified over silica gel (eluent:methylene chloride/hexane (1/1) to give 0.38 g (63% yield) of III. $^1$H NMR (CDCl$_3$): 7.82 (s, 1H), 7.66 (b, 1H), 4.46 (s, 3H), 3.46 (s, 3H), 1.38 (s, 9H).

Example 106

(Compound IV of Scheme 12 where R=tert-butyl, R'=methyl, R"=methyl). To a mixture of 380 mg of Compound III and 5 ml of dry THF at −78° C., was added 1.0 ml of 1 M DIBAL. The mixture was warmed to room temperature and checked by TLC. Ethyl acetate 15 ml and water 10 ml were added to the reaction mixture. The organic layer was dried over $MgSO_4$ and evaporated under reduced pressure. The residual oil was purified over silica gel (eluent:methylene chloride/hexane (1:1) to give 112 mg (yield: 77%) Compound IV. $^1$H NMR (CDCl$_3$): 10.11 (s, 1H), 7.86 (s, 1H), 7.66 (b, 1H), 4.54 (s, 3H), 3.46 (s, 3H), 1.38 (s, 9H).

Example 107

(Compound V of Scheme 12, where R=tert-butyl, R'=methyl, R"=methyl). A mixture of 112 mg (0.367 mmol) of Compound IV, 340 mg (1.46 mmol,) of triethyl 3-methyl-4-phosophonocrotonate in 10 ml of THF and 1 ml of DMPU was cooled to −78° C. N-BuLi (1.6M) 0.9 ml was slowly added to the solution. The reaction was warmed to room temperature and stirred overnight. Water was added (15 ml) and the solution was extracted with ethyl acetate. The organic layer was washed with water and brine, then dried over $MgSO_4$. Evaporation of the solvents gave a yellow oil.

The residual oil was purified over silica gel (eluent:methylene chloride/hexane (1:1) to give 170 mg (yield: 47%) Compound V as a mixture of isomers. $^1$H NMR (CDCl$_3$): 7.86 (s, 1H), 7.66 (b, 1H), 7.14 (dd, 2H), 6.59 (s, 1H), 4.46 (s, 3H) 4.18 (m, 2H), 3.46 (s, 3H), 2.32, 2.23 (s,s, 3H), 1.38 (s, 9H), 1.30 (t, 3H).

Example 108

(L63, Compound VI of Scheme 12, where R=tert-butyl, R'=methyl, R"=methyl). To a mixture of 170 mg of Compound V in 10 ml of ethanol was added 1 ml of 6 N NaOH. The solution was heated to reflux until completion (TLC monitoring). After cooling, water was added and the mixture as extracted with ethyl acetate. The organic layer was washed with water and brine and dried over MgSO$_4$. The solvents were evaporated under reduced pressure, and the residual oil was crystallized from acetonitrile to yield 20 mg of Compound VI. $^1$H NMR (CDCl$_3$): 7.86 (s, 1H), 7.66 (b, 1H), 7.14 (dd, 2H), 6.59 (s, 1H), 4.45 (s, 3H), 3.46 (s, 3H), 2.32, 2.23 (s,s, 3H), 1.38 (s, 9H), 1.30 (t, 3H).

Synthesis of "Non Symmetrical" RXR Modulators

In a preferred embodiment, the following Schemes depict the synthetic method employed in the synthesis of RXR modulators wherein R$^2$ differs from R$^4$.

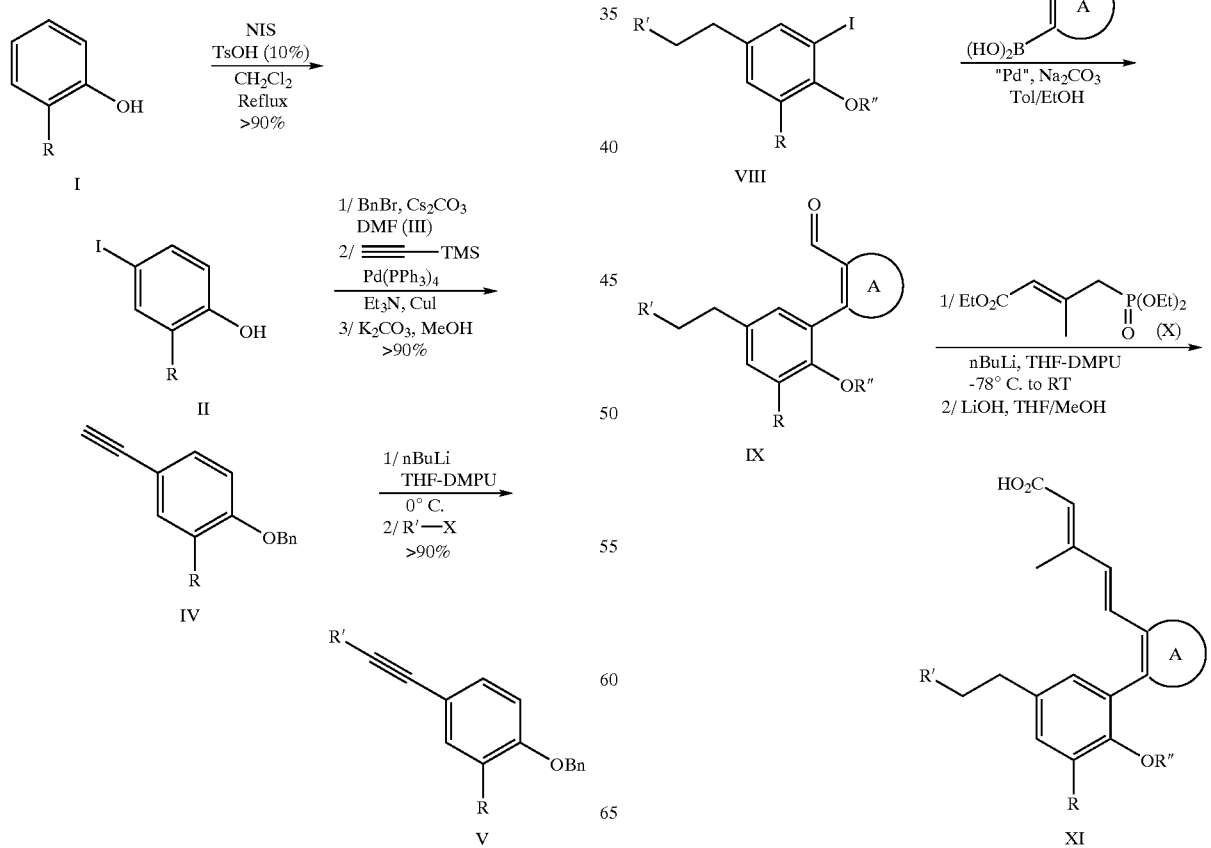

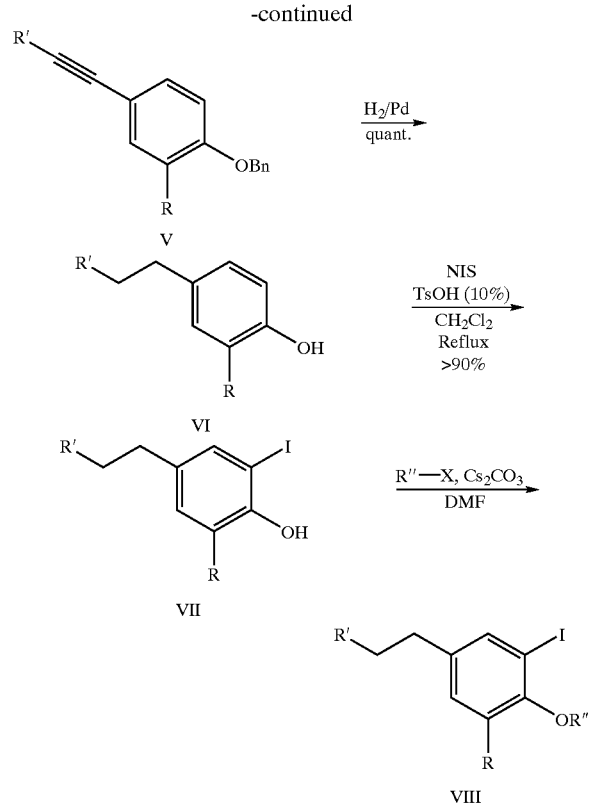

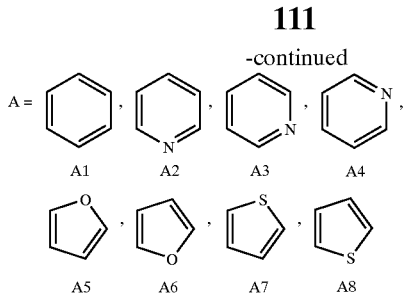

Scheme 13 depicts the synthetic method employed in the preparation of compounds of the type XI, wherein the substituents of $R^2$ and $R^4$ differ.

Example 109

(Compound II of Scheme 13, where R=tert-butyl). A mixture of 3.02 g (20.1 mmol) of 2-tert-butyl phenol, 5.43 g (24.1 mmol) of NIS and 0.38 g (2 mmol) of p-toluenesulfonic acid in 30 ml of $CH_2Cl_2$ was heated to reflux overnight. After cooling at room temperature, the purple solution was treated with a 10% aqueous $Na_2S_2O_3$ solution and dried over $MgSO_4$. After evaporation of the solvents, the phenol was purified over a short pad of silica gel (eluent: 5/95 ethyl acetate/hexane) to afford 5 g (18.1 mmol, yield: 90%) of II. $^1$H NMR (400 MHz, $CDCl_3$) δ: 7.51 (d, J=2.3 Hz, 1H), 7.34 (dd, J=8.1, 2.0 Hz, 1H), 6.44 (d, J=8.1 Hz, 1H), 2.77 (s, 1H), 1.37 (s, 9H).

Example 110

(Compound III of Scheme 13, where R=tert-butyl). A mixture of 3.65 g (13.2 mmol) of II, 6.5 gm (20.0 mmol) of $Cs_2CO_3$ and 1.9 ml (2.7 g, 15.8 mmol) of benzyl bromide in 20 ml of dry DMF was stirred at room temperature overnight. Water (100 ml) was added and the mixture was extracted with ethyl acetate. The organic layer was dried over $MgSO_4$. After evaporation of the solvents, the crude oil was purified over a short pad of silica gel (eluent: 5/95 ethyl acetate/hexane) to afford 4.25 g (11.6 mmol, yield: 88%) of III. $^1$H NMR (400 MHz, $CDCl_3$) δ: 7.55 (d, J=2.2 Hz, 1H), 7.41 (m, 6H), 6.68 (d, J=8.5 Hz, 1H), 5.08 (s, 2H), 1.38 (s, 9H).

Example 111

(Compound IV of Scheme 13 where R=tert-butyl). A mixture of 1.5 g (4.1 mmol) of III 800 mg (8.2 mmol) of trimethylsilyl acetylene, 80 mg (0.4 mmol) of CuI and 236 mg (0.2 mmol) of tetrakistriphenylphosphine palladium in 20 ml of dry $Et_3N$ was stirred at reflux for an hour and at room temperature overnight. Aqueous $NH_4Cl$ (100 ml) was added and the mixture was extracted with ethyl acetate. The organic layer was dried over $MgSO_4$. After evaporation of the solvents, the crude oil was diluted in 10 ml of methanol, and 100 mg (0.72 mmol) of $K_2CO_3$ was added. The suspension was stirred at room temperature overnight and the solvent was evaporated. Chromatography over silica gel (eluent: 10/90 ethyl acetate/hexane) afford 1.02 g (3.86 mmol, yield: 94%) of IV. $^1$H NMR (400 MHz, $CDCl_3$) δ: 7.69 (d, J=2.0 Hz, 1H), 7.41 (m, 6H), 6.68 (d, J=8.4 Hz, 1H), 5.12 (s, 2H), 2.98 (s, 1H), 1.39 (s, 9H).

Example 112

(Compound V of Scheme 13 where R=tert-butyl, R'=methyl). To a solution of 1.0 g (3.8 mmol) of IV in 4 ml of THF and 2 ml of DMPU, was added 1.8 ml of nBuLi at 0° C. The mixture was stirred 15 minutes and 0.31 ml (697 mg, 4.9 mmol) of methyl iodide diluted in 1 ml of dry THF was added dropwise. After complexion of the reaction (TLC analysis), aqueous $NH_4Cl$ (10 ml) was added and the mixture was extracted with ethyl acetate. The organic layer was dried over $MgSO_4$. After evaporation of the solvents, the crude oil was purified over a short silica gel pad (eluent: 5/95 ethyl acetate/hexane) to give 1.0 g (3.6 mmol, yield: 94%) of V. $^1$H NMR (400 MHz, $CDCl_3$) δ: 7.43 (d, J=7.0 Hz, 2H), 7.39 (t, J=7.4 Hz, 2H), 7.30 (m, 2H), 7.20 (d, J=8.4 Hz, 1H), 6.83 (d, J=8.3 Hz, 1H), 5.10 (s, 2H), 2.03 (s, 3H), 1.38 (s, 9H).

Example 113

(Compound VII of Scheme 13, where R=tert-butyl, R'=methyl). To a solution of 1.0 g (3.6 mmol) of VI and 100 mg of 10% Pd/C in 10 ml of ethyl acetate was stirred at room temperature overnight under $H_2$ atmosphere (balloon). After complexion (TLC analysis), the solution was filtrated over a celite plug and the plug washed 3 times with ethyl acetate. After evaporation of the solvents, the crude oil was directly diluted in 10 ml of $CH_2Cl_2$. p-toluenesulfonic acid (75 mg, 0.39 mmol) and NIS (1.0 g, 4.38 mmol) were successively added and the mixture was stirred until complexion (TLC analysis) of the reaction. Aqueous $Na_2S_2O_3$ was added to the purple solution and the organic layer was separated and dried over $MgSO_4$. After evaporation of the solvents and purification over a short pad of silica gel (eluent: 15/85 ethyl acetate/hexane), 995 mg (3.12 mmol, yield: 82%, 2 steps) of VII were isolated as an oil. $^1$H NMR (400 MHz, $CDCl_3$) δ: 7.34 (d, J=1.8 Hz, 1H), 7.03 (d, J=1.8 Hz, 1H), 5.33 (s, 1H), 2.46 (t, J=7.5 Hz, 2H), 1.61 (m, 2H), 1.38 (s, 9H), 0.93 (t, J=7.3 Hz, 3H).

Example 114

(Compound VIII of Scheme 13, where R=tert-butyl, R'=methyl, R"=n-propyl). A mixture of 210 mg (0.58 mmol) of VII, 1.14 g (3.5 mmol) of $Cs_2CO_3$ and 0.26 ml (344 mg, 2.8 mmol) of bromo propane in 5 ml of dry DMF was stirred at room temperature overnight. Water (20 ml) was added and the mixture was extracted with ethyl acetate. The organic layer was dried over $MgSO_4$. After evaporation of the solvents, the crude oil was purified over a short pad of silica gel (eluent: 5/95 ethyl acetate/hexane) to afford 720 mg (2.0 mmol, yield: 86%) of VIII. $^1$H NMR (400 MHz, $CDCl_3$) δ: 7.50 (d, J=2.1 Hz, 1H), 7.09 (d, J=2.1 Hz, 1H), 3.93 (t, J=6.8 Hz, 2H), 2.47 (t, J=7.3 Hz, 2H), 1.95 (m, 2H), 1.62 (m, 2H), 1.38 (s, 9H), 1.08 (t, J=7.4 Hz, 3H), 0.94 (t, J=7.3 Hz, 3H).

Example 115

(Compound IX in Scheme 13, where R=tert-butyl, R'=methyl, R"=propyl, A=A7). A mixture of 710 mg (2.33 mmol) of VIII, 136 mg (0.87 mmol) of 2-formyl-3-thiophene boronic acid, 34 mg (0.03 mmol) of $Pd(PPh_3)_4$ in toluene/ethanol aqueous $Na_2CO_3$ (5/2.5/1 ml respectively) was refluxed overnight. After cooling at room temperature, water (30 ml) was added and the mixture was extracted with ethyl acetate. The organic layer was dried over $MgSO_4$. After evaporation of the solvents, the crude oil was purified over a short pad of silica gel (eluent: 5/95 ethyl acetate/hexane) to afford 154 mg (0.45 mmol, yield: 77%) IX. $^1$H NMR (400 MHz, $CDCl_3$) δ: 9.76 (s, 1H), 7.79 (m, 1H), 7.68 (d, J=2.1 Hz, 1H), 7.21 (m, 2H), 3.32 (t, J=6.2 Hz, 2H), 2.56 (t, J=7.6 Hz, 2H), 1.55 (m, 2H), 1.55 (m, 2H), 1.41 (s, 9H), 0.97 (t, J=7.3 Hz, 3H), 0.77 (t, J=7.2 Hz, 3H).

Example 116

(Compound X in Scheme 13, where R=tert-butyl, R'=methyl, R"=n-propyl, A=A7). To a solution of 0.36 ml (384 mg, 1.45 mmol) of triethyl-3-methylphosphonocrotonate in THF/DMPU (4/1 ml respectively) was added 0.73 ml of nBuLi at −78° C. After stirring for 10 minutes, 154 mg (0.45 mmol) of IX (diluted in 1 ml of dry THF) was added dropwise. After complexion of the reaction, the solvents were evaporated and the crude product directly purified over silica gel column chromatography (eluent: 5/95 ethyl acetate/hexane) to afford 181 mg (0.4 mmol, yield: 89%) X. $^1$H NMR (400 MHz, CDCl$_3$) δ: 7.32 (d, J=8.3 Hz, 1H), 7.24 (d, J=1.9 Hz, 1H), 7.12 (d, J=15.8 Hz, 1H), 7.02 (d, J=15.3 Hz, 1H), 6.89 (d, J=1.9 Hz, 1H), 6.62 (dd, J=15.7, 9.3 Hz, 1H), 5.84 (s, 1H), 4.18 (dd, J=14.7, 7.3 Hz, 2H), 3.34 (t, J=6.1 Hz, 2H), 2.55 (t, J=7.5 Hz, 2H), 2.24 (s, 3H), 1.62 (m, 2H), 1.55 (m, 2H), 1.42 (s, 9H), 1.28 (t, J=7.1 Hz, 3H), 0.97 (t, J=7.2 Hz, 3H), 0.77 (t, J=7.3 Hz, 3H).

Example 117

(L64, Compound XI in Scheme 13, where R=tert-butyl, R'=methyl, R"=propyl, A=A7). Saponification (methanol/THF/aqueous LiOH, reflux) of 181 mg (0.4 mmol) afford after work-up and recrystallization from acetonitrile 128 mg (0.3 mmol, yield: 75%) of X. $^1$H NMR (400 MHz, CDCl$_3$) δ: 7.28 (d, J=5.2 Hz, 1H), 7.13 (d, J=2.1 Hz, 1H), 7.10 (d, J=5.2 Hz, 1H), 7.07 (d, J=15.8 Hz, 1H), 6.89 (d, J=2.1 Hz, 1H), 6.64 (d, J=15.8 Hz, 1H), 5.86 (s, 1H), 3.33 (t, J=6.3 Hz, 2H), 2.55 (t, J=7.5 Hz, 2H), 2.25 (s, 3H), 1.62 (m, 2H), 1.42 (s, 9H), 0.96 (t, J=7.3 Hz, 3H), 0.76 (t, J=7.4 Hz, 3H).

Example 118

(L65, Compound XI of Scheme 13, where R=tert-butyl, R'=n-propyl, R"=n-propyl, A=A7). This compound was prepared in the manner previously described for Compound XI in Example 117 except that propyl iodide was used instead of methyl iodide in Example 112. $^1$H NMR (400 MHz, CDCl$_3$) δ: 7.28 (d, J=5.1 Hz, 1H), 7.14 (d, J=2.2 Hz, 1H), 7.11 (d, J=5.0 Hz, 1H), 7.07 (d, J=15.8 Hz, 1H), 6.89 (d, J=2.2 Hz, 1H), 6.64 (d, J=15.8 Hz, 1H), 5.86 (s, 1H), 3.33 (t, J=6.3 Hz, 2H), 2.56 (t, J=7.8 Hz, 2H), 2.26 (s, 3H), 1.62 (m, 2H), 1.42 (s, 9H), 1.41 (m, 2H), 1.36 (m, 4H), 0.90 (t, J=6.8 Hz, 3H), 0.76 (t, J=7.4 Hz, 3H).

Example 119

(L66, Compound XI of Scheme 13, where R=cyclopentyl, R'=H, R"=n-butyl, A=A7). This compound was prepared in the manner previously described for Compound XI in Example 117, except that 2-cyclopentyl phenol was used instead of 2-tert-butyl phenol in Example 109, Compound VI was synthesized directly from IV, yielding R'=H and bromobutane was used in Example 114 instead of bromopropane. $^1$H NMR (400 MHz, CDCl$_3$) δ: 7.26 (d, J=4.4 Hz, 1H), 7.14 (d, J=5.1 Hz, 1H), 7.11 (d, J=2.1 Hz, 1H), 7.10 (d, J=15.7 Hz), 6.88 (d, J=2.1 Hz, 1H), 6.66 (d, J=15.7 Hz, 1H), 5.87 (s, 1H), 3.41 (m, 1H), 3.37 (t, J=6.5 Hz, 2H), 2.62 (dd, J=15.2, 7.6 Hz, 2H), 2.27 (s, 3H), 2.09 (m, 2H), 1.82 (m, 2H), 1.72 (m, 2H), 1.60 (m, 2H), 1.43 (m, 2H), 1.25 (t J=7.4 Hz, 3H), 0.78 (t, J=7.3 Hz, 3H).

Example 120

(L17, Compound XI of Scheme 13, where R=cyclopentyl, R'=H, R"=fluorobutyl, A=A7). This compound was prepared in the manner previously described for Compound XI in Example 117, except that 2-cyclopentyl phenol was used instead of 2-tert-butyl phenol in Example 109, Compound VI was synthesized directly from IV, yielding R'=H, and 3-fluoropropyl bromide was used instead of bromopropane in example 114. $^1$H NMR (400 MHz, CDCl$_3$) δ: 7.26 (d, J=5.2 Hz, 1H), 7.25 (d, J=2.2 Hz, 1H), 7.121 (d, J=5.3 Hz, 1H), 7.06 (d, J=15.8 Hz, 1H), 6.89 (d, J=2.2 Hz, 1H), 6.66 (d, J=15.8 Hz, 1H), 5.87 (s, 1H), 4.45 (t, J=6.0 Hz, 1H), 4.34 (t, J=6.0 Hz, 1H), 3.49 (t, J=5.9 Hz, 2H), 3.35 (m, 1H), 2.63 (dd, J=15.1, 7.5 Hz, 2H), 2.26 (s, 3H), 2.16 (m, 2H), 1.72 (m, 6H), 1.24 (t, J=7.5 Hz, 3H).

Example 121

(L67, Compound XI of Scheme 13, where R=cyclopentyl, R'=H, R"=propyl, A=A7). This compound was prepared in the manner previously described for Compound XI in Example 117, except that 2-cyclopentyl phenol was used instead of 2-tert-butyl phenol in Example 109 and Compound VI was synthesized directly from IV, yielding R'=H. $^1$H NMR (400 MHz, CDCl$_3$) δ: 7.25 (d, J=4.70 Hz, 1H), 7.15 (d, J=5.1 Hz, 1H), 7.11 (d, J=2.1 Hz, 1H), 7.10(d, J=15.8 Hz), 6.89 (d, J=2.1 Hz, 1H), 6.66 (d, J=15.8 Hz, 1H), 5.87 (s, 1H), 3.37 (m, 1H), 3.33 (t, J=6.3 Hz, 2H), 2.63 (dd, J=15.2, 7.5 Hz, 2H), 2.28 (s, 3H), 2.18 (m, 2H), 1.85 (m, 2H), 1.72 (m, 2H), 1.61, (m, 2H), 1.46 (m, 2H), 1.24 (t J=7.5 Hz, 3H), 0.79 (t, J=7.4 Hz, 3H).

Example 121a (L16, Compound XI of Scheme 13 where R=tert-butyl, R'=H, R"=1,1-trifluorobutyl, A=A7). This compound was prepared in the manner previously described for Compound XI in Example 117, except that Compound VI was synthesized directly from IV, yielding R'=H and 1,1,1-trifluoro-4-bromobutane was used instead of bromopropane in Example 114. $^1$H NMR (400 MHz, CDCl$_3$) δ: 7.32 (d, J=5.10 Hz, 1H), 7.18 (d, J=2.2 Hz, 1H), 7.09 (d, J=5.2 Hz, 1H), 6.99 (d, J=15.9 Hz), 6.93 (d, J=2.1 Hz, 1H), 6.65 (d, J=15.9 Hz, 1H), 5.87 (s, 1H), 3.42 (m, 2H), 2.63 (dd, J=15.1, 7.5 Hz, 1H), 2.00 (m, 2H), 1.72 (m, 2H), 1.42 (s, 9H), 1.24 (t J=7.2 Hz, 3H).

Example 122

(L68, Compound XI of Scheme 13, where R=tert-butyl, R'=methyl, R"=1,1-difluoroethyl, A=A7). This compound was prepared in the manner previously described for Compound XI in Example 117, except that ethyl iodide was used instead of methyl iodide in Example 112 and 2-fluoroethyl bromide was used instead of bromopropane in Example 114. $^1$H NMR (400 MHz, CDCl$_3$) δ: 7.33 (d, J=5.2 Hz, 1H), 7.17 (d, J=2.2 Hz, 1H), 7.11 (d, J=5.2 Hz, 1H), 6.99 (d, J=15.8 Hz, 1H), 6.92 (d, J=2.2 Hz, 1H), 6.67 (d, J=15.8 Hz, 1H), 5.63 (dt, J=55.4, 6.9 Hz, 1H), 3.59 (td, J=13.3, 5.3 Hz, 1H), 2.56 (t, J=7.4 Hz, 2H), 2.25 (s, 3H), 1.65 (m, 2H), 1.43 (s, 9H), 0.97 (t, J=7.3 Hz, 3H).

Example 123

(L69, Compound XI of Scheme 13, where R=cyclopentyl, R'=1-isopropyl, R"=fluoropropyl, A=A7). This compound was prepared in the manner previously described for Compound XI in Example 117, except that 2-cyclopentyl phenol was used instead of 2-tert-butyl phenol in Example 109, isopropyl iodide was used instead of methyl iodide in Example 112 and 3-fluoroethyl bromide was used instead of bromopropane in Example 114. $^1$H NMR (400 MHz, CDCl$_3$) δ: 7.25 (d, J=5.3 Hz, 1H), 7.12 (d, J=5.3 Hz, 1H), 7.09 (d, J=2.1 Hz, 1H), 7.01 (d, J=15.9 Hz, 1H), 6.88 (d, J=2.1 Hz, 1H), 6.64 (d, J=15.9 Hz, 1H), 5.89 (s, 1H), 4.46 (t, J=6.0 Hz, 1H), 4.34 (t, J=6.0 Hz, 1H), 3.49 (t, J=5.9 Hz, 2H), 2.54 (m, 2H), 2.28 (s, 3H), 2.09 (m, 2H), 1.76 (m, 4H), 1.5 (8H), 0.95 (s, 6H).

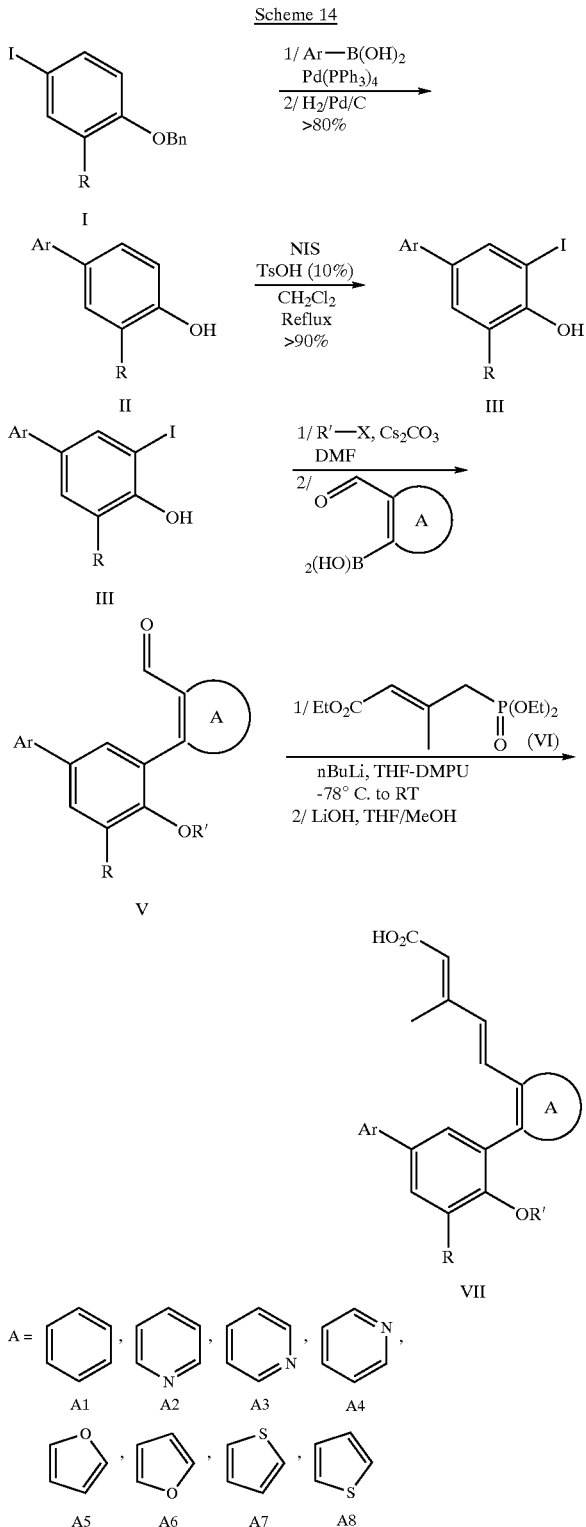

Scheme 14 depicts a method of preparation of unsymmetrical modulators wherein various substituents are introduced at $R^2$ and $R^4$.

Example 124

(Compound II of Scheme 14, where R=tert-butyl). A mixture of 593 mg (1.62 mmol) of 1 (2-tert-butyl-4-benzyloxo-phenol), 94 mg (0.08 mmol) of Pd(PPh$_3$)$_4$, 300 mg (2.40 mmol) of phenylboronic acid dissolved in 6 ml of toluene, 3 ml of ethanol and 1.7 ml of 2N aqueous Na$_2$CO$_3$ was heated to reflux overnight. After work-up, the crude product was filtrated over a short plug of silica gel to remove the catalyst impurities and directly dissolved into 5 ml of ethyl acetate. 100 mg of 10% Pd/C was added and the mixture was stirred under H$_2$ atmosphere overnight. Filtration and purification over silica gel column chromatography, 332 mg (1.46 mmol, yield: 90%, 2 steps) of II (2-tert-butyl-4-phenyl phenol) was isolated as a pasty solid. $^1$H NMR (400 MHz, CDCl$_3$) δ: 7.56 (dd, J=7.8, 1.0 Hz, 2H), 7.52 (d, J=2.2 Hz, 1H), 7.43 (d, J=8.1 Hz, 2H), 7.31 (m, 2H), 6.75 (d, J=8.1 Hz, 1H), 4.94 (s, 1H), 1.47 (s, 9H).

Example 125

(Compound III of Scheme 14, where R=tert-butyl). A mixture of 332 mg (1.46 mmol) of II (2-tert-butyl-4-phenylphenol), 394 mg (1.75 mmol) of NIS and 30 mg (0.15 mmol) of P-toluenesulfonic acid in 5 ml of dry CH$_2$Cl$_2$ was stirred at room temperature until complexion of the reaction (TLC analysis). An aqueous solution of Na$_2$S$_2$O$_3$ (20 ml) was added and the mixture was extracted with CH$_2$Cl$_2$. The organic layer was dried over MgSO$_4$. After evaporation of the solvents, the crude oil was purified over a short pad of silica gel (eluent: 5/95 ethyl acetate/hexane) to afford 493 mg (1.4 mmol, yield: 96%) of III. $^1$H NMR (400 MHz, CDCl$_3$) δ: 7.76 (d, J=2.0 Hz, 1H), 7.49 (m, 2H), 7.47 (d, J=2.0 Hz, 1H), 7.42 (t, J=7.4 Hz, 2H), 7.32 (t, J=7.2 Hz, 1H), 5.53 (s, 1H), 1.44 (s, 9H).

Example 126

(Compound IV of Scheme 14, where R=tert-butyl, R'=n-propyl). A mixture of 205 mg (0.58 mmol) of III, 93 mg (0.76 mmol) of 1-bromopropane and 284 mg (0.87 mmol) of Cs$_2$CO$_3$ in 5 ml of dry DMF was stirred at room temperature until complexion of the reaction (TLC analysis). After work-up and evaporation of the solvents, the crude oil was purified over a short pad of silica gel (eluent: 5/95 ethyl acetate/hexane) to afford 191 mg (0.49 mmol, yield: 83%) of IV. $^1$H NMR (400 MHz, CDCl$_3$) δ: 7.91 (d, J=1.90 Hz, 1H), 7.62 (m, 2H), 7.54 (d, J=1.9 Hz, 1H), 7.50 (m, 1H), 7.44 (m, 2H), 7.38 (t, J=7.2 Hz, 1H), 4.00 (t, J=6.9 Hz, 1H), 1.95 (m, 2H), 1.45 (s, 9H), 1.11 (t, J=7.6 Hz, 3H).

Example 127

(Compound V of Scheme 14, where R=tert-butyl, R'=n-propyl, A=A7). A mixture of 191 mg (0.48 mmol) of IV, 113 mg (0.73 mmol) of 2-formyl-3-thiopheneboronic acid, 28 mg (0.02 mmol) of Pd(PPh$_3$)$_4$ in toluene/ethanol/aqueous Na$_2$CO$_3$ (5/2.5/0.5 ml respectively) was refluxed overnight. After cooling at room temperature, water (30 ml) was added and the mixture was extracted with ethyl acetate. The organic layer was dried over MgSO$_4$. After evaporation of the solvents, the crude oil was purified over a short pad of silica gel (eluent: 5/95 ethyl acetate/hexane) to afford 166 mg (0.44 mmol, yield: 90%) V. $^1$H NMR (400 MHz, CDCl$_3$) δ: 7.78 (d, J=4.9 Hz, 1H), 7.65 (d, J=2.3 Hz, 1H), 7.62 (d, J=4.2 Hz, 1H), 7.58 (m, 2H), 7.44 (m, 2H), 7.39 (d, J=2.3 Hz, 1H), 7.31 (m, 1H), 3.40 (t, J=6.2 Hz, 1H), 1.55 (m, 2H), 1.49 (s, 9H), 0.81 (t, J=7.4 Hz, 3H).

Example 128

(Compound VI of Scheme 14, where R=tert-butyl, R'=n-propyl, A=A7). To a solution of 0.27 ml (289 mg, 1.09 mmol) of triethyl-3-methylphosphonocrotonate in THF/DMPU (4/1 ml respectively) was added 0.57 ml of nBuLi at −78° C. After stirring for 10 minutes, 166 mg (0.44 mmol) of V (diluted in 1 ml of dry THF) was added dropwise. After complexion of the reaction, the solvents were evaporated and the crude directly purified over silica gel column chromatography (eluent: 5/95 ethyl acetate/hexane) to afford 197 mg (0.41 mmol, yield: 95%) VI. $^1$H NMR (400 MHz, CDCl$_3$) δ: 7.65 (m, 2H), 7.42 (m, 2H), 7.33 (m, 4H), 7.14 (d, J=5.3 Hz, 1H), 7.03 (d, J=15.8 Hz, 1H), 6.64 (d, J=15.8 Hz, 1H), 5.85 (s, 1H), 4.17 (dd, J=14.2, 7.1 Hz, 2H), 3.41 (t, J=6.1 Hz, 2H), 2.26 (s, 3H), 1.50 (m, 2H), 1.49 (s, 9H), 1.29 (t, J=7.1 Hz, 3H), 0.79 (t, J=7.4 Hz, 3H).

Example 129

(L70. Compound VII of Scheme 14, where R=tert-butyl, R'=n-propyl, A=A7). Saponification (aqueous LiOH, THF, methanol) of VI followed by usual acidic work-up and recrystallization from acetonitrile afford 138 mg (0.3 mmol, yield: 75%) of VII. $^1$H NMR (400 MHz, CDCl$_3$) δ: 7.56 (m, 2H), 7.42 (t, J=7.5 Hz, 1H), 7.31 (m, 2H), 7.14 (d, J=5.1 Hz, 1H), 7.09 (d, J=15.8 Hz, 1H), 6.66 (d, J=15.8 Hz, 1H, 5.87 (s, 1H), 3.40 (t, J=4.5 Hz, 2H), 2.27 (s, 3H), 1.51 (m, 2H), 1.49 (s, 9H), 0.79 (t, J=7.4 Hz, 3H).

Scheme 15

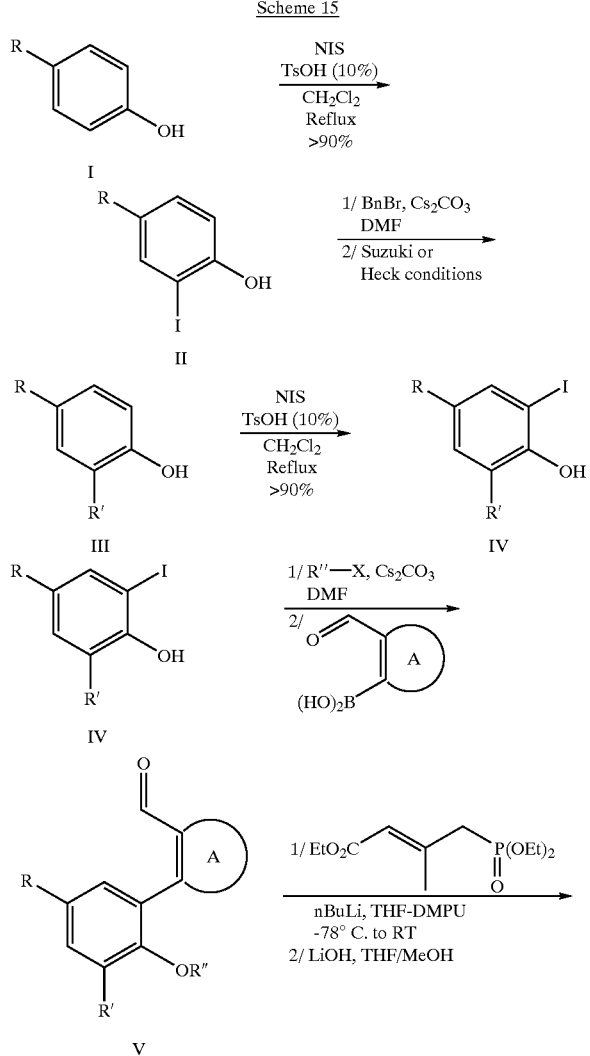

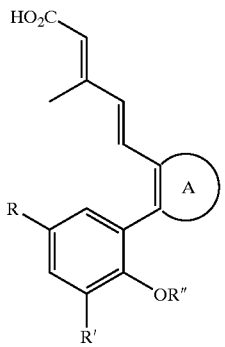

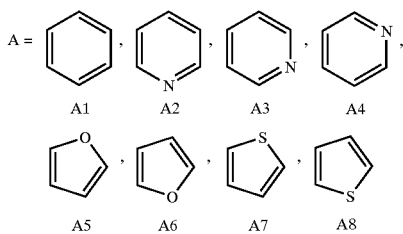

Scheme 15 depicts an alternative method of introducing a variety of substituents at the $R^2$ and $R^4$ positions.

Example 130

(Compound II of Scheme 15, where R=ethyl). A mixture of 12.2 g (0.1 mol) of I (4-ethyl phenol), 1.9 g (0.01 mol) of p-toluenesulfonic acid and 25 g (0.11 mol) of NIS in 100 ml of CH$_2$Cl$_2$ was stirred at room temperature until complexion (TLC analysis). Aqueous Na$_2$S$_2$O$_3$ was added to the purple solution and the organic layer was separated and dried over MgSO$_4$. After evaporation of the solvents and purification over a short pad of silica gel (eluent: 15/85 ethyl acetate/hexane), 22.3 g (0.09 mol, yield: 90%) of II were isolated as an oil. $^1$H NMR (400 MHz, CDCl$_3$) δ: 7.49 (d, J=1.8 Hz, 1H), 7.07 (dd, J=8.3, 1.8 Hz, 1H), 6.91 (d, J=8.1 Hz, 1H), 5.12 (s, 1H), 2.55 (dd, J=13.5, 7.4 Hz, 2H), 1.94 (t, J=7.4 Hz, 3H).

Example 131

(Compound III of Scheme 15, where R=ethyl, R'=cyclohexene). A mixture of 2.54 g (10.2 mmol) of II (2-iodo-4-ethyl phenol), 57 mg (0.26 mmol) of Pd(OAc)$_2$, 5.2 ml (4.2 g, 51 mmol) of cyclohexene, 67 mg (026 mmol) of Pd(PPh$_3$)$_4$, 3 g (30.6 mmol) of KOAc and 2.8 g (10.2 mmol) of nBu$_4$NCl in 20 ml of DMF were heated to 60° C. overnight. Water (100 ml) was added after cooling to room temperature and the solution was extracted with ethyl acetate. The organic layer was separated and dried over MgSO$_4$. After evaporation of the solvents and column chromatography purification silica gel (eluent: 15/85 ethyl acetate/hexane), 1.0 g (4.94 mmol, yield: 48%) of III were isolated as an oil. $^1$H NMR (400 MHz, CDCl$_3$) δ: 7.01 (d, J=1.9 Hz, 1H), 6.92 (dd, J=7.4, 1.9 Hz, 1H), 6.68 (d, J=7.4 Hz, 1H), 5.78 (m, 2H), 4.64 (s, 1H), 3.11 (m, 1H), 2.59 (m, 1H), 2.58 (dd, J=13.5, 7.4 Hz, 2H), 2.31 (m, 1H), 2.25 (m, 4H), 1.92 (m, 1H), 1.85 (m, 1H), 1.21 (t, J=7.3 H, 3H).

Example 132

(Compound III of Scheme 15, where R=ethyl, R'=cyclohexane). A mixture of 1.0 g (4.9 mmol) of II (2-cyclohexe-2-ene-4-ethyl phenol) and 100 mg of 10% Pd/C in 10 ml of ethyl acetate was stirred at room temperature under hydrogen atmosphere (balloon) overnight. The mixture was filtrated over celite and the solvents evaporated to give 1.0 g (4.9 mmol, yield: 100%) of III as an oil. $^1$H NMR (400 MHz, CDCl$_3$) δ: 6.99 (d, J=1.8 Hz, 1H), 6.88 (dd, J=8.0, 1.8 Hz, 1H), 6.68 (d, J=8.0 Hz, 1H), 4.56 (s, 1H), 2.78 (m, 1H), 2.57 (dd, J=15.1, 7.6 Hz, 2H), 1.89 (m, 4H), 1.75 (m, 2H), 1.49 (m, 6H), 1.20 (t, J=7.4 H, 3H).

Example 133

(Compound IV of Scheme 15, where R=ethyl, R'=cyclohexane). A mixture of 1.0 g (1.9 mmol) of III, 94 mg (0.5 mmol) of p-toluenesulfonic acid and 1.2 g (5.4 mmol) of NIS in 20 ml of CH$_2$Cl$_2$ was stirred at room temperature until complexion (TLC analysis). Aqueous Na$_2$S$_2$O$_3$ was added to the purple solution and the organic layer was separated and dried over MgSO$_4$. After evaporation of the solvents and purification over a short pad of silica gel (eluent: 15/85 ethyl acetate/hexane), 1.4 g (4.1 mmol, yield: 83%) of IV were isolated as an oil. $^1$H NMR (400 MHz, CDCl$_3$) δ: 7.31 (d, J=1.4 Hz, 1H), 6.97 (d, J=1.4 Hz, 1H), 5.12 (s, 1H), 2.92 (m, 1H), 2.53 (dd, J=15.2, 7.5 Hz, 2H), 1.88 (m, 4H), 1.72 (m, 2H), 1.40 (m, 4H), 1.19 (t, J=7.9 Hz, 3H).

Example 134

(L104, Compound VIII of Scheme 15 where R=ethyl, R'=cyclohexane, R"=n-propyl, A=A7). This compound was prepared as previously described for Compound VII in Example 129 except that IV of Example 133 was used in the synthetic route instead of Compound IV of Example 125. $^1$H NMR (400 MHz, CDCl$_3$) δ: 7.25 (d, J=5.1 Hz, 1H), 7.12 (d, J=15.8 Hz, 1H), 7.07 (d, J=2.3 Hz, 1H), 6.88 (d, J=2.3 Hz, 1H), 6.65 (d, J=15.8 Hz, 1H), 5.86 (s, 1H), 3.31 (t, J=6.4 Hz, 2H), 2.97 (m, 1 H), 2.62 (dd, J=15.2, 7.6 Hz, 2H), 2.27 (s, 3H), 1.77 (m, 4H), 1.42 (m, 6H), 1.24 (t, J=7.5 Hz, 3H), 0.82 (t, J=7.4 Hz, 3H).

Example 135

(L72, Compound VII of Scheme 15 where R=ethyl, R'=cyclohexane, R"=1-fluoropropyl, A=A7). This compound was prepared in the manner previously described for Compound VI in Example 134 except that 1-fluoro-3-bromopropane was used instead of 1-bromopropane in Example 126. $^1$H NMR (400 MHz, CDCl$_3$) δ: 7.25 (d, J=5.2 Hz, 1H), 7.12 (d, J=5.2 Hz, 1H), 7.08 (d, J=3.6 Hz, 1H), 7.05 (d, J=15.8 Hz, 1H), 6.89 (d, J=3.6 Hz, 1H), 6.66 (d, J=15.8 Hz, 1H), 5.87 (s, 1H), 4.50 (t, J=6.0 Hz, 2H), 4.39 (t, J=6.0 Hz, 1H), 3.48 (t, J=5.9 Hz, 2H), 2.92 (m, 1H), 263 (dd, J=15.1 7.5 Hz, 2H), 2.26 s, 3H), 1.83 (m, 2H), 1.79 (m, 2H), 1.55 (m, 2H), 1.40 (m, 2H), 1.24 (t, J=7.5 Hz, 3H).

Example 136

(Compound III of Scheme 15 where R=ethyl, R'=phenyl). A mixture of 2.3 g (9.2 mmol) of II (2-iodo-4-ethyl phenol), 1.4 g (10 mmol) of phenyl boronic acid and 213 mg of Pd(PPh$_3$)$_4$ in 20 ml of toluene, 10 ml of ethanol and 10 ml of aqueous 2N Na$_2$CO$_3$ was stirred at reflux overnight. After work-up the solvents were evaporated and the crude product was purified over column chromatography (eluent: 10/90 ethyl acetate/hexane) to give 0.7 g (3.8 mmol, yield: 40%) of III as a pasty solid. $^1$H NMR (400 MHz, CDCl$_3$) δ: 7.49 (m, 4H), 7.42 (m, 1H), 7.08 (m, 2H), 6.90 (d, J=8.1 Hz, 1H), 5.06 (s, 1H), 2.63 (dd, J=15.2, 7.6 Hz, 2H), 1.24 (t, J=7.1 H, 3H).

Example 137

(Compound IV of Scheme 15 where R=ethyl, R'=phenyl). A mixture of 0.75 g (3.8 mmol) of III, 72 mg (0.4 mmol) of p-toluenesulfonic acid and 1.0 g (4.6 mmol) of NIS in 10 ml of CH$_2$Cl$_2$ was stirred at room temperature until complexion (TLC analysis). Aqueous Na$_2$S$_2$O$_3$ was added to the purple solution and the organic layer was separated and dried over MgSO$_4$. After evaporation of the solvents and purification over a short pad of silica gel (eluent: 15/85 ethyl acetate/hexane), 1.4 g (4.1 mmol, yield: 83%) of IV were isolated as a pasty yellow solid. $^1$H NMR (400 MHz, CDCl$_3$) δ: 7.52 (d, J=1.4 Hz, 1H), 7.48 (m, 4H), 7.40 (m, 1H), 7.08 (d, J=1.4 Hz, 1H), 5.40 (s, 1H), 2.59 (dd, J=15.2, 7.6 Hz, 2H), 1.23 (t, J=7.5 Hz, 3H).

Example 138

(L72, Compound VII of Scheme 15 where R=ethyl, R'=phenyl, R"=n-propyl, A=A7). This compound was prepared in the manner previously described for Compound VI of Example 134 except that benzene was used instead of cyclohexene in Example 131. $^1$H NMR (400 MHz, CDCl$_3$) δ: 7.61 (d, J=7.6 Hz, 2H), 7.42 (t, J=7.3 Hz, 2H), 7.34 (d, J=7.3 Hz, 1H), 7.27 (m, 1H), 7.21 (d, J=2.1 Hz, 1H), 7.17 (d, J=9.6 Hz, 1H), 7.18 (d, J=15.2 Hz, 1H), 7.07 (d, J=2.1 Hz, 1H), 6.69 (d, J=15.8 Hz, 1H), 5.90 (s, 1H), 3.13 (t, J=6.3 Hz, 2H), 2.68 (dd, J=15.2, 7.5 Hz, 2H), 2.34 (s, 3H), 1.28 (t, J=7.6 Hz, 2H), 1.15 (m, 2H), 0.53 (t, J=7.4 Hz, 3H).

Example 139

(L73, Compound VII of Scheme 15 where R=ethyl, R'=phenyl, R"=1-fluoropropyl, A=A7). This compound was prepared in the manner previously described for Compound VI of Example 134 except that benzene was used instead of cyclohexene in Example 131 and 1-fluoro-3-bromopropane was used instead of 1-bromopropane in Example 126. $^1$H NMR (400 MHz, CDCl$_3$) δ: 7.57 (d, J=7.6 Hz, 2H), 7.42 (t, J=7.3 Hz, 2H), 7.36 (d, J=7.3 Hz, 1H), 7.27 (m, 1H), 7.21 (d, J=1.9 Hz, 1H), 7.17 (d, J=5.6 Hz, 1H), 7.09 (d, J=15.9 Hz, 1H), 7.07 (d, J=1.9 Hz, 1H), 6.69 (d, J=15.9 Hz, 1H), 5.91 (s, 1H), 4.12 (t, J=6.1 Hz, 1H), 4.00 (t, J=6.2 Hz, 1H), 3.28 (t, J=5.8 Hz, 2H), 2.69 (dd, J=15.0, 7.4 Hz, 2H), 2.34 (s, 3H), 1.56 (m, 2H), 1.29 (t, J=7.3 Hz, 3H).

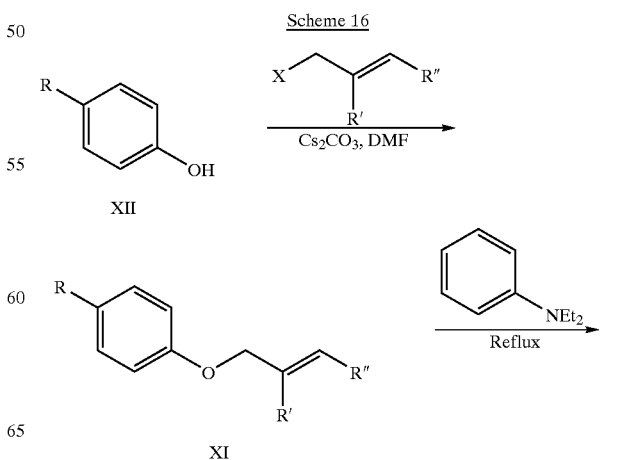

Scheme 16

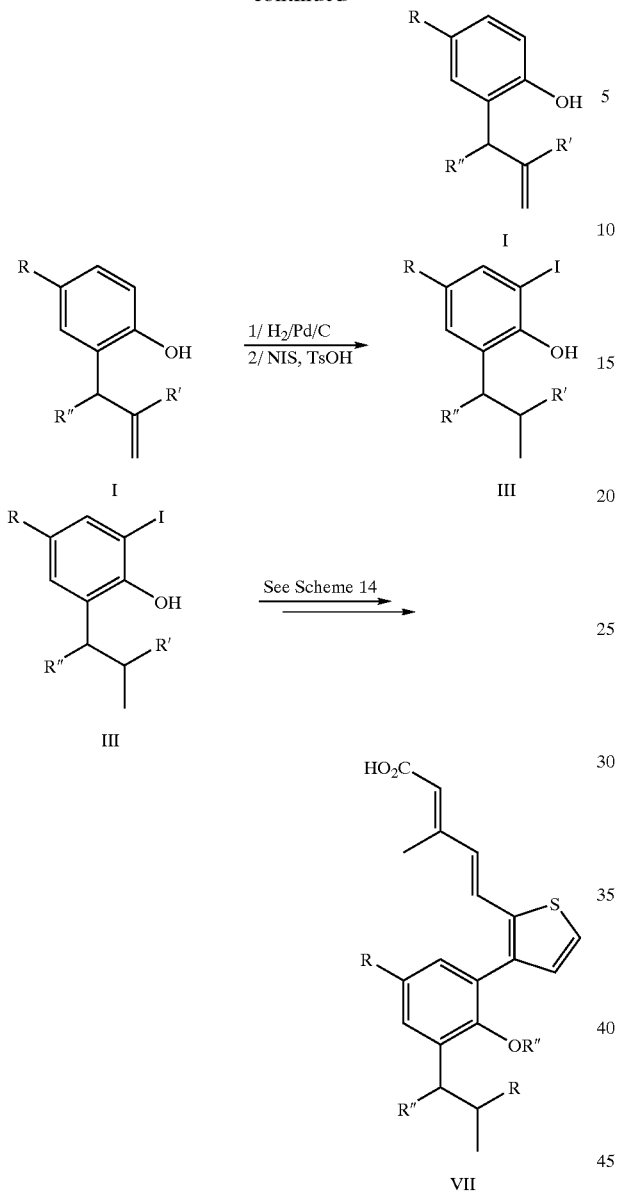

Scheme 16 depicts another alternative method for preparing modulators with a variety of substituents at the $R^2$ and $R^4$ positions.

Example 140

(Compound XI of Scheme 16 where R=tert-butyl, R'=H, R"=H). A mixture of 5.2 g (35 mmol) of 4-tert-butyl phenol, 17.0 g (52 mmol) of $Cs_2CO_3$ and 3.6 ml (5.0 g, 42.5 mmol) of allyl bromide in 70 ml of dry DMF was stirred at room temperature overnight. Water (200 ml) was added and the mixture was extracted with ethyl acetate. The organic layer was dried over $MgSO_4$. After evaporation of the solvents, the crude oil was purified over a short pad of silica gel (eluent: 5/95 ethyl acetate/hexane) to afford 9.5 mg (50 mmol, yield: 96%) of XI. $^1$H NMR (400 MHz, $CDCl_3$) δ: 7.30 (d, J=6.9 Hz, 2H), 6.88 (d, J=6.9 Hz, 2H), 6.09 (m, 1H), 5.41 (d, J=17.6 Hz, 1H), 5.27 (d, J=10.6 Hz, 1H), 4.53 (m, 2H), 1.30 (s, 9H).

Example 141

(Compound I of Scheme 16 where R=tert-butyl, R'=H, R"=H). A mixture of 1.9 g (10 mmol) of XI, in 20 ml of N,N-diethylaniline was stirred at reflux for 2 hours. After cooling, the solution was triturated with 2N aqueous solution (200 ml) and extracted with ethyl acetate. The organic layer was dried over $MgSO_4$. After evaporation of the solvents, the crude oil was purified over a short pad of silica gel (eluent:hexane and 5/95 ethyl acetate/hexane) to afford 1.3 g (6.8 mmol, yield: 68%) of I. $^1$H NMR (400 MHz, $CDCl_3$) δ: 7.15 (dd, J=8.4, 2.2 Hz, 1H), 7.11 (d, J=2.2 Hz, 1H), 6.75 (d, J=8.4 Hz, 1H), 6.05 (m, 1H), 5.19 (m, 2H), 4.86 (broad s, 1H), 3.41 (d, J=6.3 Hz, 2H), 1.29 (s, 9H), 1.26 (t, J=7.0 Hz, 3H).

Example 142

(Compound II of Scheme 16 where R=tert-butyl, R'=H, R"=H). Hydrogenation (Pd/C, ethyl acetate, 1 atm $H_2$) of 1.3 g (6.8 mmol) of I afford 1.3 g (6.8 mmol, yield: 100%) of II. $^1$H NMR (400 MHz, $CDCl_3$) δ: 7.12 (d, J=2.2 Hz, 1H), 7.09 (dd, J=8.2, 2.2 Hz, 1H), 6.69 (d, J=8.2 Hz, 1H), 4.54 (broad s, 1H), 2.57 (t, J=7.4 Hz, 2H), 1.65 (m, 2H), 1.29 (s, 9H), 0.98 (t, J=7.1 Hz, 3H).

Example 143

(L74, Compound VIII of Scheme 16 where R=tert-butyl, R'=H, R"=H, R'''=n-propyl). Compound was prepared in the manner previously described for Compound VIII in Example 129, except that Compound II of Example 142 was used instead of Compound II of Example 124 in the synthetic route. $^1$H NMR (400 MHz, $CDCl_3$) δ: 7.26 (d, J=5.1 Hz, 1H), 7.20 (d, J=2.4 Hz, 1H), 7.18 (d, J=5.3 Hz, 1H), 7.11 (d, J=15.8 Hz, 1H), 7.06 (d, J=2.4 Hz, 1H), 6.67 (d, J=15.8 Hz, 1H), 5.87 (s, 1H), 3.33 (t, J=6.4 Hz, 2H), 2.64 (dd, J=7.5 Hz, 2H), 2.27 (s, 3H), 1.69 (m, 2H), 1.48 (m, 2H), 1.32 (s, 9H), 1.00 (t, J=7.3 Hz, 3H), 0.82 (t, J=7.4 Hz, 3H).

Example 144

(L106, Compound XI of Scheme 16 where R=tert-butyl, R'=H, R"=H, R'''=n-butyl). Compound was prepared in the manner previously described for Compound VII in Example 129, except that benzyloxo-phenol was used instead of 2-tert-butyl-4-benzyloxo-phenol in Example 124. $^1$H NMR (400 MHz, $CDCl_3$) δ: 7.34 (dd, J=8.6, 2.5 Hz, 1H), 7.25 (d, J=5.2 Hz, 1H), 7.22 (d, J=2.5 Hz, 1H), 7.16 (d, J=5.2 Hz, 1H), 7.07 (d, J=15.8 Hz, 1H), 6.92 (d, J=8.6 Hz, 1H), 6.68 (d, J=15.8 Hz, 1H), 5.87 (s, 1H), 3.93 (t, J=6.5 Hz, 2H), 2.25 (s, 3H), 1.65 (m, 2H), 1.36 (m, 2H), 1.31 (s, 9H), 0.89 (t, J=7.4 Hz, 3H).

Scheme 17

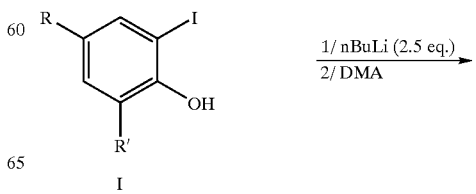

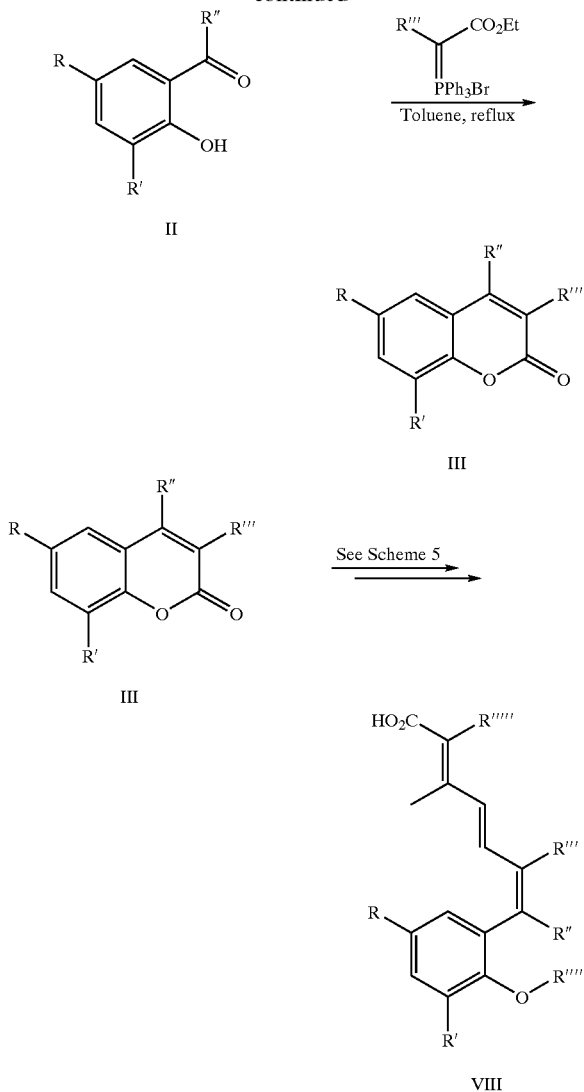

Scheme 17 depicts an alternate method of preparing unsymmetrical modulators of type VIII, in which R, R', R", R'", and R"" can all be modified.

Example 145

(Compound II of Scheme 17 where R=ethyl, R'=tert-butyl, R"=methyl). To a solution of 5.4 g (17.6 mmol) 2-tert-butyl-4-ethyl-6-iodo phenol in 45 ml of dry ether, was added 18 ml of nBuLi (1.6 M in hexane) at −78° C. The mixture is warmed-up to room temperature until complete consumption of the starting material (TLC analysis) and, then cooled to −78° C. again. N,N-dimethyl acetamide (5 ml) diluted in 5 ml of dry ether was then added dropwise and the mixture was allowed to warm-up to room temperature. After complexion of the reaction (2–5 hours), water was added and the solution was extracted with ethyl acetate. The organic layers were combined, dried over $MgSO_4$ and evaporated after filtration. The crude oil was purified over column chromatography (eluent: 5/95 ethyl acetate/hexane) to give 1.9 g (8.4 mmol, yield: 48%) of II. $^1$H NMR (400 MHz, $CDCl_3$) δ: 10.56 (broad s, 1H), 7.41 (d, J=1.9 Hz, 1H), 7.32 (d, J=1.9 Hz, 1H), 2.63 (s, 3H), 2.60 (dd, J=15.2, 7.5 Hz, 2H), 1.42 (s, 9H), 1.23 (t, J=7.2 Hz, 3H).

Example 146

(Compound III of Scheme 17 where R=ethyl, R'=tert-butyl, R"=methyl, R'"=H). A mixture of 1.9 g (8.4 mmol) 2-hydroxy-3-tert-butyl-5-ethyl acetophenone and 9.0 g (26 mmol) of (carbethoxy-ethylidene)triphenylphosphorane in 40 ml of dry toluene was refluxed overnight. After cooling et room temperature, the solvents were evaporated and the crude coumarin directly purified over column chromatography (eluent: 10/90 ethyl acetate/hexane) to give 1.9 g (7.6 mmol, yield: 90%) of III. $^1$H NMR (400 MHz, $CDCl_3$) δ: 7.35 (d, J=1.6 Hz, 1H), 7.28 (d, J=1.6 Hz, 1H), 6.26 (s, 1H), 2.70 (dd, J=15.2, 7.6 Hz, 2H), 2.43 (s, 3H), 1.49 (s, 9H), 1.27 (t, J=7.7 Hz, 3H).

Example 147

(L75, Compound VIII of Scheme 17 where R=ethyl, R'=tert-butyl, R"=methyl, R'"=H, R""=n-propyl, R""'=H). This compound was prepared in the manner previously described for Compound VIII in Scheme 5. $^1$H NMR (400 MHz, $CDCl_3$) δ: 7.09 (d, J=2.8 Hz, 1H), 6.77 (d, J=2.8 Hz, 1H), 6.62 (dd, J=15.2, 11.1 Hz, 2H), 6.23 (d, J=15.2 Hz, 1H), 6.19 (d, J=11.1 Hz, 1H), 5.76 (s, 1H), 3.69 (m, 1H), 3.64 (m, 1H), 2.59 (dd, J=15.1, 7.5 Hz, 2H), 2.21 (s, 3H), 2.15 (s, 3H), 1.67 (m, 2H), 1.40 (s, 9H), 1.22 (t, J=7.5 Hz, 3H), 0.94 (t, J=7.4 Hz, 3H).

Example 148

(L76, Compound VIII of Scheme 17 where R=ethyl, R'=tert-butyl, R"=methyl, R'"=H, R""=n-butyl, R""'=H). This compound was prepared in the manner previously described for Compound VIII in Scheme 5. $^1$H NMR (400 MHz, $CDCl_3$) δ: 7.08 (d, J=2.8 Hz, 1H), 6.78 (d, J=2.8 Hz, 1H), 6.62 (dd, J=15.3, 11.1 Hz, 2H), 6.23 (d, J=15.3 Hz, 1H), 6.20 (d, J=11.1 Hz, 1H), 5.76 (s, 1H), 3.70 (m, 2H), 2.59 (dd, J=15.1, 7.6 Hz, 2H), 2.21 (s, 3H), 2.15 (s, 3H), 1.61 (m, 2H), 1.55 (m, 2H), 1.39 (s, 9H), 1.22 (t, J=7.5 Hz, 3H), 0.91 (t, J=7.4 Hz, 3H).

Example 149

(L77, Compound VIII of Scheme 17 where R=ethyl, R'=tert-butyl, R"=methyl, R'"=H, R""=1-fluoropropyl, R""'=H). This compound was prepared in the manner previously described for Compound VIII in Scheme 5. $^1$H NMR (400 MHz, $CDCl_3$) δ: 7.09 (d, J=2.1 Hz, 1H), 6.80 (d, J=2.1 Hz, 1H), 6.57 (dd, J=15.2, 11.1 Hz, 2H), 6.24 (d, J=15.2 Hz, 1H), 6.22 (d, J=11.1 Hz, 1H), 5.76 (s, 1H), 4.55 (m, 1H), 4.50 (m, 1H), 3.82 (m, 2H), 2.60 (dd, J=15.2, 7.5 Hz, 2H), 2.22 (s, 3H), 2.13 (s, 3H), 2.01 (m, 2H), 1.39 (s, 9H), 1.23 (t, J=7.6 Hz, 3H).

Example 150

(L78, Compound VIII of Scheme 17 where R=ethyl, R'=tert-butyl, R"=methyl, R'"=H, R""=thiomethoxymethyl, R""'=H). This compound was prepared in the manner previously described for Compound VIII in Scheme 5. $^1$H NMR (400 MHz, $CDCl_3$) δ: 7.12 (d, J=2.7 Hz, 1H), 6.79 (d, J=2.7 Hz, 1H), 6.59 (dd, J=15.1, 11.0 Hz, 1H), 6.26 (d, J=15.1 Hz), 6.23 (d, J=11.0 Hz, 1H), 5.77 (s, 1H), 4.80 (d, J=10.1 Hz, 1H), 4.71 (d, J=10.1 Hz, 1H), 2.60 (dd, J=15.1, 7.6 Hz, 2H), 2.23 (s, 3H), 2.15 (s, 3H), 1 .44 (s, 9H), 1.22 (t, J=7.7 Hz, 3H).

Example 151

(L79, Compound VIII of Scheme 17 where R=ethyl, R'=tert-butyl, R"=methyl, R""=H, R""=1,1-di-fluoroethyl, R''''''=H). This compound was prepared in the manner previously described for Compound VIII in Scheme 5. ¹H NMR (400 MHz, CDCl₃) δ: 7.12 (d, J=2.0 Hz, 1H), 6.81 (d, J=2.0 Hz, 1H), 6.56 (dd, J=15.1, 11.1 Hz, 2H), 6.28 (d, J=15.2 Hz, 1H), 6.27 (d, J=1 1.1 Hz, 1H), 5.95 (dt, J=55.5, 4.0 Hz, 1H), 5.78 (s, 1H), 3.95 (m, 2H), 2.60 (dd, J=15.1, 7.5 Hz, 2H), 2.21 (s, 3H), 2.14 (s, 3H), 1.40 (s, 9H), 1.23 (t, J=7.5 Hz, 3H).

Example 152

(L80, Compound VIII of Scheme 17 where R=ethyl, R'=tert-butyl, R''=methyl, R'''=H, R''''=1,1,2,2-tetrafluoropropyl, R'''''=H). This compound was prepared in the manner previously described for Compound VIII in Scheme 5. ¹H NMR (400 MHz, CDCl₃) δ: 7.26 (d, J=2.0 Hz, 1H), 7.13 (d, J=2.0 Hz, 1H), 6.48 (dd, J=14.9, 11.1 Hz, 2H), 6.28 (d, J=15.2 Hz, 1H), 6.27 (d, J=11.1 Hz, 1H), 5.88 (dt, J=49.1, 4.0 Hz, 1H), 5.79 (s, 1H), 4.10 (m, 2H), 2.61 (dd, J=15.1, 7.5 Hz, 2H), 2.20 (s, 3H), 2.13 (s, 3H), 1.39 (s, 9H), 1.23 (t, J=7.5 Hz, 3H).

Scheme 18

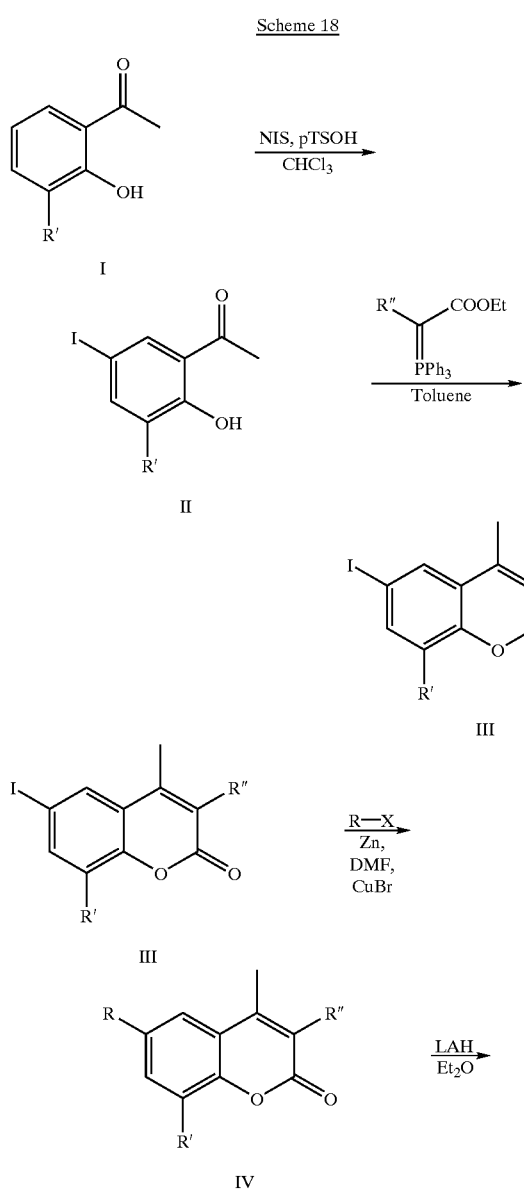

-continued

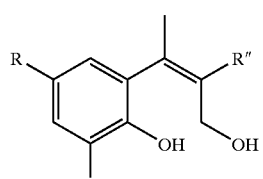

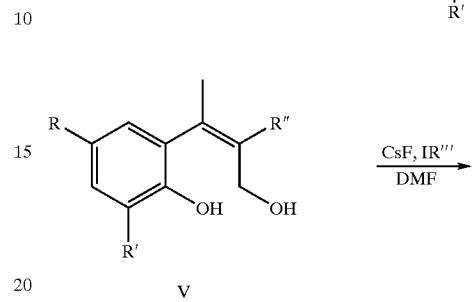

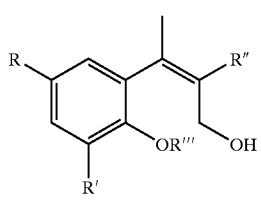

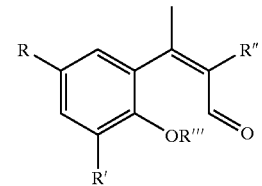

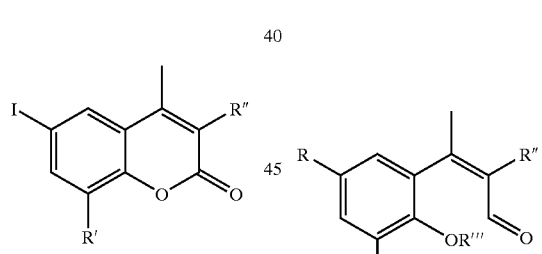

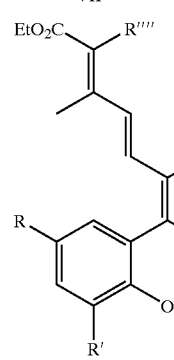

-continued

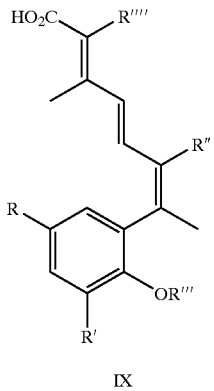

IX

Example 153

(Compound I of Scheme 18, where R'=isopropyl). Into a 1L round-bottomed flask was added 2-hydroxy-3-isopropylbenzoic acid (10.0 g, 55.49 mmoles) and THF (500 mL). This solution was cooled to 0° C. and methyllithium (311 mL of a 1.4 M solution, 435.0 mmoles) was added dropwise via addition funnel. The reaction was subsequently stirred at 0° C. for 1 h and then gradually warmed to room temperature for 72 h. At this time, the reaction was quenched with ethyl acetate, isopropanol, and saturated aqueous Ammonium Chloride. This crude mixture was concentrated in-vacuo, extracted with 5% ethyl acetate/hexanes, and filtered over a silica plug affording 7.9 g of I (43.76 mmoles, 79% yield) $^1$H NMR (400 MHz, CDCl$_3$) δ: 10.32 (s, 1H), 7.60 (d, J=8.0 Hz, 1H), 7.42 (d, J=8.1 Hz, 1H), 6.87 (t, J=7.7 Hz, 1H), 3.39 (m, 1H), 2.63 (s, 3H), 1.24 (d, J=6.8 Hz, 6H).

Example 154

(Compound II of Scheme 18, where R'=isopropyl). Into a 500 mL round-bottomed flask fitted with a reflux condenser was added hydroxy-3-isopropylphenyl)ethanone (7.7 g, 43.20 mmoles), N-iodosuccinimide (10.69 g, 47.52 mmoles), p-toluenesulfonic acid (0.822 g, 4.32 mmoles), and chloroform (216 mL). This solution was heated to reflux for 2 h. At this time, the reaction was quenched with a saturated aqueous solution of sodium thiosulfate and extracted with methylene chloride. The organic layer was then passed directly over a pad of silica gel and washed with methylene chloride to elute the product. Removal of the solvent in-vacuo afforded 12.8 g of II (42.19 mmoles, 98% yield). $^1$H NMR (400 MHz, CDCl$_3$) δ: 10.9 (s, 1H), 7.87 (d, J=2.2 Hz, 1H), 7.62 (d, J=2.0 Hz, 1H), 3.32 (m, 1H) 2.61 (s, 3H), 1.21 9d, J=6.6 Hz, 6H).

Example 155

(Compound III of Scheme 18, where R'=isopropyl, R"=H). Into a 500 mL round-bottomed flask fitted with a Dean-Stark apparatus and a reflux condenser was added 1-(2-Hydroxy-5-iodo-3-isopropyl-phenyl)-ethanone (12.8 g, 42.19 mmoles) and Toluene (300 mL). To this was added (Carbethoxymethylene)triphenylphosphorane (34.0 g, 97.0 mmoles), and the solution was heated to reflux overnight using a Dean-Stark trap. The reaction was then passed directly over a pad of silica gel and washed with hexanes to elute the Toluene. A 10% Ethyl Acetate/Hexanes solution was then used to elute the product off of the silica gel. Removal of the Solvent in-vacuo afforded 6.6 g of III (20.1 mmoles, 47% yield). $^1$H NMR (400 MHz, CDCl$_3$) δ: 7.75 (d, J=1.9 Hz, 1H), 7.70 (d, J=2.0 Hz, 1H), 6.29 (s, 1H), 3.58 (m, 1H), 2.41 (s, 3H), 1.28 (d, J=6.9 Hz, 6H).

Example 156

(Compound IV of Scheme 18, where R'=isopropyl, R=1,1,1,2,2-pentafluoroethyl, R"=H). Into a flame-dried 250 mL round-bottomed flask equipped with a cold-finger condenser was added Zinc(s) (3.98 g, 60.95 mmoles) and DMF (50 mL). This mixture was heated to 40° C. and Perfluoroethyliodide(g) was bubbled into reaction mixture until the Zinc dissolution was complete. This solution was allowed to cool to room temperature. At this time, the perfluoroethylzinc reagent was slowly cannulated into a slurry of CuBr (4.81 g, 33.53 mmoles) and DMF (50 mL) making sure to keep the temperature less than 30° C. III (5.0 g, 15.24 mmoles) was then added and the solution was heated under nitrogen to 65° C. for 6 h. The resultant mixture was quenched with NH$_4$Cl(aq) and extracted 2× with EtOAc. The organic layer was washed with Brine, collected and filtered over a pad of Celite. The solvent was removed in-vacuo and the crude oil was chromatographed on Silica gel (10% Ethyl Acetate/Hexanes) affording 3.96 g (12.37 mmoles, 81% yield) of IV. $^1$H NMR (400 MHz, CDCl$_3$) δ: 7.67 (s, 1H), 7.64 (s, 1H), 6.39 (s, 1H), 3.67 (m, 1H), 2.49 (s, 3H), 1.33 (d, J=6.8 Hz, 6H).

Example 157

(Compound V of Scheme 18, where R=1,1,1,2,2-pentafluoroethyl, R'=isopropyl, R"=H). Into a flame-dried 250 mL round-bottomed flask equipped for magnetic stirring was added of IV (0.820 g, 2.56 mmoles) and Et$_2$O (25 mL). This solution was cooled to 0° C. and LiAlH$_4$ (97mg, 2.56 mmoles) was added and then allowed to stir for 1 h. At this point, the reaction was complete by TLC analysis, therefore no additional LiAlH$_4$ was added. The reaction was quenched with a 10% (w/v) NaOH solution (Only enough to quench the reaction). This heterogeneous mixture was filtered over a small pad of silica gel using EtOAc to elute V. The filtrate was concentrated and dried in-vacuo affording a crude oil that was used without further purification. $^1$H NMR (400 MHz, CDCl$_3$) δ: 7.32 (s, 1H), 7.10 (s, 1H), 6.12 (broad s, 1H), 6.03 (t, J=7.3 Hz, 1H), 3.92 (d, J=7.3 Hz, 2H), 3.33 (m, 1H), 2.06 (s, 3H), 1.39 (t, J=6.9 Hz, 1H), 1.25 (d, J=7.0 Hz, 6H).

Example 158

(Compound VI of Scheme 18, where R=1,1,1,2,2-pentafluoroethyl, R'=isopropyl, R"=H, R'''=ethyl). Into a 100 mL round-bottomed flask equipped for magnetic stirring was added crude V (2.56 mmoles max) and DMF (20 mL). Cesium Carbonate (4.17 g, 12.8 mmoles) and Iodoethane (0.215 mL, 2.69 mmoles) were then added and the solution was stirred at room temperature overnight. At this point a 10% EtOAc/Hexanes solution was added and the resultant mixture was filtered over a silica plug using a 10% EtOAc/Hexanes solution to elute VI. The filtrate was concentrated and dried in-vacuo affording a yellow oil that was used without further purification. $^1$H NMR (400 MHz, CDCl$_3$) δ: 7.38 (d, J=2.2 Hz, 1H), 7.14 (d, J=2.2 Hz, 1H), 5.87 (t, 7.7 Hz, 1H), 3.83 (m, 4H), 3.37 (m, 1H), 1.37 (t, J=7.2 Hz, 3H), 1.24 (m, 7H).

Example 159

(Compound VII of Scheme 18, where R=1,1,1,2,2-pentafluoroethyl, R'=isopropyl, R"=ethyl). Into a 100 mL round-bottomed flask was added crude V (2.56 mmoles max), dichloromethane (20 mL), and NMO (1.0 g, 8.54 mmoles). TPAP (Catalytic, Spatula tip) was then added and the solution was stirred at RT for 1 h. The crude solution was then passed directly over a silica plug and the aldehyde was eluted with dichloromethane. The filtrate was concentrated and dried in-vacuo affording crude VII which was used without further purification. $^1$H NMR (400 MHz, CDCl$_3$) δ: 9.39 (d, J=8.1 Hz, 1H), 7.49 (d, J=2.1 Hz, 1H), 7.22 (d, J=2.1 Hz, 1H), 6.17 (d, J=8.0 Hz, 1H), 3.81 (q, J=7.0 Hz, 2H), 3.39 (m, 1H), 2.35 (s, 3H), 1.34 (t, J=7.0 Hz, 3H), 1.26 (d, J=6.9 Hz, 6H).

Example 160

(Compound VIII of Scheme 18, where R=1,1,1,2,2-pentafluoroethyl, R'=isopropyl, R"=H, R'"=ethyl, R""=H). Into a flame dried round-bottomed flask was added triethyl-3-methyl-4-phosphonocrotonate (2.45 mL, 10.24 mmoles), THF (30 mL), and DMPU (5 mL). This solution was cooled to −78° C. and n-BuLi (4.0 mL of a 2.5M solution in hexanes, 9.98 mmoles) was added dropwise via syringe. The reaction was then allowed to stir for 30 min at −78° C. At this time VII (2.56 mmoles max) was added in THF (10 mL) and the solution was allowed to stir at −78° C. for 2 h. Subsequently, the reaction was quenched with distilled water and extracted with a 10% EtOAc/Hexanes solution. The organic layer was directly passed over a silica gel plug and the ester was eluted using 10% EtOAc/Hexanes. The filtrate was concentrated and dried in-vacuo affording a yellow oil that was essentially pure VIII by NMR. $^1$H NMR (400 MHz, CDCl$_3$) δ: 7.41 (d, J=2.2 Hz, 1H), 7.14 (d, J=2.2 Hz, 1H), 6.44 (dd, J=15.2 Hz, 11.0, 1H), 6.28 (d, J=9.7, 1H), 6.25 (d, J=15.0 Hz, 1H), 5.75 (s, 1H), 4.15 (q, J=7.1 Hz, 2H), 3.80 (broad s, 2H), 3.40 (m, 1H), 2.20 (s, 3H), 2.11 9s, 3H), 1.27 (m, 12H).

Example 161

(L15, Compound IX of Scheme 18, where R=1,1,1,2,2-pentafluoroethyl, R'=isopropyl, R"=H, R'"=ethyl, R""=H). Into a 100 mL round-bottomed flask fitted with a reflux condenser was added crude VIII (2.56 mmoles max), EtOH (30 mL) and LiOH (7.68 mL of a 1N solution, 7.68 mmoles). This solution was then heated to reflux for 2 h. The resultant mixture was quenched with HCl(aq) and extracted 2× with EtOAc. The organic layer was washed with Brine, collected and filtered over a pad of Celite. The solvent was removed in-vacuo and the crude product was crystallized three times using acetonitrile affording IX which was >99% pure by HPLC and NMR. $^1$H NMR (400 MHz, CDCl$_3$) δ: 7.41 (s, 1H), 7.13 (s, 1H), 7.47 (dd, J=15.2 Hz, 11.0 Hz, 1H), 6.28 (d, J=9.1 Hz, 1H), 6.26 (d, J=15.4 Hz, 1H), 5.77 (s, 1H), 3.79 (broad s, 2H), 3.40 (m, 1H), 2.21 (s, 3H), 2.11 (s, 3H), 1.32 (t, J=6.9 Hz, 3H), 1.26 (d, J=6.7 Hz, 6H).

Example 162

(L81, Compound IX of Scheme 18, where R=1,1,1,2,2-pentafluoroethyl, R'=isopropyl, R"=H, R'"=propyl, R""=H). This compound was prepared as described previously for Compound IX in Example 161 except that iodopropane was used instead of iodoethane in Example 158. $^1$H NMR (400 MHz, CDCl$_3$) δ: 7.41 (d, J=2.1 Hz, 1H), 7.14 (d, J=2.1 Hz, 1H), 6.48 (dd, J=15.3 Hz, 10.9 Hz, 1H), 6.29 (d, J=7.9 Hz, 1H), 6.27 (d, J=15.5 Hz, 1H), 5.77 (s, 1H), 3.67 (broad s, 2H), 3.39 (m, 1H), 2.21 (s, 3H), 2.12 (s, 3H), 1.71 (m, 2H), 1.26 (d, J=6.8 Hz, 6H), 0.98 (t, J=7.5 Hz, 3H).

Example 163

(L82, Compound IX of Scheme 18, where R=1,1,1,2,2-pentafluoroethyl, R'=isopropyl, R"=H, R'"=1,1,1-trifluorobutyl, R""=H). This compound was prepared as described previously for Compound IX in Example 161 except that 1,1,1-trifluoro-4-iodobutane was used instead of iodoethane in Example 158. $^1$H NMR (400 MHz, CDCl$_3$) δ: 7.41 (d, J=2.1 Hz, 1H), 7.14 (d, J=2.1 Hz, 1H), 6.41 (dd, J=15.2 Hz, 10.8 Hz, 1H), 6.29 (d, J=10.8 Hz, 1H), 6.27 (d, J=15.2 Hz), 5.76 (s, 1H), 3.74 (broad s, 2H), 3.29 (m, 1H), 2.26 (m, 2H), 2.18 (s, 3H), 2.09 (s, 3H), 1.92 (m, 2H), 1.24 (d, J=6.8 Hz, 6H).

Example 164

(L83, Compound IX of Scheme 18, where R=1,1,1,2,2-pentafluoroethyl, R'=isopropyl, R"=H, R'"=n-butyl, R""=H). This compound was prepared as described previously for Compound IX in Example 161 except that iodobutane was used instead of iodoethane in Example 158. $^1$H NMR (400 MHz, CDCl$_3$) δ: 7.41 (d, J=2.1 Hz, 1H), 7.14 (d, J=2.1 Hz, 1H), 6.48 (dd, J=15.3 Hz, 10.9 Hz, 1H), 6.28 (d, J=7.6 Hz, 1H), 6.27 (d, J=15.4, 1H), 5.77 (s, 1H), 3.71 (broad s, 2H), 3.38 (m, 1H), 2.20 (s, 3H), 2.12 (s, 3H), 1.67 (m, 2H), 1.43 (m, 2H), 1.25 (d, J=6.8 Hz, 6H), 0.93 (t, J=7.3 Hz, 3H).

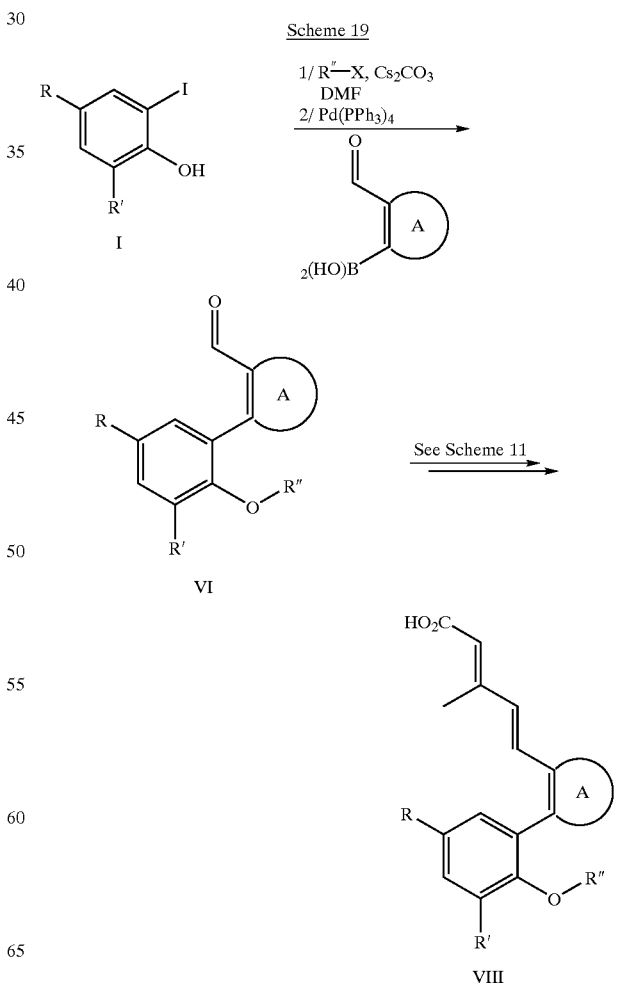

Scheme 19

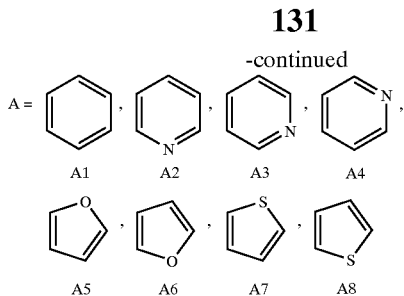

Scheme 19 depicts an alternate method to introducing a variety of substituents at $R^2$ and $R^4$ in modulators of type VIII.

Example 165

(L84, Compound VIII of Scheme 19, where R=ethyl, R'=tert-butyl, R"=1-fluoropropyl, A=A7). This compound was prepared as described previously for Compound VIII in Example 82 according to Scheme 5. $^1$H NMR (400 MHz, CDCl$_3$) δ: 7.32 (d, J=5.1 Hz, 1H), 7.17 (d, J=2.0 Hz, 1H), 7.10 (d, J=5.2 Hz, 1H), 7.00 (d, J=15.8 Hz, 1H), 6.93 (d, J=1.9 Hz, 1H), 6.65 (d, J=15.8 Hz, 1H), 5.87 (s, 1H), 4.45 (t, J=5.4, Hz, 1H), 4.32 (t, J=5.4 Hz, 1H), 3.51 (m, 2H), 2.63 (dd, J=15.2, 7.6 Hz, 2H), 2.24 (s, 3H), 1.85 (m, 1H), 1.75 (m, 1H), 1.43 (s, 9H), 1.25 (t, J=7.5 Hz, 3H).

Example 166

(L85, Compound VIII of Scheme 19, where R=tert-butyl, R'=methyl, R"=n-butyl, A=A7). This compound was prepared as described previously for Compound VIII in Example 82 according to Scheme 5. $^1$H NMR (400 MHz, CDCl$_3$) δ: 7.25 (d, J=3.1 Hz, 1H), 7.20 (d, J=2.3 Hz, 1H), 7.18 (d, J=5.3 Hz, 1H), 7.10 (d, J=15.8 Hz, 1H), 7.05 (d, J=2.4 Hz, 1H), 6.67 (d, J=15.8 Hz, 1H), 5.88 (s, 1H), 3.41 (t, J=6.4 Hz, 2H), 2.33 (s, 3H), 2.26 (s, 3H), 1.45 (m, 2H), 1.31 (s, 9H), 1.28 (m, 2H), 0.79 (t, J=7.3 Hz, 3H).

Example 167

(L86, Compound VIII of Scheme 19, where R=ethyl, R'=tert-butyl, R"=1,1-difluoroethyl, A=A7). This compound was prepared as described previously for Compound VIII in Example 82 according to Scheme 5. $^1$H NMR (400 MHz, CDCl$_3$) δ: 7.34 (d, J=5.2 Hz, 1H), 7.19 (d, J=1.9 Hz, 1H), 7.11 (d, J=5.0 Hz, 1H), 6.99 (d, J=15.9 Hz, 1H), 6.95 (d, J=1.9 Hz, 1H), 6.68 (d, J=15.9 Hz, 1H), 5.89 (s, 1H), 5.63 (tt, J=55.4, 4.2 Hz, 1H), 3.58 (m, 2H), 2.64 (dd, J=15.2, 7.6 Hz, 2H), 2.25 (s, 3H), 1.43 (s, 9H), 0.88 (t, J=6.5 Hz, 3H).

Example 168

(L87, Compound VIII of Scheme 19, where R=ethyl, R'=tert-butyl, R"=1,1-difluoroethyl, A=A1). This compound was prepared as described previously for Compound VIII in Example 82 according to Scheme 5. $^1$H NMR (400 MHz, CDCl$_3$) δ: 7.73 (m, 1H), 7.39 (m, 3H), 7.20 (s, 1H), 6.89 (d, J=16.1, Hz, 1H), 6.77 (d, J=16.1 Hz, 1H), 5.88 (s, 1H), 5.36 (dt, J=56.3, 4.3 Hz, 1H), 3.52 (m, 2H), 2.64 (dd, J=15.1, 7.6 Hz, 2H), 2.18 (s, 3H), 1.65 (m, 2H), 1.42 (s, 9H), 1.25 (t, J=6.9 Hz, 3H).

Example 169

(L88, Compound VIII of Scheme 19, where R=ethyl, R'=tert-butyl, R"=n-butyl, A=A1). This compound was prepared as described previously for Compound VIII in Example 82 according to Scheme 5. $^1$H NMR (400 MHz, CDCl$_3$) δ: 7.70 (t, J=5.0 Hz, 1H), 7.36 (m, 3H), 7.16 (d, J=1.9 Hz, 1H), 6.96 (d, J=16.1 Hz, 1H), 6.86 (d, J=1.9 Hz, 1H), 6.76 (d, J=16.1 Hz, 1H), 5.87 (s, 1H), 3.34 (m, 1H), 3.29 (m, 1H), 2.62 (dd, J=15.2, 7.6 Hz, 2H), 2.19 (s, 3H), 1.42 (s, 9H), 1.31 (m, 2H), 1.24 (t, J=7.4 Hz, 3H), 1.12 (m, 2H), 0.67 (t, J=7.2 Hz, 3H).

Example 170

(L89, Compound VIII of Scheme 19, where R=ethyl, R'=tert-butyl, R"=fluoropropyl, A=phenyl). This compound was prepared as described previously for Compound VIII in Example 82 according to Scheme 5. $^1$H NMR (400 MHz, CDCl$_3$) δ: 7.62 (m, 1H), 7.38 (m, 3H), 7.18 (d, J=2.1 Hz, 1H), 6.92 (d, J=16.1 Hz, 1H), 6.89 (d, J=2.1 Hz, 1H), 6.78 (d, J=16.1 Hz, 1H), 5.89 (s, 1H), 4.24 (m, 2H), 3.47 (m, 1H), 3.40 (m, 1H), 2.63 (dd, J=15.2, 7.6 Hz, 2H), 2.19 (s, 3H), 1.62 (m, 2H), 1.42 (s, 9H), 1.25 (t, J=7.7 Hz, 3H).

Example 171

(L90, Compound VIII of Scheme 19, where R=ethyl, R'=tert-butyl, R"=propyl, A=A1). This compound was prepared as described previously for Compound VIII in Example 82 according to Scheme 5. $^1$H NMR (400 MHz, CDCl$_3$) δ: 7.69 (t, J=5.4 Hz, 1H), 7.35 (m, 3H), 7.16 (d, J=2.2 Hz, 1H), 6.96 (d, J=16.0 Hz, 1H), 6.87 (d, J=2.2 Hz, 1H), 6.76 (d, J=16.0 Hz, 1H), 5.87 (s, 1H), 3.34 (m, 1H), 3.32 (m, 2H), 2.62 (dd, J=15.2, 7.6 Hz, 2H), 2.19 (s, 3H), 1.42 (s, 9H), 1.30 (m, 2H), 1.24 (t, J=7.5 Hz, 3H), 0.62 (t, J=7.5 Hz, 3H).

Example 172

(L91, Compound VIII of Scheme 19, where R=ethyl, R'=tert-butyl, R"=fluoroethyl, A=phenyl). This compound was prepared as described previously for Compound VIII in Example 82 according to Scheme 5. $^1$H NMR (400 MHz, CDCl$_3$) δ: 7.71 (m, 1H), 7.37 (m, 3H), 7.19 (d, J=1.9 Hz, 1H), 6.94 (d, J=16.1 Hz, 1H), 6.89 (d, J=1.9 Hz, 1H), 6.76 (d, J=16.0 Hz, 1H), 5.89 (s, 1H), 4.25 (t, J=2.0 Hz, 1H), 4.13 (t, J=2.0 Hz, 1H), 3.55 (m, 2H), 2.62 (dd, J=15.0, 7.6 Hz, 2H), 2.20 (s, 3H), 1.44 (s, 9H), 1.25 (t, J=7.5 Hz, 3H).

Example 173

(L92, Compound VIII of Scheme 19, where R=ethyl, R'=tert-butyl, R"=ethyl, A=A1). This compound was prepared as described previously for Compound VIII in Example 82 according to Scheme 5. $^1$H NMR (400 MHz, CDCl$_3$) δ: 7.70 (dd, J=5.5, 3.6 Hz, 1H), 7.36 (m, 3H), 7.16 (d, J=2.1 Hz, 1H), 6.98 (d, J=16.0 Hz, 1H), 6.86 (d, J=2.1 Hz, 1H), 6.78 (d, J=16.0 Hz, 1H), 5.88 (s, 1H), 3.35 (m, 2H), 2.62 (dd, J=15.1, 7.6 Hz, 2H), 2.21 (s, 3H), 1.43 (s, 9H), 1.24 (t, J=7.5 Hz, 3H), 0.91 (t, J=7.5 Hz, 3H).

Scheme 20

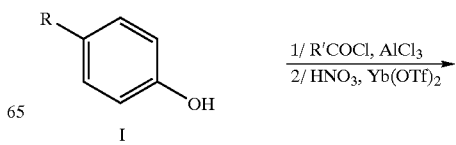

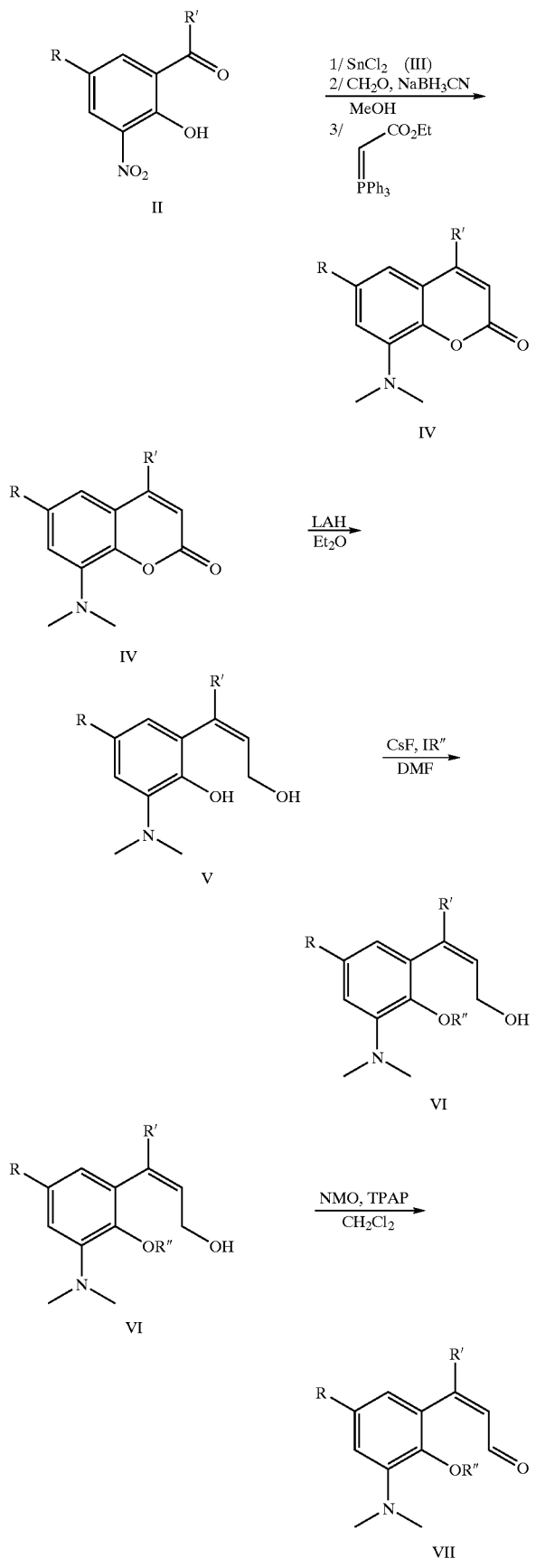
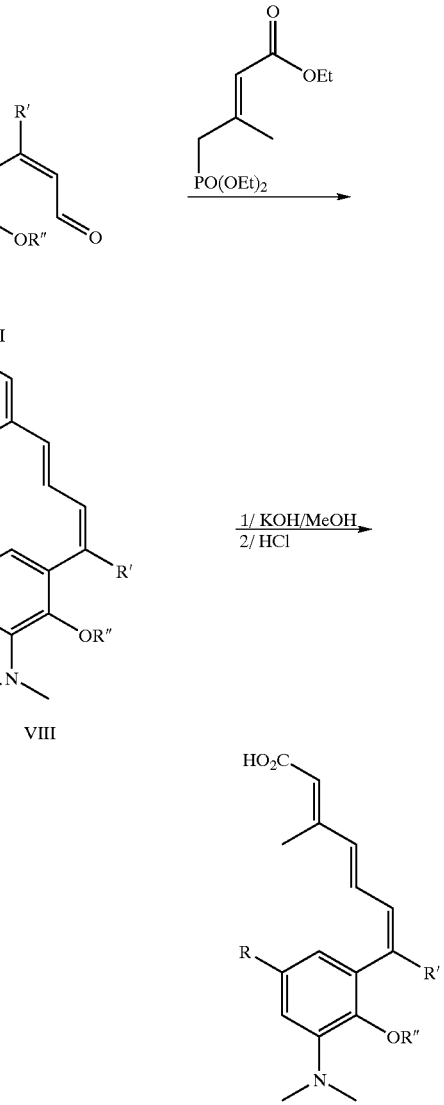

Scheme 20 depicts a method for introducing amine groups at the $R^4$ position of the RXR unsymmetrical modulators.

Example 174

(Compound III of Scheme 20, where R=methyl, R'=methyl). A mixture of 5.0 g (32.6 mmol) of 2-acetyl-4-methyl-6-nitrophenol and 500 mg of 10% Pd/C in 20 ml of ethyl acetate was stirred under hydrogen atmosphere for 16 hours. The mixture was filtrated over celite and the solvents evaporated under reduced pressure. The crude aniline was directly dissolved into 60 ml of methanol, and 1.4 g (10.3 mmol) of $ZnCl_2$ followed by 5.2 ml of formaldehyde (37% in water) were added. The solution was cooled to 0° C. and $NaBH_3CN$ (excess) was added portionwise. After complexion of the reaction (TLC analysis), the solvents were removed and he residue purified over silica gel column chromatography (eluent: 10/90 ethyl acetate/hexane) to afford 2.9 g (15 mmol, yield: 73%) of III. $^1$H NMR (400 MHz, $CDCl_3$) δ: 10.75 (s, 1H), 7.15 (d, J=1.7 Hz, 1H), 6.90 (d, J=1.7 Hz, 1H), 2.81 (s, 9H), 2.61 (s, 3H), 2.29 (s, 3H).

Example 175

(Compound IV of Scheme 20, where R=methyl, R'=methyl). A mixture of 1.9 g (10 mmol) and 8.7 g (25 mmol) of carbethoxy triphenylphoshonoacetate in toluene was refluxed for 16 hours. After complexion of the reaction (TLC analysis), the solvents were removed and he residue purified over silica gel column chromatography (eluent: 15/85 ethyl acetate/hexane) to afford 1.9 g (8.7 mmol, yield: 87%) of IV. $^1$H NMR (400 MHz, CDCl$_3$) δ: 6.95 (d, J=1.8 Hz, 1H), 6.89 (d, J=1.8 Hz, 1H), 6.24 (s, 1H), 2.90 (s, 6H), 2.39 (s, 3H), 2.38 (s, 3H), 2.37 (s, 3H).

Example 176

(L93, Compound XII of Scheme 20, where R=methyl, R"=methyl, R'"=n-butyl). This compound was prepared as described previously for Compound VII according to Scheme 5. $^1$H NMR (400 MHz, CDCl$_3$) δ: 6.66 (d, J=2.1 Hz, 1H), 6.57 (dd, J=15.5, 10.9 Hz, 1H), 6.47 (broad s, 1H), 6.21 (d, J=14.6 Hz, 2H), 5.74 (s, 1H), 3.73 (m, 2H), 2.82 (s, 6H), 2.28 (s, 3H), 2.17 (s, 3H), 2.13 (s, 3H), 1.57 (m, 2H), 1.39 (m, 2H), 0.89 (t, J=7.4 Hz, 3H).

Example 177

(L94, Compound XII of Scheme 20, where R=methyl, R"=methyl, R'"=n-propyl). This compound was prepared as described previously for Compound VII according to Scheme 5. $^1$H NMR (400 MHz, CDCl$_3$) δ: 6.66 (s, 1H), 6.57 (dd, J=15.5, 10.8 Hz, 1H), 6.47 (s, 1H), 6.21 (d, J=15.4 Hz, 1H), 5.74 (s, 1H), 3.70 (m, 2H), 2.81 (s, 6H), 2.17 (s, 3H), 2.14 (s, 3H), 1.61 (m, 2H), 0.93 (t, J=7.4 Hz, 3H).

Example 178

(L95, Compound XII of Scheme 20, where R=methyl, R"=methyl, R'"=1-fluoropropyl). This compound was prepared as described previously for Compound VII according to Scheme 5. $^1$H NMR (460 MHz, CDCl$_3$) δ: 6.67 (s, 1H), 6.53 (dd, J=15.3, 10.8 Hz, 1H), 6.50 (d, J=10.8 Hz, 1H), 6.22 (d, J=15.3 Hz, 1H), 6.20 (s, 1H), 5.75 (s, 1H), 4.62 (t, J=6.0 Hz, 1H), 4.50 (t, J=6.0 Hz, 1H), 3.86 (t, J=5.6 Hz, 2H), 2.80 (s, 6H), 2.26 (s, 3H), 2.16 (s, 3H), 2.13 (s, 3H), 1.96 (m, 2H).

Example 179

(Compound II of Scheme 20, where R=phenyl, R"=methyl). To a flame dried 250 ml round bottom flask, 1 g (3.85 mmol) 5-Bromo-2-hydroxy-3-nitroacetophenone, 0.56 g (4.60 mmol) phenol boronic acid, 0.22 g (0.15 mmol)tetrakis(triphenylphosphine)palladium, and 5.77 ml (11.5 mmol) of a 2M sodium carbonate solution was added to 1:1 toluene:ethanol (2M) and heated to reflux for 12 hrs. The reaction was then diluted with 250 ml of 25% ethyl acetate/hexane solution and filtered through a silica packed plug using a gradient solvent system (eluent: hexanes to 20% ethyl acetate/hexanes). The crude fractions were then combined and concentrated under reduced pressure to a dark brown solid. The solid was further purified using flash silica gel column chromatography using a gradient solvent system (eluent: Hexanes (0.1% acetic acid) to 10% ethyl acetate/hexanes (0.1% acetic acid)) solvent system. The solid was further purified by recrystallization from 10% ethyl acetate/hexanes resulting in 0.36 g (1.4 mmol) of II as an orange/yellow solid in 37% yield. $^1$H NMR (500 MHz, CDCl$_3$) δ: 12.97 (s, 1H), 8.44 (d, J-=2.4 Hz, 1H), 8.26 (d, J=2.4 Hz, 1H), 7.57 (dd, J=8.5 Hz, 1.2, 2H), 7.51 (t, J=7.6 Hz, 2H), 7.44 (t, J=7.0 Hz, 1H), 2.79 (s, 3H).

Example 180

(Compound III of Scheme 20, where R=phenyl, R'=methyl). To a 100 ml round bottom flask was added 2.0 g (7.8 mmol) of 5-phenyl-2-hydroxy-3-nitroacetophenone and a catalytic amount (0.8 mmol) of palladium on activated charcoal in 39 ml ethyl acetate (0.2M) under a hydrogen balloon. The reaction was allowed to stir for 12 hrs. at which time the mix was filtered through a celite packed plug using ethyl acetate as the eluent. The fractions were collected and concentrated under reduced pressure to a dark brown oil. Due to low stability the aminophenol was carried on to the next step without further purification.

Crude 0.5 g (2.2 mmol) 5-phenyl-2-hydroxy-3-aminoacetophenone was added to a 100 ml round bottom flask followed by addition of 4.59 ml (44.0 mmol) of a 36% wt solution of formaldehyde in water, and 0.23 g (3.3 mmol) zinc chloride in 20 ml (0.2M) methanol. The mixture was cooled to 0C using an ice water bath and 1.38 g (22.0 mmol) sodium cyanoborohydride was added to the mix under nitrogen in small 0.2 g portions. After addition of the reducing agent, the reaction was allowed to warm to room temperature and stir for 1 hr. The reaction was quenched with water and pH brought to 7 using 1N HCl. The reaction was partitioned with ethyl acetate and washed 3× with ethyl acetate. The organic layers were combined and washed 1× with brine, dried using sodium sulfate, filtered and concentrated under reduced pressure to a yellow oil. The oil was purified using flash column chromatography (eluent: hexanes to 20% ethyl acetate/hexane) affording 0.16 g (0.6 mmol) of III in 29% yield. $^1$H NMR (500 MHz, CDCl$_3$) δ: 7.54 (m, 2H), 7.45 (m, 3H), 7.36 (m, 1H), 7.30 (d, J=2.1 Hz, 1H), 2.90 (s, 6H), 2.70 (s, 3H).

Example 181

Compound IV of Scheme 20, where R=phenyl, R"=methyl). To a 100 ml pear shaped flask was added 0.16 g (0.6 mmol) of 5-phenyl-2-hydroxy-3NN-dimethyacetophenone and 0.44 g (1.3 mmol) carbethoxymethylene triphenylphosphorane in 23 ml (0.2 M) toluene. The reaction was heated to reflux and allowed to stir for 12 hrs. The reaction was diluted with 250 mLs 10% ethyl acetate/hexanes and purified using flash silica gel column chromatography (eluent:hexanes to 20% hexanes/ethyl acetate) affording 0.15 g (0.5 mmol) of IV as a yellow solid in 86% yield. $^1$H NMR (500 MHz, CDCl$_3$) δ: 7.59 (m, 2H), 7.47 (m, 2H), 7.39 (m, 1H), 7.34 (d, J=2.1 Hz, 1H), 7.28 (d, J=2.1 Hz, 1H), 6.33 (d, J=1.2 Hz, 1H), 3.00 (s, 6H), 2.48 (d, J=1.2 Hz, 3H).

Example 182

(Compound V of Scheme 20 where R=phenyl, R'=methyl). To a flame dried 100 ml pear shaped flask was added 0.19 g (0.7 mmol) 6-Phenyl-8-NN-dimethyl-4-methyl-chromen-2-one in a 9:1 mixture of diethyl ether:tetrahydrofuran under nitrogen. The solution was cooled to 0C using an ice bath and allowed to stir for 15 min. at which time 0.03 g (0.7 mmol) lithium aluminum hydride was added and the reaction was allowed to stir for 1.5 hrs at 0C The reaction was quenched with 1N sodium hydroxide bringing the pH to 7. The mixture was filtered through a celite packed plug using ethyl acetate as the eluent. The organic layers were combined and dried using sodium sulfate, filtered, and concentrated under reduced pressure to a white foam. Due to lack of stability, V was carried on to next step without further purification.

Example 183

(Compound VI of Scheme 20 where R=phenyl, R'=methyl, R"=1,1-difluoroethyl). To a flame dried 100 ml pear shaped flask was added 0.2 g (0.7 mmol) V as a crude white foam in 10 ml (0.1 M) N,N-Dimethylformamide. 0.1 g (0.8 mmol) Difluorobromoethane was added, followed by addition of 0.3 g (1.0 mmol) cesium carbonate under nitrogen. The reaction was allowed to stir for 12 hrs. at room temperature at which time 250 ml of a 10% ethyl acetate/hexanes mix was used to dilute the mixture. The reaction was filtered through a silica packed plug and the organic layers were combined and concentrated under reduced pressure affording 0.07 g (0.2 mmol) of VI as an oil in 29% yield. $^1$H NMR (500 MHz, CDCl$_3$) δ: 7.54 (m, 2H), 7.43 (m, 2H), 7.33 (m, 1H), 7.06 (d, J=2.1 Hz, 1H), 6.92 (d, J=2.1 Hz, 1H), 6.03 (m, 1H), 5.87 (m, 1H), 4.11 (mr, 2H), 3.94 (d, J=7.3 Hz, 2H), 2.86 (s, 6H), 2.11 (s, 3H).

Example 184

(Compound VII of Scheme 20 where R=phenyl, R'=methyl, R"=1,1-difluoroethyl). To a flame dried 100 ml pear shaped flask 0.07 g (0.2 mmol) VI in 3 ml (0.1 M) dichloromethane was added 0.04 g (0.3 mmol) 4-methylmorpholine N-oxide and 7 mg (0.02 mmol) Tetrapropylammonium perruthenate. The reaction was allowed to stir for 1.5 hrs at room temperature at which time the reaction was filtered through a celite packed plug using dichloromethane as the eluent. The organic layers were combined and concentrated under reduced pressure to a dark brown oil. Due to lack of stability, the product was carried on without further purification.

Example 185

(Compound VIII of Scheme 20 where R=phenyl, R'=methyl, R"=1,1-difluoroethyl). To a flame dried 100 ml pear shaped flask under nitrogen was added 0.15 g (0.6 mmol) triethyl-3-methyl-4-phosphonocrotonate in 2 ml (0.3 M) 2:1 tetrahydorfuran:DMPU(1,3-dimethyl-3,4,5,6-tetrahydo-2-(1H)-pyrimidinone). The mix was cooled to −78° C. using an acetone/dry ice bath. 0.23 ml (0.6 mmol) of n-BuLi (2.5 M solution in hexanes) was added dropwise via syringe. The reaction was allowed to stir at −78° C. for 30 min. at which time 0.07 g (0.2 mmol) 3-[2-(2,2-difluoroethoxy)-3-NN-dimethyl-5-phenyl]-but-2-enal in 1 ml (0.2 M) 2:1 tetrahydrofuran:DMPU(1,3-dimethyl-3,4,5,6-tetrahydo-2-(1H)-pyrimidinone) was added to the mix via cannula and the reaction was allowed to warm to −40° C. and stir for 2 hrs. The reaction was quenched with water and extracted 3× with ethyl acetate. The organics were combined and washed with brine, dried using sodium sulfate, filtered, and concentrated under reduced pressure to a yellow oil. The oil was purified using flash silica gel column chromatography (eluent: 10% ethyl acetate/hexanes) affording 18 mgs (0.004 mmol) of VIII as an oil in 21% yield. $^1$H NMR (500 MHz, CDCl$_3$) δ: 7.55 (d, J=8.2 Hz, 2H), 7.43 (t, J=7.9 Hz, 2H), 7.34 (m, 1H), 7.10 (s, 1H), 6.93 (d, J=2.1 Hz, 1H), 6.52 (dd, J=15.8, 11.1 Hz, 1H), 6.30 (d, J=10.7 Hz, 1H), 6.25 (d, J=15.3 Hz, 1H), 6.01 (m, 1H), 5.76 (s, 1H), 4.16 (m, 4H), 2.89 (s, 3H), 2.88 (s, 3H), 2.21 (s, 3H), 2.13 (s, 3H), 1.28 (t, J=7.0 Hz, 3H).

Example 186

(L96 Compound IX of Scheme 20, where R=phenyl, R'=methyl, R"=1,1-difluoroethyl). In a 50 ml pear shaped flask was added 18 mgs (0.04 mmol) VIII in 2.5 ml (0.02M) of a 2:2:1 mixture of tetrahydrofuran:ethanol:water. 10 mgs (0.2 mmol) lithium hydroxide was added to the mixture and the reaction was heated to reflux and allowed to stir for 3 hrs. The reaction was quenched with 6N HCl making the solution acidic (pH around 1) followed by 3× extraction with ethyl acetate. The organic layers were combined and washed with brine, dried with sodium sulfate, filtered, and concentrated under reduced pressure to a white solid. The solid was purified using reverse phase HPLC (eluent: 80/20 methanol/water (0.1% trifluoroaceticacid) resulting in 9 mgs (0.02 mmol) 1× in a 52% yield. $^1$H NMR (500 MHz, CDCl$_3$) δ: 7.48 (m, 6H), 7.35 (d, J=2.14 Hz, 1H), 6.51 (dd, J=12.07, 10.4 Hz, 1H), 6.43 (d, J=12.2 Hz, 1H), 6.39 (d, J=15.3 Hz, 1H), 6.18 (tt, J=4.9, 4.5 Hz, 1H), 5.83 (s, 1H), 4.70 (bs, 1H), 4.22 (m, 2H), 3.29 (s, 6H), 2.24 (s, 3H), 2.14 (s, 3H).

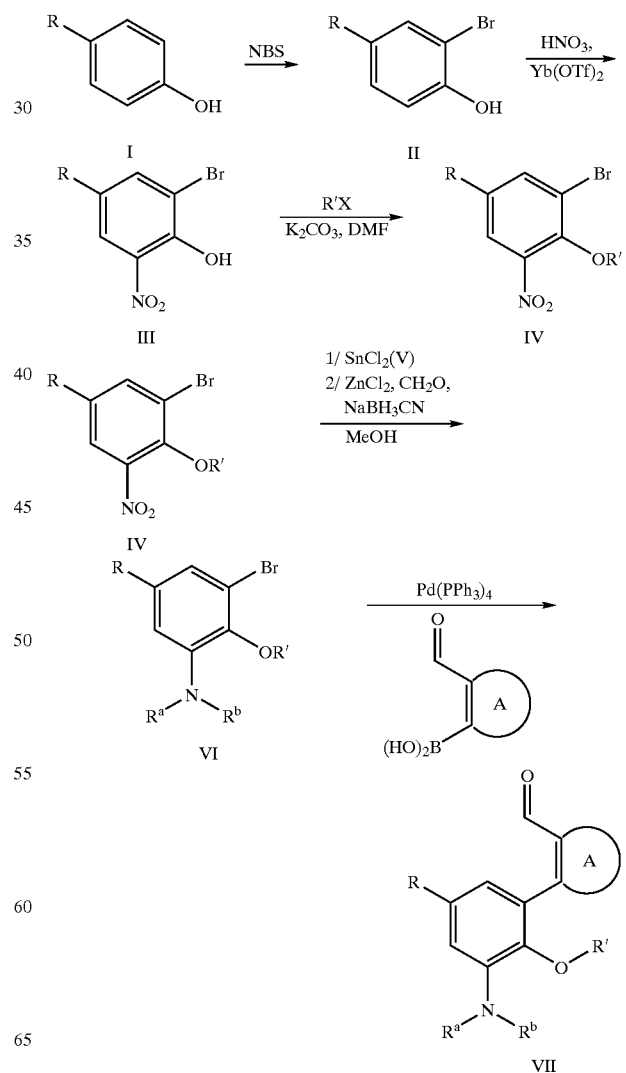

Scheme 21

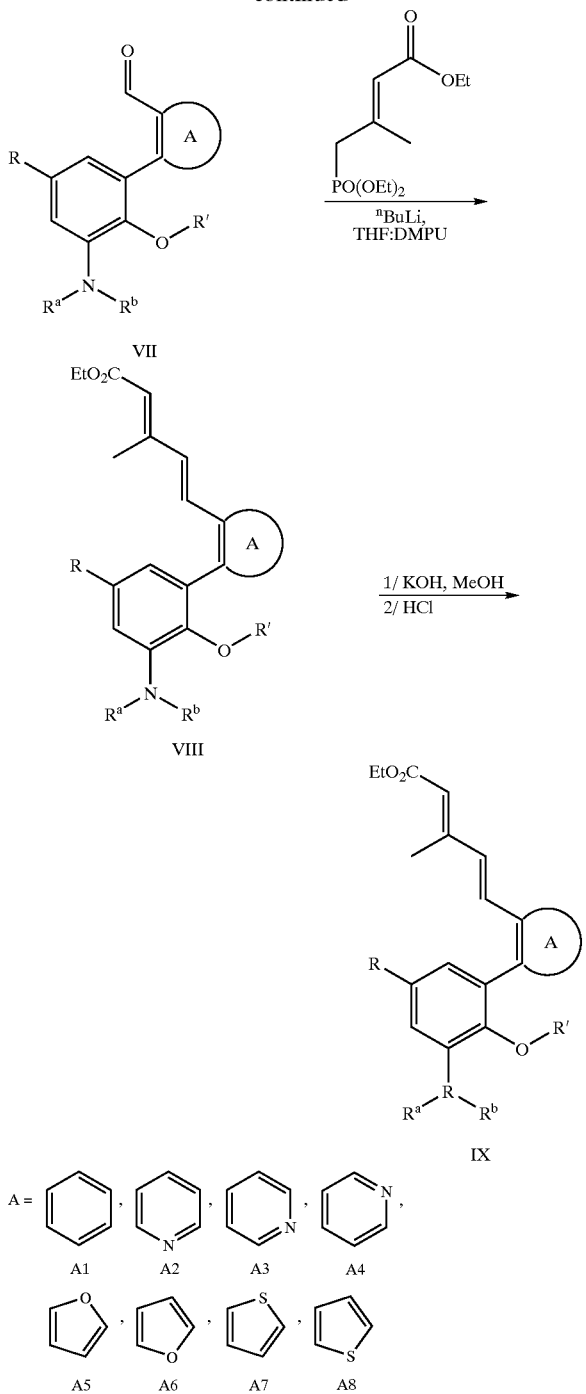

Example 187

(Compound II of Scheme 21, where R=ethyl). To a mixture of 35 g (0.286 mol) of 4-ethyl phenol and 0.5 g (0.029 mol) of p-toluenesulfonic acid in 300 ml of CH$_2$Cl$_2$ was added portionwise 56 g (0.315 mol) of NBS. After complexion of the reaction (TLC monitoring), water was added and the aqueous layer was extracted with CH$_2$Cl$_2$. The organic layers were combined, dried over MgSO$_4$ and evaporated under reduced pressure. The crude product was purified over a large pad of silica gel (eluent: 5/95 ethyl acetate/hexane) to afford 56.3 g (0.28 mol, yield: 98%) of II. $^1$H NMR (400 MHz, CDCl$_3$) δ: A mettre.

Example 188

(Compound III of Scheme 21, where R=ethyl). To a mixture of 0.5 g (0.8 mmol) of Yb(Otf)$_2$ in 20 ml of 1,1-dichloroethane was added 1 ml of concentrated nitric acid at room temperature. The mixture was stirred for 10 minutes and a white biphasic precipitate appears on the bottom of the flask. Then 3.24 g (16.1 mmol) of 2-bromo-4-ethyl phenol diluted in 5 ml of 1,1-dichloroethane was added via a syringe. The mixture becomes yellow and is stirred until complexion of the reaction (TLC monitoring). The organic layer was then separated and dried over MgSO$_4$ and evaporated under reduced pressure. The crude product was purified over a large pad of silica gel (eluent: 10/90 ethyl acetate/hexane) to afford 3.7 g (15 mmol, yield: 93%) of III. $^1$H NMR (400 MHz, CDCl$_3$) δ: 10.97 (s, 1H), 7.90 (d, J=2.2 Hz, 1H), 7.71 (d, J=2.2 Hz, 1H), 2.64 (dd, J=15.2, 7.6 Hz, 2H), 1.25 (t, J=7.6 Hz, 3H).

Example 189

(Compound IV of Scheme 21 where R=ethyl, R'=n-propyl). A mixture of 1.47 g (5.97 mmol) of 2-bromo-4-ethyl-6-nitro phenol, 0.9 ml (1.45 g, 7.76 mmol) of 1-iodobutane and 1.23 g (8.9 mmol) of K$_2$CO$_3$ in 8 ml of dry DMF was heated to 60° C. overnight. After cooling at room temperature, water (50 ml) was added and the solution was extracted with ethyl acetate. The organic layer was then separated, dried over MgSO$_4$ and evaporated under reduced pressure. The crude product was purified over a short pad of silica gel (eluent: 5/95 ethyl acetate/hexane) and directly used in the next step. $^1$H NMR (400 MHz, CDCl$_3$) δ: 7.60 (d, J=1.7 Hz, 1H), 7.55 (d, J=1.7 Hz, 1H), 4.09 (t, J=6.4 Hz, 2H), 2.65 (dd, J=15.2, 7.6 Hz, 2H), 1.82 (m, 2H), 4.52 (m, 2H), 1.25 (t, J=7.8 Hz, 3H), 0.98 (t, J=7.5 Hz, 3H).

Example 190

(Compound V of Scheme 21 where R=ethyl, R'=n-propyl). A mixture of crude 2-bromo-4-ethyl-6-nitro propyloxyphenol, 6.7 g (30.0 mmol) of SnCl$_2$ in 20 ml of ethyl acetate was heated to reflux. After the reaction was completed, (TLC monitoring), and cooling at room temperature, water (100 ml) was added. The milky solution was filtrated over a celite plug and extracted with ethyl acetate. The organic layer was then separated, dried over MgSO$_4$ and evaporated under reduced pressure. The crude product was directly used in the next step. $^1$H NMR (400 MHz, CDCl$_3$) δ: 8.2 (broad s, 2H), 7.49 (d, J=1.7 Hz, 1H), 7.44 (d, J=1.7 Hz, 1H), 4.19 (t, J=6.8 Hz, 2H), 2.64 (dd, J=14.9, 7.5 Hz, 2H), 1.90 (m, 2H), 1.42 (m, 2H), 1.26 (t, J=7.3 Hz, 3H), 0.97 (t, J=7.4 Hz, 3H).

Example 191

(Compound VI of Scheme 21 where R=ethyl, R'=n-propyl, R$^a$=R$^b$=methyl). A mixture of crude 2-amino-6-bromo-4-ethyl propyloxyphenol, 1.65 g (12.0 mmol) of ZnCl$_2$ 7.5 ml of formaldehyde (37% solution in water) in 20 ml of methanol was cooled to 0° C. An excess of NaBH$_3$CN was then added portionwise, until the reaction was complete (TLC monitoring). Evaporation of the solvent followed by silica gel column chromatography afford 1.14 g (3.79 mmol, yield: 64%, 3 steps) of VI. $^1$H NMR (400 MHz, CDCl$_3$) δ: 6.95 (d, J=1.8 Hz, 1H), 6.63 (d, J=1.8 Hz, 1H), 3.92 (t, J=6.6 Hz, 2H), 2.81 (s, 6H), 2.54 (dd, J=15.2, 7.6 Hz, 2H), 1.81 (m, 2H), 1.53 (m, 2H), 1.21 (t, J=7.7 Hz, 3H), 0.98 (t, J=7.4 Hz, 3H).

Example 192

(Compound VII of Scheme 21, where R=ethyl, R'=n-butyl, R$^a$=R$^b$=methyl, A=A7). A mixture of 380 mg (1.27 mmol) of 1-bromo-2-propyloxy-4-N,N-dimethylamino-5-ethyl benzene, 73 mg (0.06 mmol) of Pd(PPh$_3$)$_4$, 257 mg (1.65 mmol) of 2-formyl-3-thiophene boronic acid dissolved in 5 ml of toluene, 3 ml of ethanol and 1.3 ml of 2N aqueous Na$_2$CO$_3$ was heated to reflux overnight. After work-up and purification over silica gel column chromatography, 115 mg (0.35 mmol, yield: 27%) of VII was isolated as an oil. $^1$H NMR (400 MHz, CDCl$_3$) δ: 9.78 (s, 1H), 7.68 (d, J=4.9 Hz, 1H), 7.20 (d, J=4.9 Hz, 1H), 6.79 (d, J=1.9 Hz, 1H), 6.74 (d, J=1.9 Hz, 1H), 3.60 (t, J=6.5 Hz, 2H), 2.85 (s, 6H), 2.62 (dd, J=15.2, 7.6 Hz, 2H), 1.38 (m, 2H), 1.26 (t, J=7.4 Hz, 3H), 1.17 (m, 2H), 0.75 (t, J=7.5 Hz, 3H).

Example 193

(Compound VIII of Scheme 21, where R=ethyl, R'=n-butyl, R$^a$=R$^b$=methyl, A=A7). To a solution of 0.22 ml (239 mg, 0.090 mmol) of triethyl-3-methylphosphonocrotonate in 5 ml of THF/DMPU (4/1 ml respectively) was added 0.5 ml of nBuLi at −78° C. After stirring for 10 minutes, 115 mg (0.35 mmol) of 2-formyl-3-(2-butyloxy-4-N,N-dimethylamino-6-ethylbenzene)-thiophene (diluted in 1 ml of dry THF) was added dropwise. After complexion of the reaction, the solvents were evaporated and the crude ester directly purified over silica gel column chromatography (eluent: 5/95 ethyl acetate/hexane) to afford 150 mg (0.34 mmol, yield: 98%) of VIII. $^1$H NMR (400 MHz, CDCl$_3$) δ: 7.21 (d, J=5.1 Hz, 1H), 7.09 (d, J=5.1 Hz, 1H), 7.04 (d, J=15.8 Hz, 1H), 6.75 (d, J=1.9 Hz, 1H), 6.62 (d, J=1.9 Hz, 1H), 6.62 (d, J=15.8 Hz, 1H), 4.17 (dd, J=14.2, 7.6 Hz, 2H), 3.59 (t, J=6.3 Hz, 2H), 2.87 (s, 6H), 2.60 (dd, J=15.1, 7.5 Hz, 2H), 1.39 (m, 2H), 1.28 (t, J=7.2 Hz, 3H), 1.25 (t, J=7.6 Hz, 3H), 1.18 (m, 2H), 0.75 (t, J=7.4 Hz, 3H).

Example 194

(L97, Compound IX of Scheme 21, where R=ethyl, R'=n-butyl, R$^a$=R$^b$=methyl, A=A7). The compound was prepared in the manner previously described for Compound IX of Example 186 except that Compound VIII of Example 194 was employed in the synthesis. $^1$H NMR (400 MHz, CDCl$_3$) δ: 7.21 (s, 1H), 7.10 (s, 1H), 7.07 (d, J=16.8 Hz, 1H), 6.74 (s, 1H), 6.65 (s, 1H), 6.64 (d, J=14.2 Hz, 1H), 5.87 (s, 1H), 3.56 (t, J=6.1 Hz, 2H), 2.86 (s, 6H), 2.61 (m, 2H), 2.25 (s, 3H), 1.41 (m, 2H), 1.28 (m, 4H), 0.74 (t, J=7.2 Hz, 3H).

Scheme 22

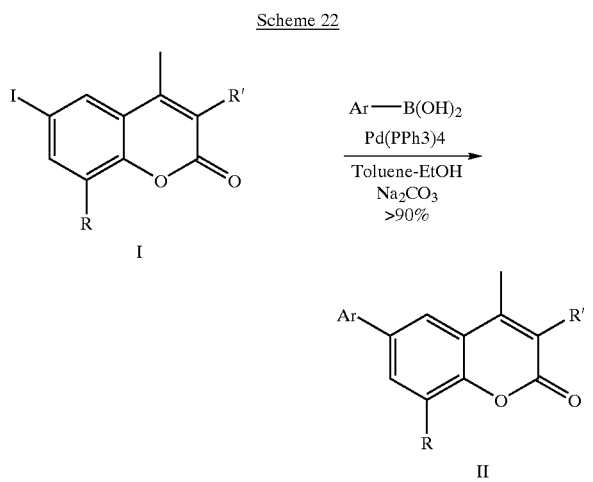

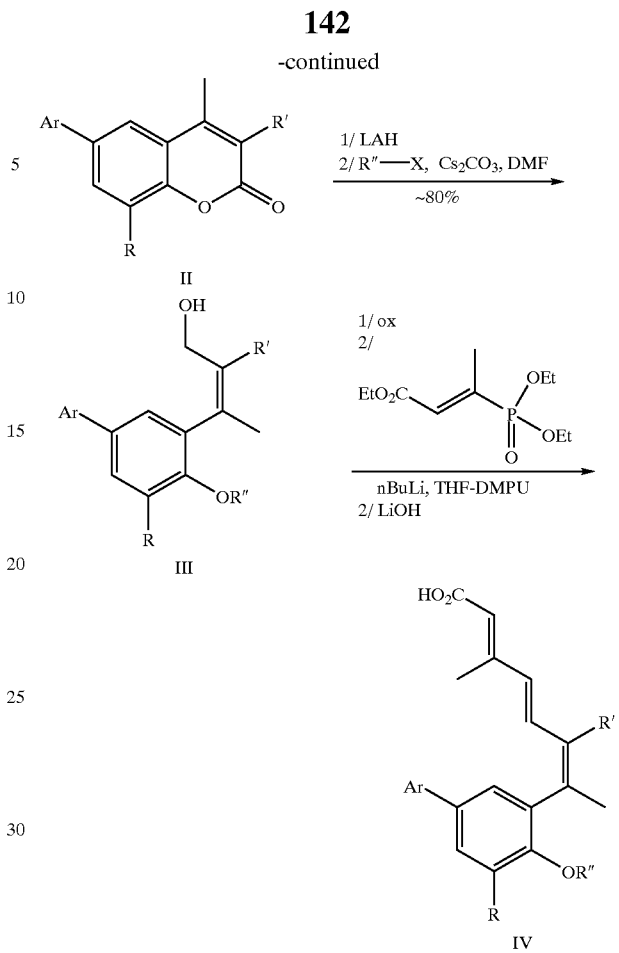

Scheme 22 depicts an alternative method for the preparation of RXR modulators, wherein aryl or heterocyclic groups can be independently introduced at the R$^2$ and R$^4$ positions.

Example 195

(Compound II of Scheme 22, where R=isopropyl, R'=H, Ar=2-fluorobenzene). A mixture of 108 mg (0.329 mmol) of 4-methyl-7-iodo-9-isopropyl coumarin, 70 mg (0493 mmol) of 2-fluorobenzene boronic acid, 19 mg (0.016 mmol) of Pd(PPh$_3$)$_4$, 0.33 ml of a 2N aqueous solution of Na$_2$CO$_3$ in 5 ml of toluene and 3 ml of ethanol was refluxed. After complexion of the reaction (TLC analysis), the mixture is cooled to room temperature and diluted in water (10 ml). After extraction with ethyl acetate, the organic layer separated and dried over MgSO$_4$. After evaporation, the crude coumarin was purified over silica gel (eluent: 10/90 ethyl acetate/hexane) to afford 91 mg (0.307 mmol, yield: 93%) of II as a yellow solid. $^1$H NMR (400 MHz, CDCl$_3$) δ: 7.62 (m, 2H), 7.45 (td, J=7.8, 1.7 Hz, 1H), 7.37 (m, 1H), 7.26 (dd, J=7.4, 1.0 Hz, 1H), 7.19 (m, 1H), 6.33 (s, 1H), 3.70 (dt, J=13.8, 6.9 Hz, 1H), 2.47 (s, 3H), 1.34 (d, J=6.9 Hz, 6H).

Example 196

(Compound II of Scheme 22, where R=isopropyl, R'=H, Ar=3-fluorobenzene). This compound was prepared in the manner previously described for Compound II in Example 85 except that 3-fluorobenzene boronic acid was used instead of 2-fluorobenzene boronic acid. ¹H NMR (400 MHz, CDCl₃) δ: 7.64 (d, J=1.9 Hz, 1H), 7.59 (d, J=1.9 Hz, 1H), 7.45 (m, 1H), 7.38 (m, 1H), 7.28 (m, 1H), 7.09 (m, 1H), 6.34 (s, 1H), 3.68 (dt, J=13.7, 6.8 Hz, 1H), 2.49 (s, 3H), 1.34 (d, J=6.9 Hz, 6H).

Example 197

(Compound II of Scheme 22, where R=isopropyl, R'=H, Ar=3-fluorobenzene). This compound was prepared in the manner previously described for Compound II in Example 85 except that 4-fluorobenzene boronic acid was used instead of 2-fluorobenzene boronic acid. ¹H NMR (400 MHz, CDCl₃) δ: 7.61 (d, J=2.2 Hz, 1H), 7.55 (d, J=2.1 Hz, 1H), 7.54 (m, 2H), 7.17 (t, J=8.7 Hz, 2H), 7.28 (m, 1H), 7.09 (m, 1H), 6.34 (s, 1H), 3.69 (dt, J=13.8, 6.8 Hz, 1H), 2.49 (s, 3H), 1.34 (d, J=6.9 Hz, 6H).

Example 198

(Compound II of Scheme 22, where R=isopropyl, R'=H, Ar=3,5-difluorobenzene). This compound was prepared in the manner previously described for Compound II in Example 85 except that 3,5-difluorobenzene boronic acid was used instead of 2-fluorobenzene boronic acid. ¹H NMR (400 MHz, CDCl₃) δ: 7.61 (d, J=2.0 Hz, 1H), 7.57 (d, J=2.0 Hz, 1H), 7.11 (m, 2H), 6.88 (m, 1H), 6.35 (s, 1H), 3.69 (dt, J=13.7, 6.8 Hz, 1H), 2.50 (s, 3H), 1.34 (d, J=7.0 Hz, 6H).

Example 199

(Compound II of Scheme 22, where R=isopropyl, R'=H, Ar=pyridine). This compound was prepared in the manner previously described for Compound II in Example 85 except that pyrindyl boronic acid was used instead of 2-fluorobenzene boronic acid. ¹H NMR (400 MHz, CDCl₃) δ: 8.72 (dd, J=4.9, 2.0 Hz, 1H), 8.11 (d, J=2.0 Hz, 1H), 8.07 (d, J=2.0 Hz, 1H), 7.78 (m, 2H), 7.18 (m, 1H), 3.60 (dt, J=13.8, 6.9 Hz, 1H), 2.54 (s, 3H), 1.37 (d, J=7.1 Hz, 6H).

Example 200

(Compound II of Scheme 22, where R=isopropyl, R'=H, Ar=thiophene). This compound was prepared in the manner previously described for Compound II in Example 85 except that thiophene boronic acid was used instead of 2-fluorobenzene boronic acid. ¹H NMR (400 MHz, CDCl₃) δ: 7.68 (d, J=2.1 Hz, 1H), 7.61 (d, J=2.1 Hz, 1H), 7.32 (m, 2H), 7.11 (dd, J=4.9, 3.5 Hz, 1H), 6.33 (s, 1H), 3.66 (dt, J=13.8, 6.9 Hz, 1H), 2.49 (s, 3H), 1.34 (d, J=7.0 Hz, 6H).

Example 201

(Compound II of Scheme 22, where R=isopropyl, R'=H, Ar=2-furan). This compound was prepared in the manner previously described for Compound II in Example 85 except that 2-furan boronic acid was used instead of 2-fluorobenzene boronic acid. 1H NMR (400 MHz, CDCl₃) δ: 7.75 (d, J=2.0 Hz, 1H), 7.72 (d, J=2.0 Hz, 1H), 7.33 (m, 2H), 7.15 (m, 1H), 6.69 (s, 1H), 3.66 (dt, J=13.9, 6.8 Hz, 1H), 2.49 (s, 3H), 1.33 (d, J=7.1 Hz, 6H).

Example 202

(L98, Compound IV of Scheme 22, where R=isopropyl, R'=H, R"=difluoroethyl, Ar=pyridine). This compound was prepared as described previously for Compound VIII according to Scheme 5. ¹H NMR (400 MHz, CDCl₃) δ: 8.23 (t, J=7.8 Hz, 1H), 7.92 (d, J=8.1 Hz, 1H), 7.85 (J=2.2 Hz, 1H), 7.67 (t, J=6.5 Hz, 1H), 7.49 (J=2.2 Hz, 1H), 6.42 (d, J=14.8 Hz, 1H), 6.40 (dd, J=14.8, 10.7 Hz, 1H), 6.30 (d, J=14.7 Hz, 1H), 5.97 (dt, J=55.1, 4.0 Hz, 1H), 5.78 (s, 1H), 4.00 (m, 2H), 3.44 (dt, J=13.8, 6.8 Hz, 1H), 2.26 (s, 3H), 2.10 (s, 3H), 1.31 (d, J=7.0 Hz, 6H).

Example 203

(L99, Compound IV of Scheme 22, where R=isopropyl, R'=H, R"=difluoroethyl, Ar=4-fluorobenzene). This compound was prepared as described previously for Compound VIII according to Scheme 5. ¹H NMR, (400 MHz, CDCl₃) δ: 7.50 (dd, J=8.6, 5.4 H, 2H), 7.38 (d, J=2.3 Hz, 1H), 7.13 (dd, J=8.6, 5.4 Hz, 2H), 7.10 (d, J=2.4 Hz, 1H), 6.56 (dd, J=15.3, 11.0 Hz, 1H), 6.32 (d, J=11.5 Hz, 1H), 5.96 (dt, J=55.2, 4.0 Hz, 1H), 5.79 (s, 1H), 4.17 (td, J=13.6, 4.0 Hz, 2H), 3.40 (dt, J=13.8, 6.9 Hz, 1H), 2.23 (s, 3H), 2.14 (s, 3H), 1.29 (d, J=6.9 Hz, 6H).

Example 204

(L100, Compound IV of Scheme 22, where R=isopropyl, R'=H, R"=difluoroethyl, Ar=3-fluorobenzene). This compound was prepared as described previously for Compound VIII according to Scheme 5. ¹H NMR (400 MHz, CDCl₃) δ: 7.42 (d, J=2.2 Hz, 1H), 7.38 (dd, J=8.1, 5.9Hz, 1H), 7.23 (m, 1H), 7.14 (d, J=2.2 Hz, 1H), 7.04 (m, 1H), 6.55 (dd, J=15.5, 11.0 Hz, 1H), 6.34 (d, J=11.0 Hz, 1H), 6.30 (J=15.5 Hz, 1H), 5.97 (dt, J=55.3, 3.9 Hz, 1H), 5.97 (s, 1H), 3.93 (td, J=13.4, 3.9 Hz, 2H), 3.40 (dt, J=13.9, 6.9 Hz, 1H), 2.24 (s, 3H), 2.14 (s, 3H), 1.30 (d, J=6.9 Hz, 6H).

Example 205

(L19, Compound IV of Scheme 22, where R=isopropyl, R'=H, R"=difluoroethyl, Ar=2-fluorobenzene). This compound was prepared as described previously for Compound VIII according to Scheme 5. ¹H NMR (400 MHz, CDCl₃) δ: 7.39 (m, 2H), 7.31 (m, 1H), 7.20 (t, J=7.4 Hz, 1H), 7.14 (m, 2H), 6.65 (dd, J=15.2, 10.9 Hz, 1H), 6.33 (d, J=10.5 Hz, 1H), 6.30 (d, J=15.1 Hz, 1H), 5.98 (dt, J=55.2, 3.9 Hz, 1H), 5.98 (s, 1H), 3.94 (m, 2H), 3.40 (dt, J=13.9, 6.9 Hz, 1H), 2.23 (s, 3H), 2.17 (s, 3H), 1.29 (d, J=6.9 Hz, 6H).

Example 206

(L101, Compound IV of Scheme 22, where R=isopropyl, R'=H, R"=difluoroethyl, Ar=thiophene). This compound was prepared as described previously for Compound VIII according to Scheme 5. ¹H NMR (400 MHz, CDCl₃) δ: 7.45 (d, J=2.2 Hz, 1H), 7.25 (m, 2H), 7.18 (d, J=2.2 Hz, 1H, 7.07 (dd, J=4.8, 3.9 Hz, 1H), 6.56 (dd, J=15.3, 11.0 Hz, 1H), 6.33 (d, J=11.0 Hz, 1H), 6.30 (d, J=15.3 Hz, 1H), 5.96 (dt, J=55.2, 4.0 Hz, 1H), 5.79 (s, 1H), 3.90 (td, J=13.6, 4.0 Hz, 2H), 3.37 (dt, J=13.9, 6.9 Hz, 1H), 2.23 (s, 3H), 2.14 (s, 3H), 1.28 (d, J=6.9 Hz, 6H).

Scheme 23

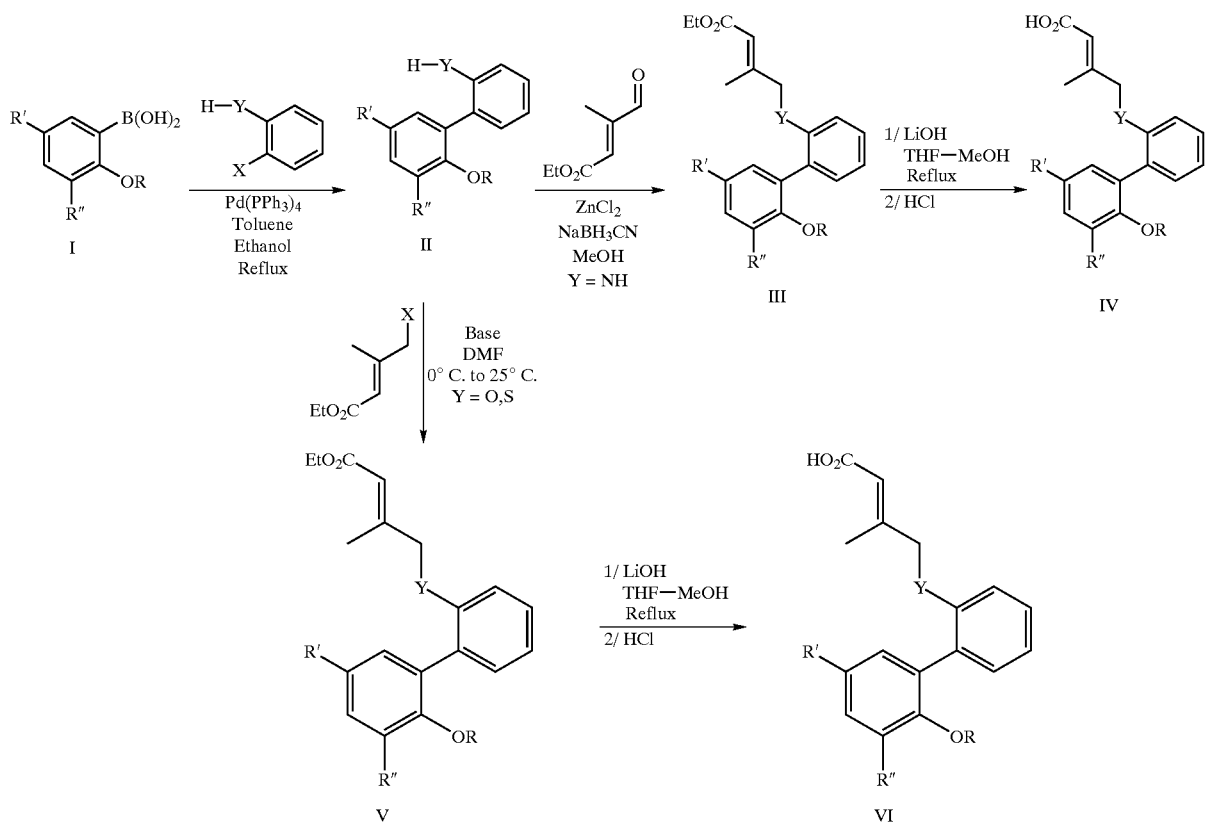

Scheme 23 depicts the synthesis of compounds of the type VI.

Example 207

(Compound II of Scheme 23, where R=ethyl, R'=R"= isopropyl, Y=NH). To a mixture of 90 mg (0.140 mmol) of 2-Iodoaniline and 24 mg (0.02 mmol, 5%) of Pd(PPh$_3$)$_4$ in toluene (5 ml) was added 153 mg (0.611 mmol) of 2-ethoxy-3,5-di isopropyl benzene boronic acid diluted in 3 ml of ethanol. To this yellow solution, 0.41 ml of a 2N Na$_2$CO$_3$ solution was added, and the resulting mixture was heated to reflux until completion. After cooling at room temperature, water was added and the mixture was extracted with ethyl acetate. The organic layers were combined and dried over MgSO$_4$. The solvents were evaporated under reduced pressure and the resulting oil was purified over silica gel (eluent: 10/90 ethyl acetate/hexane) to give 70 mg (0.235 mmol, yield: 57%) of II as a clear brown oil. $^1$H NMR (CDCl3), δ: 7.17 (m, 2H), 7.10 (d, J=2.2 Hz, 1H), 6.97 (d, J=2.2 Hz, 1H), 6.83 (td, J=8.2, 0.9 Hz, 1H), 6.78 (d, J=7.9 Hz, 1H), 3.90 (broad s, 2H), 3.54 (dd, J=9.2, 7.1 Hz, 2H), 3.42 (ddd, J=13.9, 6.9, 6.9 Hz, 1H), 2.90 (ddd, J=13.8, 6.8, 6.8 Hz, 1H), 1.25 (d, J=6.9 Hz, 12 H), 1.07 (t, J=7.0 Hz, 3H).

Example 208

(Compound III of Scheme 23, where R=ethyl, R'=R"= isopropyl, Y=NH). To a mixture of 65 mg (0.218 mmol) of 2-(2-ethoxy-3, 5-di isopropyl benzene)-aniline and 24 mg (0.176 mmol, 0.75 equivalent) of zinc chloride and 50 μl (50 mg, 0.352 mmol) of ethyl-3-methyl-4-oxo crotonate in 3 ml of methanol was added 44 mg (0.705 mmol, 4 equivalents) of NaBH$_3$CN portionwise at 0° C. The mixture was stirred at this temperature until complexion and the solvents were evaporated under reduced pressure. The residue was then purified over silica gel column chromatography (eluent: ethyl acetate/hexane: 5/95) to give 25 mg (0.06 mmol, yield: 27%) of III as a clear oil. $^1$H NMR (CDCl$_3$), δ: 7.19 (m, 2H), 7.11 (d, J=2.3 Hz, 1H), 6.96 (d, J=2.3 Hz, 1H), 6.77 (t, J=8.2 Hz, 1H), 6.50 (d, J=8.1 Hz, 1H), 5.94 (s, 1H), 4.39 (broad t, J=6.0 Hz, 1H), 4.12 (dd, J=14.1, 7.0 Hz, 2H), 3.79 (d, J=5.9 Hz, 2H), 3.54 (dd, J=14.0, 7.1 Hz, 2H), 3.42 (ddd, J=13.8,.6.9, 6.9 Hz, 1H), 2.88 (m, 1H), 2.16 (s, 3H), 1.25 (m, 12 H), 1.07 (t, J=7.0 Hz, 3H), 1.05 (t, J=7.0 Hz, 3H).

Example 209

(L102, Compound IV of Scheme 23, where R=ethyl, R'=R"=isopropyl, Y=NH). A mixture of 25 mg (0.06 mmol) of 2-[(2-ethoxy-3, 5-di isopropyl benzene)-4-(ethyl-3-methyl crotonate)]-aniline, 1 ml of THF, 1 ml of methanol and 0.5 ml of a 2M LiOH aqueous solution was heated to reflux until complete consumption of starting material. After cooling at room temperature, the solvents were evaporated under reduced pressure and the aqueous layer was acidified with 2N aqueous HCl (pH=1–2) and extracted 2 times with ethyl acetate. The organic layers were combined and dried over MgSO$_4$. After removal of the solvents, the residual oil was purified by preparative plate (1000μ, eluent: 25/75 ethyl acetate/hexane) to give 3 mg (0.008 mmol, yield: 13%) of IV as a pasty oil. $^1$H NMR (CDCl3), δ: 7.20 (t, J=8.1 Hz, 1H), 7.16 (d, J=7.4 Hz, 1H), 7.11 (d, J=1.9 Hz, 1H), 6.95 (d, J=2.1 Hz, 1H), 6.78 (t, J=7.4 Hz, 1H), 6.48 (d, J=8.1 Hz, 1H), 5.98 (s, 1H), 4.41 (broad s, 1H), 3.81 (s, 2H), 3.54 (dd, J=14.0, 7.1 Hz, 2H), 3.41 (ddd, J=13.7, 6.9, 6.9 Hz, 1H), 2.89 (ddd, J=13.7, 6.8, 6.8 Hz, 1H), 2.16 (s, 3H), 1.26 (d, J=6.9 Hz, 6H), 1.25 (d, J=6.8 Hz, 6H), 1.05 (t, J=7.0 Hz, 3H).

BIOLOGICAL ACTIVITY

Example 210

Evaluation of Retinoid Receptor Subfamily Activity In Vitro

Utilizing the "cis-trans" or "co-transfection" assay described by Evans et al., Science, 240:889–95 (May 13, 1988), the disclosure of which is herein incorporated by reference, the dimer-selective RXR modulator compounds of the present invention were tested and found to have strong, specific activity as selective RXR modulators, including activity as full agonists, partial agonists and/or full antagonists of RXR homodimers and/or heterodimers. This assay is described in further detail in U.S. Pat. Nos. 4,981, 784 and 5,071,773, the disclosures of which are incorporated herein by reference.

The co-transfection assay provides a method for identifying functional agonists which mimic, or antagonists which inhibit, the effect of native hormones, and quantifying their activity for responsive IR proteins. In this regard, the co-transfection assay mimics an in vivo system in the laboratory. Importantly, activity in the co-transfection assay correlates very well with known in vivo activity, such that the co-transfection assay functions as a qualitative and quantitative predictor of a tested compounds in vivo pharmacology. See, e.g., T. Berger et al. 41 J. Steroid Biochem. Molec. Biol. 773 (1992), the disclosure of which is herein incorporated by reference.

In the co-transfection assay, cloned cDNA for one or more IRs (e.g., human RARα, RXRα, or PPARγ), alone or in combination (i.e. for heterodimer assays) under the control of a constitutive promoter (e.g., the SV 40, RSV or CMV promoter) is introduced by transfection (a procedure to introduce exogenous genes into cells) into a background cell substantially devoid of endogenous IRs. These introduced gene(s) direct the recipient cells to make the IR protein(s) of interest. A further gene is also introduced (co-transfected) into the same cells in conjunction with the IR gene(s). This further gene, comprising the cDNA for a reporter protein, such as firefly luciferase (LUC), controlled by an appropriate hormone responsive promoter containing a hormone response element (HRE). This reporter plasmid functions as a reporter for the transcriptional-modulating activity of the target IR(s). Thus, the reporter acts as a surrogate for the products (mRNA then protein) normally expressed by a gene under control of the target receptor(s) and their native hormone(s).

The co-transfection assay can detect small molecule agonists or antagonists, including partial agonists and antagonist, of target IRs. Exposing the transfected cells to an agonist ligand compound increases reporter activity in the transfected cells. This activity can be conveniently measured, e.g., by increasing luciferase production and enzymatic activity, which reflects compound-dependent, IR-mediated increases in reporter transcription. To detect antagonists, the co-transfection assay is carried out in the presence of a constant concentration of an known agonist to the target IR (e.g., 4-[(3,5,5,8,8-Pentamethyl-5,6,7,8-tetrahydro-2-naphthyl)ethenyl]benzoic acid (LGD1069, Ligand Pharmaceuticals, Inc.) for RXRα) known to induce a defined reporter signal. Increasing concentrations of an antagonist will decrease the reporter signal (e.g., luciferase production). The co-transfection assay is therefore useful to detect both agonists and antagonists of specific IRs. Furthermore, it determines not only whether a compound interacts with a particular IR, but whether this. interaction mimics (agonizes) or blocks (antagonizes) the effects of native or synthetic regulatory molecules on target gene expression, as well as the specificity and strength of this interaction.

The activity of the dimer-selective RXR retinoid modulator compounds of the present invention were evaluated utilizing the co-transfection assay according to the following illustrative Examples.

Example 210A

RXR Homodimer Co-transfection Assay

CV-1 cells (African green monkey kidney fibroblasts) were cultured in the presence of Dulbecco's Modified Eagle Medium (DMEM) supplemented with 10% charcoal resin-stripped fetal bovine serum then transferred to 96-well microtiter plates one day prior to transfection.

To determine agonist and antagonist activity of the modulator compounds of the present invention, the CV-1 cells were transiently transfected by calcium phosphate coprecipitation according to the procedure of Berger et al., 41 J. Steroid Biochem. Mol. Biol., 733 (1992) with the receptor expressing plasmid pRShRXRα, Mangelsdorf et al., 345 Nature, 224 (1990), the disclosures of which are herein incorporated by reference at a concentration of 10 ng/well. The receptor expression plasmid was cotransfected along with a reporter plasmid at 50 ng/well, the internal control plasmid pRS-β-Gal at 50 ng/well and filler DNA, pGEM, at 90 ng/well.

The reporter plasmid CRBPIITKLUC, which contains an RXRE (retinoid X receptor response element, as described in Mangelsdorf et al., 66 Cell, 555 (1991), the disclosure of which is herein incorporated by reference, was used in transfections for the RXR homodimer assay. This reporter plasmid contains the cDNA for firefly luciferase (LUC) under the control of a promoter containing the RXR response element. As noted above, pRS-β-Gal, coding for constitutive expression of E. coli β-galactosidase (β-Gal), was included as an internal control for evaluation of transfection efficiency and compound toxicity.

Six hours after transfection, media was removed and the cells were washed with phosphate-buffered saline (PBS). Media containing compounds of the present invention in concentrations ranging from $10^{-10}$ to $10^{-5}$ M were added to the cells. Similarly, the reference compounds all-trans retinoic acid (ATRA)(Sigma Chemical), LGD1069 (4-[(3,5,5, 8,8-Pentamethyl-5,6,7,8-tetrahydro-2-naphthyl)ethenyl] benzoic acid: Ligand Pharmaceuticals, Inc.) and LG100268 (6-[1-(3,5,5,8,8-pentamethyl-5,6,7,8-tetrahydronaphthalen-2-yl)cyclopropyl]nicotinic acid: Ligand Pharmaceuticals, Inc.), compounds with known agonist activity on RXRs, were added at similar concentrations to provide a reference point for analysis of the agonist activity of the compounds of the present invention. When determining the antagonist activity of the compounds of the present invention, the compounds were added to the cells in the presence of a fixed concentration ($3.2 \times 10^{-8}$ M) of the known RXR agonist LGD1069 (4-[(3,5,5,8,8-Pentamethyl-5,6,7,8-tetrahydro-2-naphthyl)ethenyl]benzoic acid: Ligand Pharmaceuticals, Inc.). Retinoid purity was established as greater than 99% by reverse phase high-performance liquid chromatography. Retinoids were dissolved in dimethylsulfoxide for use in the transcriptional activation assays. Two to three replicates were used for each sample. Transfections and subsequent procedures were performed on a Biomek 1000 automated workstation.

After 40 hours, the cells were washed with PBS, lysed with a detergent-based buffer and assayed for LUC and β-Gal activities using a luminometer or spectrophotometer, respectively. For each replicate, the normalized response (NR) was calculated as:

LUC response/β-Gal rate where β-Gal rate=β-Gal.1×10⁵/β-Gal incubation time.

The mean and standard error of the mean (SEM) of the NR were calculated. Data were plotted as the response of the compound compared to the reference compounds over the range of the dose-response curve. For the agonist activity of the compounds of the present invention, the effective concentration that produced 50% of the maximum response ($EC_{50}$) was quantified. Antagonist activity was determined by testing the amount of LUC expression in the presence of the RXR agonists described above at the $EC_{50}$ concentration for such known compounds. The concentration of compounds of the present invention that inhibited 50% of LUC expression induced by the reference agonist was quantified ($IC_{50}$). In addition, the efficacy of antagonists was determined as a function (%) of maximal inhibition.

Example 210B

RXR and RAR Binding

In addition to the cotransfection data, the binding of selected compounds of the present invention to the RAR and RXR receptors was also investigated according to the methodology described in M. F., Boehm, et al., "Synthesis and Structure-Activity Relation-ships of Novel Retinoid X Receptor Selective Retinoids", 37 *J. Med. Chem.*, 2930 (1994); M. F. Boehm, et al., "Synthesis of High Specific Activity [³H]-9-cis Retinoic Acid and Its Application for Identifying Retinoids with Unusual Binding Properties", 37 *J. Med. Chem.*, 408 (1994), and E. A. Allegretto, et al., "Characterization and Comparison of Hormone-Binding and Transactivation Properties of Retinoic Acid and Retinoid X Receptors Expressed in Mammalian Cells and Yeast", 268 *J. Biol. Chem.*, 22625 (1993), the disclosures of which are herein incorporated by reference.

Non-specific binding was defined as that binding remaining in the presence of 500 nM of the appropriate unlabelled compound. At the end of the incubation period, bound ligand was separated from free. The amount of bound tritiated retinoid was determined by liquid scintillation counting of an aliquot (700 μL) of the supernatant fluid or the hydroxylapatite pellet.

After correcting for non-specific binding, $IC_{50}$ values were determined. The $IC_{50}$ value is defined as the concentration of competing ligand needed to reduce specific binding by 50%. The $IC_{50}$ value was determined graphically from a log-logit plot of the data. The $K_i$ values were determined by application of the Cheng-Prussof equation to the $IC_{50}$ values, the labeled ligand concentration and the $K_d$ of the labeled ligand.

The RXRα binding activity and agonist and antagonist activity in the RXRα homodimer cotransfection assay of selected compounds of the present invention are shown in Table 3 below.

TABLE 3

Activity in RXRα binding and RXRα homodimer cotransfection assays of selected dimer-selective RXR modulator compounds of the present invention. $EC_{50}$ and $IC_{50}$ values were not calculated (NC) if efficacy was <10%. Values represent mean of n > 3 independent experiments.

| Cmpd. No. | RXRα Binding $K_i$ (nM) | RXRα Homodimer Cotransfection Assay ||||
|---|---|---|---|---|---|
| | | Agonist Efficacy (%) | Agonist $EC_{50}$ (nM) | Agonist Efficacy (%) | Antagonist $IC_{50}$ (nM) |
| ATRA | 53 | 100 | 919 | 0 | NC |
| LGD1069 | 36 | 85 | 76 | 0 | NC |
| LG100268 | 3.0 | 73 | 15 | 0 | NC |
| L1 | 1.1 | 62 | 33 | 7 | NC |
| L2 | 13 | 11 | 14 | 62 | 9 |
| L3 | 1.1 | 2 | NC | 90 | 5 |
| L4 | 0.9 | 1 | NC | 92 | 9 |
| L5 | 0.6 | 0 | NC | 94 | 10 |

As can be seen in Table 3, all of the dimer-selective RXR modulator compounds displayed high affinity binding to RXRα. Compound L1 displayed agonist activity similar in efficacy and potency to the known RXR agonist, LG100268, in the context of an RXR:RXR homodimer in the cotransfection assay. Compound L2 acted as a partial agonist, demonstrating significant efficacy as both an agonist and an antagonist. Compounds L3, L4 and L5 displayed highly efficacious and potent antagonist activity with little or no agonist activity. Thus, compounds of the present invention display properties ranging from full agonists to partial agonists to full antagonists in the context of RXR homodimers.

Example 210C

RXR Heterodimer Co-transfection Assays

The RXR modulator compounds of the present invention were further tested for activity on RXR heterodimers with RARα, RARγ or PPARγ utilizing the cotransfection assay in CV-1 cells as described in Example 210A. The RXR:RAR heterodimer cotransfection assays utilized the following expression plasmids and reporter plasmid: pRShRARα (10 ng/well, Giguere et al., 330 *Nature*, 624 (1987) the disclosure of which is herein incorporated by reference) or pRShRARγ (10 ng/well, Ishikawa et al., 4 *Mol. Endocrin.*, 837 (1990) the disclosure of which is herein incorporated by reference) with Δ-MTV-LUC (50 ng/well, Hollenberg and Evans, 55 *Cell*, 899 (1988), the disclosure of which is herein incorporated by reference) containing an RARE which is referred to as two copies of the TRE-palindromic response element described in Umesono et al., 336 *Nature*, 262 (1988), the disclosure of which is herein incorporated by reference. For the RXR:PPARγ heterodimer cotransfection assay, the RXRα receptor expression plasmid, pRShRXRα (10 ng/well), was cotransfected with the PPARγ expression plasmid, pCMVhPPARγ (10 ng/well), and a reporter plasmid containing three copies of a PPARγ response element (pPREA3-tk-LUC, 50 ng/well; Mukherjee et al. 272 *Journ. Biol. Chem.*, 8071–8076 (1997) and references cited therein, the disclosures of which are herein incorporated by reference).

Cotransfections were performed as described in Example 210A. For determination of agonist activity in the context of the RXR:RAR heterodimer or the RXR:PPARγ heterodimer, media containing compounds of the present invention in concentrations ranging from $10^{-10}$ to $10^{-5}$ M were added to the cells. Similarly, the reference compounds all-trans retinoic acid (ATRA)(Sigma Chemical) and TTNPB ((E)-4-[2-(5,6,7,8-tetrahydro-5,5,8,8-tetramethyl-2-naphthalenyl)-1-propenyl]benzoic acid: Hoffman LaRoche, Inc.), known RAR agonist compounds, or BRL 49653, a compound with known agonist activity on PPARγ, were added at similar concentrations to provide a reference point for analysis of the agonist activity of the compounds of the present invention. When evaluating the antagonist activity of the compounds of the present invention on RARγ, the compounds were added to the cells in the presence of a fixed concentration ($1 \times 10^{-8}$ M) of the known RAR selective agonist TTNPB ((E)-4-[2-(5,6,7,8-tetrahydro-5,5,8,8-tetramethyl-2-naphthalenyl)-1-propenyl]benzoic acid: Hoffman LaRoche, Inc.). Antagonist efficacy and $IC_{50}$ values were determined as in Example 210A.

Compounds of the present invention were also tested for the ability to synergize with a PPARγ agonist in the context of an RXR heterodimer. For these assays the compounds were added to the cells with a fixed concentration of BRL 49653 ($1 \times 10^{-7}$ M) for the RXR:PPARγ heterodimer assay. Efficacy of the compounds of the present invention in the agonist and synergy assays was calculated as the maximum response obtained over the range of the dose response curve relative to the maximum response obtained by the reference agonist. Antagonist efficacy was determined as a function (%) of maximal inhibition.

RAR suppresses RXR ligand binding and transactivation of typical RXR agonists (e.g., LGD1069, LG100268) via allosteric interactions. Forman, B. M., Umesono, K., Chen, J., & Evans, R. M., *Cell* 81, 541–550 (1995) and Kurokawa, R., et. al. *Nature* 371, 528–531 (1994). However, when RAR is occupied, typical RXR agonists activate the heterodimer. . Forman, B. M., Umesono, K., Chen, J., & Evans, R. M., *Cell* 81, 541–550 (1995) and Roy, B., Taneja, R., & Chambon, P., *Mol. Cell. Biol.* 15, 6481–6487 (1995). To examine the effects of the compounds of the present invention on the transcriptional properties of the RXR:RAR heterodimer, a heterodimer cotransfection assay as described above was employed. Table 4 below shows the activity of selected compounds of the present invention in terms of agonist or antagonist efficacy in the RXR:RAR heterodimer cotransfection assay.

activate or are inactive on the RXR:RAR heterodimer, ATRA and the RAR selective activator TTNPB strongly transactivate this heterodimer. Compound L1 of the present invention displayed weak agonist activity alone. Compound L2, which displayed partial RXR agonist activity, was not active in the RXR:RAR assay. Compounds L3, L4 and L5 were also not active as RXR:RAR agonists. In fact, they displayed significant RXR:RAR antagonist activity as indicated by their efficacy in the antagonist assay. Thus, there appears to be a continuum of activities from the dimer-selective RXR modulator compounds of the present invention on the RXR:RAR heterodimer such that as the length of the carbon chain at the $R^7$ position increases the RXR:RAR agonist activity tends to decrease and the RXR:RAR antagonist activity tends to increase.

RXR:PPARγ heterodimers have previously been shown to be responsive to both RXR and PPAR ligands. Kliewer, et al., *Nature* 358, 771–774 (1992). To examine the effects of the compounds of the present invention on the transcriptional properties of the RXR:PPARγ, a heterodimer cotransfection assay as described above was employed. Table 5 below shows the activity of reference compounds and of selected compounds of the present invention in terms of agonist or synergy efficacy in the RXR:PPARγ heterodimer cotransfection assay. As can be seen in Table 5, the known RXR agonists LGD 1069 and LG 100268 when tested alone induce transactivation of the RXRα:PPARγ heterodimer as does a PPARγ ligand, the thiazolidinedione BRL 49653. In addition, when the RXR agonists were tested in combination with the PPARγ ligand (i.e. synergy mode), they showed even stronger agonist activity. The dimer-selective RXR modulator compounds of the present invention, as was seen for the RXR:RAR heterodimer assay, also display a continuum of activities on the RXRα:PPARγ heterodimer. Compound L1 displays both agonist and synergistic activity similar to that seen with LGD 1069 and LG 100268. L2 is a partial agonist alone and shows stronger activity in combination with the PPARγ ligand. Compounds L3 and L4 were only weakly active alone, but they were active in the presence of the PPARγ ligand. Finally, Compound L5 was not active as an agonist on the RXRα:PPARγ heterodimer either alone or in combination the PPARγ ligand.

TABLE 4

Activity in RXRα:RAR heterodimer cotransfection assays of selected dimer-selective RXR modulator compounds of the present invention. Values represent mean of n > 3 independent experiments.

| Cmpd. No. | RXRα:RAR Heterodimer Cotransfection Assay | |
|---|---|---|
| | Agonist Efficacy (%)[1] | Antagonist Efficacy (%)[2] |
| ATRA | 100 | — |
| TTNPB | 115 | — |
| LGD1069 | 33 | 0 |
| LG100268 | 6 | 0 |
| L1 | 21 | 19 |
| L2 | 6 | 49 |
| L3 | 5 | 84 |
| L4 | 2 | 88 |
| L5 | 5 | 68 |

[1]Efficacy calculated as maximal response relative to response of ATRA.
[2]Efficacy calculated relative to maximal repression (100%) in presence of 10 nM TTNPB.

As shown in Table 4, whereas RXR agonists, such as LGD1069 and LG100268 by themselves, either weakly

TABLE 5

Activity in RXRα:PPARγ heterodimer cotransfection assays of selected dimer-selective RXR modulator compounds of the present invention. Values represent mean of n > 3 independent experiments.

| Cmpd. No. | RXRα:PPARγ Heterodimer Cotransfection Assay | |
|---|---|---|
| | Agonist Efficacy (%)[1] | Synerg Efficacy (%)[2] |
| BRL 49653 | 100 | — |
| LGD1069 | — | 64 |
| LG100268 | 59 | 183 |
| L1 | 59 | 166 |
| L2 | 14 | 69 |
| L3 | 6 | 25 |
| L4 | 3 | 20 |
| L5 | 4 | 6 |

[1]Efficacy calculated as maximal response relative to response of BRL 49653.
[2]Efficacy calculated as maximal response in presence of 100 nM BRL relative to response of BRL alone.

Thus, although all of the compounds of the present invention directly and specifically bind RXR, they manifest distinct properties in the RXR:RXR homodimer assay as compared to the RXR:RAR and RXR:PPARγ heterodimer assays. The various RXR modulator compounds of the present invention have a range of activities when compared with each other and are truly dimer-selective RXR modulators, such that their actual function as either agonist, partial agonist and/or antagonist change depending upon the RXR partner and whether the partner is bound by ligand.

Example 211

Evaluation of Activity In Vivo

In Vivo Method

Rodents that are genetically defective in the leptin pathway are commonly used as animal models of NIDDM. db/db mice and ZDF rats develop frank diabetes that progresses to include β-cell failure and the accompanying precipitous drop in plasma insulin levels. Both strains are profoundly obese, hyperglycemic, hyperinsulinemic, and hypertriglyceridemic. fa/fa rats, on the other hand, are obese and insulin resistant but do not develop frank diabetes and the associated hyperglycemia. Using all 3 models we have examined the efficacy of oral dosing with rexinoid modulators on diabetes, insulin sensitivity, food consumption and body weight gain.

All animal experiments were conducted in a United States Department of Agriculture registered facility in accordance with NIH guidelines for the care and use of laboratory animals. The Ligand Institutional Animal Care and Use committee (IACUC) approved each study. Mice (obtained from Jackson Laboratory), ZDF rats (obtained from Genetic Models Inc.) and fa/fa rats (obtained from either Charles River, or Harlan) were maintained on 12-hour light/dark cycle. Mice (age 28–42 days) were caged in groups of 5–6 and rats (age 7 weeks) were housed individually. All animals were allowed ad libitum access to water and food (Purina 5015 for mice and 5008 for rats). Compounds were administered at the specified doses by oral gavage on the morning of each day of any experiment. Blood samples were obtained 3 hours after dosing from fed animals under anesthesia and collected into heparinized capillary tubes from the tail vein.

Mice transgenic for the human apolipoprotein A-I gene (obtained from Jackson Laboratory) were used to evaluate PPARalpha mediated effects on HDL cholesterol. The mice were handled as described above for db/db mice, except that they were fed Purina 5001.

Rexinoids that are full agonists at the RXR homodimer, such as LG100268, are efficacious insulin sensitizers in rodent models of Type II Diabetes. However, such compounds raise triglycerides and suppress the thyroid hormone axis in these animals. On the other hand, full antagonists, such as L5, have no effect on glucose, triglycerides or the thyroid status in these same model systems. We have identified a specific subset of rexinoids that maintain the desirable insulin sensitizing activity and minimize both the suppression of the thyroid axis and triglyceride elevations (e.g., L3, L4, L6, L7, L8, L9, L13, L14, L15, L16, L17, L18, L19). These compounds are heterodimer selective modulators of RXR activity. They bind to RXR with high affinity ($K_i$<20 nM) and produce potent activation of the RXR:PPARgamma heterodimer. This activation of PPARgamma in vitro is presumably a major determinant of the antidiabetic efficacy of the compounds in vivo. In addition, to minimize the undesirable increases in triglyceride levels and suppression of thyroid hormone axis, the modulators must not significantly activate the RXR:RAR heterodimer and must have substantial RXR:RAR antagonist activity. This requirement is clearly demonstrated by the two related compounds L2, L3. The striking in vitro characteristic for these two compounds is that L3 has twice the RXR:RAR antagonist activity as L2; this correlates with the distinction in vivo where L2 suppresses thyroid hormone axis while L3 does not. Analogous results are obtained in normal Sprague Dawley rats where both T4 and TSH can be monitored. In this acute model these heterodimer selective RXR modulators suppress neither TSH nor T4.

When administered to obese, insulin resistant db/db mice (100 mg/kg by daily oral gavage for 14 days) these heterodimer selective RXR modulators lower both plasma glucose and triglycerides. However, unlike either full agonists (e.g., LG100268, L1) or partial agonists that exhibit some activity at the RXR:RAR heterodimer (e.g., L2), they do not substantially suppress total circulating levels of T4, or substantially increase triglycerides.

Four week old db/db mice are essentially normoglycemic, they have not yet developed hyperglycemia. Treatment of such mice with 1392 (30 mg/kg by daily oral gavage) prevents the development of hyperglycemia. This treatment has been shown to successfully control plasma glucose levels for up to 11 weeks (when the mice are 15 weeks old).

Treatment of 7 week old db/db mice with metformin (300 mg/kg by daily oral gavage) lowers plasma glucose. However the maximum effect is seen following the first week of treatment. Over 3 subsequent weeks the efficacy of metformin decreases. At this point treatment with metformin plus the addition of 1392 (100 mg/kg by daily oral gavage) lowered plasma glucose to the level of age matched lean. These data suggest that the RXR modulator could be efficacious in cases of secondary failure of metformin.

When administered to obese, insulin resistant fa/fa rats (100 mg/kg by daily oral gavage for 14 days) these heterodimer selective RXR modulators (such as 1392) produce insulin sensitization as demonstrated using an oral glucose tolerance test. In response to the oral glucose challenge both insulin and glucose rise significantly less than in untreated control animals. These 1392 treated animals consume the same amount of food and gain the same amount of weight as vehicle treated control animals. When fa/fa animals are treated with a thiazolinedione insulin sensitizer they consume significantly more food and gain significantly more weight than control animals. In contrast, animals treated with a combination of the thiazolidinedione and 1392 consume the same amount of food and gain the same amount of weight as the control animals; 1392 blocks the thiazolidinedione induced increases in both food consumption and body weight gain.

When administered to transgenic mice carrying the human apo A-I gene all of these compounds increase HDL cholesterol, but both LG100268 and L1 also substantially raise triglycerides. The modulators that do not activate the RXR:RAR heterodimer and have greater than 50% RXR:RAR antagonists activity do not substantially raise triglycerides in the transgenic mouse model, consistent with their heterodimer selectivity. This effect is consistent with activation of PPARalpha, and in fact in vivo these compounds synergize with the weak PPARalpha agonist fenofibrate.

Example 212

Evaluation of Teratogenicity In Vivo

Teratogenicity is commonly evaluated by examination of fetuses obtained by cesarean section from pregnant mice dosed daily with test compound between gestation days 6–18. We have conducted a blinded study using time-mated female Crl:CD-1® (ICR)BR mice to evaluate potential developmental toxicity (teratogenicity) following administration of L6 at either 30 or 200 mg/kg-day by daily oral gavage for the specified 12 days of gestation. Each test group consisted of 7–8 pregnant females and produced approx. 100 live fetuses per test group. As a positive control, pregnant female mice were treated with the retinoid LG100268 at a dose of either 30 mg/kg-day or 100 mg/kg-day. Teratogenicity was observed in fetuses from mice treated with the LG100268 at both dosage groups. In contrast, no teratogenic effects were observed in fetuses from mice treated with L6. Compared to controls dosed with vehicle, no effects were observed on the number of Corpora lutea, implantation sites, live or dead fetuses, early or late resorptions, fetal weight or sex, gross external morphology or visceral morphology of the cranial region in fetuses from mice treated with L6 at either dose. The highest dose of L6 tested (200 mg/kg-day) is twice the dose required to produce maximum antidiabetic activity in db/db mice (100 mg/kg-day).

While we have described a number of embodiments of this invention, it is apparent that our basic constructions may be altered to provide other embodiments which utilize the processes and products of this invention. Therefore it will be appreciated that the scope of this invention is to be defined by the appended claims, rather than by the specific embodiments which have been presented by way of example.

What is claimed is:

1. A compound having the structure:

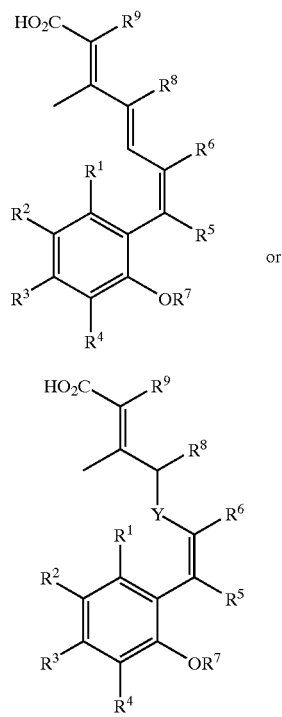

wherein:

$R^1$ is selected from the group of hydrogen, F, Cl, Br, I, $C_1$–$C_3$ alkyl, $C_1$–$C_3$ haloalkyl, $C_2$–$C_3$ alkenyl, $C_2$–$C_3$ haloalkenyl, $C_2$–$C_3$ alkynyl, $C_2$–$C_3$ haloalkynyl, and $C_1$–$C_3$ alkoxy, wherein said alkyl, haloalkyl, alkenyl, haloalkenyl, alkynyl, haloalkynyl, and alkoxy groups may be optionally substituted;

$R^2$ and $R^4$ are independently selected from the group of hydrogen, $NR^{10}R^{11}$, $C_1$–$C_6$ alkyl, $C_1$–$C_6$ haloalkyl, $C_3$–$C_8$ cycloalkyl, $C_2$–$C_6$ alkenyl, $C_2$–$C_6$ haloalkenyl, $C_2$–$C_6$ alkynyl, $C_2$–$C_6$ haloalkynyl, aryl, heteroaryl, $C_1$–$C_6$ alkoxy, and aryloxy, wherein said alkyl, haloalkyl, cycloalkyl, alkenyl, haloalkenyl, alkynyl, haloalkynyl, aryl, heteroaryl, alkoxy, aryloxy groups may be optionally substituted;

$R^3$ is selected from the group of hydrogen, $C_1$–$C_6$ alkyl, $C_1$–$C_6$ haloalkyl, $C_3$–$C_8$ cycloalkyl, $C_2$–$C_6$ alkenyl, $C_2$–$C_6$ haloalkenyl, $C_2$–$C_6$ alkynyl, $C_2$–$C_6$ haloalkynyl, aryl, heteroaryl, $C_1$–$C_6$ alkoxy, and aryloxy, wherein said alkyl, haloalkyl, cycloalkyl, alkenyl, haloalkenyl, alkynyl, haloalkynyl, aryl, heteroaryl, alkoxy, aryloxy groups may be optionally substituted;

$R^5$ and $R^6$ are independently selected from the group of hydrogen, F, Cl, Br, I, CN, $NH_2$, OH, SH, $C_1$–$C_6$ alkyl, $C_1$–$C_6$ haloalkyl, $C_2$–$C_6$ alkenyl, $C_1$–$C_6$ haloalkenyl, $C_1$–$C_6$ alkoxy, and aryloxy wherein said alkyl, haloalkyl, alkenyl, haloalkenyl, alkoxy and aryloxy groups may be optionally substituted;

$R^7$ is optionally substituted $C_2$–$C_6$ haloalkyl;

$R^8$ is selected from the group of hydrogen, F, Cl, Br, I, CN, $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_1$–$C_6$ alkoxy, and aryloxy, wherein said alkyl, haloalkyl, alkenyl, haloalkenyl, alkynyl, alkoxy and aryloxy groups may be optionally substituted;

$R^9$ is selected from the group of hydrogen, F, Cl, Br, I, methyl, and optionally substituted methyl;

$R^{10}$ and $R^{11}$ each independently is hydrogen or optionally substituted $C_1$–$C_6$ alkyl; or $R^{10}$ and $R^{11}$ taken together with nitrogen form an optionally substituted five- or six-membered heterocyclic ring;

Y is selected from the group of $NR^{12}$, O and S;

$R^{12}$ is selected from the group of hydrogen, optionally substituted $C_1$–$C_6$ alkyl, and optionally substituted $C_1$–$C_6$ haloalkyl; and pharmaceutically acceptable salts thereof.

2. A compound according to claim 1, wherein $R^1$ is selected from the group of hydrogen, optionally substituted $C_1$–$C_3$ alkyl and optionally substituted $C_1$–$C_3$ haloalkyl.

3. A compound according to claim 2, wherein $R^1$ is hydrogen.

4. A compound according to claim 2, wherein $R^3$ is selected from the group of hydrogen, optionally substituted $C_1$–$C_6$ alkyl and optionally substituted $C_1$–$C_6$ haloalkyl.

5. A compound according to claim 4, wherein $R^3$ is hydrogen.

6. A compound according to claim 4, wherein $R^8$ is selected from the group of hydrogen, optionally substituted $C_1$–$C_6$ alkyl and optionally substituted $C_1$–$C_6$ haloalkyl.

7. A compound according to claim 6, wherein $R^8$ is hydrogen.

8. A compound according to claim 6, wherein $R^9$ is hydrogen, F, Cl, Br, or I.

9. A compound according to claim 8, wherein $R^9$ is hydrogen.

10. A compound according to claim 1, wherein $R^5$ and $R^6$ each independently is selected from the group of hydrogen, F, Cl, Br, I, and $C_1$–$C_4$ alkyl wherein said alkyl group may be optionally substituted; or $R^5$ and $R^6$ taken together form a three- to eight-membered carbocyclic ring, a three- to eight-membered heterocyclic ring, an aryl group or a heteroaryl group, wherein said carbocyclic ring, heterocyclic ring, aryl and heteroaryl groups may be optionally substituted.

11. A compound according to claim 10, wherein
$R^5$ is optionally substituted $C_1$–$C_4$ alkyl and $R^6$ is hydrogen.

12. A compound according to claim 10, wherein
$R^5$ and $R^6$ taken together form a five- to six-membered carbocyclic ring, a five- to six-membered heterocyclic ring, an aryl group or a heteroaryl group, wherein said carbocyclic ring, heterocyclic ring, aryl and heteroaryl groups may be optionally substituted.

13. A compound according to claim 1, wherein
$R^2$ and $R^4$ are independently selected from the group of $NR^{10}R^{11}$, $C_1$–$C_6$ alkyl, $C_1$–$C_6$ haloalkyl, $C_3$–$C_8$ cycloalkyl, aryl, and heteroaryl, wherein said alkyl, haloalkyl, cycloalkyl, aryl and heteroaryl groups may be optionally substituted.

14. A compound according to claim 13, wherein
$R^2$ and $R^4$ are independently selected from the group of aryl, $C_1$–$C_6$ alkyl and $C_1$–$C_6$ haloalkyl, wherein said aryl, alkyl and haloalkyl groups may be optionally substituted.

15. A compound according to claim 14, wherein
$R^2$ and $R^4$ each independently is optionally substituted $C_1$–$C_6$ alkyl.

16. A compound according to claim 15, wherein $R^2$ is selected from the group of etyl, i-propyl, t-butyl, and t-amyl.

17. A compound according to claim 13, wherein $R^4$ is selected from the group of $NR^{10}R^{11}$, i-propyl, t-butyl, and t-amyl.

18. A compound according to claim 1, wherein
$R^1$ is selected from the group of hydrogen, optionally substituted $C_1$–$C_3$ alkyl, and optionally substituted $C_1$–$C_3$ haloalkyl;
$R^3$, $R^6$, and $R^8$ are independently selected from the group of hydrogen, optionally substituted $C_1$–$C_6$ alkyl, and optionally substituted $C_1$–$C_6$ haloalkyl;
$R^2$ and $R^4$ are independently selected from the group of $C_1$–$C_6$ alkyl, $C_1$–$C_6$ haloalkyl, $C_5$–$C_6$ cycloalkyl, aryl, and heteroaryl, wherein said alkyl, haloalkyl, cycloalkyl, aryl and heteroaryl groups may be optionally substituted;
$R^5$ is optionally substituted $C_1$–$C_6$ alkyl; and
$R^9$ is hydrogen, F, Cl, Br, or I.

19. A compound according to claim 1, wherein
$R^1$ is selected from the group of hydrogen, optionally substituted $C_1$–$C_3$ alkyl, and optionally substituted $C_1$–$C_3$ haloalkyl;
$R^3$, $R^6$, and $R^8$ are independently selected from the group of hydrogen, optionally substituted $C_1$–$C_6$ alkyl, and optionally substituted $C_1$–$C_6$ haloalkyl;
$R^2$ and $R^4$ are independently selected from the group of $C_1$–$C_4$ alkyl, $C_1$–$C_4$ haloalkyl, $C_5$–$C_6$ cycloalkyl, aryl, and heteroaryl, wherein said alkyl, haloalkyl, cycloalkyl, aryl and heteroaryl groups may be optionally substituted;
$R^5$ is optionally substituted $C_1$–$C_6$ alkyl; and
$R^9$ is hydrogen, F, Cl, Br, or I.

20. A compound according to claim 1, wherein
$R^1$, $R^3$, $R^8$ and $R^9$ are hydrogen;
$R^2$ and $R^4$ are independently selected from the group of $C_1$–$C_6$ alkyl, $C_1$–$C_6$ haloalkyl, $C_3$–$C_6$ cycloalkyl, aryl and heteroaryl, wherein alkyl, haloalkyl, cycloalkyl, aryl and heteroaryl may be optionally substituted;

$R^5$ and $R^6$ taken together form a five- to six-membered carbocyclic ring, a five- to six-membered heterocyclic ring, an aryl group or a heteroaryl group, wherein said carbocyclic ring, heterocyclic ring, aryl and heteroaryl groups may be optionally substituted; and
$R^7$ is an optionally substituted $C_2$–$C_5$ alkyl.

21. A compound according to claim 1, wherein
$R^1$, $R^3$, $R^8$ and $R^9$ are hydrogen;
$R^2$ and $R^4$ are independently selected from the group of $C_1$–$C_6$ alkyl, $C_1$–$C_6$ haloalkyl, $C_3$–$C_6$ cycloalkyl, aryl and heteroaryl, wherein alkyl, haloalkyl, cycloalkyl, aryl and heteroaryl may be optionally substituted;
$R^5$ and $R^6$ taken together form a five- to six-membered carbocyclic ring, a five- to six-membered heterocyclic ring, an aryl group or a heteroaryl group, wherein said carbocyclic ring, heterocyclic ring, aryl and heteroaryl groups may optionally substituted; and
$R^7$ is optionally substituted $C_2$–$C_5$ haloalkyl.

22. A compound according to claim 1, wherein said compound, when administered to an individual, decreases blood glucose levels but does not substantially raise triglyceride levels.

23. A compound according to claim 1 wherein said compound does not substantially suppress thyroid hormone axis in an individual.

24. A compound according to claim 1 wherein said compound is non-teratogenic.

25. A compound according to claim 1 wherein said modulator compound is selected from the group of:

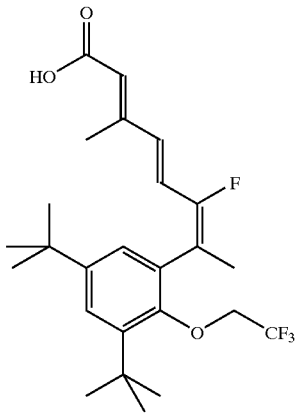

L20

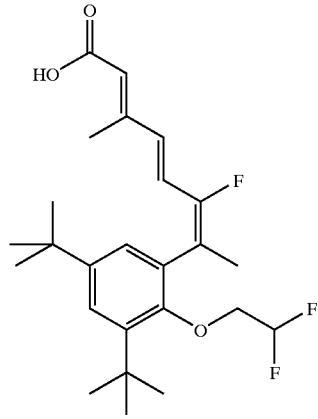

L21

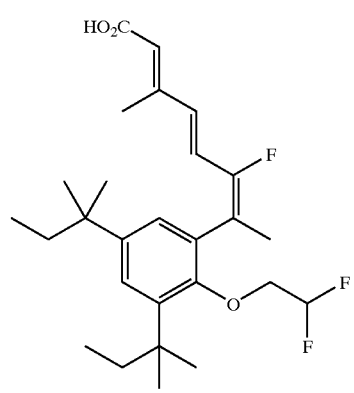 L22
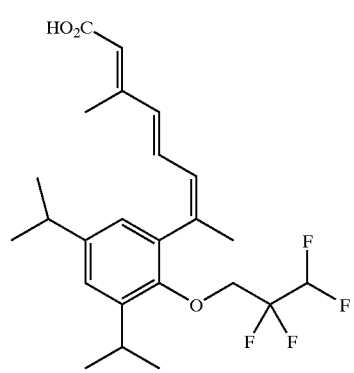 L26
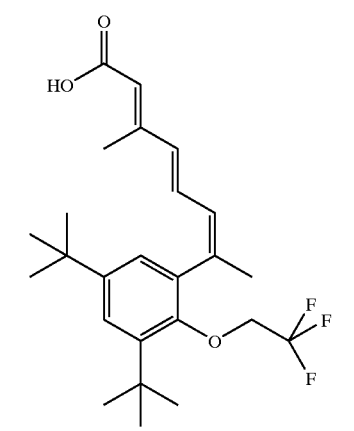 L23
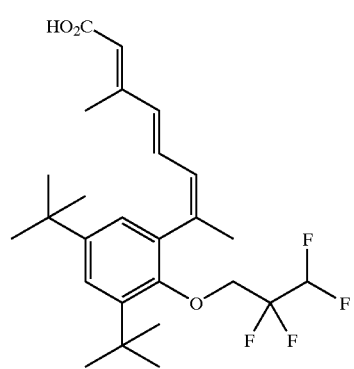 L27
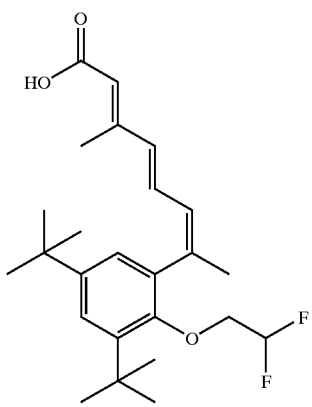 L13
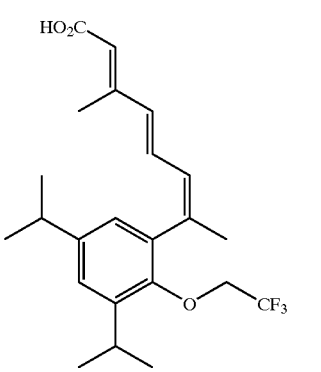 L28
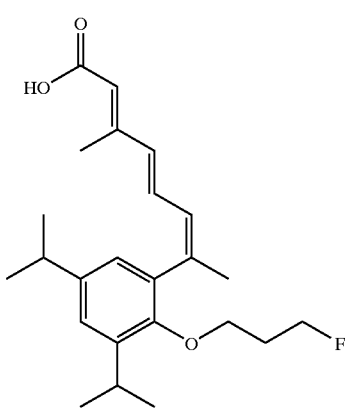 L24
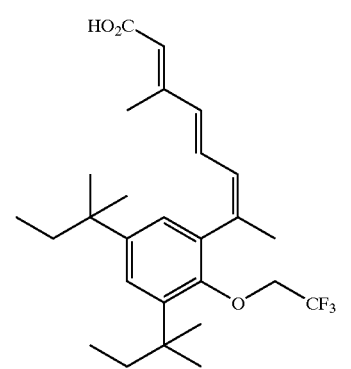 L29

-continued
L30
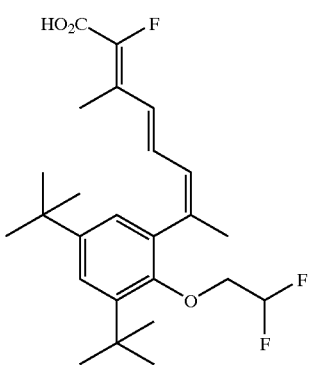
L82
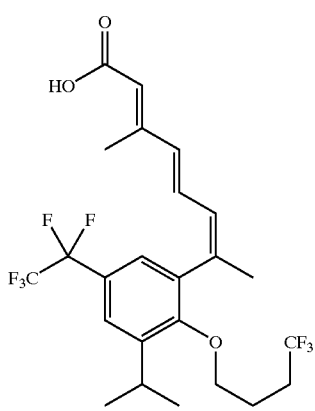
L77
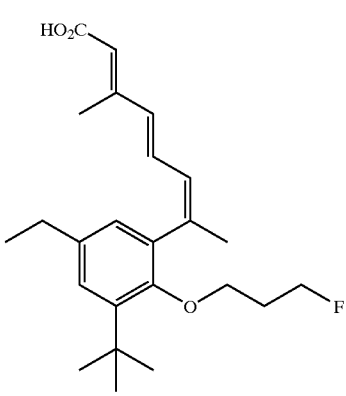
L95
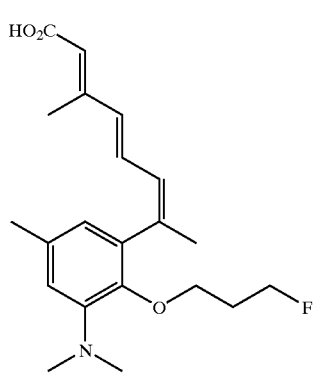
-continued
L79
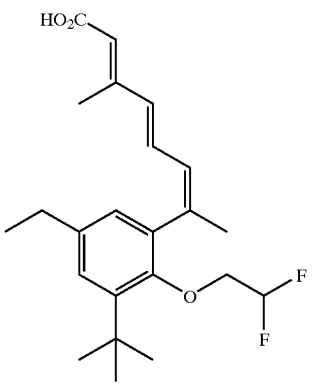
L96
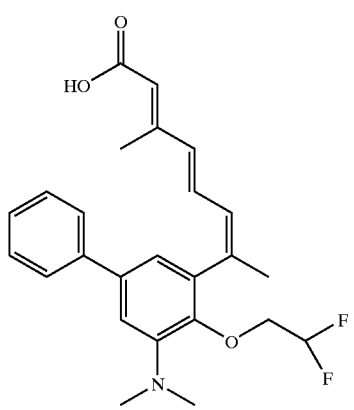
L80
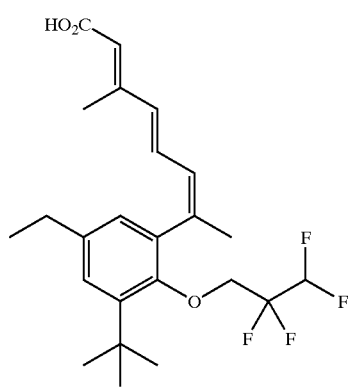
L98
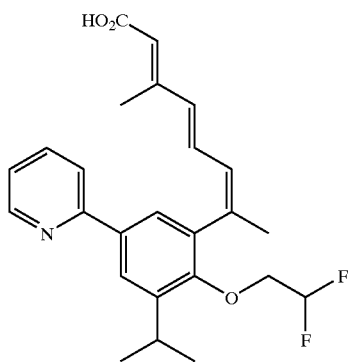

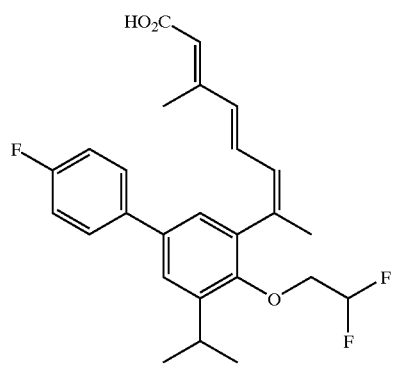
L99
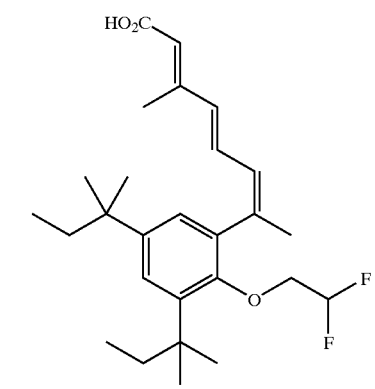
L18
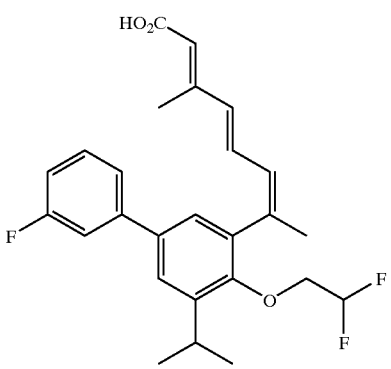
L100
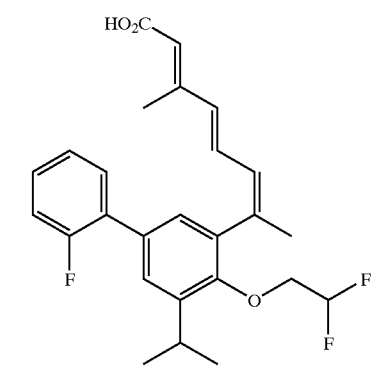
L19
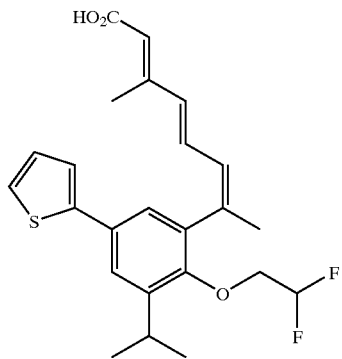
L101
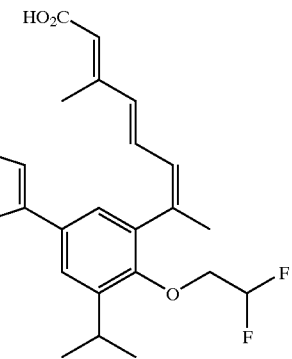
and
26. A compound of claim 25 wherein said compound is selected from the group of:
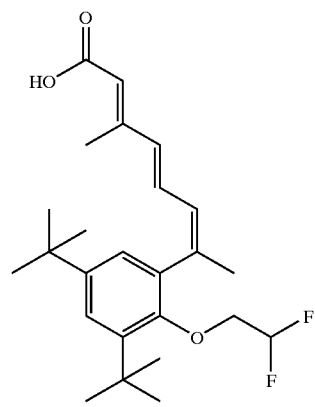
L13
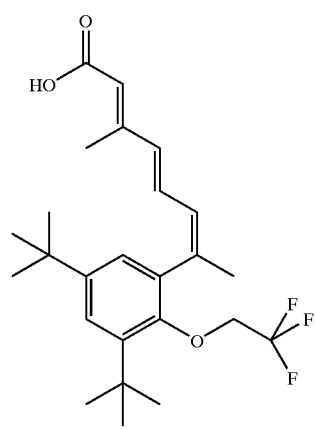
L23
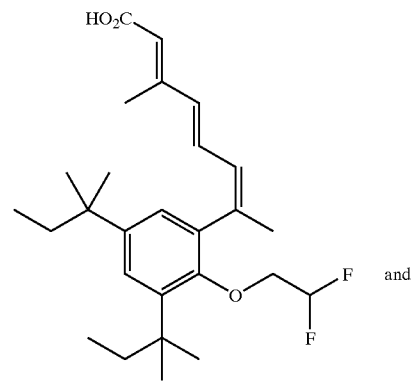
L18
and -continued

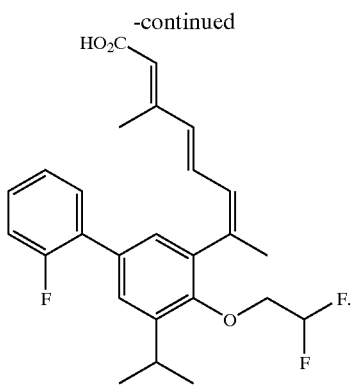

27. A pharmaceutical composition comprising a compound according to any one of claims 1, 25 or 26 and a pharmaceutically acceptable carrier.

28. A method for modulating RXR activity in an individual comprising administering to said individual a pharmaceutically effective amount of a compound according to any one of claims 1, 25 or 26.

29. A method for treating an individual having a disease condition selected from the group of syndrome X, NIDDM, diabetes, obesity and cardiovascular disease comprising administering to said individual a pharmaceutically effective amount of a compound according to any one of claims 1, 25 or 26.

30. A method for treating an individual having a disease condition selected from the group of breast cancer, photoaging, acne, and psoriasis comprising administering to said individual a pharmaceutically effective amount of a compound according to any one of claims 1, 25 or 26.

31. A method for treating an individual at risk for developing a disease condition selected from the group of syndrome X, NIDDM, diabetes, obesity and cardiovascular disease comprising administering to said individual a pharmaceutically effective amount of a compound according to any one of claims 1, 25 or 26.

32. A method for treating an individual at risk for developing a disease condition selected from the group of breast cancer, photoaging, acne, and psoriasis comprising administering to said individual a pharmaceutically effective amount of a compound according to any one of claims 1, 25 or 26.

33. A method for lowering blood glucose levels in an individual without substantially raising said individual's serum triglyceride levels comprising administering to said individual a pharmaceutically effective amount of a compound according to any one of claims 1, 25 or 26.

34. A method of claim 33 further comprising administering to said individual a PPARγ agonist.

35. A method for increasing HDL cholesterol levels and reducing triglyceride levels in an individual comprising administering to said individual a pharmaceutically effective amount of a compound according to any one of claims 1, 25 or 26.

36. A method for modulating lipid metabolism in an individual comprising administering to said individual a pharmaceutically effective amount of a compound according to any one of claims 1, 25 or 26.

37. The method of claim 35 further comprising the administration of a PPARα agonist.

38. A method for modulating RXR:PPAR heterodimer activity in an individual comprising administering to said individual a pharmaceutically effective amount a compound according to any one of claims 1, 25 or 26.

39. The method of claim 38 further comprising administering to said individual a PPAR agonist.

40. A process for preparing a compound of structural formula 1:

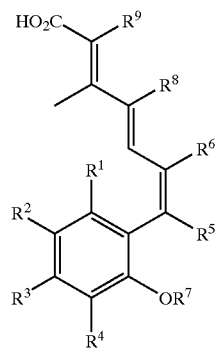

comprising the step of treating a coumarin intermediate of structural formula 4:

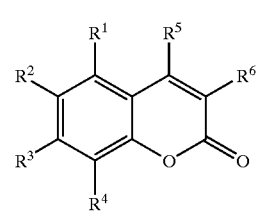

with a reducing agent to form a diol of structural formula 7:

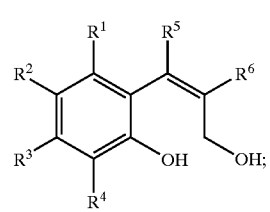

wherein
$R^1$ is selected from the group of hydrogen, F, Cl, Br, I, $C_1$–$C_3$ alkyl, $C_1$–$C_3$ haloalkyl, $C_2$–$C_3$ alkenyl, $C_2$–$C_3$ haloalkenyl, $C_2$–$C_3$ alkynyl, $C_2$–$C_3$ haloalkynyl, and $C_1$–$C_3$ alkoxy, wherein said alkyl, haloalkyl, alkenyl, haloalkenyl, alkynyl, haloalkynyl, and alkoxy groups may be optionally substituted;

$R^2$ and $R^4$ are independently selected from the group of hydrogen, $NR^{10}R^{11}$, $C_1$–$C_6$ alkyl, $C_1$–$C_6$ haloalkyl, $C_3$–$C_8$ cycloalkyl, $C_2$–$C_6$ alkenyl, $C_2$–$C_6$ haloalkenyl, $C_2$–$C_6$ alkynyl, $C_2$–$C_6$ haloalkynyl, aryl, heteroaryl, $C_1$–$C_6$ alkoxy, and aryloxy, wherein said alkyl, haloalkyl, cycloalkyl, alkenyl, haloalkenyl, alkynyl, haloalkynyl, aryl, heteroaryl, alkoxy, aryloxy groups may be optionally substituted;

$R^3$ is selected from the group of hydrogen, $C_1$–$C_6$ alkyl, $C_1$–$C_6$ haloalkyl, $C_3$–$C_8$ cycloalkyl, $C_2$–$C_6$ alkenyl, $C_2$–$C_6$ haloalkenyl, $C_2$–$C_6$ alkynyl, $C_2$–$C_6$ haloalkynyl, aryl, heteroaryl, $C_1$–$C_6$ alkoxy, and aryloxy, wherein said alkyl, haloalkyl, cycloalkyl, alkenyl, haloalkenyl, alkynyl, haloalkynyl, aryl, heteroaryl, alkoxy, aryloxy groups may be optionally substituted;

$R^5$ and $R^6$ are independently selected from the group of hydrogen, F, Cl, Br, I, CN, $NH_2$, OH, SH, $C_1$–$C_6$ alkyl, $C_1$–$C_6$ haloalkyl, $C_2$–$C_6$ alkenyl, $C_1$–$C_6$ haloalkenyl, $C_1$–$C_6$ alkoxy, and aryloxy wherein said alkyl, haloalkyl, alkenyl, haloalkenyl, alkoxy and aryloxy groups may be optionally substituted; or $R^5$ and $R^6$ taken together form a three- to eight-membered carbocyclic ring, a three- to eight-membered heterocyclic ring, an aryl group or a heteroaryl group, wherein said carbocyclic ring, heterocyclic ring, aryl and heteroaryl groups may be optionally substituted;

$R^7$ is selected from the group of $C_2$–$C_6$ alkyl, $C_2$–$C_6$ alkenyl, and $C_2$–$C_6$ haloalkyl, wherein said alkyl, alkenyl, and haloalkyl groups may be optionally substituted;

$R^8$ is selected from the group of hydrogen, F, Cl, Br, I, CN, $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_1$–$C_6$ alkoxy, and aryloxy, wherein said alkyl, haloalkyl, alkenyl, haloalkenyl, alkynyl, alkoxy and aryloxy groups may be optionally substituted;

$R^9$ is selected from the group of hydrogen, F, Cl, Br, I, methyl, and optionally substituted methyl;

$R^{10}$ and $R^{11}$ each independently is hydrogen or optionally substituted $C_1$–$C_6$ alkyl; or $R^{10}$ and $R^{11}$ taken together with nitrogen form an optionally substituted five- or six-membered heterocyclic ring; and pharmaceutically acceptable salts thereof.

41. A process according to claim 40 further comprising the steps of:

(a) selectively alkylating the phenol oxygen of the diol of structural formula 7 with $R^7X$ in the presence of a base to form a primary allylic alcohol of structural formula 8:

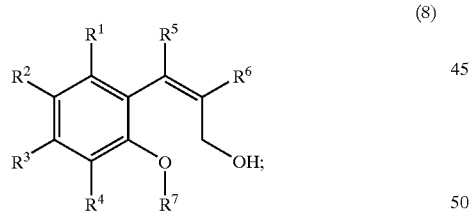

(8)

(b) treating the allylic alcohol of structural formula 8 with an oxidant to form an aldehyde of structural formula 9:

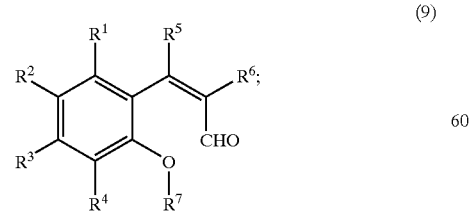

(9)

(c) treating the aldehyde of structural formula 9 with a phosphonate of structural formula 10:

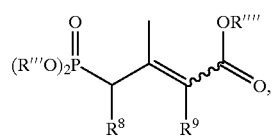

(10)

to form an ester of formula 1-E:

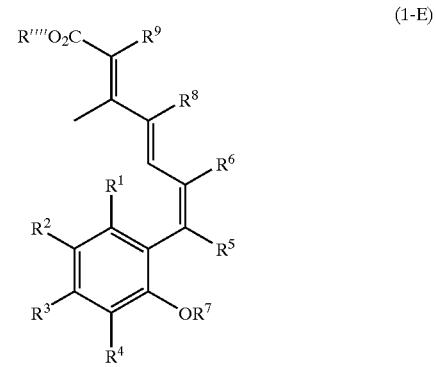

(1-E)

and hydrolyzing the ester, 1-E;
wherein:
R''' and R'''' each independently is alkyl or aryl;
X is a halogen.

42. A process according to claim 41 wherein R''' and R'''' each independently is methyl, ethyl or iso-propyl.

43. A process for preparing a compound of structural formula 1:

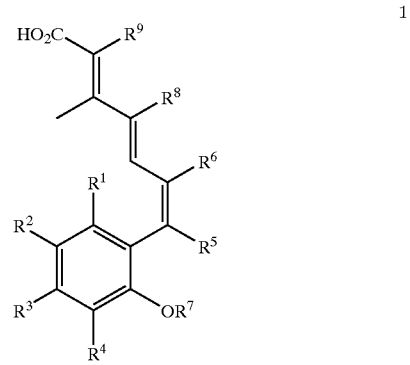

1 comprising the steps of:

(a) treating alkoxyarylhalide 12

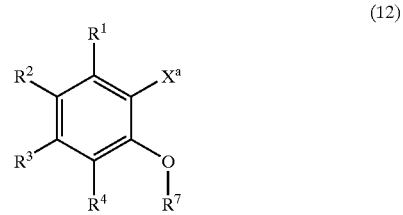

(12)

with a trialkyl borate and a base under Pd-catalysis to form a compound of structural formula 14

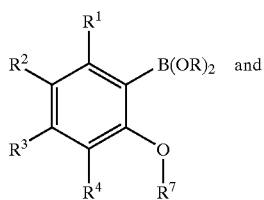

(14)

(b) treating the compound of structural formula 14 with a compound of structural formula 15:

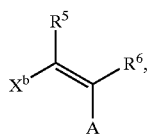

(15)

to form a compound of structural formula 16:

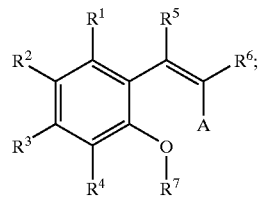

(16)

wherein:
A is COOR' or COP$^g$, wherein P$^g$ is a protecting group;
R and R$^1$ each independently is hydrogen or alkyl;
X$^a$ and X$^b$ each independently is halogen;
R$^1$ is selected from the group of hydrogen, F, Cl, Br, I, $C_1$–$C_3$ alkyl, $C_1$–$C_3$ haloalkyl, $C_2$–$C_3$ alkenyl, $C_2$–$C_3$ haloalkenyl, $C_2$–$C_3$ alkynyl, $C_2$–$C_3$ haloalkynyl, and $C_1$–$C_3$ alkoxy, wherein said alkyl, haloalkyl, alkenyl, haloalkenyl, alkynyl, haloalkynyl, and alkoxy groups may be optionally substituted;
R$^2$ and R$^4$ are independently selected from the group of hydrogen, NR$^{10}$R$^{11}$, $C_1$–$C_6$ alkyl, $C_1$–$C_6$ haloalkyl, $C_3$–$C_8$ cycloalkyl, $C_2$–$C_6$ alkenyl, $C_2$–$C_6$ haloalkenyl, $C_2$–$C_6$ alkynyl, $C_2$–$C_6$ haloalkynyl, aryl, heteroaryl, $C_1$–$C_6$ alkoxy, and aryloxy, wherein said alkyl, haloalkyl, cycloalkyl, alkenyl, haloalkenyl, alkynyl, haloalkynyl, aryl, heteroaryl, alkoxy, aryloxy groups may be optionally substituted;
R$^3$ is selected from the group of hydrogen, $C_1$–$C_6$ alkyl, $C_1$–$C_6$ haloalkyl, $C_3$–$C_8$ cycloalkyl, $C_2$–$C_6$ alkenyl, $C_2$–$C_6$ haloalkenyl, $C_2$–$C_6$ alkynyl, $C_2$–$C_6$ haloalkynyl, aryl, heteroaryl, $C_1$–$C_6$ alkoxy, and aryloxy, wherein said alkyl, haloalkyl, cycloalkyl, alkenyl, haloalkenyl, alkynyl, haloalkynyl, aryl, heteroaryl, alkoxy, aryloxy groups may be optionally substituted;
R$^5$ and R$^6$ are independently selected from the group of hydrogen, F, Cl, Br, I, CN, NH$_2$, OH, SH, $C_1$–$C_6$ alkyl, $C_1$–$C_6$ haloalkyl, $C_2$–$C_6$ alkenyl, $C_1$–$C_6$ haloalkenyl, $C_1$–$C_6$ alkoxy, and aryloxy wherein said alkyl, haloalkyl, alkenyl, haloalkenyl, alkoxy and aryloxy groups may be optionally substituted; or
R$^5$ and R$^6$ taken together form a three- to eight-membered carbocyclic ring, a three- to eight-membered heterocyclic ring, an aryl group or a heteroaryl group, wherein said carbocyclic ring, heterocyclic ring, aryl and heteroaryl groups may be optionally substituted;
R$^7$ is selected from the group of $C_2$–$C_6$ alkyl, $C_2$–$C_6$ alkenyl, and $C_2$–$C_6$ haloalkyl, wherein said alkyl, alkenyl, and haloalkyl groups may be optionally substituted;
R$^8$ is selected from the group of hydrogen, F, Cl, Br, I, CN, $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_1$–$C_6$ alkoxy, and aryloxy, wherein said alkyl, haloalkyl, alkenyl, haloalkenyl, alkynyl, alkoxy, and aryloxy groups may be optionally substituted;
R$^9$ is selected from the group of hydrogen, F, Cl, Br, I, methyl, and optionally substituted methyl;
R$^{10}$ and R$^{11}$ each independently is hydrogen or optionally substituted $C_1$–$C_6$ alkyl; or
R$^{10}$ and R$^{11}$ taken together with nitrogen form an optionally substituted five- or six-membered heterocyclic ring; and pharmaceutically acceptable salts thereof.

44. A process for preparing a compound of the structural formula 1:

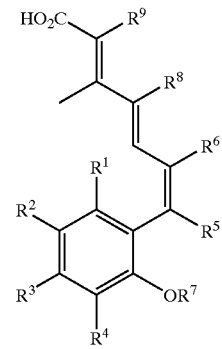

(1)

comprising the step of:

(a) treating a ketone of structural formula VI:

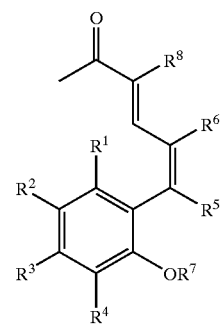

(VI)

with a phosphonate of structural formula 10b:

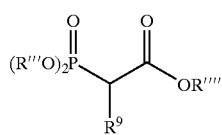
(10b)

wherein:
R''' and R'''' each independently is alkyl or aryl;
R$^1$ is selected from the group of hydrogen, F, Cl, Br, I, $C_1$–$C_3$ alkyl, $C_1$–$C_3$ haloalkyl, $C_2$–$C_3$ alkenyl, $C_2$–$C_3$ haloalkenyl, $C_2$–$C_3$ alkynyl, $C_2$–$C_3$ haloalkynyl, and $C_1$–$C_3$ alkoxy, wherein said alkyl, haloalkyl, alkenyl, haloalkenyl, alkynyl, haloalkynyl, and alkoxy groups may be optionally substituted;
R$^2$ and R$^4$ are independently selected from the group of hydrogen, NR$^{10}$R$^{11}$, $C_1$–$C_6$ alkyl, $C_1$–$C_6$ haloalkyl, $C_3$–$C_8$ cycloalkyl, $C_2$–$C_6$ alkenyl, $C_2$–$C_6$ haloalkenyl, $C_2$–$C_6$ alkynyl, $C_2$–$C_6$ haloalkynyl, aryl, heteroaryl, $C_1$–$C_6$ alkoxy, and aryloxy, wherein said alkyl, haloalkyl, cycloalkyl, alkenyl, haloalkenyl, alkynyl, haloalkynyl, aryl, heteroaryl, alkoxy, aryloxy groups may be optionally substituted;
R$^3$ is selected from the group of hydrogen, $C_1$–$C_6$ alkyl, $C_1$–$C_6$ haloalkyl, $C_3$–$C_8$ cycloalkyl, $C_2$–$C_6$ alkenyl, $C_2$–$C_6$ haloalkenyl, $C_2$–$C_6$ alkynyl, $C_2$–$C_6$ haloalkynyl, aryl, heteroaryl, $C_1$–$C_6$ alkoxy, and aryloxy, wherein said alkyl, haloalkyl, cycloalkyl, alkenyl, haloalkenyl, alkynyl, haloalkynyl, aryl, heteroaryl, alkoxy, aryloxy groups may be optionally substituted;
R$^5$ and R$^6$ are independently selected from the group of hydrogen, F, Cl, Br, I, CN, NH$_2$, OH, SH, $C_1$–$C_6$ alkyl, $C_1$–$C_6$ haloalkyl, $C_2$–$C_6$ alkenyl, $C_1$–$C_6$ haloalkenyl, $C_1$–$C_6$ alkoxy, and aryloxy wherein said alkyl, haloalkyl, alkenyl, haloalkenyl, alkoxy and aryloxy groups may be optionally substituted; or
R$^5$ and R$^6$ taken together form a three- to eight-membered carbocyclic ring, a three- to eight-membered heterocyclic ring, an aryl group or a heteroaryl group, wherein said carbocyclic ring, heterocyclic ring, aryl and heteroaryl groups may be optionally substituted;
R$^7$ is selected from the group of $C_2$–$C_6$ alkyl, $C_2$–$C_6$ alkenyl, and $C_2$–$C_6$ haloalkyl, wherein said alkyl, alkenyl, and haloalkyl groups may be optionally substituted;
R$^8$ is selected from the group of hydrogen, F, Cl, Br, I, CN, $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_1$–$C_6$ alkoxy, and aryloxy, wherein said alkyl, haloalkyl, alkenyl, haloalkenyl, alkynyl, alkoxy, and aryloxy groups may be optionally substituted;
R$^9$ is selected from the group of hydrogen, F, Cl, Br, I, methyl, and optionally substituted methyl;
R$^{10}$ and R$^{11}$ each independently is hydrogen or optionally substituted $C_1$–$C_6$ alkyl; or R$^{10}$ and R$^{11}$ taken together with nitrogen form an optionally substituted five- or six-membered heterocyclic ring;
and pharmaceutically acceptable salts thereof.

45. A process according to claim 44, wherein R$^9$ is F.

46. A process for preparing a compound of structural formula 1b:

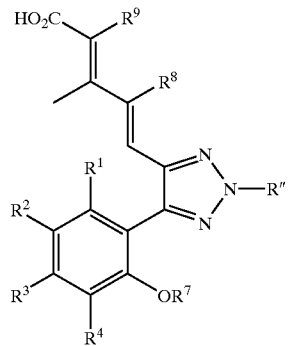
(1b)

comprising the step of:
(a) treating a compound of the structural formula I:

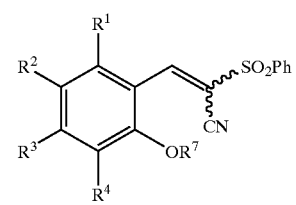
(I)

with sodium azide to form a triazole of formula II:

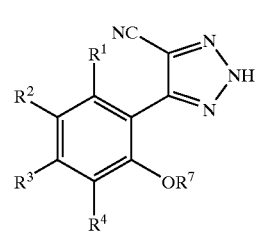
(II)

wherein:
R'' is $C_1$–$C_6$ alkyl;
R$^1$ is selected from the group of hydrogen, F, Cl, Br, I, $C_1$–$C_3$ alkyl, $C_1$–$C_3$ haloalkyl, $C_2$–$C_3$ alkenyl, $C_2$–$C_3$ haloalkenyl, $C_2$–$C_3$ alkynyl, $C_2$–$C_3$ haloalkynyl, and $C_1$–$C_3$ alkoxy, wherein said alkyl, haloalkyl, alkenyl, haloalkenyl, alkynyl, haloalkynyl, and alkoxy groups may be optionally substituted;
R$^2$ and R$^4$ are independently selected from the group of hydrogen, NR$^{10}$R$^{11}$, $C_1$–$C_6$ alkyl, $C_1$–$C_6$ haloalkyl, $C_3$–$C_8$ cycloalkyl, $C_2$–$C_6$ alkenyl, $C_2$–$C_6$ haloalkenyl, $C_2$–$C_6$ alkynyl, $C_2$–$C_6$ haloalkynyl, aryl, heteroaryl, $C_1$–$C_6$ alkoxy, and aryloxy, wherein said alkyl, haloalkyl, cycloalkyl, alkenyl, haloalkenyl, alkynyl, haloalkynyl, aryl, heteroaryl, alkoxy, aryloxy groups may be optionally substituted;
R$^3$ is selected from the group of hydrogen, $C_1$–$C_6$ alkyl, $C_1$–$C_6$ haloalkyl, $C_3$–$C_8$ cycloalkyl, $C_2$–$C_6$ alkenyl, $C_2$–$C_6$ haloalkenyl, $C_2$–$C_6$ alkynyl, $C_2$–$C_6$ haloalkynyl, aryl, heteroaryl, $C_1$–$C_6$ alkoxy, and aryloxy, wherein said alkyl, haloalkyl, cycloalkyl, alkenyl, haloalkenyl, alkynyl, haloalkynyl, aryl, heteroaryl, alkoxy, aryloxy groups may be optionally substituted;

$R^7$ is selected from the group of $C_2$–$C_6$ alkyl, $C_2$–$C_6$ alkenyl, and $C_2$–$C_6$ haloalkyl, wherein said alkyl, alkenyl, and haloalkyl groups may be optionally substituted;

$R^8$ is selected from the group of hydrogen, F, Cl, Br, I, CN, $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_1$–$C_6$ alkoxy, and aryloxy, wherein said alkyl, haloalkyl, alkenyl, haloalkenyl, alkynyl, alkoxy, and aryloxy groups may be optionally substituted;

$R^9$ is selected from the group of hydrogen, F, Cl, Br, I, methyl, and optionally substituted methyl;

$R^{10}$ and $R^{11}$ each independently is hydrogen or optionally substituted $C_1$–$C_6$ alkyl; or $R^{10}$ and $R^{11}$ taken together with nitrogen form an optionally substituted five- or six-membered heterocyclic ring; and pharmaceutically acceptable salts thereof.

47. A process for preparing a compound of the structural formula 1a:

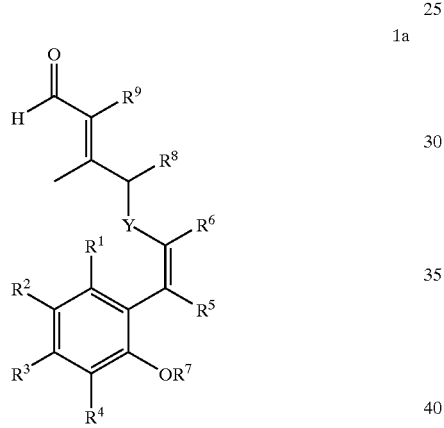

comprising the steps of:

(a) treating an arylboronic acid of structural formula I:

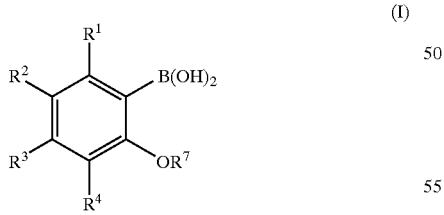

with a compound of structural formula XI:

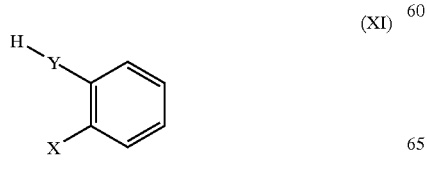

to form a compound of structural formula II:

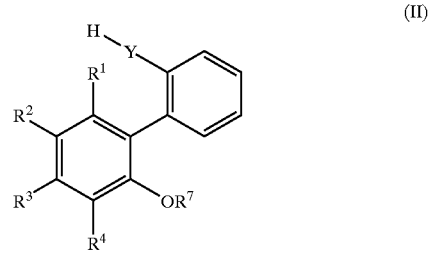

wherein:

X is halogen;

$R^1$ is selected from the group of hydrogen, F, Cl, Br, I, $C_1$–$C_3$ alkyl, $C_1$–$C_3$ haloalkyl, $C_2$–$C_3$ alkenyl, $C_2$–$C_3$ haloalkenyl, $C_2$–$C_3$ alkynyl, $C_2$–$C_3$ haloalkynyl, and $C_1$–$C_3$ alkoxy, wherein said alkyl, haloalkyl, alkenyl, haloalkenyl, alkynyl, haloalkynyl, and alkoxy groups may be optionally substituted;

$R^2$ and $R^4$ are independently selected from the group of hydrogen, $NR^{10}R^{11}$, $C_1$–$C_6$ alkyl, $C_1$–$C_6$ haloalkyl, $C_3$–$C_8$ cycloalkyl, $C_2$–$C_6$ alkenyl, $C_2$–$C_6$ haloalkenyl, $C_2$–$C_6$ alkynyl, $C_2$–$C_6$ haloalkynyl, aryl, heteroaryl, $C_1$–$C_6$ alkoxy, and aryloxy, wherein said alkyl, haloalkyl, cycloalkyl, alkenyl, haloalkenyl, alkynyl, haloalkynyl, aryl, heteroaryl, alkoxy, aryloxy groups may be optionally substituted;

$R^3$ is selected from the group of hydrogen, $C_1$–$C_6$ alkyl, $C_1$–$C_6$ haloalkyl, $C_3$–$C_8$ cycloalkyl, $C_2$–$C_6$ alkenyl, $C_2$–$C_6$ haloalkenyl, $C_2$–$C_6$ alkynyl, $C_2$–$C_6$ haloalkynyl, aryl, heteroaryl, $C_1$–$C_6$ alkoxy, and aryloxy, wherein said alkyl, haloalkyl, cycloalkyl, alkenyl, haloalkenyl, alkynyl, haloalkynyl, aryl, heteroaryl, alkoxy, aryloxy groups may be optionally substituted;

$R^5$ and $R^6$ are independently selected from the group of hydrogen, F, Cl, Br, I, CN, $NH_2$, OH, SH, $C_1$–$C_6$ alkyl, $C_1$–$C_6$ haloalkyl, $C_2$–$C_6$ alkenyl, $C_1$–$C_6$ haloalkenyl, $C_1$–$C_6$ alkoxy, and aryloxy wherein said alkyl, haloalkyl, alkenyl, haloalkenyl, alkoxy and aryloxy groups may be optionally substituted; or $R^5$ and $R^6$ taken together form a three- to eight-membered carbocyclic ring, a three- to eight-membered heterocyclic ring, an aryl group or a heteroaryl group, wherein said carbocyclic ring, heterocyclic ring, aryl and heteroaryl groups may be optionally substituted;

$R^7$ is selected from the group of $C_2$–$C_6$ alkyl, $C_2$–$C_6$ alkenyl, and $C_2$–$C_6$ haloalkyl, wherein said alkyl, alkenyl, and haloalkyl groups may be optionally substituted;

$R^8$ is selected from the group of hydrogen, F, Cl, Br, I, CN, $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_1$–$C_6$ alkoxy, and aryloxy, wherein said alkyl, haloalkyl, alkenyl, haloalkenyl, alkynyl, alkoxy, and aryloxy groups may be optionally substituted;

$R^9$ is selected from the group of hydrogen, F, Cl, Br, I, methyl, and optionally substituted methyl;

$R^{10}$ and $R^{11}$ each independently is hydrogen or optionally substituted $C_1$–$C_6$ alkyl; or $R^{10}$ and $R^{11}$ taken together with nitrogen form an optionally substituted five- or six-membered heterocyclic ring;

Y is selected from the group of $NR^{12}$, O and S;

$R^{12}$ is selected from the group of hydrogen, optionally substituted $C_1$–$C_6$ alkyl, and optionally substituted $C_1$–$C_6$ haloalkyl; and pharmaceutically acceptable salts thereof.

48. A process according to claim 47, wherein Y is $NR^{12}$.

49. A compound having the structure:

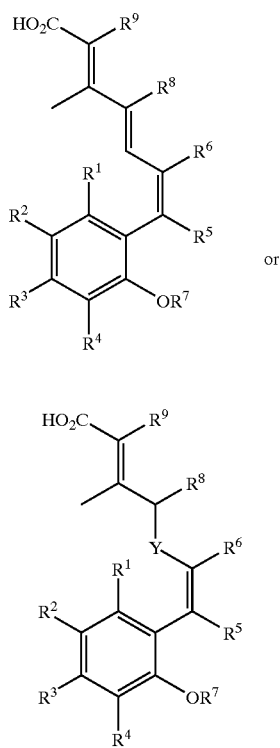

wherein:

$R^1$ is selected from the group of hydrogen, F, Cl, Br, I, $C_1$–$C_3$ alkyl, $C_1$–$C_3$ haloalkyl, $C_2$–$C_3$ alkenyl, $C_2$–$C_3$ haloalkenyl, $C_2$–$C_3$ alkynyl, $C_2$–$C_3$ haloalkynyl, and $C_1$–$C_3$ alkoxy, wherein said alkyl, haloalkyl, alkenyl, haloalkenyl, alkynyl, haloalkynyl, and alkoxy groups may be optionally substituted;

$R^2$ is optionally substituted $C_1$–$C_6$ haloalkyl;

$R^3$ is selected from the group of hydrogen, $C_1$–$C_6$ alkyl, $C_1$–$C_6$ haloalkyl, $C_3$–$C_8$ cycloalkyl, $C_2$–$C_6$ alkenyl, $C_2$–$C_6$ alkynyl, $C_2$–$C_6$ haloalkynyl, aryl, heteroaryl, $C_1$–$C_6$ alkoxy and aryloxy, wherein said alkyl, haloalkyl, cycloalkyl, alkenyl, haloalkenyl, alkynyl, haloalkynyl, aryl, heteroaryl, alkoxy, aryloxy groups may be optionally substituted;

$R^4$ is selected from the group of hydrogen, $NR^{10}R^{11}$, $C_1$–$C_6$ alkyl, $C_1$–$C_6$ haloalkyl, $C_3$–$C_8$ cycloalkyl, $C_2$–$C_6$ alkenyl, $C_2$–$C_6$ haloalkenyl, $C_2$–$C_6$ alkynyl, $C_2$–$C_6$ haloalkynyl, aryl, heteroaryl, $C_1$–$C_6$ alkoxy, and aryloxy, wherein said alkyl, haloalkyl, cycloalkyl, alkenyl, haloalkenyl, alkynyl, haloalkynyl, aryl, heteroaryl, alkoxy, aryloxy groups may be optionally substituted;

$R^5$ and $R^6$ are independently selected from the group of hydrogen, F, Cl, Br, I, CN, $NH_2$, OH, SH, $C_1$–$C_6$ alkyl, $C_1$–$C_6$ haloalkyl, $C_2$–$C_6$ alkenyl, $C_1$–$C_6$ haloalkenyl, $C_1$–$C_6$ alkoxy, and aryloxy wherein said alkyl, haloalkyl, alkenyl, haloalkenyl, alkoxy and aryloxy groups may be optionally substituted;

$R^7$ is selected from the group of $C_2$–$C_6$ alkyl, $C_2$–$C_6$ alkenyl, and $C_2$–$C_6$ haloalkyl, wherein said alkyl, alkenyl, and haloalkyl groups may be optionally substituted;

$R^8$ is selected from the group of hydrogen, F, Cl, Br, I, CN, $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_1$–$C_6$ alkoxy, and aryloxy, wherein said alkyl, haloalkyl, alkenyl, haloalkenyl, alkynyl, alkoxy and aryloxy groups may be optionally substituted;

$R^9$ is selected from the group of hydrogen, F, Cl, Br, I, methyl, and optionally substituted methyl;

$R^{10}$ and $R^{11}$ each independently is hydrogen or optionally substituted $C_1$–$C_6$ alkyl; or $R^{10}$ and $R^{11}$ taken together with nitrogen form an optionally substituted five- or six-membered heterocyclic ring;

Y is selected from the group of $NR^{12}$, O and S;

$R^{12}$ is selected from the group of hydrogen, optionally substituted $C_1$–$C_6$ alkyl, and optionally substituted $C_1$–$C_6$ haloalkyl; and pharmaceutically acceptable salts thereof.

50. A compound according to claim 48, wherein $R^1$ is selected from the group of hydrogen, optionally substituted $C_1$–$C_3$ alkyl and optionally substituted $C_1$–$C_3$ haloalkyl.

51. A compound according to claim 49, wherein $R^1$ is hydrogen.

52. A compound according to claim 49, wherein $R^3$ is selected from the group of hydrogen, optionally substituted $C_1$–$C_6$ alkyl and optionally substituted $C_1$–$C_6$ haloalkyl.

53. A compound according to claim 51, wherein $R^3$ is hydrogen.

54. A compound according to claim 51, wherein $R^8$ is selected from the group of hydrogen, optionally substituted $C_1$–$C_6$ alkyl and optionally substituted $C_1$–$C_6$ haloalkyl.

55. A compound according to claim 53, wherein $R^8$ is hydrogen.

56. A compound according to claim 53, wherein $R^9$ is hydrogen, F, Cl, Br, or I.

57. A compound according to claim 55, wherein $R^9$ is hydrogen.

58. A compound according to claim 48, wherein $R^5$ and $R^6$ each independently is selected from the group of hydrogen, F, Cl, Br, I, and $C_1$–$C_4$ alkyl wherein said alkyl group may be optionally substituted.

59. A compound according to claim 57, wherein $R^5$ is optionally substituted $C_1$–$C_4$ alkyl and $R^6$ is hydrogen.

60. A compound according to claim 57, wherein $R^7$ is selected from the group of $C_2$–$C_5$ alkyl and $C_2$–$C_5$ haloalkyl, wherein said alkyl and haloalkyl groups may be optionally substituted.

61. A compound according to claim 59, wherein $R^7$ is an optionally substituted $C_2$–$C_5$ alkyl.

62. A compound according to claim 48, wherein $R^4$ is selected from the group of $NR^{10}R^{11}$, $C_1$–$C_6$ alkyl, $C_1$–$C_6$ haloalkyl, $C_3$–$C_8$ cycloalkyl, aryl, and heteroaryl, wherein said alkyl, haloalkyl, cycloalkyl, aryl and heteroaryl groups may be optionally substituted.

63. A compound according to claim 61, wherein
R⁴ is selected from the group of aryl, $C_1$–$C_6$ alkyl and $C_1$–$C_6$ haloalkyl, wherein said aryl, alkyl and haloalkyl groups may be optionally substituted.

64. A compound according to claim 62, wherein
R⁴ is optionally substituted $C_1$–$C_6$ alkyl.

65. A compound according to claim 48, wherein
R¹ is selected from the group of hydrogen, optionally substituted $C_1$–$C_3$ alkyl, and optionally substituted $C_1$–$C_3$ haloalkyl;
R³, R⁶, and R⁸ are independently selected from the group of hydrogen, optionally substituted $C_1$–$C_6$ alkyl, and optionally substituted $C_1$–$C_6$ haloalkyl;
R⁴ is selected from the group of $C_1$–$C_6$ alkyl, $C_1$–$C_6$ haloalkyl, $C_5$–$C_6$ cycloalkyl, aryl, and heteroaryl, wherein said alkyl, haloalkyl, cycloalkyl, aryl and heteroaryl groups may be optionally substituted;
R⁵ is optionally substituted $C_1$–$C_6$ alkyl;
R⁷ is optionally substituted $C_2$–$C_5$ alkyl; and
R⁹ is hydrogen, F, Cl, Br, or I.

66. A compound according to claim 48, wherein
R¹ is selected from the group of hydrogen, optionally substituted $C_1$–$C_3$ alkyl, and optionally substituted $C_1$–$C_3$ haloalkyl;
R³, R⁶, and R⁸ are independently selected from the group of hydrogen, optionally substituted $C_1$–$C_6$ alkyl, and optionally substituted $C_1$–$C_6$ haloalkyl;
R⁴ is selected from the group of $C_1$–$C_4$ alkyl, $C_1$–$C_4$ haloalkyl, $C_5$–$C_6$ cycloalkyl, aryl, and heteroaryl, wherein said alkyl, haloalkyl, cycloalkyl, aryl and heteroaryl groups may be optionally substituted;
R⁵ is optionally substituted $C_1$–$C_6$ alkyl;
R⁷ is optionally substituted $C_2$–$C_5$ haloalkyl; and
R⁹ is hydrogen, F, Cl, Br, or I.

67. A compound according to claim 48, wherein
R¹, R³, R⁸ and R⁹ are hydrogen;
R⁴ is selected from the group of $C_1$–$C_6$ alkyl, $C_1$–$C_6$ haloalkyl, $C_3$–$C_6$ cycloalkyl, aryl and heteroaryl, wherein alkyl, haloalkyl, cycloalkyl, aryl and heteroaryl may be optionally substituted; and
R⁷ is an optionally substituted $C_2$–$C_5$ alkyl.

68. A compound according to claim 48, wherein
R¹, R³, R⁸ and R⁹ are hydrogen;
R⁴ is selected from the group of $C_1$–$C_6$ alkyl, $C_1$–$C_6$ haloalkyl, $C_3$–$C_6$ cycloalkyl, aryl and heteroaryl, wherein alkyl, haloalkyl, cycloalkyl, aryl and heteroaryl may be optionally substituted; and
R⁷ is optionally substituted $C_2$–$C_5$ haloalkyl.

69. A compound according to claim 48, wherein said compound, when administered to an individual, decreases blood glucose levels but does not substantially raise triglyceride levels.

70. A compound according to claim 48 wherein said compound does not substantially suppress thyroid hormone axis in an individual.

71. A compound according to claim 48 wherein said compound is non-teratogenic.

72. A compound according to claim 48 wherein said modulator compound is selected from the group of:

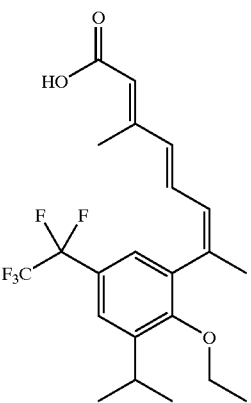

L15

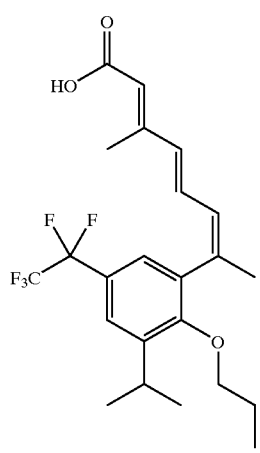

L81

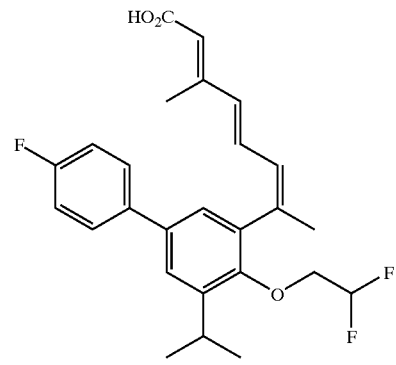

L99

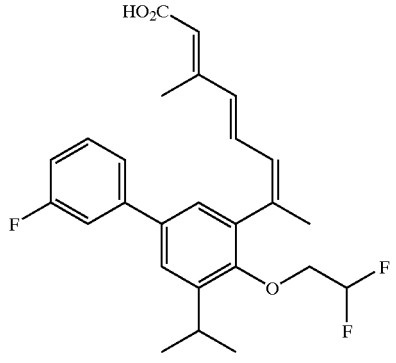

L100

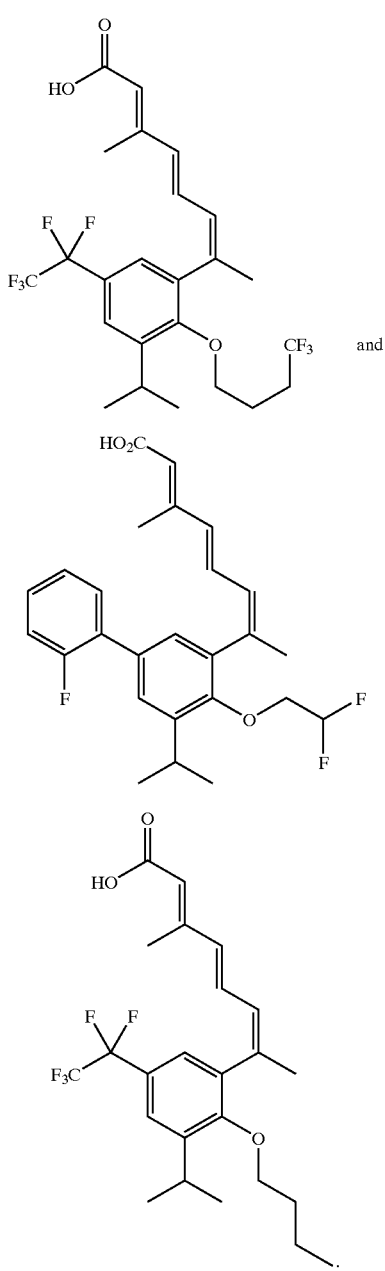

73. A pharmaceutical composition comprising a compound according to claim 48 and a pharmaceutically acceptable carrier.

74. A method for modulating RXR activity in an individual comprising administering to said individual a pharmaceutically effective amount of a compound according to claim 48.

75. A method for treating an individual having a disease condition selected from the group of syndrome X, NIDDM, diabetes, obesity and cardiovascular disease comprising administering to said individual a pharmaceutically effective amount of a compound according to claim 48.

76. A method for treating an individual having a disease condition selected from the group of breast cancer, photoaging, acne, and psoriasis comprising administering to said individual a pharmaceutically effective amount of a compound according to claim 48.

77. A method for treating an individual at risk for developing a disease condition selected from the group of syndrome X, NIDDM, diabetes, obesity and cardiovascular disease comprising administering to said individual a pharmaceutically effective amount of a compound according to claim 48.

78. A method for treating an individual at risk for developing a disease condition selected from the group of breast cancer, photoaging, acne, and psoriasis comprising administering to said individual a pharmaceutically effective amount of a compound according to claim 48.

79. A method for lowering blood glucose levels in an individual without substantially raising said individual's serum triglyceride levels comprising administering to said individual a pharmaceutically effective amount of a compound according to claim 48.

80. A method of claim 78 further comprising administering to said individual a PPARγ agonist.

81. A method for increasing HDL cholesterol levels and reducing triglyceride levels in an individual comprising administering to said individual a pharmaceutically effective amount of a compound according to claim 48.

82. A method for modulating lipid metabolism in an individual comprising administering to said individual a pharmaceutically effective amount of a compound according to claim 48.

83. The method of claim 81 further comprising the administration of a PPARα agonist.

84. A method for modulating RXR:PPAR heterodimer activity in an individual comprising administering to said individual a pharmaceutically effective amount a compound according to claim 48.

85. The method of claim 83 further comprising administering to said individual a PPAR agonist.

* * * * *